US012655468B2

(12) United States Patent
Holsboer

(10) Patent No.: US 12,655,468 B2
(45) **Date of Patent: *Jun. 16, 2026**

(54) GENETIC PREDICTORS OF A RESPONSE TO TREATMENT WITH CRHR1 ANTAGONISTS

(71) Applicant: HMNC Holding GmbH, Munich (DE)

(72) Inventor: Florian Holsboer, Munich (DE)

(73) Assignee: HMNC Holding GmbH, Munich (DE)

( * ) Notice: Subject to any disclaimer, the term of this patent is extended or adjusted under 35 U.S.C. 154(b) by 1311 days.

This patent is subject to a terminal disclaimer.

(21) Appl. No.: 17/145,681

(22) Filed: Jan. 11, 2021

(65) Prior Publication Data

US 2021/0207199 A1 Jul. 8, 2021

Related U.S. Application Data

(63) Continuation-in-part of application No. 15/562,454, filed as application No. PCT/EP2016/057229 on Apr. 1, 2016, now abandoned.

(60) Provisional application No. 62/141,879, filed on Apr. 2, 2015.

(51) Int. Cl.

| | |
|---|---|
| ***C12Q 1/68*** | (2018.01) |
| ***A61K 31/4166*** | (2006.01) |
| ***A61K 31/4985*** | (2006.01) |
| ***A61K 31/53*** | (2006.01) |
| ***A61K 45/06*** | (2006.01) |
| ***C12Q 1/6827*** | (2018.01) |
| ***G16B 40/00*** | (2019.01) |

(52) U.S. Cl.

CPC ........ *C12Q 1/6827* (2013.01); *A61K 31/4166* (2013.01); *A61K 31/4985* (2013.01); *A61K 31/53* (2013.01); *A61K 45/06* (2013.01); *G16B 40/00* (2019.02); *C12Q 2600/156* (2013.01)

(58) Field of Classification Search

None

See application file for complete search history.

(56) References Cited

FOREIGN PATENT DOCUMENTS

| | | | |
|---|---|---|---|
| WO | 2005/054500 | A1 | 6/2005 |
| WO | 2012/027446 | A1 | 3/2012 |
| WO | 2013/160315 | A2 | 10/2013 |
| WO | 2013/160317 | A2 | 10/2013 |
| WO | 2014/202541 | A1 | 12/2014 |
| WO | WO2016/156575 | A2 | 10/2018 |

OTHER PUBLICATIONS

PCT International Search Report and Written Opinion for PCT Application No. PCT/EP2016/057229 mailed Sep. 27, 2016 (17 pages).

Kalinin et al; Future Medicine, vol. 19, pp. 629-650, 2018.

Liu et al; PLOS One, vol. 10, pp. 1-11, 2015.

KP055277233—https://www.ncbi.nlm.nih.gov/SNP/snp_ss.cgi?subsnp_id=161060780.

KP055291832—http://www.ncbi.nlm.nih.gov/projects/SNP/snp_ss.cgi?subsnp_id=244304589.

PCT International Search Report and Written Opinion for PCT Application No. PCT/EP2016/057230 mailed Aug. 22, 2016 (16 Pages).

*Primary Examiner* — Jehanne S Sitton

(74) *Attorney, Agent, or Firm* — BALLARD SPAHR LLP

(57) ABSTRACT

The present disclosure provides methods for predicting a treatment response of a subject to a treatment with a CRHR1 antagonist and methods of detecting a polymorphism genotype associated with a treatment response of a subject to treatment with a CRHR1 antagonist. Sets of at least one polymorphism genotype useful in such methods are also disclosed. Further, methods of treating a condition which is treatable by a CRHR1 antagonist in a subject in need thereof are provided. Compositions, kits and arrays and uses thereof are also disclosed, which can be used in the methods of the invention.

58 Claims, 1 Drawing Sheet

Specification includes a Sequence Listing.

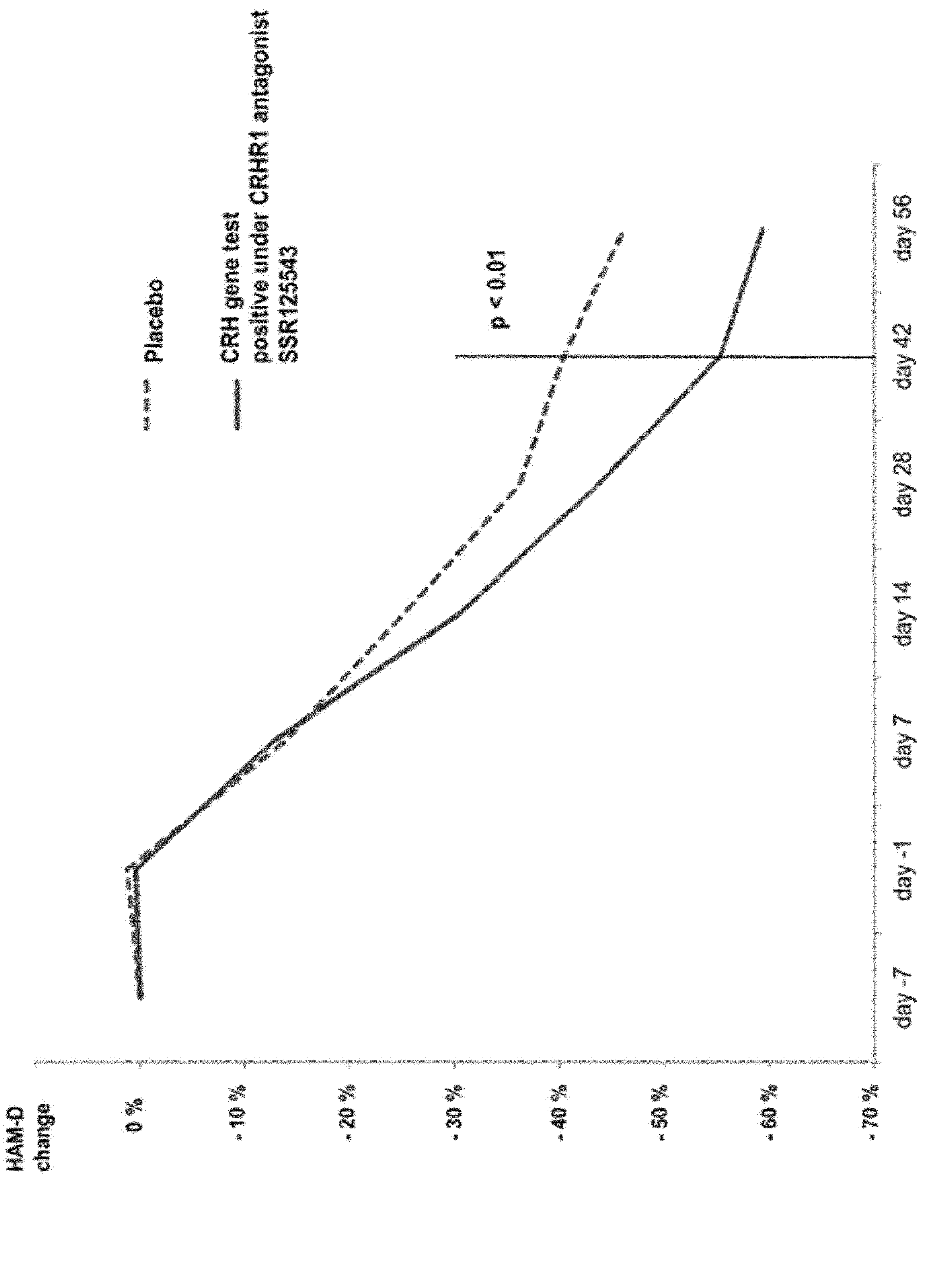
HAM-D change
0 %
- 10 %
- 20 %
- 30 %
- 40 %
- 50 %
- 60 %
- 70 %
day -7
day -1
day 7
day 14
day 28
day 42
day 56
Placebo
CRH gene test positive under CRHR1 antagonist SSR125543
p < 0.01

SEQUENCE LISTING

```
<160> NUMBER OF SEQ ID NOS: 548

<210> SEQ ID NO 1
<211> LENGTH: 121
```

<212> TYPE: DNA
<213> ORGANISM: Homo sapiens
<220> FEATURE:
<221> NAME/KEY: source
<222> LOCATION: 1..121
<223> OTHER INFORMATION: /mol_type="unassigned DNA"
/organism="Homo sapiens"
<220> FEATURE:
<221> NAME/KEY: variation
<222> LOCATION: 61
<223> OTHER INFORMATION: /allele="[A/G]"

<400> SEQUENCE: 1
atgagtctcc aggactctat ggcttccttc atgtcatcgt ccactctgcc aagggattta 60
agcaatcagc cagtaagtgc cctggccagg acgaggttgg gtgggccatt gtggattctg 120
c 121

<210> SEQ ID NO 2
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 2
atgaagatct acgacagaga tgaattgagg ggacaaatgt cagagctcac agacgactgt 60
atctctgttc aggaccgctt ccacctcact gaaattcact ccctcaatgt gctggagggc 120
a 121

<210> SEQ ID NO 3
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 3
aacagcagga tcagaagcct atttttaatg tcattccacc aattcccgtt ggttccgaaa 60
attggaatag gtgccaagga tctggagatg acaacttgac ttctctgggg actctgaact 120
t 121

<210> SEQ ID NO 4
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61

<223> OTHER INFORMATION: /allele="[A/G]"

<400> SEQUENCE: 4
ccaaagaatc attaactcct ggtagagaag aaaaccccag cagtgtgctt gctcaggaga 60
agggagatgt gatggacttc tataaaaccc taagaggagg agctactgtg aaggtttctg 120
c 121

<210> SEQ ID NO 5
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 5
atatgtttga caatttttat ttttagctag tcatcaaagc tcttacaagt cagaatttca 60
aacttgacca ggactatagt ttatttactg gagtgctagg agagaatgca aaagtgatgg 120
t 121

<210> SEQ ID NO 6
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 6
ttgatcatgc attcccaata ttcgtatatg tatttataaa ttacataatg ggcagggtgc 60
aatggctcac acctgtaatc ccagcactgg gggaagctga ggtgggtgga tcacctgaag 120
t 121

<210> SEQ ID NO 7
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 7
cactggatat tctaaggagt gttttgaact aatcttgttc ccttgaagtt cctggagttt 60
attagcagat gtaagtagta tggagtaagt tcatacctct caaaaagcac tataatttag 120
g 121

<210> SEQ ID NO 8
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 8
cgacgatgta taccagaata tttgttcaga ttaatatttt ccttattctg gcttattaaa 60
atagtaacgc ctgttcttat taaggttgat tttgcctgta attagaagtc atgggcaact 120
t 121

<210> SEQ ID NO 9
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 9
aaacactcct tagaatatcc agtggaaagc actgggactg attttcattc gttgagcatt 60
acccaaggta gtgtgcccta aaaagaagtg taccttatga acagaatagt agaaactatc 120
c 121

<210> SEQ ID NO 10
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 10
gtgcatgtgg gatttattct tctgactcag gaaagcaatt tgatgaagtg acatgtttct 60
actaaacagc acacatcaag acacgttatg ctgcttctgt ttatcccacc tactggaagg 120
a 121

<210> SEQ ID NO 11
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"

<220> FEATURE:
<221> NAME/KEY: variation
<222> LOCATION: 61
<223> OTHER INFORMATION: /allele="[A/T]"

<400> SEQUENCE: 11
catataatat cttaatttaa caagtaaatg cagatgcctt aagattccct atcttggagt 60
agttggctga caccttctcc agaaagcata gttaacctgc tgcatgacaa agggcaagtt 120
a 121

<210> SEQ ID NO 12
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 12
catcaggcag ccctccagct gaatgatttt tgtctgtgcc tggcccagtc cctgagtcca 60
aagtggtttt taggattcac atcggttaca ggaccgggcc atggtctgcc cacctgaagc 120
t 121

<210> SEQ ID NO 13
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 13
taaaaaatat gtgaaaatgc attttccccc tattccttct ggaaagcaac attagggtcc 60
agcagttctg tctggaagga gggagatgca ggagcagcat cctggcttat gaccgcgtgg 120
c 121

<210> SEQ ID NO 14
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 14
cagtatttaa gatgaaagga gatcagattt ggtttcggag aacagagcag atgtcgtggc 60
atcagtaatc actagggtgt ccctttaagg atatgaggac tgtggtgagc agggatggct 120
a 121

<210> SEQ ID NO 15
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 15
ccggagccag ctcggcactg gaaccggcgt cctctggtgg cagagagaga gcgctactgg 60
agattttcgg accgaatcgg cacgctcgtc agatccaagc aggcgggact ggcctggagc 120
a 121

<210> SEQ ID NO 16
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 16
agaggcaact gtgtctcggg aaggtaaagt gaacatctca gggtcatgta agtcggaagc 60
aacacagcgg tgacttacac tcagatcctt actctccaga gttagtgctc ttaaccagta 120
g 121

<210> SEQ ID NO 17
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[C/G]"

<400> SEQUENCE: 17
ttcacagcat caagcagtcc acagcagtct gagctggcag gtcatggagc agcccccaaa 60
cagctgtggc tggggggatg acggccaggc tccctgacca ccctgcctgt ggaggtgacc 120
t 121

<210> SEQ ID NO 18
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 18
cttctagttg tatttattgt taaaatgaca tcataatatt acaggaaatc cccccagcct 60
accctcaccc tgctgtgatt ttactgatca ttatctcccc ctgttcttta ctcaggtgta 120
t 121

<210> SEQ ID NO 19
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 19
tgcatgaact tgggtcccag agggtcctat tatgaaagct ggatcaattg caatgggaaa 60
agggctaacg ttattgtacc tagaatgctg aagtggtcaa ctacctaaat aaagattaca 120
c 121

<210> SEQ ID NO 20
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 20
aatattagaa gtttcctttg tctcccctta ttttgtcacc aggagtaaaa attaacttta 60
agaaaaggaa atttgctggg gtcaccttgt accttgtcct ggctttgttc tcgggtgctg 120
g 121

<210> SEQ ID NO 21
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 21
aaggaaagaa ataacagtaa aaattcaata aaattgaaac aaatatataa gaaaatcaac 60
aaaactaaaa gtgtttttaa aaagattaat gcagttgata agcttctagc aagactattc 120
a 121

<210> SEQ ID NO 22
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 22
tctgagggcg ggaaccaggt ctcctttacc ctgggatgca tgggagctca gaaatgtgga 60
atgaagtcgt taatttacac agcacctacc gtgcacctgg agaaggtgag aacatggctg 120
g 121

<210> SEQ ID NO 23
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 23
caagcaacct gcctcctgct agacaattag ctttatccat gagttaccaa agagggagcc 60
aaaacccagg gaagctgaaa gagctgttga ttgtcaccct gtgagttggt gatagaaaga 120
t 121

<210> SEQ ID NO 24
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 24
gattgtaccc accaaaatct ataaacaata aggaactgtg gttgtttgct gcaaataact 60
atgataaacc acactgtttg tatcacatgt attagcccat tgtgacattg tcaattgacc 120
a 121

<210> SEQ ID NO 25
<211> LENGTH: 121
<212> TYPE: DNA

<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 25
gtagggtatt gagtgagggg ttgttatctt cagtcaatcc atcaattaat ttgtattaga 60
acattctgtg tgccagtcac agtacatgcc ctcatcattc ccaactcttg aggagcttag 120
t 121

<210> SEQ ID NO 26
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/T]"

<400> SEQUENCE: 26
attttgcagt tatctcagaa tattaactag aatatatggc tcatgagagc aggccctgtg 60
actgccttcc tcactctcat gtcactaggg actagcacat agtaggcact caagaaacgt 120
t 121

<210> SEQ ID NO 27
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 27
gcgcttagtt tcctgccaca gggagacagt aagaaaggtg acgtcaatct gagatgagag 60
agagagcaaa acagttcttt tgaccacctt gaccccgacc ttgaaataag gtggaactaa 120
t 121

<210> SEQ ID NO 28
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 28
acgggctttg tgcgaagttc gtcggcgctg gtgtccacag caagtgaagt gggttcagtt 60
agtcccaggt tccaatggtt gaggcggaaa ggcaaaggta taaataccct tgatagcctt 120
t 121

<210> SEQ ID NO 29
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 29
ggcctctgct tcccaccaag gtgctggggg aagtgggctg ctgtggaccc ccaccccgga 60
acactctgct ttctgcagga tcctcatgct ccccaaggac ccagagaggc tggggtgggg 120
g 121

<210> SEQ ID NO 30
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 30
cacaacattg atgctctctg aacactatga cctctgatta tttatcaacc tccaagagct 60
atcactgtca ctggggacag agagcagaca aaataaaaca cctgggagtg gggtgcagaa 120
g 121

<210> SEQ ID NO 31
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[C/G]"

<400> SEQUENCE: 31
tgggctgggc tcccctcttc tgtgagagcc aaacagagcc cttcctgagt cccatccatt 60
cgcagggtcc tactgttgtc cgccccctcg ttcccactgc cagctctggg ggagctgggc 120
t 121

<210> SEQ ID NO 32
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 32
cttgcctcta tctgggtcct tttcattgct ctacaaagaa tcctttcttc ctcccaggcc 60
acactaagta ataacaactg gggacttttc tcacgccaac ttctgagccg cttcaagtgt 120
c 121

<210> SEQ ID NO 33
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 33
aggcccggcc catcaatgcc cacgctacac gaggcatact agacagtcgc tgcctaagcc 60
aaagtcagat caccgatatt cttccaggaa aaggctcctc ttgccccctt tcccacaaga 120
a 121

<210> SEQ ID NO 34
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 34
tacttttgaa gtttctgtca aagaatgtca gagaatatat agttttgtgt ggctatctct 60
atttttctta tatattatcc ctgttaatgc agggcatact gttactcttg aatgttttaa 120
c 121

<210> SEQ ID NO 35
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:

<221> NAME/KEY: variation
<222> LOCATION: 61
<223> OTHER INFORMATION: /allele="[A/G]"

<400> SEQUENCE: 35
tctgtgaacg tgttggcact aactgaaaat gaatgtttgc tacattatag tccattaggt 60
atggtcatag ttgccagtgg tgagcagaat cctcccagga gtaataaatt catcagtata 120
c 121

<210> SEQ ID NO 36
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 36
gcaatcaata catcatgatg taatgtagtc atatagacta ggacacttag attagccccc 60
atgacgcaag gcgtgttctg agtaacagtc tcaaattaag tggagacttt gtgatcactg 120
c 121

<210> SEQ ID NO 37
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 37
gttttttaaa ggttttagta ttgcaatgtg gaatccaaaa ctgttatcaa tgaacttttg 60
attgttacat tgaaatatgt cagtctatct tgcactttga atgtatcttt tacccatgca 120
t 121

<210> SEQ ID NO 38
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 38
aagagcaaag ctccgtctta aaaaaaaaaa aaaaaaaaaa aagaacacag cctcccacct 60
aatatttcct gacacggggc ctcaggatgg cactaacggt tccctcaccc agggaggtag 120
a 121

<210> SEQ ID NO 39
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 39
tctgttccct aaaattttga tgtacccaga aaagcatatt gtaaaaaatg ttcagatggt 60
aagagtttta ctttctaata aagcatacag atttgtgatg gggagttcag ttcatgggca 120
g 121

<210> SEQ ID NO 40
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 40
gaaagtggtg agggacaggc ctggacagtg tccactgggc agagagagcc gattccgtgc 60
agctcctggt gctgatgtgc agcgtctggg gatcccgtcg tctgttttac tctggggata 120
t 121

<210> SEQ ID NO 41
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 41
ttaatgtcag cacactaata ttcaaacatc cttgacctca tctcatataa ataaatccaa 60
atgcaaatat cagtcagtca atatatgttg tatgtctagc tcccacacaa tttttatagc 120
a 121

<210> SEQ ID NO 42
<211> LENGTH: 121
<212> TYPE: DNA
<213> ORGANISM: HOMO SAPIENS
<220> FEATURE:
<221> NAME/KEY: source
<222> LOCATION: 1..121

-continued

<223> OTHER INFORMATION: /mol_type="unassigned DNA"
      /organism="HOMO SAPIENS"
<220> FEATURE:
<221> NAME/KEY: variation
<222> LOCATION: 61
<223> OTHER INFORMATION: /allele="[A/G]"

<400> SEQUENCE: 42
cctgcactat ccaagattct ggatgtcttt aaggtaacaa gtgtccatgt tgttccttga 60
aagcctggag aaatctggtg tgggaaatgt aggactcttg gtgtgggggg actgttcaag 120
a 121

<210> SEQ ID NO 43
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
      /organism="HOMO SAPIENS"
<220> FEATURE:
<221> NAME/KEY: variation
<222> LOCATION: 61
<223> OTHER INFORMATION: /allele="[A/G]"

<400> SEQUENCE: 43
tagcaatgtt cctctgtctg cacttaagcc ataagaactc tttttccttg taagcccatc 60
agtactcaat gaaatgcctg cagagatttg gtgcatagct attttcgctt ctgctgagaa 120
c 121

<210> SEQ ID NO 44
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
      /organism="HOMO SAPIENS"
<220> FEATURE:
<221> NAME/KEY: variation
<222> LOCATION: 61
<223> OTHER INFORMATION: /allele="[A/G]"

<400> SEQUENCE: 44
ctccttcatc ctcccacaga gccttggcat gctcatagaa ttcctgaaag tgaacacaag 60
aaagtttaga gaaaggcaag agcttgaact aatcaacaac actgtcattc aaaccctgag 120
a 121

<210> SEQ ID NO 45
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
      /organism="HOMO SAPIENS"
<220> FEATURE:
<221> NAME/KEY: variation
<222> LOCATION: 61
<223> OTHER INFORMATION: /allele="[A/C]"

<400> SEQUENCE: 45
tggatctgaa gatcttagcc aaggcaggaa agcacacgat caggtaacct ccagattcac 60
agccctggtg ccccggttct cctgggaact ggtcctgaga tcttggacaa atccctggtt 120
c 121

<210> SEQ ID NO 46
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 46
aaaacatttt ttactcgcat taactctttc aatttcacaa caaatctaag aaaaatgcaa 60
aaacaggaaa attaaaacaa atggaaacat taaaagtatc catcaatata tacaaatatt 120
g 121

<210> SEQ ID NO 47
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 47
taaccaaatt agtctaaaac actatcatct cctcctggat tactgcaaca gactccttct 60
atgcttgccc ccttcggcct attcacacag tttctatagt gatcctttca aaatttcaga 120
t 121

<210> SEQ ID NO 48
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 48
gctttggggc tgtttttcct ggaaaaacga ctgccttcta aggccaaagg tcagtttaaa 60
aagggctgct ggaccgccaa accccaccga acagggaata tttagggcag aaataaggac 120
t 121

<210> SEQ ID NO 49
<211> LENGTH: 121
<212> TYPE: DNA
<213> ORGANISM: HOMO SAPIENS

```
<220> FEATURE:
<221> NAME/KEY: source
<222> LOCATION: 1..121
<223> OTHER INFORMATION: /mol_type="unassigned DNA"
      /organism="HOMO SAPIENS"
<220> FEATURE:
<221> NAME/KEY: variation
<222> LOCATION: 61
<223> OTHER INFORMATION: /allele="[A/G]"

<400> SEQUENCE: 49

taatagagca cagtatccaa gagagtagga tcttaataac cccctgaaaa agcaagcaga     60

aatggctttc taaaagcagg agaacaagag aaatacttcc aacacgcatg gtggtcagat    120

t                                                                    121


<210> SEQ ID NO 50
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
      /organism="HOMO SAPIENS"
<220> FEATURE:
<221> NAME/KEY: variation
<222> LOCATION: 61
<223> OTHER INFORMATION: /allele="[A/C]"

<400> SEQUENCE: 50

tgcgactcaa gcccaccctg cctggcctgc accaggtgga accccatgcg cttgcctagc     60

aaggaccaga caccgagggg ccgttggttc taggacggcg agggtcagaa ggagaggcct    120

g                                                                    121


<210> SEQ ID NO 51
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
      /organism="HOMO SAPIENS"
<220> FEATURE:
<221> NAME/KEY: variation
<222> LOCATION: 61
<223> OTHER INFORMATION: /allele="[A/G]"

<400> SEQUENCE: 51

aatcccaata aaagctctaa taccacctaa aaccatttct gttctctacc tctgtcatta     60

atgcttaaat gaaacaaggc tgaaaatcaa ataatgcaga aatgtgcctt cgtcaataag    120

t                                                                    121


<210> SEQ ID NO 52
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
      /organism="HOMO SAPIENS"
<220> FEATURE:
<221> NAME/KEY: variation
<222> LOCATION: 61
<223> OTHER INFORMATION: /allele="[A/C]"
```

<400> SEQUENCE: 52
atgacacagc acaggttcta tatctttaga tggtaaatta aaaattcctg gctgaatttg 60
attgattgtc atttttaaaa attgttaaag acttgtaaga gggaagaata ggccagacat 120
t 121

<210> SEQ ID NO 53
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 53
aatgatcctg ggtaacaaat gtgatatgaa tgacaaaaga caagtgtcaa aagaaagagg 60
agagaaggta aatgtgaatg gaatggataa aggttggaat ctactcacat taagcatttc 120
t 121

<210> SEQ ID NO 54
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 54
aaaataataa tttctcacgc tcacttcggc agcacatata ctaaaataat aatttctccc 60
agttctttat tattagcctc caaagagtat acctgcagca gctttaaaca acatgccact 120
c 121

<210> SEQ ID NO 55
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 55
tgctatttta cattgggtga tcaggaaatg ctcctaggag gaggtggtat ttgagcaggg 60
atatgggtga agtaagagag gtcatgcaag ggctagaaga agactactcc aggcagagga 120
g 121

<210> SEQ ID NO 56

<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 56
aaaatctggc aagatagcct atacaacatg gtgagaccct gtctctacaa aaattaaaaa 60
atatatatat agccgaacat agtggctata ttggagtgca gcaggtggaa ggagtgcttg 120
a 121

<210> SEQ ID NO 57
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 57
agttctccag aggacctgcc tacctccaga cggctcactc actcccactc attctgtata 60
aactgctagt gaagcctttc tgacacagca cacccaccac attactctct aattcatgga 120
c 121

<210> SEQ ID NO 58
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 58
ttaagacctc agaaaactct tgttaaaatg gaaatctatt ccctaaaaga gattatacac 60
atatccatta tggacattca catgctagca gtgattcatt gatcaaatta gttgtcactt 120
t 121

<210> SEQ ID NO 59
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 59
gtttatttgt tgattttatc tgtggaagat cagtccaacg tttaaagtgg ggtgttgaag 60
actccagcta ctattttatt aggggcttat ctctatgttt acctctaata atattttctt 120
t 121

<210> SEQ ID NO 60
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 60
tttgctaaga agtgttaatt ctctaagagg aaaatgtcat ttctccaaaa caaaacttta 60
agcaggtgat tttttttaaa agccctgtca ggttgacaag tgctataaga taataaacct 120
t 121

<210> SEQ ID NO 61
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 61
tccaaatcac gtaacaaggt tacctccaga aaaaaaggct attgctgaac agaggctttc 60
atttttactt ttattcccca gaatttttg aatgctttag aacattgatt ctcaaaccgt 120
a 121

<210> SEQ ID NO 62
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 62
gagggaagct ggctctcttt gaatggaaat ttaaccagaa gttaaaataa attccattca 60
atcgtataga atagttttgt tccttttcac ttaaaaatat ttttctctct tttatgtgcc 120
t 121

<210> SEQ ID NO 63
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 63
ctcgaggagg ggctcacacc gagatcaatc catgatgaca gcacttcatg gcccgtctca 60
aacacacagg cccactccct ggtctggccc aggctggggt gctcagggcc tctgtgttgt 120
t 121

<210> SEQ ID NO 64
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 64
aaaatgatgg gataatctaa ttcatctaac ttgctttaca aatgaggaaa ctgataatcc 60
aaaagattta atctcatagg aaccaggtga cagagcagga aataggccac tggtctcctg 120
c 121

<210> SEQ ID NO 65
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 65
catctgcaga tttaacgatt tcattgaaaa aaaaatcctc cagatcaggt attttagaat 60
attaaataac accaatcctg aggcccgtct gtaaccactc aaagggtcca ccttgcccac 120
t 121

<210> SEQ ID NO 66
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"

/organism="HOMO SAPIENS"
<220> FEATURE:
<221> NAME/KEY: variation
<222> LOCATION: 61
<223> OTHER INFORMATION: /allele="[A/G]"

<400> SEQUENCE: 66
cttggggatt ccactgggct atgtgtccat ttatttattc attcaataaa tatttactga 60
atgtccacca ggccctatag ataccatggg aaacagacag tggcccctgt tctcaagtgg 120
c 121

<210> SEQ ID NO 67
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 67
gaaggactaa aggggtcaag atacaaggag tcaccaaaga atgcagaaga gacaagttca 60
agaagactac cacatacgta ttggttaccc agagagaacc tgaaaacagc agcaccattg 120
g 121

<210> SEQ ID NO 68
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 68
tggttcaggt ggctctggat aaggtcagtg aggcttagtt caaaccaacc tgatttataa 60
acataagaac attctactac taattcttgt taatattggt cttagaaaag gaaatttctg 120
a 121

<210> SEQ ID NO 69
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 69
tcaggaggtc tgttgctaat cccaaccagc atgatttacg ggaagtaaat catctatgac 60
atgcccaaag agaataaaag tacatacagg atgcttctac ttagggcttt tttggtagag 120
a 121

<210> SEQ ID NO 70
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 70
atcctgatca gcctgtctca caaacattgg gttctataga cgctcctaga ttgcattttc 60
atttaagctg agccttgatg gtctgctgga atatggtagg ctacacttta cacacacaag 120
g 121

<210> SEQ ID NO 71
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 71
tccttttgtt cccagtgcct tgacagggta tggggggacc tgcatgacta gcattaaatg 60
aaggactggg ctttgccaga atgaagaaat cctctgagaa tgtgcagtag agcaaaacaa 120
g 121

<210> SEQ ID NO 72
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 72
tggacattta taaccaggga tctgtgcgtt ttgctataat tcagaaagta gcagactact 60
agacacgtgt catttggcaa gggattttaa gagcacatag tatacttaga ataatcatgc 120
t 121

<210> SEQ ID NO 73
<211> LENGTH: 121
<212> TYPE: DNA
<213> ORGANISM: HOMO SAPIENS
<220> FEATURE:

<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 73
gagagggagg aaaagtcggt tcgagaaccc aggtggaaaa tagattgagg gaagcaaaac 60
aagatgttac aggaggaata tgggtgattg tcttttcctt ttatatttct gcatgttttg 120
t 121

<210> SEQ ID NO 74
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 74
taaaaaataa ttttaaagca gtgtggtctc aatcttagta gaagagtaga aagcaagata 60
atttctactt ggaataaaca agtgcacagt ggaagtgatt aactcttact ctcaatgtta 120
t 121

<210> SEQ ID NO 75
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 75
aaatagaggg ctctggacat cttcagaggg tcccacttta gacttcactg atctcttttt 60
aacatttttt atcaatacat aatatttgta cattttatgg ggtatttgtg atattttgct 120
a 121

<210> SEQ ID NO 76
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 76
cctaatctca ttcacaaata tatctgaata aaaatggtaa atccaaagac aacaacatca 60
ataactatct tagctatatc ccttactgga aataataaat gtaaagtgtg aaagaatcaa 120
t 121

<210> SEQ ID NO 77
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 77
cctcgcctct ctcttctgat ttatctggct cttgcctctc cccctccatc aaaagaccac 60
actatctctc tcctcttttc catttgaacg attttgccat tcatcaaact gattgctaat 120
g 121

<210> SEQ ID NO 78
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 78
cttcagagac ttcgtaatta aaggaacaga gtgagagaca tcatcaagtg gagagaaatc 60
atagtttaaa ctgcattata aattttataa cagaattaaa gtagatttta aaagataaaa 120
t 121

<210> SEQ ID NO 79
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 79
ctggtatggg agccagggtt gaagtcactc acgggtcctc tccgagaact cgagtggtga 60
aatggagagc cggggcctgc ccttgtccct gcagcaggac tggggaggag ggggtgcctg 120
a 121

<210> SEQ ID NO 80
<211> LENGTH: 121

<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 80
gtctgtgtga cagagcaaga ccctgtctct taaaaaaaaa aaaagtgatg tagccatttc 60
ataaagacag ttgggcaata actatcaaat ttaaaatgca tatcaccttt gcacttccag 120
g 121

<210> SEQ ID NO 81
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 81
accacacggt ccctcaggct gcttgttacc gtggaagctt cctgaactct ctccagaccc 60
acagacctcc cttcttgggg gctgccgctg aggagcttct ggctagtgag ctctgaagca 120
c 121

<210> SEQ ID NO 82
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 82
aagggaaatg ttttcatttt tctcttccca acccaatccc ctctctctaa atcttggtat 60
aggtgaggtg ctaacagaca gtgaaacaag aaagtggttg gagtcattcc aaaaggggaa 120
c 121

<210> SEQ ID NO 83
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61

<223> OTHER INFORMATION: /allele="[C/G]"

<400> SEQUENCE: 83
tatgagttct gtaagaacag gtactggggt caggcttttc accactgagt ccccctagaa 60
cccagcatgg tgccttgaac acagaaggtg ttcagaaaac atatattgaa tgatgaacga 120
a 121

<210> SEQ ID NO 84
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 84
ggaagaccca tttgcttcct ttccccaatt ctaccaacac atttattgag cacttactat 60
ataactggca attgagatga aagtacacat aacaaggtga acatgcaagg ggtccaccag 120
t 121

<210> SEQ ID NO 85
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[C/G]"

<400> SEQUENCE: 85
ggcatcttta gaccaaagaa tctactgcac ttcaaattct tcatgtgtgt aatgagaata 60
ctgatggcac tacctttgta gtgtttggga atgatttggg gagatacttt tttgtgtaaa 120
g 121

<210> SEQ ID NO 86
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 86
tcctggactt tgccatgtcc ttctaagtga cccgagcact tccagtctca tttgggcagc 60
atccttcccg aattccattc tgtacacttc aagcaaatta gttttagagc atagctctga 120
t 121

<210> SEQ ID NO 87
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 87
aaaaaaaaaa aaaaaaaaag aatagaatag aatagagagt ttggaaaaag atacacataa 60
atatgcttga ttcattttgc taatgcaaag acaatttcat ggaaaagtga taacctttaa 120
g 121

<210> SEQ ID NO 88
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 88
ttgttgagtg ttggtgatgc tgatagttgg agatacccag acagataagg tatattgccc 60
actttcaaaa cttggctgcg ttagttacat ccctatcgat gcaattttct tttcttttg 120 a 121

<210> SEQ ID NO 89
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 89
ttcttctaag actgctcttc ctggcttgca gatggccgcc ttcatgctgg gtctttacac 60 aaccttttc actgtgctac cacattcctg aaggacacca gtcatattga ttagagtccc 120
a 121

<210> SEQ ID NO 90
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"

<220> FEATURE:
<221> NAME/KEY: variation
<222> LOCATION: 61
<223> OTHER INFORMATION: /allele="[A/G]"

<400> SEQUENCE: 90
cgattttgga gcagtagggg actggctgcc gagggggcat ctagattgag ataggtggga 60
aggcaggaca agacccctaa gctcactgcc tcctcgattc cagtcgtcag actccataag 120
t 121

<210> SEQ ID NO 91
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 91
tacacttaca aaagaataga gaatcggcta taaatttgct gagtcagaac attatactgg 60
acatccactt tctcacttct ttgtttttcc agaatgagca cttttgccaa tcccggtttg 120
t 121

<210> SEQ ID NO 92
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 92
caagaccggc ctgggcaaca tatcaaggac ccatctctac aaaattgaaa aaaaaaaaaa 60
agggggaagc aggaaaaggt gatcatggtg gaccacacaa agctttagaa tgaattcttt 120
t 121

<210> SEQ ID NO 93
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 93
gactgaggaa gctccatttt ctttgaggta catcaacatc aataacagat caatggaccc 60
acttaatgga gctcttaatt gagtagaaaa aaatatttaa gagttttgcc gctctacggc 120
a 121

<210> SEQ ID NO 94
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 94
tgcggcctgc agcctgacct catggcttag ctgtgcctcc tggacaccat ccctctctgc 60
aatggcgtgt ggtcctgagt cactgacagc actgacccgc tcctctgagc accagccctg 120
t 121

<210> SEQ ID NO 95
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 95
ttatatggtg gtaaggtgtt ggggaggggg aggggaattg ttttttaatc tttatgatta 60
aatctcagtt ttttttagtg ggtctgaatc cctgggctgt gactttcaga aatgagacaa 120
g 121

<210> SEQ ID NO 96
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 96
gaggcattat ttggtgagaa tcaccattta aaaatgcaaa atattgtgtc actggcttaa 60
actgcagatt cctaggccag aggcaatcaa tacatcatga tgtaatgtag tcatatagac 120
t 121

<210> SEQ ID NO 97
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 97 caccccctgac ccactcatat gtctgttctc actcagaggt gaggccctgt gtcttcagcc 60
atggtaaact caggacctct ggacaggcag gcccagggtg taggcaccat gacttttcct 120
g 121

<210> SEQ ID NO 98
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 98
ctgggggtta gggggacaga gaagtaacgt cacaagattt taagcttggg ccagatatgg 60
aaaataattt aatcctagat cacattttac acatgaataa ctgagaacag aaagaagtga 120
t 121

<210> SEQ ID NO 99
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 99
atagggttga aagtagagca gaaagggcaa gcagagaact agacagagaa gacagatgac 60
agaggagagg aggggaatga ctgccagggc caggtcccag gagagtggga aggtattatt 120
a 121

<210> SEQ ID NO 100
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/T]"

<400> SEQUENCE: 100
tatgtcattt gtaaaatttt aatcataagg tacaatttcc ttgaggcttc ttcacaatga 60
acattgagcc catggtgata tccccagtct tcttgcccta gaggcagcca catatgctta 120
t 121

<210> SEQ ID NO 101
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 101
aaaaaaaaaa aaaaaaaaaa aaagaacaca gcctcccacc tcatatttcc tgacacgggg 60
actcaggatg gcactaacgg ttccctcacc cagggaggta gaaggacttg gacacaagac 120
g 121

<210> SEQ ID NO 102
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 102
caacacactt aatcttgggg aatctgagtt tattagagga atgtagggag gaagcaggct 60
acatgccctc ccagcttaga tttagattta gccagaagaa tgtctgcact tctttgctag 120
a 121

<210> SEQ ID NO 103
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 103
agcaatcctc ccacctcagc ttcccaaagt gctgagatta caggcgtgag ccactgcacc 60
aggcccatct tcctttagac tgtcttgatg aagtcactag agcatatgat aaaaggagag 120
a 121

<210> SEQ ID NO 104
<211> LENGTH: 121
<212> TYPE: DNA

<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 104
aaggaaataa agaacatgac agaaaaaccg tctatcattt taaagaatat atatatatat 60
ataatcatta ggagaatatt catagaaata aaaacattaa aggtgtttct ggtgagatct 120
c 121

<210> SEQ ID NO 105
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 105
agaagtaatt tgagtatctt ttccttgttt ttctcttttg tccagcttat atttatccac 60
aattttataa atctggctca gcaaagcatg ttggaaggga tctcatttta aacaattctg 120
t 121

<210> SEQ ID NO 106
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 106
ggtcgtcttc tagtacagta agggcaaagg gcactgcaat tgctattaaa ctgtaagaag 60
aaggaaaaaa tggacagatt tcgtagccta gtccatcaaa atcattactt tgtagttgat 120
a 121

<210> SEQ ID NO 107
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 107
tctggaaggg atcccccgga actgggggaa tttccaggca catgaggctc tgtcaaccca 60
accaggaaca tccgcccctg ccatctgctc cagacgtcat tgcagagtct gtgtgagagg 120
a 121

<210> SEQ ID NO 108
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 108
aaaaaaaagt atgaatgaaa gtagatttta agtatgccat gttagataaa taatacgtac 60
atattttggc actaaatgaa taactgctgg aaaaatttat tttaagtggc ttttaaaatg 120
c 121

<210> SEQ ID NO 109
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 109
ttaaaattag tagttttaca taaaaatctg aatgtctggc ttttcttgga aaattggaaa 60
atctggccat gccagacctc atttttaaat ggcaattgca tgtgcccctg caagcaggga 120
t 121

<210> SEQ ID NO 110
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 110
ataggtgtgt gtaccacagc tcccagctgc atgtacttta aaaatgtgtc taagccaggc 60
atggtggctc acgcccgtaa tcccagcact ttgggaggcg gaggcgggtg gatcacctga 120
g 121

<210> SEQ ID NO 111
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 111
tgcaataatg tgcaaacaga aaaatcagaa cctgctcatg ctgccatatt aataggaacc 60
atcagtcagc cagagaggga ctcacatatc agacttacat attactaaac tattttctgt 120
g 121

<210> SEQ ID NO 112
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 112
cagagcttgg tatctgagcc tggggccctt tgagccagct gtgttggggg aggtggaggc 60
aggaagttgt aaggtttgag actttgagag ggagccttga gtgtgtagtt actaagggaa 120
a 121

<210> SEQ ID NO 113
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[C/G]"

<400> SEQUENCE: 113
gaaactggga taatacagcc atgcgctacc tactggcatt cccgtcagtg cgtacacgat 60
catggtccca gactgcaatt tttttttttt ttttttgaga cagagtctca ctctgtcacc 120
c 121

<210> SEQ ID NO 114
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:

<221> NAME/KEY: variation
<222> LOCATION: 61
<223> OTHER INFORMATION: /allele="[A/G]"

<400> SEQUENCE: 114
tccttaactt aactgctttc ctcattggct tggtctccat agtgattcat tttgctgtaa 60
aaagtagaca attatagaca attatgaaaa atatgaatac tgtggtctct gagtctgaat 120
t 121

<210> SEQ ID NO 115
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 115
aaattagtat actacctaac ctgggaaata aattaaaaac tgtgatttga ttttcataat 60
aaagaataga aactatcctt taggtcattt ctaattacaa aaaaatttcc attcaaatca 120
t 121

<210> SEQ ID NO 116
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 116
atatgaatga aagaataaaa ctcatcttaa ttttcagaga cttatctaca tagaaaaaat 60
aaagtatttt agaattaaca agattggaag attgctgaca taaaaatcaa tttttagtag 120
t 121

<210> SEQ ID NO 117
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 117
gggtggtgag gcctaagctg aacctgagag gtgaggaaaa cagaccaagc tgaccaaacc 60
actccaggcc cttcctccac tcacagggat gctcctcccg tggtgccttc ctctagacac 120
t 121

<210> SEQ ID NO 118
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 118
tgcacaccat gcgaactgtg gagtatctca gtaagagtgt taggaggaat attttatagg 60
acttgtgctt gtattaggtg attttgggga gtttaagaaa gcagagcttt ctcgattgga 120
t 121

<210> SEQ ID NO 119
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 119
tctaattgac ttttattagg gatttatgaa tcaggcagta ttccatctag gaaatgtcta 60
aaaaggtgct ccacccccatt ggcagaacag ttgtttgaga tttgttgttg ttattttgct 120
t 121

<210> SEQ ID NO 120
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 120
aatgggaagc agcagggtgt gatgtggacc ctggattgta tgtattccct ctcttagggc 60
atggctgctt tttatttgca gctttaccat tgccatgctg gaaaatcatc acatatttca 120
a 121

<210> SEQ ID NO 121
<211> LENGTH: 121
<212> TYPE: DNA
<213> ORGANISM: HOMO SAPIENS
<220> FEATURE:
<221> NAME/KEY: source
<222> LOCATION: 1..121

<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/T]"

<400> SEQUENCE: 121
ggcagtccta aaggaaggtc accctgggat catctcacct ttgacgaggc tggccaggga 60
agctgctgag aatgaaataa actcttctct cttttgcttg gagaaaagaa atcatgggta 120
g 121

<210> SEQ ID NO 122
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 122
ctgggctaga ggcaaaagca gagatgtgag ctgtaaattt gaatgaagga ccagatagaa 60
agtagaaagt ggaaaatgga acctagagct ttggacaggg ctcaaaggaa aacaagcatt 120
t 121

<210> SEQ ID NO 123
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 123
ttgaaatatg attctatatt taataggaaa aggaaacagc agcctattaa aaatgtatca 60
aaacaataac tttttattag tcctactaac atctgaactt ttatgttcct acctacaagt 120
c 121

<210> SEQ ID NO 124
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 124
ccactgtggg ggacggcaga ctgatgggaa cattggttga gtgaccacaa gtgctgttga 60
aagttttttg gtaacagttt taagtgtttt ggttaagcta gacctgaaaa aaatggtata 120
g 121

<210> SEQ ID NO 125
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 125
ataaatttgt caaataaata aactttaaag aaatggccaa cttgggaagg acattaggcc 60
atcagtttgt agtcttacgt caattcttga tctccaagca aaattagttt cagttctctg 120
a 121

<210> SEQ ID NO 126
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 126
agggagggga gaccaagggc tctgagcagc ccccaaagct ccttgtccct cagggtggct 60
atgtggggag cggcctacct ctgagatctt ctggaactgg ttgttggact ggctgcactt 120
c 121

<210> SEQ ID NO 127
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 127
attagaatac tttactctac ttaattaatc aatcatattt agtttgactc accttcccag 60
aaccttctag ttctttctta tctttcagtg cttgtccaga caacattttc atttcaacaa 120
c 121

<210> SEQ ID NO 128
<211> LENGTH: 121
<212> TYPE: DNA
<213> ORGANISM: HOMO SAPIENS

<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 128
ccagattcat gaagaaccct gtatcattga tatcacctag accaccacaa aacaaacata 60
acatttatgt ctctttagtc tccattaaaa ataaacatgt aaaaatgaat caaactcatt 120
t 121

<210> SEQ ID NO 129
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 129
aatgaactta cattctacct gcctccctgt atattttgct ttggttctaa ttattgttaa 60
atgaatcaca acatgtgata tacctctcag ttacttccaa ttgaatcaag agtttttctg 120
a 121

<210> SEQ ID NO 130
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 130
tgataaactg tgctccataa cacaaataat ttcattcttc ttcctttctt gccgagtagt 60
aaaaaaaaga ggatggctgg tttatctcaa gtaatcagac atttaataat aatatagaaa 120
a 121

<210> SEQ ID NO 131
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 131
ccaacagctc atgagcaagg aggccaaaac cctgcgtgga cggtctgctt ccctgcccctt 60 accccccgac ctttattttt tttttgagac gaagtctcgc tctgtcacct aggctgaagt 120
a 121

<210> SEQ ID NO 132
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 132
agagactgcc cactcttgtt aacttcctgg gtttgttttg attccatcaa gggagtagca 60
atgtctcata cttttgtctt ccccacgggg aagggcacat atttggcact caatacatgt 120
a 121

<210> SEQ ID NO 133
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 133
ctttctattc tatttttagc agcctatgga ttctaggagt gacccagctc cagggatagg 60
acttgattaa tctaaattta gagaatggat ttagattaat ccaatcttgg taattccccg 120
t 121

<210> SEQ ID NO 134
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 134
cagaggctgg atgaagatgt acgcaagctc tttcctcctg agacccagtg agggaggcaa 60
aggaggctcc ctagctaaag agggagctca aagttgcagc ctttcctcat gcaaggcaag 120
g 121

<210> SEQ ID NO 135

-continued

<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 135
gctgtggtaa agcattaatg aagcacaggg cctatcacgc agtcaggctc agtataaggt 60
aaggtgtttt ttttttaatc caggtaacat aagaagcacc tgttagcatg agttccatac 120
a 121

<210> SEQ ID NO 136
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 136
tggggtgggt catactcaaa ttgatacaca gcctttgtcc tgagtgtttg tcttccaaaa 60
aaatctcttt gcttagagat ctcagaaaat atttgctgtg ttaggggcag attcctggat 120
t 121

<210> SEQ ID NO 137
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 137
ccttattcat agagtagtat tgcttaaaaa ctgctccaac cacttcttaa acctgaaacc 60
atagacagaa acatctccta agactgataa atcctaagct ttatgctgtt agagactggg 120
t 121

<210> SEQ ID NO 138
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 138
ctgcttgtat tacctgaaca gttctttgtg ttttgattct attgtgttct gtgttgctga 60
atagcagttg gtaagcaatg gcatgtcatc cttgtccctg attttggccg aatgaggaca 120
t 121

<210> SEQ ID NO 139
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 139
tcttacagta aatccccact tatcaaatct tcagatgtgt agagaaggaa taaggcaggg 60
ataatggggg agtgggacag agagatgccc tttctggagt ttgcacaacg gttgcatgct 120
g 121

<210> SEQ ID NO 140
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 140
gtcttcgtga atctgcgtaa attgctgcat ctctcttggc ctcagttttc ttagccacac 60
agacaggact gaactaaatg atctctaaag tacttctcaa gtctataatt ctatgattct 120
c 121

<210> SEQ ID NO 141
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 141
agaggattag aatgacttgc tcctcacaat ttccctgcgt ctgtaactgc acccatgtag 60
acctcatcac ctagagcctt agcctcctaa ataatagtag ctggcactta ctgagaatgc 120
t 121

<210> SEQ ID NO 142
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 142
agtgattata ttttccatta tcccatatat atgtaatggt atgtaatttg tatcattctc 60
atttcatagg agagttattt cattacacaa caagaatgcc atagggtggc atttctgaaa 120
g 121

<210> SEQ ID NO 143
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 143
gaggccgtgt gaatgcttgg gagaagcgcg ctttcggcca ggggtctgga atgcttgcac 60
agggttcttc tctataaaca gtgcagacca gggcctcctg ggcaagcgca gggggtgggc 120
g 121

<210> SEQ ID NO 144
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 144
tattgtggca ataacttctg ctgaaaaact aacctgttct actgagaatt ctatcaatgt 60
aaatagataa acagatgctg gattacacat atctgtacag aactttccta atgctctatc 120
t 121

<210> SEQ ID NO 145
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"

/organism="HOMO SAPIENS"
<220> FEATURE:
<221> NAME/KEY: variation
<222> LOCATION: 61
<223> OTHER INFORMATION: /allele="[A/G]"

<400> SEQUENCE: 145
tctaatggga agagagaaac aaggagagag agaaaaacaa acaggcaaat tggagaaaca 60
atgcatacaa agtagacatt tccaccgtgc gctgcagttt tttccatcat tatttgtttg 120
g 121

<210> SEQ ID NO 146
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 146
acatctaagc ccactccagc cggcccccag aggtgggagg gtccgccacc tcccacagcg 60
agcacctggg ttaccatagg tgcagttaca gcagaagcga ataatgagga gaatctccat 120
g 121

<210> SEQ ID NO 147
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 147
ccataatttg tattagcaca ttaaagaccc cgagaggttc tgcaaaagga aactagttgt 60
accaacttgg tacaactcag catttccaaa atatttggtt acagagcact ttttgcatgt 120
g 121

<210> SEQ ID NO 148
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 148
tcagggtgga ttttgaaatt tccattatat gcaaagccca tgaaaggcta aatatcagtt 60

-continued aagaggggag aggagggtgg ctcctaggtc ctctaatggg caggaaagta tttaaaacaa 120
c 121

<210> SEQ ID NO 149
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 149
tgagattagt gtttgtaaat gcacactgtt gggggaaccc tcttcctagt ccttgtttcc 60
atgtttccca ggaatgaaca ctagtggagc agcacttccc atttcccccc actctttact 120
c 121

<210> SEQ ID NO 150
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 150
taccacctct tcagcaccct ctcgcatccc cacccgtcca gcagcagcac aaaggggccc 60
aaaggtgcag cattagggaa tctaatggcc tgaggaataa gttctcgccc actgtgactc 120
c 121

<210> SEQ ID NO 151
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 151
cccttcccaa gccatgggca aaaacagctc aggtagtaat gaaggtgtgg ctatagctga 60
acaattggat ttaaatccca cagagccatg gtgctgggaa gaggggctgc cctggccagt 120
c 121

<210> SEQ ID NO 152
<211> LENGTH: 121
<212> TYPE: DNA
<213> ORGANISM: HOMO SAPIENS
<220> FEATURE:

<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 152
aagtggaatt acatcaaact aaattacatc atcagagtaa agagacaatt tacaaaaagg 60
aaagaaatat ttaaaaacca cacatcggat aaggggctaa tttccaaaat atatgaggaa 120
c 121

<210> SEQ ID NO 153
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 153
ctccagcgcg cctgaggctc atgcatttgg ctaatgagct gcggtttctc ttcaggtcgg 60
aatggatctt gaaggggacc gcaatggagg agcaaagaag aagaactttt ttaaactgaa 120
c 121

<210> SEQ ID NO 154
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 154
taagacaaag ctggctccag gcaaagaata ctaccagcaa caaagaggaa catttcagat 60
aataaaagag acaattcatt gggtggatca caagctcagg agttcgagac cagcctggcc 120
a 121

<210> SEQ ID NO 155
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/T]"

<400> SEQUENCE: 155
tctgcctaga aggactagcc tgctgcttca tttcccccct cctctgcagc cgatttcaga 60
aggctgcagc agagaaagcg agacccccac accttgtttg tgtgtaccct tccttccgca 120
c 121

<210> SEQ ID NO 156
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 156
taaaaagcaa atattagtaa cctggaaaac atacatggag gtatgttcat taacggcagt 60
aaaaaaccaa accaaatttt agagatgagc ggtaccttag aagatttagt caggggaaaa 120
g 121

<210> SEQ ID NO 157
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 157
caggaacatc cagctgcctg catgactttt ctaagtgtct aaaaagcatc ttaaacttaa 60
attcttgatt ccctctcctt tactccacga caaaaatcca gctcttccca ttgtcttctc 120
t 121

<210> SEQ ID NO 158
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 158
tttatgcttg aaaatcatag aaattgtgtc taaggatatg ctttgggata tttggacttc 60
acttttgttt tagtttttag ttagctgttg agtttaaagt aatttagtgc tctgatattt 120
g 121

<210> SEQ ID NO 159
<211> LENGTH: 121

<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 159
tgcgggtaca ccggcaggca ggaaaaccca ggcttctctc cacatggtgt ttacgtcgtg 60
aggggagaga gactagggac gcacgagtag agaagatccc tttggtttat gttaagtgca 120
g 121

<210> SEQ ID NO 160
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 160
tgattcctag gctgcctgta ctagtgatag tgaggctcac taccatccac cacctaaatt 60
agaaccgctt gatgacacag cacaggttct atatctttag atggtaaatt aaaaattcct 120
g 121

<210> SEQ ID NO 161
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 161
acaagtcggg gtgtagctta cgggagggaa gtcaaagtca ggcacgttca tcacactcag 60
aatgtagtcc actctgaact ggttctcggg gttggccagc tccacggggg gcaccaggtt 120
g 121

<210> SEQ ID NO 162
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61

<223> OTHER INFORMATION: /allele="[A/C]"

<400> SEQUENCE: 162
gtagtagatg ctcattgtaa gattcaaaaa cattccagct tacaaaacat atccagctta 60
aattttaact catggtcttt agcaagtata gattcctcaa gtgaaagggc attgaggcag 120
a 121

<210> SEQ ID NO 163
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 163
gcaatgctag aaatatgggg attaaaataa tgggaaaatc agttttagtg taatacaagg 60
aaaaacatta aacatgaagc tgtccagcag tagaacaaat tgccttgcaa agagctgcaa 120
a 121

<210> SEQ ID NO 164
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 164
gcccaagatt ctatatttga acaagcttct gggtaatatt tatgacaggg aagtcttgag 60
aaaatttgga ctataggtcg tcttttaagg ttcttgccaa ctctaagact gccatcccat 120
a 121

<210> SEQ ID NO 165
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 165
agctacctca gagtactttg tcttttaatg ggattataat agaatctcat gaccttgtta 60
aacttaaata agtcaataaa tggaacattt caaacagtgc ctggttcaca gtggtattat 120
c 121

<210> SEQ ID NO 166
<211> LENGTH: 120
<212> TYPE: DNA
<213> ORGANISM: HOMO SAPIENS
<220> FEATURE:
<221> NAME/KEY: source
<222> LOCATION: 1..120
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele=
"[-/CACTTACCTTCTTTGTGCCACAGTTTCCCTATCTAAAACACAAGGTTATCAGTTATCAACAT
CTCTTGGGATTGTGAGGACTAAAGTAATGCACATAAAG]"

<400> SEQUENCE: 166
ctttgttaaa tgttttttct gcatctattg agctgatcat atgctttctc ttgctaatgt 60
ggctttgtac agtgcctgtt acatggtata ctttcaacat tagtagtagt agatgttgta 120

<210> SEQ ID NO 167
<211> LENGTH: 120
<212> TYPE: DNA
<213> ORGANISM: HOMO SAPIENS
<220> FEATURE:
<221> NAME/KEY: source
<222> LOCATION: 1..120
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele=
"[-/AAATTACCCTGTTAGGTTTCAATGAAACACCTTTTCTCTTGTAACAAACATCTCCTCCAAGC
TAGAATTTCAAAACAG]"

<400> SEQUENCE: 167
tttttctaag tttatgtctt aacctaacaa taactcaaaa gagaaacaag tatctctcca 60
tgttaccatc cactaggtaa taatttttat gctagcaaca aaacccaaaa tatgtgttca 120

<210> SEQ ID NO 168
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 168
ttggttatga ttttttttc atttgaagta aatatccacc tttgtatcta attttgcatt 60
aaaaaaaaaa ttttttttt ttactttaag ttgaatccct acaattgtat aaccttcagg 120
t 121

<210> SEQ ID NO 169
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"

<220> FEATURE:
<221> NAME/KEY: variation
<222> LOCATION: 61
<223> OTHER INFORMATION: /allele="[A/G]"

<400> SEQUENCE: 169
ccagctagtt ttattttta atagtgttct tgcacatgag gagaaagact gaattcaatt 60
acactattct ataactaatt ataagttata ataaaaatga aacaaaaaca tttcaactga 120
t 121

<210> SEQ ID NO 170
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 170
aagaaggtgg cgtgtcactt cgtttgactt cagctgggaa catgcatatc agtcgactca 60
aattttttgc tattctgtgc ttatccacga atcgatagga aagcaagtgt ggatttgggg 120
g 121

<210> SEQ ID NO 171
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 171
aatgacacag atcgtcacac agttttaaga caaatgtttt tacctatttg acctagtctg 60
acaatcccta tttgggcaaa aatcttcatt tgcaggtcat gattggaggc aggcacagaa 120
a 121

<210> SEQ ID NO 172
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 172
aattctttga tgtgctacaa acctgaaact ggtaagacaa gcacaaagca acgtgcaata 60
aaaaaatcgt atctcaaggg aaaatactca aagaaagaaa agtggcagca cttatattag 120
t 121

<210> SEQ ID NO 173
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 173
caaaagtgat aaaagtaact ttcaaggcta gatcatgcaa gacaaggcaa catagcttct 60
acctggttct atgaagacat ttgcctttgg ctccctgagc ctccatccaa gaagtcgaag 120
t 121

<210> SEQ ID NO 174
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 174
gaggtccagg ctgcagtgag ctatgatcac atgccttcac tccagcctgg gtgacagagc 60
aagacactga ctcaaaacaa aatacataaa ttaatttgtt taattcatga ttagttacta 120
t 121

<210> SEQ ID NO 175
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 175
aatgtgggcc acatgtgacc aacaagataa ttatgaaacc tgactgctgg atatgctgat 60
acagccaaaa aacatcaagg actgtgagtg agtttggagg tgggagcaga gaaaatttct 120
g 121

<210> SEQ ID NO 176
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 176
gcaatcagaa aggtcctctt taaatgtgag ttagatcatg ttactgctct gctcaaaata 60
atgcagtggt tttccattgc acagagtggc agattgcatt ttccaaaaga caattgcaat 120
g 121

<210> SEQ ID NO 177
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 177
ctagcatgat ttattaatat tagcctttct tctctccccg tttatgcttt ggtgggtact 60
agacagaaac cccacaaatt ttaagacagt tttaagagaa atagtaactg gttaaatatc 120
c 121

<210> SEQ ID NO 178
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 178
aggtcataca gcaaataact ggcattcctg gaacccaaat tccaggtgtc ttgttccaaa 60
acccatgttc tttattctat tctgcctctg ccaaacaaaa cccaaaccaa aaatgtcttc 120
t 121

<210> SEQ ID NO 179
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 179

-continued

```
agtcaataaa cccaaatgat aatttaaaat tcaccctgat gatggttcca ataaatatat     60

aaatagtgta gctctagttc ggtttcataa gaattgtgca gcaataattc tttctgtaat    120

t                                                                    121
```

<210> SEQ ID NO 180
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 180

```
tatgccacca tacccgctaa tttttgtatt taatagaaac agggtttcgc catgttgaca     60

agctggactt gaactcctca cttgaactcc tcacgtcaag tgatctgcct gctttagcct    120

c                                                                    121
```

<210> SEQ ID NO 181
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 181

```
aaacaaacaa acaaacaaac tgaggtttag gtttaggtag ctggagttta taggcatggc     60

acataggtca gagcctcaat tttctagcta aatgtcaatg tttcccactt attttattgc    120

c                                                                    121
```

<210> SEQ ID NO 182
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 182

```
gcttacagcc agggctacac agaagtgagc aaagctggtg aagatgggga tgggggagtg     60

aagtgagttg acgctagaaa gggatgtagc aaatgtaact attattccag aatccaagtg    120

t                                                                    121
```

<210> SEQ ID NO 183
<211> LENGTH: 121
<212> TYPE: DNA

<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 183
ctactagcta cataatgtga tgccatatta aactgtaatc acctttccac caaactaata 60
aagacaacat gctaattttt gtattaagac acagtgcaat aacacacaat tgaatgatgc 120
t 121

<210> SEQ ID NO 184
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 184
tgtgtactcc caaaattcat atgttgatac ctaatctcca aagcaatagt attaagggtg 60
agtgcctttg ggaggtgatt ggataatgag ggcagagctt tcatgtacag aattagtact 120
c 121

<210> SEQ ID NO 185
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 185
gaaacagagg cttagacagt ttacttatgt gcccaaggac acaaaatcag aaacaggtac 60
aaggagcact tgaaccaaaa ccaatactgt cttgccatac caaacagtat ttatttattt 120
a 121

<210> SEQ ID NO 186
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 186
cctgtggccg ttggttttcc tgggtgggga agggtgctgg cctcattcac aacagcagat 60
actcattcct ccagggtcag gctatggggc tcaacgtgat caggacagat ctgagccccg 120
t 121

<210> SEQ ID NO 187
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 187
actgggcttg tagcttaaat tattcacact ttactcatgt aatgatgaac agttttaggt 60
acttataata tgtagaggct aactctctct ttctctcact ctgtctttcc ctctgtttgt 120
c 121

<210> SEQ ID NO 188
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 188
tcaacccaag gcagagagag ccctgtctca aaacagattt ctgagtgtgg cttctgtcca 60
agcatgtgaa ttaacatgta acacaaaaga gaagaaagaa atgttaagga aattatacca 120
g 121

<210> SEQ ID NO 189
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 189
attttctctc tctcgtagct gagagagtca tgactatggc gtgttctctg tactctgagg 60
acctgaaccc actcatgggt tactctggcc tttggtcagg tagttttgcc aactcgctat 120
t 121

<210> SEQ ID NO 190
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 190
gcagtactca ccatgggcct taaggtgaga ctcagagatg tgctggcttc aggtataacc 60
aagcacattt gaaactatag cggctatggg gagagattcc ttctgcttga gaaaaggaga 120
g 121

<210> SEQ ID NO 191
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[C/G]"

<400> SEQUENCE: 191
gtgtatgctt tgtgaggata ggtagctttt cttactcact gttgttacca gtacctagaa 60
ccaagcctga ccttattagg ttctttcaaa tatttgaaag atattttaaa atattcacat 120
a 121

<210> SEQ ID NO 192
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 192
tgatctcatt accttaattc ctttgcttat aaaatgagtt cattggtcag aagcaacgct 60
atgtacaata ccaagaatat gaatatgtca tttacagaat gacaagctcg tcaatttcag 120
t 121

<210> SEQ ID NO 193
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:

<221> NAME/KEY: variation
<222> LOCATION: 61
<223> OTHER INFORMATION: /allele="[A/G]"

<400> SEQUENCE: 193
gcaaagaatc actggttacc attatctttg aaatggctcc tcataaaaca cagaaaataa 60
acattaagac atgaaagcta caaggcccac aatgcgggaa ttttaacctt gaaaactgtc 120
c 121

<210> SEQ ID NO 194
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 194
tcagagttta ggattttggc cattctaaga gatgtgcagt agtaactcag tgttttattt 60
acaattccct aatgacatat gatgttaagt atcttctaat atgctcattt gtcatctgca 120
t 121

<210> SEQ ID NO 195
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/T]"
<220> FEATURE:
<221> NAME/KEY: misc_feature
<222> LOCATION: (51) ... (54)
<223> OTHER INFORMATION: "n" is any nucleic acid

<400> SEQUENCE: 195
ttttaatatt tgtttagata tgacatttat tcaaagttaa aagcaaacac nnnnagaatt 60
atgaagaggt atctgtttaa catttcctca gtcaagttca gagtcttcag agacttcrta 120
a 121

<210> SEQ ID NO 196
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 196
gttttccttt aacattccat tatcctattg ttcattcttt ggagctgtga tttgtttaat 60
atatttcagg cttcttaata aatcaagtca tgtaagttat tatttggatc atttcgaaac 120
t 121

<210> SEQ ID NO 197
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 197
gtggttctaa agcttcggtg aatattagaa tggcctcaag agctagtaaa aaacacagcc 60
agcctggatt attcaagtag gctagggttt ggccttttat ttttataata ttccgaggtg 120
a 121

<210> SEQ ID NO 198
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 198
gttggtgaga aggcatatgg ggaaaaaata aggcaggaaa ggaagacgga aaatgctgtg 60
agtagggtgg cattttaaat actgtggtca gggaagcctc accaaaaatg tgacatctga 120
a 121

<210> SEQ ID NO 199
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 199
ttgtctttta ttggttttat aaaggatcta agtgtttgga aaggtgtggg accatgtact 60
attggagatt tcagtgtttg actatgagag aaggaaatgt tattttttgg gaatgttatt 120
t 121

<210> SEQ ID NO 200
<211> LENGTH: 121
<212> TYPE: DNA

<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 200
gaagcatcac ctcttttatc atatgaagcc ttttcacaaa ggagggaatg atgattgact 60
aagttttgtg tctattctat acactgtact gtcaaagcat gcagagcatg tattgcatat 120
a 121

<210> SEQ ID NO 201
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 201
ctctttgtgt taaggttgta tcatctacct gtagtcactg cagtcagctg aattttacca 60
agagaatctg acagtcgttg cccagtcaaa ttagtttaga tccatctgta acaggttcct 120
a 121

<210> SEQ ID NO 202
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 202
ctgattcctg ctctgtagcc acacagatgc caacagctgg cacttgtcca agaaacatgt 60
actcaaggtc aggtgcagtg gctcatgcct gtaatcctag gtttttggga agctgaggag 120
g 121

<210> SEQ ID NO 203
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 203
aatagagacc agaaaggatt atttgatgtt catttagcaa gcaacatagt aaaataattt 60
attccactgt ttgtatgtat ccttgactgt ttctaacaag tgacccattc tttcttaata 120
t 121

<210> SEQ ID NO 204
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 204
aaaataaagc ccagatgcct ttccggctcc ccccacgggg ttgccctgat ggtttaagac 60
aataacagat atgaaaatcc tctgtaaaca ggaaggcttc accactcttg gaactcaaga 120
t 121

<210> SEQ ID NO 205
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 205
tgtgacgatg ccttatgaca aacaactcta catctcagtg tcttacacca atgagctcat 60
aagcctgcag gttggctgtg gtgactgctc ctggcttggc cccatgggtg tctcatccca 120
g 121

<210> SEQ ID NO 206
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 206
ttatgctctt tattctaagg aagtgccccc taaaacaaag ctcaggagcc tcaacccggc 60
agggaagaca gtttcctcac gaggcaggca agcaacacca ggtggctctc tttcccaaga 120
t 121

<210> SEQ ID NO 207
<211> LENGTH: 100
<212> TYPE: DNA
<213> ORGANISM: HOMO SAPIENS
<220> FEATURE:
<221> NAME/KEY: source
<222> LOCATION: 1..100
<223> OTHER INFORMATION: /mol_type="unassigned DNA"
/organism="HOMO SAPIENS"
<220> FEATURE:
<221> NAME/KEY: variation
<222> LOCATION: 40
<223> OTHER INFORMATION: /allele="[A/G]"

<400> SEQUENCE: 207
ttactagtta tgcaatgcac tcgaatccag tttaagttca gcgctctcat ctgtaaaagt 60
ggggcaagaa tttgcctttt gatgttggga gatcaagttc 100

<210> SEQ ID NO 208
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 208
gccctataga taccatggga aacagacagt ggcccctgtt ctcaagtggc ttagactcta 60
atgggaaaga catttatttt ttcttttttt ttttttttta gagacggagt ctcgctctgt 120
c 121

<210> SEQ ID NO 209
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 209
agtatctaag cttattggcc ctaagtaaat cttaggttag gtagagctca gttcccaggg 60
acattcaaga ttcataaaga agtgatattt ttcccagcta aaatattttt cttcttacca 120
g 121

<210> SEQ ID NO 210
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61

<223> OTHER INFORMATION: /allele="[A/G]"

<400> SEQUENCE: 210
cttttatttt aaactttttc ttaagtaatt ttacaattgc tgaaaagtaa aagagcctca 60
atgaattcct gaataccctt tacctgtttt cctgaatgtt cctaaaaata cctagcaatg 120
a 121

<210> SEQ ID NO 211
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 211
ctgagcacct tctatttgcc aacaactgtt ttaggcactg gggatatagt gataaacaga 60
acaaccacaa atccctgtcc tctggaactc accgtcagag tgaggaaggc ctgagtcccc 120
t 121

<210> SEQ ID NO 212
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 212
gggtgtgatt tggttgctaa tttctcttca cttctgggaa accagcccct tataaatcaa 60
actataggcc agagaggctg ccacatgctc ccaggctgtt tatttgaaga gagacttaca 120
t 121

<210> SEQ ID NO 213
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 213
aaataaaagc aacacagagc agtatgtaca ggacagcgtt agaatatacc agagaacaag 60
aacacaatct acaatcattt ccagtgaatg caggatgtta aagagatgca taaaatcccc 120
t 121

<210> SEQ ID NO 214
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 214
gactgcccag agcacagcgt ggagaaggcg ctcggccccc gcccaggcag gcagagcacc 60
atgatgggtt cacgatgccc tatgccaggg tcgtgggtga caggtgtgtt tgccatctct 120
a 121

<210> SEQ ID NO 215
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/T]"

<400> SEQUENCE: 215
gactaaaaag catagtattc tgttcttcag ggagttgtgg gttcggatct gtgcaaagat 60
aggaggtagc tgaataaaca tagttgcaaa ttataacctc ccaaatgtgc cctgaggaca 120
c 121

<210> SEQ ID NO 216
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 216
aaataaacac gaagaacaaa gccccaccac cgtgctgtgc tgtttgtgtg gccccactgc 60
atcgaggcca caggctagct gctagacgca tctagagttc cctgattcct aaaattattt 120
a 121

<210> SEQ ID NO 217
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"

<220> FEATURE:
<221> NAME/KEY: variation
<222> LOCATION: 61
<223> OTHER INFORMATION: /allele="[A/G]"

<400> SEQUENCE: 217
cattttaatt ttcaaattgc ttgattaaaa tggcaaacag tttgaaaatt gtatacctct 60
atatcattca gttaaaaaac aataaagtga cattcttaaa aacatcaagg actttcccct 120
c 121

<210> SEQ ID NO 218
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 218
catttataca ggataatgga aaagggggtt tctcccgagt agagaactta aacagtgtga 60
agcacagtgt gttccacact atagctgatg ggttggcctc agggggggatg ttcaggtata 120 c 121

<210> SEQ ID NO 219
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 219
taatatatga agggtgcatt attctaattt aatggattaa tcatactttt taaaaacagt 60
attactaaat tctgtaataa catggtgatt ttatatacac atgactaggt gaaaggatat 120
t 121

<210> SEQ ID NO 220
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 220
gcaaggtggc actcttagga gttgaatcca gctctggtgt gtgggacagg caggaggaga 60
agaagagagg gaggaaaagt cggttcgaga acccaggtgg aaaatagatt gagggaagca 120
a 121

<210> SEQ ID NO 221
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 221
gcaggcgccc cctttccccg ctccccaggc gcttcagcac cgcggacagc gcccatccga 60
atcactgagg ccaaagccca gcacgtctaa ggcagtcccg taggaagacc ccgtgtgcac 120
c 121

<210> SEQ ID NO 222
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 222
aggaccattt tagaaatctg tgaaccacag tggtgaaaga aggaacacat tctctacaga 60
aatgtatatt aagtgtctgt taacctggca ttgtcctccc caaccaaaac tatttctatt 120
g 121

<210> SEQ ID NO 223
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 223
agagcagggg aaagagagtg gaagtaccag gtgggcaaag tttacaattt taagtaggat 60
agtcagggca gacctcatta aggagataac tttgagccaa gacgggatag agcagaagga 120
a 121

<210> SEQ ID NO 224
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 224
cttcttgcac atgattcttt ccatgacacc tagtgccctt ctccatctag agctacctct 60
atatgtccac gttccttctc tctaagctca tgatagacct caggagaaag tcaggtaggc 120
c 121

<210> SEQ ID NO 225
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 225
cgtatggaac cttttggcat tggctttttc tactcagcat aatttcctgg agagtcatcc 60
aaattgctgc atgtatggat agcttgttcc atttcattgc tgagttcatt tgcttttttt 120
t 121

<210> SEQ ID NO 226
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 226
gcaactttac ctgctaatga ctatatacac ccatttttct catttttaa aaatatcatc 60 acatattact ttaaaatgtc aagaactgct tcaacagcca ggcaatgatg gctggtatgc 120
t 121

<210> SEQ ID NO 227
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/T]"

<400> SEQUENCE: 227

```
aagcaaagca attgctacaa ggaggattat gggtgaaagt catggatgga ttatgagtta     60

atcacacacc tagagaagca tgtaaaatgt gcaggtaaat tacacccatt cattcaggca    120

g                                                                    121


<210> SEQ ID NO 228
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
      /organism="HOMO SAPIENS"
<220> FEATURE:
<221> NAME/KEY: variation
<222> LOCATION: 61
<223> OTHER INFORMATION: /allele="[A/G]"

<400> SEQUENCE: 228

cccgcccacc tgagcacagt gtccatatag gaacatgagt gacagccctg cacatgggca     60

agagcatcca aaccacactt caggcaaaac tacatttcag tgatgtccat ccttaggaaa    120

a                                                                    121


<210> SEQ ID NO 229
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
      /organism="HOMO SAPIENS"
<220> FEATURE:
<221> NAME/KEY: variation
<222> LOCATION: 61
<223> OTHER INFORMATION: /allele="[A/C]"

<400> SEQUENCE: 229

cttactttaa catccaaaaa taactaaaaa gtcctagaaa attaaacttt tccaaatttc     60

aaaagtactt gtgctgtatg aattctactt catgtatcat acacaaacaa gttatgacaa    120

a                                                                    121


<210> SEQ ID NO 230
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
      /organism="HOMO SAPIENS"
<220> FEATURE:
<221> NAME/KEY: variation
<222> LOCATION: 61
<223> OTHER INFORMATION: /allele="[A/G]"

<400> SEQUENCE: 230

acatattcca gaaattctcc ataatttctg atccactctt acattcctct cctttccagc     60

actattattg atctcttctt cttcttttga aaatctttgt tccctccatc tatcatttca    120

g                                                                    121


<210> SEQ ID NO 231
<211> LENGTH: 121
<212> TYPE: DNA
```

<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 231
gcagggtcca cgggcttctg gacacctccc tacctgggcc ggcttcatcc tcctacgacc 60
aacagtcgtg ttgatgacat gcacctgtcc cgggacttcc cccagccccc agccagctgc 120
g 121

<210> SEQ ID NO 232
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 232
aaaaataatg ttcctttcta aatatgctaa attatttcca taaaactcat aaacttttat 60
acctagaaat ttatgaaaac ctattgacaa cttttatgcc tgaaaagatc tgaaagattg 120
a 121

<210> SEQ ID NO 233
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 233
ggccacaaag cccttgcaca ggcacagcta taatttttgt ctctcttctg ttggaaaggt 60
acaaagttaa ctggagtgat gtgtgtaatt gatggtataa tggtaagcaa aaatcacaaa 120
t 121

<210> SEQ ID NO 234
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 234
gaagagagga gtgaggtgct atgtactttt aaacaacaag atatcatgag aactcactcc 60
atatcacaag aagagcaccc tgggggatgg tattaaatca ttagaaacca cctcatgatc 120
c 121

<210> SEQ ID NO 235
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 235
aaactaggaa gaatattgaa ggtagccaga aaagaaaaaa aggcacattg catgcagagg 60
aacaaagatg agaatcacag caaacttctc tttagaaaca atataagttg taagacaatg 120
g 121

<210> SEQ ID NO 236
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 236
ggctgagtga atgaccacca ctctgtggtt caccaaaaaa ccacatcagg ttttccccag 60
acaccttggg acagtttgaa atgtccaaat agtaaagcaa tgaactgcca taaatgtagt 120
t 121

<210> SEQ ID NO 237
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[C/G]"

<400> SEQUENCE: 237
gttgagggga gcctggagaa gttggctggg acagatgaca ccacttggag accatattta 60
cgctctcaga ctttatccaa gtgggactgt tgtttaaagg tttgaaaaaa catggcttat 120
a 121

<210> SEQ ID NO 238
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 238
cactcacagg tctcccctgg attgtgcaga accagacatt gctgcctttg cctaggcagg 60
ataatagata tcatgagggc ttgggaagct tcggggggaa agttaggcta tctgcccacc 120
c 121

<210> SEQ ID NO 239
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 239
agtatagtcc tgagaaagtt ttggccaagc caatggagag ccccatagcc aaagctgccc 60
attagaggaa tcccatatca agtagaattg gatgggtgag aattctcagg tggctgagag 120
t 121

<210> SEQ ID NO 240
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 240
caagaagaga ggataaccaa cacacaaatg agtaaataaa atgattgctg attgctatta 60
atgctaacaa ggaaagagat cctgttccat gtgagtgaga tcatgcccat tgcttcatca 120
t 121

<210> SEQ ID NO 241
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:

<221> NAME/KEY: variation
<222> LOCATION: 61
<223> OTHER INFORMATION: /allele="[A/G]"

<400> SEQUENCE: 241
catggcacac agtcacagaa acatagcaag cccttgaaat caggctttct gactttgtct 60
aatctcctgc tttagcaaag acatcaattc tccctccttt tatttaaatg gtggctgggt 120
c 121

<210> SEQ ID NO 242
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 242
cacctacaca cacctacaca catgcatgca cacacacatg gcctctctct ccaggcttct 60
agagctcagg acaggtcaga tccatctctg tcgggcacaa cattgatgct ctctgaacac 120
t 121

<210> SEQ ID NO 243
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 243
ctgagagttt cgtacagacc tggtccaaaa attccaattt cataggtgtg gagttttcat 60
acaagtactt caattgctac actcaaagag aaagatttaa cacctagaaa tctagctgtc 120
t 121

<210> SEQ ID NO 244
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 244
aataatgcat aaggtttttg taagaattag aattaataaa gtacttagac cataataact 60
aattagtatt agttgttgtc tttgctatta ttttgatgtg gtggttgttt ggtttcacct 120
g 121

<210> SEQ ID NO 245
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 245
tccctgcttc ttactaatat tgtcactttg tctcttaata cagatatttt cttttgatca 60
atgtttgtaa agtaacatat gtttctgacc tcttacttta aaacttacta tggccttgta 120
a 121

<210> SEQ ID NO 246
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 246
gccttgcaga ttatgtagca ggtcctgatg taacagaatt aagattgcag gtgggattgg 60
agttgctaat cagctgactt tgagatggag aggtgatcct ggattatttt ggtggaccca 120
t 121

<210> SEQ ID NO 247
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 247
ccccctaggg agtagctgcg gcggcaccaa gagaggggtg gggggcgtgc tgcgcagagg 60
aggacctcac aaagcggcct cagagtttcg caggtcctgc tgttctaggg aagggttaaa 120
g 121

<210> SEQ ID NO 248
<211> LENGTH: 121
<212> TYPE: DNA
<213> ORGANISM: HOMO SAPIENS
<220> FEATURE:
<221> NAME/KEY: source
<222> LOCATION: 1..121

<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/T]"

<400> SEQUENCE: 248
gaccacttga acacatcctt ttaaatagat acctttttta aaatctatgg ttatgtaaca 60
actgtgtccg agggatttaa gcagaaagcc ctgtgggttt ctcttttcaa aagacagacc 120
t 121

<210> SEQ ID NO 249
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 249
gtgtcctctc taaggatggg acccctactg tccatctcag gctcagcact gccttggggc 60
aggccacttc tggcttcttt aggcctcgtt tccacgggag gggaagctgg gtccgatggt 120
g 121

<210> SEQ ID NO 250
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 250
tctgtcaccc cttctacatc ttagctcacc tgtcctcaca aataaacatc actcttgaat 60
actacaatct cactttatta gattgtaaat ttttatgagg aaaaaggtcc tgagctatgg 120
c 121

<210> SEQ ID NO 251
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 251
acacagcatt aattaaaaat ggaagttttc cacttccttg ataatttggc tatctgaata 60
aatttgtgaa tttgctaggt taagacctag ttcgtggtca catttcaaca aaacagcttg 120
a 121

<210> SEQ ID NO 252
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 252
acttatatct ctttctaaac actagcagcc cagaattctc aggccacttt tgggcattgt 60
agcaacacaa taggtgcctc ctgtggaccc catgcctcca atcagagcag ggattaccgg 120
c 121

<210> SEQ ID NO 253
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 253
atggagggga cagagtttat ctttttcacg gtttgtatat atatattttt taatcttttg 60
agagtcccag tttttgaagc attcacttgg ctgattcacc aattcataga ctggagtaga 120
a 121

<210> SEQ ID NO 254
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 254
tagtgtaagg tgaccggaaa aatctgatta aaggacaaat gttcagttca aaggtgtttc 60
aagctgagaa tagcatctct atttactcct cacgatgttc atctcaggag gcactgtact 120
t 121

<210> SEQ ID NO 255
<211> LENGTH: 121
<212> TYPE: DNA
<213> ORGANISM: HOMO SAPIENS

<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 255
agagcttttg cagaacttgt tgatgaattg aatttatggc ctgggtgagg aaaaggaatt 60
agtaatggca cttgggtttt tggtgtgaac aactagtgat taatcggagt tcccatttaa 120
c 121

<210> SEQ ID NO 256
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 256
ttctcagtgt tcaccaagtc tggttgtccc agtctcctat ctctgtctgt tcctctcctc 60
atctgtcttt atgttagtta tggccctgaa tataaaacag ataaaggaag ggtctggttg 120
a 121

<210> SEQ ID NO 257
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 257
taatttctac atttctacca aaagtcactt catggcaatc taggcttttt ctatcacatg 60
actcaaagtt ctccagcatc agcatctacc cattatgcaa ttccaactca tttccacatt 120
t 121

<210> SEQ ID NO 258
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 258
agtagaaaat aagcacaata attttagatg tttataagtt ctctgaaaac aatagagtat 60
aatgatataa cacgtttagg tagtttggaa aattatagtc gagtcaatga ccttagattc 120
a 121

<210> SEQ ID NO 259
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 259
atatctgagt attaagaaaa attgaaaccc taagcatcaa tttcttagga acttctctga 60
accattaagt tgttttaaaa ttactttcct ccatcagact cctaatcatc acctagtgat 120
a 121

<210> SEQ ID NO 260
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 260
tacatacaca catacacata catgcagata gatagataga tagataaaga tctccagtca 60
ataacctaac tttacatcta agaaactggg aaaaaagcaa ataaaacccc aaagcagcag 120
a 121

<210> SEQ ID NO 261
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 261
ctcgcagcgc ggaactctga cgcaatccag ggccgaggaa aaatgattaa aacccaacaa 60
actcgagtgc tggggtccac caagcgggcc gtcttggtta gaaggcccgc cccacacgtc 120
t 121

<210> SEQ ID NO 262

<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 262
agatcacttt ttattgcaat atgcaattta ctggagagat gaactgctcc tgctgagatt 60
attagtgtca ctgcatttta agcaggtaca acacttgaac tcactgcagt agcaacagga 120
a 121

<210> SEQ ID NO 263
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 263
gggggctcca ggcagaggga acagcttgtg caaaggccct ggggcaggcc aagggcagag 60
aacttaaggt atggaaaaaa aaaaaaaaag gcatggaaag gaggccagca tggctaggag 120
c 121

<210> SEQ ID NO 264
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 264
gtcagatgtg ttgtggaaga ataattactc tattttgtga ttttataaag tgtattttct 60
atattattat taaatgtctg attacttgag ataaaccagc catcctcttt ttttactact 120
c 121

<210> SEQ ID NO 265
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 265
taaatggtgg gtgctatttt gttgctgtta ggtctatttt cttcatctgt tatttcgcat 60
aacagtaaaa cagatactca gatgacttat ataactttca ttagtttcat taggtggtgt 120
c 121

<210> SEQ ID NO 266
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 266
gaacgaatga gaagtgagga aacgcttagc gcaaaaggaa aaagagagaa agacatacag 60
aaacaaggtt acgcggaggc cggcgaaaag cgattccccg ctcccccagg ccaagggccc 120
c 121

<210> SEQ ID NO 267
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 267
tacaaggtca ggctcaacgg aagtgaccgt cccacagtta tgcagcacta agtcaatggc 60
acatttgctt gtgtgttggt tacatttgta actcaaagct gatgccttaa gaaggttagg 120
g 121

<210> SEQ ID NO 268
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 268
cctgaagtgt ctgcttagcc gcgcacgggg tatttatatc tcaggctttg gagaactatc 60
aggtttgggg cccggctagg gcgtgcgtgt tcacgctggg acctgtcaca acctggtctt 120
a 121

<210> SEQ ID NO 269
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 269
atggatcttg aaggggaccg caatggagga gcaaagaaga agaacttttt taaactgaac 60
aataaaaggt aactagcttg tttcattttc atagtttaca tagttgcgag atttgagtaa 120
t 121

<210> SEQ ID NO 270
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 270
gtttaaaaca acactgtgat ttcacaattt ctgtggatca tgaattaagg agcagcttag 60
atggatggtc ctgggttgag tccttcctgt ggctgcagtc aagaagtcag ctggggctac 120
a 121

<210> SEQ ID NO 271
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 271
tggctactct aatttttcaa tggtaaacag accagagtta ttctaagaaa ttatgaaaag 60
aaatccattt cgaagtctta aagcaaattt agagactgac aattgaaaat acatcttctt 120
t 121

<210> SEQ ID NO 272
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"

/organism="HOMO SAPIENS"
<220> FEATURE:
<221> NAME/KEY: variation
<222> LOCATION: 61
<223> OTHER INFORMATION: /allele="[A/G]"

<400> SEQUENCE: 272
gcttgaggcc aggatttcaa gacttgcctg agcaacataa tgagatgccc tctctcaaaa 60
atttaattaa ttaatttaaa aagaaaatcc cagctactca ggaagctgag atgggaagat 120
c 121

<210> SEQ ID NO 273
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/C]"

<400> SEQUENCE: 273
aacttaaatc agcaagcaga aaacaaacaa cttcattaaa aatgagcaga ggacctgaac 60
aaacacttct cagaagaaaa cattcttatg gccaacaaat acatgaaaaa agcctcatca 120
c 121

<210> SEQ ID NO 274
<211> LENGTH: 121
<212> TYPE: DNA
<213> ORGANISM: HOMO SAPIENS
<220> FEATURE:
<221> NAME/KEY: source
<222> LOCATION: 1..121
<223> OTHER INFORMATION: /mol_type="unassigned DNA"
/organism="HOMO SAPIENS"
<220> FEATURE:
<221> NAME/KEY: variation
<222> LOCATION: 61
<223> OTHER INFORMATION: /allele="[A/G]"

<400> SEQUENCE: 274
caagggcagc atgttgcttc atgagcggtt ctggacaggg atggtgggag atgttgctag 60
agggaattgt ggccctgggc ttagaaacaa aggggcaaga aggtctcaga agctggggcc 120
t 121

<210> SEQ ID NO 275
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 275
aggactctat ggcttccttc atgtcatcgt ccactctgcc aagggattta 50

<210> SEQ ID NO 276
<211> LENGTH: 50

<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 276
acgacagaga tgaattgagg ggacaaatgt cagagctcac agacgactgt 50

<210> SEQ ID NO 277
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 277
tcagaagcct atttttaatg tcattccacc aattcccgtt ggttccgaaa 50

<210> SEQ ID NO 278
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 278
tcacagtagc tcctcctctt agggttttat agaagtccat cacatctccc 50

<210> SEQ ID NO 279
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 279
ttgcattctc tcctagcact ccagtaaata aactatagtc ctggtcaagt 50

<210> SEQ ID NO 280
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 280
attcccaata ttcgtatatg tatttataaa ttacataatg ggcagggtgc 50

<210> SEQ ID NO 281

<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 281
agtgcttttt gagaggtatg aacttactcc atactactta catctgctaa 50

<210> SEQ ID NO 282
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 282
tgacttctaa ttacaggcaa aatcaacctt aataagaaca ggcgttacta 50

<210> SEQ ID NO 283
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 283
tactattctg ttcataaggt acacttcttt ttagggcaca ctaccttggg 50

<210> SEQ ID NO 284
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 284
aggtgggata aacagaagca gcataacgtg tcttgatgtg tgctgtttag 50

<210> SEQ ID NO 285
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 285
ttgtcatgca gcaggttaac tatgctttct ggagaaggtg tcagccaact 50

<210> SEQ ID NO 286
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 286
ccctccagct gaatgatttt tgtctgtgcc tggcccagtc cctgagtcca 50

<210> SEQ ID NO 287
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 287
gtgaaaatgc attttccccc tattccttct ggaaagcaac attagggtcc 50

<210> SEQ ID NO 288
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 288
tgctcaccac agtcctcata tccttaaagg gacaccctag tgattactga 50

<210> SEQ ID NO 289
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 289
cagtcccgcc tgcttggatc tgacgagcgt gccgattcgg tccgaaaatc 50

<210> SEQ ID NO 290
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 290
agagcactaa ctctggagag taaggatctg agtgtaagtc accgctgtgt 50

<210> SEQ ID NO 291
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 291
aagcagtcca cagcagtctg agctggcagg tcatggagca gcccccaaac 50

<210> SEQ ID NO 292
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 292
gtaaagaaca gggggagata atgatcagta aaatcacagc agggtgaggg 50

<210> SEQ ID NO 293
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 293
tatttaggta gttgaccact tcagcattct aggtacaata acgttagccc 50

<210> SEQ ID NO 294
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 294
agaacaaagc caggacaagg tacaaggtga ccccagcaaa tttccttttc 50

<210> SEQ ID NO 295
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 295
tgctagaagc ttatcaactg cattaatctt tttaaaaaca cttttagttt 50

<210> SEQ ID NO 296
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 296
tctcaccttc tccaggtgca cggtaggtgc tgtgtaaatt aacgacttca 50

<210> SEQ ID NO 297
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 297
gcctcctgct agacaattag ctttatccat gagttaccaa agagggagcc 50

<210> SEQ ID NO 298
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 298
accaaaatct ataaacaata aggaactgtg gttgtttgct gcaaataact 50

<210> SEQ ID NO 299
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 299
tcaagagttg ggaatgatga gggcatgtac tgtgactggc acacagaatg 50

<210> SEQ ID NO 300
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 300
agtgcctact atgtgctagt ccctagtgac atgagagtga ggaaggcagt 50

<210> SEQ ID NO 301
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 301
ccttatttca aggtcggggt caaggtggtc aaaagaactg ttttgctctc 50

<210> SEQ ID NO 302
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 302
aagggtattt atacctttgc ctttccgcct caaccattgg aacctgggac 50

<210> SEQ ID NO 303
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 303
agcctctctg ggtccttggg gagcatgagg atcctgcaga aagcagagtg 50

<210> SEQ ID NO 304
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 304
atgctctctg aacactatga cctctgatta tttatcaacc tccaagagct 50

<210> SEQ ID NO 305
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 305
cccctcttct gtgagagcca aacagagccc ttcctgagtc ccatccattc 50

<210> SEQ ID NO 306
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 306
tctgggtcct tttcattgct ctacaaagaa tcctttcttc ctcccaggcc 50

<210> SEQ ID NO 307
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 307
catcaatgcc cacgctacac gaggcatact agacagtcgc tgcctaagcc 50

<210> SEQ ID NO 308
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 308
tcaagagtaa cagtatgccc tgcattaaca gggataatat ataagaaaaa 50

<210> SEQ ID NO 309
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 309
gaatttatta ctcctgggag gattctgctc accactggca actatgacca 50

<210> SEQ ID NO 310
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 310
catcatgatg taatgtagtc atatagacta ggacacttag attagccccc 50

<210> SEQ ID NO 311
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 311
ggttttagta ttgcaatgtg gaatccaaaa ctgttatcaa tgaacttttg 50

<210> SEQ ID NO 312
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 312
tgggtgaggg aaccgttagt gccatcctga ggccccgtgt caggaaatat 50

<210> SEQ ID NO 313
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 313
actgaactcc ccatcacaaa tctgtatgct ttattagaaa gtaaaactct 50

<210> SEQ ID NO 314
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 314
agtaaaacag acgacgggat ccccagacgc tgcacatcag caccaggagc 50

<210> SEQ ID NO 315
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 315
cacactaata ttcaaacatc cttgacctca tctcatataa ataaatccaa 50

<210> SEQ ID NO 316
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 316
ccaagattct ggatgtcttt aaggtaacaa gtgtccatgt tgttccttga 50

<210> SEQ ID NO 317
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 317
gaagcgaaaa tagctatgca ccaaatctct gcaggcattt cattgagtac 50

<210> SEQ ID NO 318
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 318
tgaatgacag tgttgttgat tagttcaagc tcttgccttt ctctaaactt 50

<210> SEQ ID NO 319
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 319
gatcttagcc aaggcaggaa agcacacgat caggtaacct ccagattcac 50

<210> SEQ ID NO 320
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"

/organism="Artificial Sequence"

<400> SEQUENCE: 320
ttactcgcat taactctttc aatttcacaa caaatctaag aaaaatgcaa 50

<210> SEQ ID NO 321
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 321
agtctaaaac actatcatct cctcctggat tactgcaaca gactccttct 50

<210> SEQ ID NO 322
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 322
tctgccctaa atattccctg ttcggtgggg tttggcggtc cagcagccct 50

<210> SEQ ID NO 323
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 323
ccatgcgtgt tggaagtatt tctcttgttc tcctgctttt agaaagccat 50

<210> SEQ ID NO 324
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 324
cttctgaccc tcgccgtcct agaaccaacg gcccctcggt gtctggtcct 50

<210> SEQ ID NO 325
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"

/note="Synthetic"
/organism="Artificial Sequence"

<400> SEQUENCE: 325
aaagctctaa taccacctaa aaccatttct gttctctacc tctgtcatta 50

<210> SEQ ID NO 326
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 326
acaggttcta tatctttaga tggtaaatta aaaattcctg gctgaatttg 50

<210> SEQ ID NO 327
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 327
aatgtgagta gattccaacc tttatccatt ccattcacat ttaccttctc 50

<210> SEQ ID NO 328
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 328
ttgtttaaag ctgctgcagg tatactcttt ggaggctaat aataaagaac 50

<210> SEQ ID NO 329
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 329
tggagtagtc ttcttctagc ccttgcatga cctctcttac ttcacccata 50

<210> SEQ ID NO 330
<211> LENGTH: 50
<212> TYPE: DNA
<213> ORGANISM: Artificial Sequence
<220> FEATURE:
<221> NAME/KEY: source
<222> LOCATION: 1..50

<223> OTHER INFORMATION: /mol_type="unassigned DNA"
/note="Synthetic"
/organism="Artificial Sequence"

<400> SEQUENCE: 330
cttccacctg ctgcactcca atatagccac tatgttcggc tatatatata 50

<210> SEQ ID NO 331
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 331
tagagagtaa tgtggtgggt gtgctgtgtc agaaaggctt cactagcagt 50

<210> SEQ ID NO 332
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 332
ctaatttgat caatgaatca ctgctagcat gtgaatgtcc ataatggata 50

<210> SEQ ID NO 333
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 333
ttattagagg taaacataga gataagcccc taataaaata gtagctggag 50

<210> SEQ ID NO 334
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 334
agtgttaatt ctctaagagg aaaatgtcat ttctccaaaa caaaacttta 50

<210> SEQ ID NO 335
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 335
gtaacaaggt tacctccaga aaaaaaggct attgctgaac agaggctttc 50

<210> SEQ ID NO 336
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 336
aagagagaaa aatattttta agtgaaaagg aacaaaacta ttctatacga 50

<210> SEQ ID NO 337
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 337
ggctcacacc gagatcaatc catgatgaca gcacttcatg gcccgtctca 50

<210> SEQ ID NO 338
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 338
gataatctaa ttcatctaac ttgctttaca aatgaggaaa ctgataatcc 50

<210> SEQ ID NO 339
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 339
gtggaccctt tgagtggtta cagacgggcc tcaggattgg tgttatttaa 50

<210> SEQ ID NO 340
<211> LENGTH: 50
<212> TYPE: DNA
<213> ORGANISM: Artificial Sequence
<220> FEATURE:

<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 340
aacaggggcc actgtctgtt tcccatggta tctatagggc ctggtggaca 50

<210> SEQ ID NO 341
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 341
aggggtcaag atacaaggag tcaccaaaga atgcagaaga gacaagttca 50

<210> SEQ ID NO 342
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 342
ccttttctaa gaccaatatt aacaagaatt agtagtagaa tgttcttatg 50

<210> SEQ ID NO 343
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 343
tgttgctaat cccaaccagc atgatttacg ggaagtaaat catctatgac 50

<210> SEQ ID NO 344
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 344
gcctgtctca caaacattgg gttctataga cgctcctaga ttgcattttc 50

<210> SEQ ID NO 345
<211> LENGTH: 50
<212> TYPE: DNA
<213> ORGANISM: Artificial Sequence

```
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 345

cccagtgcct tgacagggta tggggggacc tgcatgacta gcattaaatg                50


<210> SEQ ID NO 346
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 346

taaccaggga tctgtgcgtt ttgctataat tcagaaagta gcagactact                50


<210> SEQ ID NO 347
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 347

aaaagtcggt tcgagaaccc aggtggaaaa tagattgagg gaagcaaaac                50


<210> SEQ ID NO 348
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 348

gagtaagagt taatcacttc cactgtgcac ttgtttattc caagtagaaa                50


<210> SEQ ID NO 349
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 349

ctctggacat cttcagaggg tcccacttta gacttcactg atctcttttt                50


<210> SEQ ID NO 350
<211> LENGTH: 50
<212> TYPE: DNA
```

<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 350
tcacacttta catttattat ttccagtaag ggatatagct aagatagtta 50

<210> SEQ ID NO 351
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 351
cagtttgatg aatggcaaaa tcgttcaaat ggaaaagagg agagagatag 50

<210> SEQ ID NO 352
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 352
ttcgtaatta aaggaacaga gtgagagaca tcatcaagtg gagagaaatc 50

<210> SEQ ID NO 353
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 353
agccagggtt gaagtcactc acgggtcctc tccgagaact cgagtggtga 50

<210> SEQ ID NO 354
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 354
caaaggtgat atgcatttta aatttgatag ttattgccca actgtcttta 50

<210> SEQ ID NO 355
<211> LENGTH: 50

-continued

<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 355
ccctcaggct gcttgttacc gtggaagctt cctgaactct ctccagaccc 50

<210> SEQ ID NO 356
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 356
ttttcatttt tctcttccca acccaatccc ctctctctaa atcttggtat 50

<210> SEQ ID NO 357
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 357
ttcaatatat gttttctgaa caccttctgt gttcaaggca ccatgctggg 50

<210> SEQ ID NO 358
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 358
cccttgcatg ttcaccttgt tatgtgtact ttcatctcaa ttgccagtta 50

<210> SEQ ID NO 359
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 359
aaagtatctc cccaaatcat tcccaaacac tacaaaggta gtgccatcag 50

<210> SEQ ID NO 360

<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 360
tgctctaaaa ctaatttgct tgaagtgtac agaatggaat tcgggaagga 50

<210> SEQ ID NO 361
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 361
atcacttttc catgaaattg tctttgcatt agcaaaatga atcaagcata 50

<210> SEQ ID NO 362
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 362
ttggtgatgc tgatagttgg agatacccag acagataagg tatattgccc 50

<210> SEQ ID NO 363
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 363
atcaatatga ctggtgtcct tcaggaatgt ggtagcacag tgaaaaaggt 50

<210> SEQ ID NO 364
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 364
gcagtagggg actggctgcc gagggggcat ctagattgag ataggtggga 50

<210> SEQ ID NO 365
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 365
attggcaaaa gtgctcattc tggaaaaaca aagaagtgag aaagtggatg 50

<210> SEQ ID NO 366
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 366
attctaaagc tttgtgtggt ccaccatgat caccttttcc tgcttccccc 50

<210> SEQ ID NO 367
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 367
gctccatttt ctttgaggta catcaacatc aataacagat caatggaccc 50

<210> SEQ ID NO 368
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 368
agcctgacct catggcttag ctgtgcctcc tggacaccat ccctctctgc 50

<210> SEQ ID NO 369
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 369
ttctgaaagt cacagcccag ggattcagac ccactaaaaa aaactgagat 50

<210> SEQ ID NO 370
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 370
actacattac atcatgatgt attgattgcc tctggcctag gaatctgcag 50

<210> SEQ ID NO 371
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 371
ccactcatat gtctgttctc actcagaggt gaggccctgt gtcttcagcc 50

<210> SEQ ID NO 372
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 372
gggggacaga gaagtaacgt cacaagattt taagcttggg ccagatatgg 50

<210> SEQ ID NO 373
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 373
aagtagagca gaaagggcaa gcagagaact agacagagaa gacagatgac 50

<210> SEQ ID NO 374
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 374
tggctgcctc tagggcaaga agactgggga tatcaccatg ggctcaatgt 50

<210> SEQ ID NO 375
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 375
ccaagtcctt ctacctccct gggtgaggga accgttagtg ccatcctgag 50

<210> SEQ ID NO 376
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 376
aatcttgggg aatctgagtt tattagagga atgtagggag gaagcaggct 50

<210> SEQ ID NO 377
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 377
tatcatatgc tctagtgact tcatcaagac agtctaaagg aagatgggcc 50

<210> SEQ ID NO 378
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 378
cagaaacacc tttaatgttt ttatttctat gaatattctc ctaatgatta 50

<210> SEQ ID NO 379
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 379
ttaaaatgag atcccttcca acatgctttg ctgagccaga tttataaaat 50

<210> SEQ ID NO 380
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 380
tagtacagta agggcaaagg gcactgcaat tgctattaaa ctgtaagaag 50

<210> SEQ ID NO 381
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 381
atcccccgga actgggggaa tttccaggca catgaggctc tgtcaaccca 50

<210> SEQ ID NO 382
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 382
agccacttaa aataaatttt tccagcagtt attcatttag tgccaaaata 50

<210> SEQ ID NO 383
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 383
gcaggggcac atgcaattgc catttaaaaa tgaggtctgg catggccaga 50

<210> SEQ ID NO 384
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 384

```
gtaccacagc tcccagctgc atgtacttta aaaatgtgtc taagccaggc                 50


<210> SEQ ID NO 385
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 385

tgcaaacaga aaaatcagaa cctgctcatg ctgccatatt aataggaacc                 50


<210> SEQ ID NO 386
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 386

taactacaca ctcaaggctc cctctcaaag tctcaaacct tacaacttcc                 50


<210> SEQ ID NO 387
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 387

aatacagcca tgcgctacct actggcattc ccgtcagtgc gtacacgatc                 50


<210> SEQ ID NO 388
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 388

aactgctttc ctcattggct tggtctccat agtgattcat tttgctgtaa                 50


<210> SEQ ID NO 389
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"
```

<400> SEQUENCE: 389
tggaaatttt tttgtaatta gaaatgacct aaaggatagt ttctattctt 50

<210> SEQ ID NO 390
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 390
attgattttt atgtcagcaa tcttccaatc ttgttaattc taaaatactt 50

<210> SEQ ID NO 391
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 391
gcctaagctg aacctgagag gtgaggaaaa cagaccaagc tgaccaaacc 50

<210> SEQ ID NO 392
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 392
gcgaactgtg gagtatctca gtaagagtgt taggaggaat attttatagg 50

<210> SEQ ID NO 393
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 393
acaacaacaa atctcaaaca actgttctgc caatggggtg gagcaccttt 50

<210> SEQ ID NO 394
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 394
tgatgatttt ccagcatggc aatggtaaag ctgcaaataa aaagcagcca 50

<210> SEQ ID NO 395
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 395
ttcttttctc caagcaaaag agagaagagt ttatttcatt ctcagcagct 50

<210> SEQ ID NO 396
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 396
ggcaaaagca gagatgtgag ctgtaaattt gaatgaagga ccagatagaa 50

<210> SEQ ID NO 397
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 397
taggaacata aaagttcaga tgttagtagg actaataaaa agttattgtt 50

<210> SEQ ID NO 398
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 398
tttttcaggt ctagcttaac caaaacactt aaaactgtta ccaaaaaact 50

<210> SEQ ID NO 399
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"

/organism="Artificial Sequence"

<400> SEQUENCE: 399
caaataaata aactttaaag aaatggccaa cttgggaagg acattaggcc 50

<210> SEQ ID NO 400
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 400
cagtccaaca accagttcca gaagatctca gaggtaggcc gctccccaca 50

<210> SEQ ID NO 401
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 401
tgaaaatgtt gtctggacaa gcactgaaag ataagaaaga actagaaggt 50

<210> SEQ ID NO 402
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 402
gattcatttt tacatgttta tttttaatgg agactaaaga gacataaatg 50

<210> SEQ ID NO 403
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 403
tcttgattca attggaagta actgagaggt atatcacatg ttgtgattca 50

<210> SEQ ID NO 404
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"

/note="Synthetic"
/organism="Artificial Sequence"

<400> SEQUENCE: 404
tgctccataa cacaaataat ttcattcttc ttcctttctt gccgagtagt 50

<210> SEQ ID NO 405
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 405
atgagcaagg aggccaaaac cctgcgtgga cggtctgctt ccctgccctt 50

<210> SEQ ID NO 406
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 406
gagtgccaaa tatgtgccct tccccgtggg gaagacaaaa gtatgagaca 50

<210> SEQ ID NO 407
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 407
tatttttagc agcctatgga ttctaggagt gacccagctc cagggatagg 50

<210> SEQ ID NO 408
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 408
catgaggaaa ggctgcaact ttgagctccc tctttagcta gggagcctcc 50

<210> SEQ ID NO 409
<211> LENGTH: 50
<212> TYPE: DNA
<213> ORGANISM: Artificial Sequence
<220> FEATURE:
<221> NAME/KEY: source
<222> LOCATION: 1..50

<223> OTHER INFORMATION: /mol_type="unassigned DNA"
/note="Synthetic"
/organism="Artificial Sequence"

<400> SEQUENCE: 409
agcattaatg aagcacaggg cctatcacgc agtcaggctc agtataaggt 50

<210> SEQ ID NO 410
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 410
catactcaaa ttgatacaca gcctttgtcc tgagtgtttg tcttccaaaa 50

<210> SEQ ID NO 411
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 411
agagtagtat tgcttaaaaa ctgctccaac cacttcttaa acctgaaacc 50

<210> SEQ ID NO 412
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 412
tcggccaaaa tcagggacaa ggatgacatg ccattgctta ccaactgcta 50

<210> SEQ ID NO 413
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 413
ccgttgtgca aactccagaa agggcatctc tctgtcccac tcccccatta 50

<210> SEQ ID NO 414
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 414
atctgcgtaa attgctgcat ctctcttggc ctcagttttc ttagccacac 50

<210> SEQ ID NO 415
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 415
gtaagtgcca gctactatta tttaggaggc taaggctcta ggtgatgagg 50

<210> SEQ ID NO 416
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 416
tgccacccta tggcattctt gttgtgtaat gaaataactc tcctatgaaa 50

<210> SEQ ID NO 417
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 417
ctgcgcttgc ccaggaggcc ctggtctgca ctgtttatag agaagaaccc 50

<210> SEQ ID NO 418
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 418
ttaggaaagt tctgtacaga tatgtgtaat ccagcatctg tttatctatt 50

<210> SEQ ID NO 419
<211> LENGTH: 50
<212> TYPE: DNA
<213> ORGANISM: Artificial Sequence
<220> FEATURE:

<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 419
aatgatggaa aaaactgcag cgcacggtgg aaatgtctac tttgtatgca 50

<210> SEQ ID NO 420
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 420
ctcctcatta ttcgcttctg ctgtaactgc acctatggta acccaggtgc 50

<210> SEQ ID NO 421
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 421
aagtgctctg taaccaaata ttttggaaat gctgagttgt accaagttgg 50

<210> SEQ ID NO 422
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 422
ttttgaaatt tccattatat gcaaagccca tgaaaggcta aatatcagtt 50

<210> SEQ ID NO 423
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 423
gtttgtaaat gcacactgtt gggggaaccc tcttcctagt ccttgtttcc 50

<210> SEQ ID NO 424
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 424
tgggcgagaa cttattcctc aggccattag attccctaat gctgcacctt 50

<210> SEQ ID NO 425
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 425
gccatgggca aaaacagctc aggtagtaat gaaggtgtgg ctatagctga 50

<210> SEQ ID NO 426
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 426
acatcaaact aaattacatc atcagagtaa agagacaatt tacaaaaagg 50

<210> SEQ ID NO 427
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 427
aaaaagttct tcttctttgc tcctccattg cggtcccctt caagatccat 50

<210> SEQ ID NO 428
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 428
ctggctccag gcaaagaata ctaccagcaa caaagaggaa catttcagat 50

<210> SEQ ID NO 429
<211> LENGTH: 50
<212> TYPE: DNA

```
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 429

ggactagcct gctgcttcat ttcccccctc ctctgcagcc gatttcagaa                50


<210> SEQ ID NO 430
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 430

atattagtaa cctggaaaac atacatggag gtatgttcat taacggcagt                50


<210> SEQ ID NO 431
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 431

atgggaagag ctggattttt gtcgtggagt aaaggagagg gaatcaagaa                50


<210> SEQ ID NO 432
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 432

aaaatcatag aaattgtgtc taaggatatg ctttgggata tttggacttc                50


<210> SEQ ID NO 433
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 433

cataaaccaa agggatcttc tctactcgtg cgtccctagt ctctctcccc                50


<210> SEQ ID NO 434
<211> LENGTH: 50
```

<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 434
gctgcctgta ctagtgatag tgaggctcac taccatccac cacctaaatt 50

<210> SEQ ID NO 435
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 435
gtgtagctta cgggagggaa gtcaaagtca ggcacgttca tcacactcag 50

<210> SEQ ID NO 436
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 436
ctcattgtaa gattcaaaaa cattccagct tacaaaacat atccagctta 50

<210> SEQ ID NO 437
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 437
tttgcaaggc aatttgttct actgctggac agcttcatgt ttaatgtttt 50

<210> SEQ ID NO 438
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 438
ctatatttga acaagcttct gggtaatatt tatgacaggg aagtcttgag 50

<210> SEQ ID NO 439

<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 439
ctgtgaacca ggcactgttt gaaatgttcc atttattgac ttatttaagt 50

<210> SEQ ID NO 440
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 440
actactacta atgttgaaag tataccatgt aacaggcact gtacaaagcc 50

<210> SEQ ID NO 441
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 441
ttttgggttt tgttgctagc ataaaaatta ttacctagtg gatggtaaca 50

<210> SEQ ID NO 442
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 442 ttttttttc atttgaagta aatatccacc tttgtatcta attttgcatt 50

<210> SEQ ID NO 443
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 443
ttatttttta atagtgttct tgcacatgag gagaaagact gaattcaatt 50

<210> SEQ ID NO 444
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 444
cgtgtcactt cgtttgactt cagctgggaa catgcatatc agtcgactca 50

<210> SEQ ID NO 445
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 445
atcgtcacac agttttaaga caaatgtttt tacctatttg acctagtctg 50

<210> SEQ ID NO 446
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 446
tgtgctacaa acctgaaact ggtaagacaa gcacaaagca acgtgcaata 50

<210> SEQ ID NO 447
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 447
cttggatgga ggctcaggga gccaaaggca aatgtcttca tagaaccagg 50

<210> SEQ ID NO 448
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 448
atcatgaatt aaacaaatta atttatgtat tttgttttga gtcagtgtct 50

<210> SEQ ID NO 449
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 449
acatgtgacc aacaagataa ttatgaaacc tgactgctgg atatgctgat 50

<210> SEQ ID NO 450
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 450
gtcttttgga aaatgcaatc tgccactctg tgcaatggaa aaccactgca 50

<210> SEQ ID NO 451
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 451
ttattaatat tagcctttct tctctccccg tttatgcttt ggtgggtact 50

<210> SEQ ID NO 452
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 452
tttggtttgg gttttgtttg gcagaggcag aatagaataa agaacatggg 50

<210> SEQ ID NO 453
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 453
agaattattg ctgcacaatt cttatgaaac cgaactagag ctacactatt 50

```
<210> SEQ ID NO 454
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 454

caggcagatc acttgacgtg aggagttcaa gtgaggagtt caagtccagc                50


<210> SEQ ID NO 455
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 455

acaaacaaac tgaggtttag gtttaggtag ctggagttta taggcatggc                50


<210> SEQ ID NO 456
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 456

tctggaataa tagttacatt tgctacatcc ctttctagcg tcaactcact                50


<210> SEQ ID NO 457
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 457

cataatgtga tgccatatta aactgtaatc acctttccac caaactaata                50


<210> SEQ ID NO 458
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 458
```

caaaattcat atgttgatac ctaatctcca aagcaatagt attaagggtg 50

<210> SEQ ID NO 459
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 459
aatactgttt ggtatggcaa gacagtattg gttttggttc aagtgctcct 50

<210> SEQ ID NO 460
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 460
ttggttttcc tgggtgggga agggtgctgg cctcattcac aacagcagat 50

<210> SEQ ID NO 461
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 461
gggaaagaca gagtgagaga aagagagagt tagcctctac atattataag 50

<210> SEQ ID NO 462
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 462
gcagagagag ccctgtctca aaacagattt ctgagtgtgg cttctgtcca 50

<210> SEQ ID NO 463
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 463
tctcgtagct gagagagtca tgactatggc gtgttctctg tactctgagg 50

<210> SEQ ID NO 464
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 464
ctcaagcaga aggaatctct ccccatagcc gctatagttt caaatgtgct 50

<210> SEQ ID NO 465
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 465
gtgaggatag gtagcttttc ttactcactg ttgttaccag tacctagaac 50

<210> SEQ ID NO 466
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 466
acgagcttgt cattctgtaa atgacatatt catattcttg gtattgtaca 50

<210> SEQ ID NO 467
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 467
caaggttaaa attcccgcat tgtgggcctt gtagctttca tgtcttaatg 50

<210> SEQ ID NO 468
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 468
ggattttggc cattctaaga gatgtgcagt agtaactcag tgttttattt 50

<210> SEQ ID NO 469
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 469
ctgaagactc tgaacttgac tgaggaaatg ttaaacagat acctcttcat 50

<210> SEQ ID NO 470
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 470
aacattccat tatcctattg ttcattcttt ggagctgtga tttgtttaat 50

<210> SEQ ID NO 471
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 471
agcttcggtg aatattagaa tggcctcaag agctagtaaa aaacacagcc 50

<210> SEQ ID NO 472
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 472
aggcatatgg ggaaaaaata aggcaggaaa ggaagacgga aaatgctgtg 50

<210> SEQ ID NO 473
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 473
ttggttttat aaaggatcta agtgtttgga aaggtgtggg accatgtact 50

<210> SEQ ID NO 474
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 474
acatgctctg catgctttga cagtacagtg tatagaatag acacaaaact 50

<210> SEQ ID NO 475
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 475
taaggttgta tcatctacct gtagtcactg cagtcagctg aattttacca 50

<210> SEQ ID NO 476
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 476
ctctgtagcc acacagatgc caacagctgg cacttgtcca agaaacatgt 50

<210> SEQ ID NO 477
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 477
agaatgggtc acttgttaga aacagtcaag gatacataca aacagtggaa 50

<210> SEQ ID NO 478
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"

/organism="Artificial Sequence"

<400> SEQUENCE: 478
ccaagagtgg tgaagccttc ctgtttacag aggattttca tatctgttat 50

<210> SEQ ID NO 479
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 479
acacccatgg ggccaagcca ggagcagtca ccacagccaa cctgcaggct 50

<210> SEQ ID NO 480
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 480
tattctaagg aagtgccccc taaaacaaag ctcaggagcc tcaacccggc 50

<210> SEQ ID NO 481
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 481
tcccaacatc aaaaggcaaa ttcttgcccc acttttacag atgagagcgc 50

<210> SEQ ID NO 482
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 482
taccatggga aacagacagt ggcccctgtt ctcaagtggc ttagactcta 50

<210> SEQ ID NO 483
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"

/note="Synthetic"
/organism="Artificial Sequence"

<400> SEQUENCE: 483
cttattggcc ctaagtaaat cttaggttag gtagagctca gttcccaggg 50

<210> SEQ ID NO 484
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 484
gtatttttag gaacattcag gaaaacaggt aaagggtatt caggaattca 50

<210> SEQ ID NO 485
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 485
ggccttcctc actctgacgg tgagttccag aggacaggga tttgtggttg 50

<210> SEQ ID NO 486
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 486
tggttgctaa tttctcttca cttctgggaa accagcccct tataaatcaa 50

<210> SEQ ID NO 487
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 487
aacacagagc agtatgtaca ggacagcgtt agaatatacc agagaacaag 50

<210> SEQ ID NO 488
<211> LENGTH: 50
<212> TYPE: DNA
<213> ORGANISM: Artificial Sequence
<220> FEATURE:
<221> NAME/KEY: source
<222> LOCATION: 1..50

<223> OTHER INFORMATION: /mol_type="unassigned DNA"
/note="Synthetic"
/organism="Artificial Sequence"

<400> SEQUENCE: 488
aaacacacct gtcacccacg accctggcat agggcatcgt gaacccatca 50

<210> SEQ ID NO 489
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 489
atagtattct gttcttcagg gagttgtggg ttcggatctg tgcaaagata 50

<210> SEQ ID NO 490
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 490
taggaatcag ggaactctag atgcgtctag cagctagcct gtggcctcga 50

<210> SEQ ID NO 491
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 491
ttcaaattgc ttgattaaaa tggcaaacag tttgaaaatt gtatacctct 50

<210> SEQ ID NO 492
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 492
ggataatgga aaagggggtt tctcccaagt agagaactta aacagtgtga 50

<210> SEQ ID NO 493
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 493
cacctagtca tgtgtatata aaatcaccat gttattacag aatttagtaa 50

<210> SEQ ID NO 494
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 494
caatctattt tccacctggg ttctcgaacc gacttttcct ccctctcttc 50

<210> SEQ ID NO 495
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 495
gggtcttcct acgggactgc cttagacgtg ctgggctttg gcctcagtga 50

<210> SEQ ID NO 496
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 496
agttttggtt ggggaggaca atgccaggtt aacagacact taatatacat 50

<210> SEQ ID NO 497
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 497
aaagagagtg gaagtaccag gtgggcaaag tttacaattt taagtaggat 50

<210> SEQ ID NO 498
<211> LENGTH: 50
<212> TYPE: DNA
<213> ORGANISM: Artificial Sequence
<220> FEATURE:

<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 498
atgattcttt ccatgacacc tagtgccctt ctccatctag agctacctct 50

<210> SEQ ID NO 499
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 499
aaatgaactc agcaatgaaa tggaacaagc tatccataca tgcagcaatt 50

<210> SEQ ID NO 500
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 500
ccatcattgc ctggctgttg aagcagttct tgacatttta aagtaatatg 50

<210> SEQ ID NO 501
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 501
ttgctacaag gaggattatg ggtgaaagtc atggatggat tatgagttaa 50

<210> SEQ ID NO 502
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 502
gatggacatc actgaaatgt agttttgcct gaagtgtggt ttggatgctc 50

<210> SEQ ID NO 503
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 503
cttgtttgtg tatgatacat gaagtagaat tcatacagca caagtacttt 50

<210> SEQ ID NO 504
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 504
gaaattctcc ataatttctg atccactctt acattcctct cctttccagc 50

<210> SEQ ID NO 505
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 505
gggggctggg gggaagtccc gggacaggtg catgtcatca acacgactgt 50

<210> SEQ ID NO 506
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 506
agatcttttc aggcataaaa gttgtcaata ggttttcata aatttctagg 50

<210> SEQ ID NO 507
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 507
cccttgcaca ggcacagcta taatttttgt ctctcttctg ttggaaaggt 50

<210> SEQ ID NO 508
<211> LENGTH: 50
<212> TYPE: DNA

<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 508
gtggtttcta atgatttaat accatccccc agggtgctct tcttgtgata 50

<210> SEQ ID NO 509
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 509
gaatattgaa ggtagccaga aaagaaaaaa aggcacattg catgcagagg 50

<210> SEQ ID NO 510
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 510
atggcagttc attgctttac tatttggaca tttcaaactg tcccaaggtg 50

<210> SEQ ID NO 511
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 511
ttttttcaaa cctttaaaca acagtcccac ttggataaag tctgagagcg 50

<210> SEQ ID NO 512
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 512
atagcctaac tttccccccg aagcttccca agccctcatg atatctatta 50

<210> SEQ ID NO 513
<211> LENGTH: 50

<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 513
acctgagaat tctcacccat ccaattctac ttgatatggg attcctctaa 50

<210> SEQ ID NO 514
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 514
aatgggcatg atctcactca catggaacag gatctctttc cttgttagca 50

<210> SEQ ID NO 515
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 515
agtcacagaa acatagcaag cccttgaaat caggctttct gactttgtct 50

<210> SEQ ID NO 516
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 516
cacctacaca catgcatgca cacacacatg gcctctctct ccaggcttct 50

<210> SEQ ID NO 517
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 517
cgtacagacc tggtccaaaa attccaattt cataggtgtg gagttttcat 50

<210> SEQ ID NO 518

<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 518
caaacaacca ccacatcaaa ataatagcaa agacaacaac taatactaat 50

<210> SEQ ID NO 519
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 519
atagtaagtt ttaaagtaag aggtcagaaa catatgttac tttacaaaca 50

<210> SEQ ID NO 520
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 520
ttatgtagca ggtcctgatg taacagaatt aagattgcag gtgggattgg 50

<210> SEQ ID NO 521
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 521
tccctagaac agcaggacct gcgaaactct gaggccgctt tgtgaggtcc 50

<210> SEQ ID NO 522
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 522
ttgaaaagag aaacccacag ggctttctgc ttaaatccct cggacacagt 50

<210> SEQ ID NO 523
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 523
taaggatggg acccctactg tccatctcag gctcagcact gccttggggc 50

<210> SEQ ID NO 524
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 524
cttctacatc ttagctcacc tgtcctcaca aataaacatc actcttgaat 50

<210> SEQ ID NO 525
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 525
ttgttgaaat gtgaccacga actaggtctt aacctagcaa attcacaaat 50

<210> SEQ ID NO 526
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 526
ctttctaaac actagcagcc cagaattctc aggccacttt tgggcattgt 50

<210> SEQ ID NO 527
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 527
gtctatgaat tggtgaatca gccaagtgaa tgcttcaaaa actgggactc 50

<210> SEQ ID NO 528
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 528
cctcctgaga tgaacatcgt gaggagtaaa tagagatgct attctcagct 50

<210> SEQ ID NO 529
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 529
aactccgatt aatcactagt tgttcacacc aaaaacccaa gtgccattac 50

<210> SEQ ID NO 530
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 530
tcaccaagtc tggttgtccc agtctcctat ctctgtctgt tcctctcctc 50

<210> SEQ ID NO 531
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 531
atgagttgga attgcataat gggtagatgc tgatgctgga gaactttgag 50

<210> SEQ ID NO 532
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 532
gtcattgact cgactataat tttccaaact acctaaacgt gttatatcat 50

<210> SEQ ID NO 533
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 533
tgatgattag gagtctgatg gaggaaagta attttaaaac aacttaatgg 50

<210> SEQ ID NO 534
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 534
tggggtttta tttgcttttt tcccagtttc ttagatgtaa agttaggtta 50

<210> SEQ ID NO 535
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 535
ggaactctga cgcaatccag ggccgaggaa aaatgattaa aacccaacaa 50

<210> SEQ ID NO 536
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 536
tactgcagtg agttcaagtg ttgtacctgc ttaaaatgca gtgacactaa 50

<210> SEQ ID NO 537
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 537
ggcagaggga acagcttgtg caaaggccct ggggcaggcc aagggcagag 50

<210> SEQ ID NO 538
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 538
aaaagaggat ggctggttta tctcaagtaa tcagacattt aataataata 50

<210> SEQ ID NO 539
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 539
gtgctatttt gttgctgtta ggtctatttt cttcatctgt tatttcgcat 50

<210> SEQ ID NO 540
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 540
gcctggggga gcggggaatc gcttttcgcc ggcctccgcg taaccttgtt 50

<210> SEQ ID NO 541
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 541
ggctcaacgg aagtgaccgt cccacagtta tgcagcacta agtcaatggc 50

<210> SEQ ID NO 542
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 542
ttgtgacagg tcccagcgtg aacacgcacg ccctagccgg gccccaaacc 50

<210> SEQ ID NO 543
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 543
aaggggaccg caatggagga gcaaagaaga agaacttttt taaactgaac 50

<210> SEQ ID NO 544
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 544
gctgacttct tgactgcagc cacaggaagg actcaaccca ggaccatcca 50

<210> SEQ ID NO 545
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 545
aatttttcaa tggtaaacag accagagtta ttctaagaaa ttatgaaaag 50

<210> SEQ ID NO 546
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

<400> SEQUENCE: 546
aggatttcaa gacttgcctg agcaacataa tgagatgccc tctctcaaaa 50

<210> SEQ ID NO 547
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
/note="Synthetic"
/organism="Artificial Sequence"

-continued

```
<400> SEQUENCE: 547

agcaagcaga aaacaaacaa cttcattaaa aatgagcaga ggacctgaac          50


<210> SEQ ID NO 548
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Synthetic"
      /organism="Artificial Sequence"

<400> SEQUENCE: 548

ttctgagacc ttcttgcccc tttgtttcta agcccagggc cacaattccc          50
```

GENETIC PREDICTORS OF A RESPONSE TO TREATMENT WITH CRHR1 ANTAGONISTS

CROSS REFERENCE TO RELATED APPLICATIONS

This application is a continuation-in-part of U.S. application Ser. No. 15/562,454, filed Sep. 28, 2017, which claims the priority benefit of PCT/EP2016/057229, filed Apr. 1, 2016, which claims priority benefit of U.S. Provisional Application No. 62/141,879, filed Apr. 2, 2015. The entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on Mar. 17, 2021, is named 18744_0128 SL.txt and is 204,800 bytes in size.

BACKGROUND OF THE INVENTION

Corticotropin-releasing hormone (CRH or corticotropin-releasing factor/CRF) is pivotal in modulating the activity of the hypothalamic-pituitary-adrenal (HPA) axis during stress, stress-response and stress-adaptation, as well as in inflammation. CRH is a 41 aa peptide hormone derived from a 196-amino acid pre-prohormone, produced in the hypothalamus and transported in small vessels to the pituitary from which the peripheral stress hormone corticotropin (also known as adrenocorticotropic hormone/ACTH) is released which, in turn, induces secretion of cortisol from the adrenal gland. CRH containing nerve fibers also project to areas in the CNS implicated in behavioral adaptation to stress, including the amygdala, being implied in fear and anxiety, the prefrontal cortex and the hippocampus. Persistent stress is hypothesized to result in anxiety, depressive symptoms and other stress-related disorders in patients with inherited or acquired vulnerability. Among those patients, antagonists of CRH would appear to be the ideally tailored therapy. The effects of CRH in the brain, where CRH acts like a neurotransmitter, are conveyed via the type 1 CRH receptor (CRHR1, or CRF—R1), which mediates a variety of endocrine, behavioural, and autonomic stress-responses (Heinrichs and Koob, J Pharmacol Exp Ther. 2004 November; 311(2):427-40), including, but not being limited to, psychiatric conditions such as anxiety disorders and major depression (Holsboer and Ising, Eur J Pharmacol 2008, 583(2-3): 350-7; Koob and Zorilla, Neuropsychopharmacology 2012, 37(1):308-9). In murine models, CRHR1 deletions displayed less depression-related behaviors, while CRH over-expression in the CNS lead to an increase of several behaviors that can, within certain limitations, be extrapolated to human depression.

The World Health Organization (WHO) considers depression as one of the top ten causes of morbidity and mortality, with a lifetime prevalence for depression ranging, e.g., from 12-16% in Germany. Depressive disorders account for a worldwide number of over one million suicides annually, and create a significant burden on costs in health care, work leave, disability pension, early retirement, loss of productivity of workers, by far surmounting direct costs such as inpatient and outpatient treatments. Finally, depression also multiplies the risk for other conditions such as cardiovascular disease, diabetes and neurodegenerative disorders.

Significant effort has been focused on the development of inhibitors of neuropeptide receptor ligands as drugs for psychiatric diseases and related conditions, including CRHR1 antagonists for the treatment of anxiety and depression (Griebel and Holsboer, Nature Reviews Drug Discovery 2012, 11:462-478). However, essentially all randomized controlled trials using CRHR1 antagonists in humans produced negative results, which has lead several originators to stall CRHR1 antagonist development, see Williams, Expert Opin Ther Pat 2013, 23(8):1057-68.

The present invention rests in part on the recognition that several of these earlier trials testing CRHR1 antagonist only failed to show statistically relevant effects due to the lack of appropriate patient stratification and selection according to their individual, underlying pathophysiology. In other words, a CRHR1 antagonist can only be effective in pathologies where the underlying causality is dominated by CRH over-activity or excessive CRH secretion. In the absence of CRH over-activity, a CRHR1-antagonist is not likely to have any significant effect.

Methods and algorithms for predicting an ACTH response to CRHR1 antagonists using the dex/CRH test in patients with depressive symptoms and/or anxiety symptoms, as well as a set of genotypes of single nucleotide polymorphisms (SNPs) for use in such methods and algorithms, have been described in WO 2013/160315 (A2). Correspondingly, CRHR1 antagonists for use in the treatment of depressive symptoms and/or anxiety symptoms in patients having CRH over-activity have been described in WO 2013/160317 (A2), wherein CRH over-activity is detected by determining the status of the same set of genotypes of SNPs as in WO 2013/160315 (A2). However, there remains a need for improved methods of predicting the treatment response to CRHR1 antagonists. In particular, there is a strong need to provide a direct prediction of clinical response in subjects treated with a treatment with a CRHR1 antagonist, e.g., in subjects having depressive symptoms or anxiety symptoms, or another stress-related condition mediated by CRHR1.

The present invention rests on additional evidence unknown in the prior art, according to which many polymorphisms are present in essentially all relevant nodes of the CRH/CRHR1 signaling chain. It is, thus, an object of the present invention to provide a particularly useful set of genomic DNA polymorphisms for predicting a central CRH over-activity and/or a clinical response to treatment with a CRHR1 antagonist, in particular in, but not being limited to, patients with anxiety symptoms or depressive symptoms. Thus, the present invention provides improved methods for predicting treatment response of patients to a treatment with a CRHR1 antagonist, as well as methods of treatment comprising an CRHR1 antagonist, compositions, kits and arrays comprising polynucleotides and uses thereof in methods of predicting the treatment response.

SUMMARY OF THE INVENTION

The present invention is based, at least in part, on the recognition of polymorphism genotypes, including, but not being limited to, single nucleotide polymorphism (SNP) genotypes that are predictive of a subject's clinical responsiveness or non-responsiveness to treatment with a corticotropin releasing hormone receptor type 1 (CRHR1) antagonist. Specifically, the presence or absence of one or more of the polymorphism genotypes disclosed in Table 2 herein can be used to predict the likelihood that a given subject will or will not respond to treatment with a CRHR1 antagonist. The set and subsets of polymorphism genotypes, compositions, and methods described herein are thus useful in selecting appropriate treatment modalities (e.g., a treatment with a CRHR1 antagonist or a non-CRHR1 antagonist) for a subject having a condition treatable by a CRHR1 antagonist.

Thus, in a first aspect, the invention provides a method for predicting a treatment response of a subject to treatment with a CRHR1 antagonist, the method comprising: providing a biological sample obtained from the subject, and detecting the presence or absence of one or more polymorphism genotypes in the biological sample, wherein the one or more polymorphism genotypes comprise: (a) at least one polymorphism genotype selected from the group consisting of rs34169260 (A/G), rs796287 (A/C), rs56149945 (A/G), rs6190 (T/C), rs7179092 (T/C), rs7614867 (A/G), rs920640 (T/C), rs7167722 (T/C), rs920638 (T/C), rs7165629 (T/C), rs80049044 (T/A), rs16941058 (A/G), rs112015971 (A/G), rs10894873 (T/C), rs117455294 (T/G), rs1170303 (T/C), rs16940681 (C/G), rs968519 (T/C), rs28381866 (T/C), rs79320848 (T/G), rs114653646 (T/G), rs2589496 (T/C), rs10482650 (A/G), rs17614642 (A/G), rs73200317 (T/C), rs1380146 (T/A), rs735164 (T/C), rs730976 (T/G), rs55934524 (T/G), rs4570614 (A/G), rs4458044 (C/G), rs77850169 (A/G), rs35339359 (A/G), rs34800935 (T/C), rs72945439 (T/C), rs113959523 (A/G), rs116798177 (A/G), rs11247577 (T/G), rs75869266 (T/C), rs74372553 (T/C), rs11691508 (A/G), rs6493965 (A/G), rs4869476 (T/C), rs3730170 (T/C), rs2145288 (A/C), rs2935752 (A/C), rs146512400 (A/G), rs62057097 (T/C), rs115061314 (T/C), rs34113594 (T/G), rs61751173 (A/G), rs74338736 (A/C), rs10851726 (T/C), rs4610906 (T/C), rs59485211 (T/C), rs7060015 (T/G), rs75710780 (T/G), rs6520908 (T/C), rs487011 (T/G), rs1383699 (A/C), rs67516871 (A/G), rs114106519 (T/C), rs7220091 (A/G), rs12489026 (A/G), rs876270 (T/C), rs4968161 (T/C), rs62056907 (A/G), rs2235013 (T/C), rs16878812 (A/G), rs6549407 (A/G), rs28381848 (A/G), rs79723704 (A/C), rs72814052 (A/G), rs10152908 (T/C), rs172769 (A/C), rs78596668 (T/C), rs73307922 (T/C), rs3842 (A/G), rs7210584 (A/C), rs62402121 (T/C), rs55709291 (A/G), rs72747088 (A/G), rs929610 (G/C), rs6766242 (T/C), rs1468552 (G/C), rs78838114 (T/C), rs62489862 (T/C), rs894342 (A/G), rs58882373 (T/C), rs3811939 (A/G), rs6984688 (T/G), rs1018160 (T/C), rs76602912 (A/G), rs80067508 (A/G), rs74888440 (T/C), rs12481583 (T/C), rs66794218 (A/G), rs16946701 (A/G), rs75726724 (A/G), rs67959715 (T/A), rs11871392 (T/G), rs2044070 (A/G), rs77612799 (T/C), rs6743702 (T/C), rs616870 (T/C), rs79590198 (A/G), rs75715199 (A/G), rs13087555 (T/C), rs4869618 (T/C), rs117397046 (A/G), rs8042817 (A/G), rs2258097 (T/C), rs2260882 (C/G), rs532996 (A/G), rs11747040 (T/C), rs10034039 (T/G), rs116909369 (A/G), rs79134986 (A/G), rs117615688 (T/C), rs8032253 (T/C), rs12818653 (T/A), rs4587884 (A/C), rs77122853 (T/C), rs117615061 (T/C), rs74682905 (A/G), rs2257468 (T/C), rs2032582 (T/G), rs2235015 (T/G), rs2729794 (T/C), rs77549514 (A/G), rs74790420 (A/C), rs73129579 (T/C), rs12913346 (A/C), rs117560908 (T/C), rs72747091 (A/G), rs2935751 (A/G), rs4331446 (A/G), rs7523266 (T/C), rs7648662 (T/C), rs117034065 (A/G), rs4836256 (T/C), rs80238698 (T/C), rs3730173 (T/C), rs11687884 (T/C), rs72693005 (T/C), rs2589476 (T/C), rs9813396 (T/C), rs10482667 (A/G), rs72784444 (A/G), rs75074511 (T/C), rs7951003 (A/G), rs79584784 (A/G), rs2214102 (T/C), rs28811003 (A/G), rs6100261 (A/T), rs77152456 (A/G), rs66624622 (T/G), rs140302965 (A/G), rs11653269 (T/C), rs74405057 (A/G), rs7121 (A/G), rs16977818 (A/C), rs12490095 (T/C), rs118003903 (A/G), rs62377761 (T/C), P1_M_061510_6_34_M (–/CACTTACCTTCTTTGTGCCACAGTTTCCCTATCTAAAACAC AAGGTTATCAGTTATCAACATCTCTTGGGATTGTGAGGACTAAAGTAATGCACATAA AG), rs375115639 (–/AAATTACCCTGTTAGGTTTCAATGAAACACCTTTTCTCTTGTAACA AACATCTCCTCC AAGCTAGAATTTCAAAACAG), rs1002204 (A/C), rs10062367 (A/G), rs10482642 (A/G), rs10482658 (A/G), rs1053989 (A/C), rs10851628 (T/C), rs10947562 (T/C), rs11069612 (A/G), rs11071351 (T/C), rs11091175 (A/G), rs11638450 (T/C), rs11715827 (T/G), rs11745958 (T/C), rs11834041 (A/G), rs1202180 (T/C), rs12054781 (A/G), rs12539395 (A/G), rs12720066 (T/G), rs1279754 (A/C), rs12872047 (T/C), rs12876742 (A/C), rs12917505 (A/G), rs13066950 (T/G), rs13229143 (C/G), rs1383707 (T/C), rs1441824 (T/C), rs1652311 (A/G), rs17064 (T/A), rs17100236 (A/G), rs17149699 (A/G), rs1724386 (A/G), rs17250255 (A/G), rs17327624 (T/G), rs17616338 (A/G), rs17687796 (A/G), rs17740874 (T/C), rs17763104 (T/C), rs1880748 (T/C), rs1882478 (A/G), rs1944887 (T/C), rs2028629 (A/G), rs2143404 (A/G), rs2173530 (T/C), rs220806 (T/C), rs2235047 (A/C), rs2242071 (A/G), rs2257474 (T/C), rs2295583 (A/T), rs234629 (T/C), rs234630 (A/G), rs2436401 (A/G), rs258750 (T/C), rs2589487 (T/C), rs28364018 (T/G), rs28381774 (T/C), rs28381784 (A/G), rs2963155 (A/G), rs3133622 (T/G), rs32897 (T/C), rs33388 (A/T), rs3730168 (T/C), rs3735833 (T/G), rs3777747 (A/G), rs3786066 (T/C), rs3798346 (T/C), rs3822736 (A/G), rs389035 (T/C), rs3924144 (A/G), rs4148737 (T/C), rs4148749 (G/C), rs417968 (T/C), rs4458144 (T/C), rs4515335 (T/C), rs4728699 (A/G), rs4758040 (A/G), rs4812040 (A/G), rs4912650 (T/G), rs4957891 (T/C), rs5906392 (A/G), rs6026561 (T/C), rs6026565 (T/A), rs6026567 (A/G), rs6026593 (A/G), rs6092704 (T/G), rs6100260 (A/G), rs6128461 (T/C), rs6415328 (T/C), rs6610868 (T/C), rs6686061 (A/C), rs6730350 (T/G), rs6746197 (T/C), rs6963426 (T/C), rs7121326 (T/C), rs7721799 (A/G), rs7787082 (T/C), rs7799592 (A/C), rs796245 (T/C), rs809482 (A/C), rs8125112 (T/C), rs919196 (A/G), rs920750 (T/C), rs9332385 (A/G), rs930473 (T/G), rs9324921 (A/C), rs9348979 (A/G), rs9571939 (A/C), and rs9892359 (T/C); (b) at least one polymorphism genotype being in linkage disequilibrium with any one of the polymorphism genotypes of (a); or (c) a combination of (a) and (b); and predicting the treatment response from the presence or absence of the one or more polymorphism genotypes of (a), (b), or (c). In a preferred embodiment, the method for predicting a treatment response of a subject to treatment with a CRHR1 antagonist comprises: providing a biological sample obtained from the subject, and detecting the presence or absence of one or more polymorphism genotypes in the biological sample, wherein the one or more polymorphism genotypes comprise: (a) at least one polymorphism genotype selected from the group consisting of rs11715827 (T/G), rs2044070 (A/G), rs2028629 (A/G) and rs6026567 (A/G) as disclosed in Table 2, optionally (b) in combination with at least one polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2 and predicting the treatment response from the presence or absence of the one or more polymorphism genotypes of (a), optionally in combination with (b).

In another aspect, the invention provides a method for detecting a polymorphism genotype associated with a treatment response of a subject to treatment with a CRHR1 antagonist, the method comprising providing a biological sample obtained from the subject, and detecting the presence or absence of one or more polymorphism genotypes in the biological sample, wherein the one or more polymorphism genotypes comprise: (a) at least one polymorphism genotype selected from the group consisting of rs34169260 (A/G), rs796287 (A/C), rs56149945 (A/G), rs6190 (T/C), rs7179092 (T/C), rs7614867 (A/G), rs920640 (T/C), rs7167722 (T/C), rs920638 (T/C), rs7165629 (T/C), rs80049044 (T/A), rs16941058 (A/G), rs112015971 (A/G), rs10894873 (T/C), rs117455294 (T/G), rs1170303 (T/C), rs16940681 (C/G), rs968519 (T/C), rs28381866 (T/C), rs79320848 (T/G), rs114653646 (T/G), rs2589496 (T/C), rs10482650 (A/G), rs17614642 (A/G), rs73200317 (T/C), rs1380146 (T/A), rs735164 (T/C), rs730976 (T/G), rs55934524 (T/G), rs4570614 (A/G), rs4458044 (C/G), rs77850169 (A/G), rs35339359 (A/G), rs34800935 (T/C), rs72945439 (T/C), rs113959523 (A/G), rs116798177 (A/G), rs11247577 (T/G), rs75869266 (T/C), rs74372553 (T/C), rs11691508 (A/G), rs6493965 (A/G), rs4869476 (T/C), rs3730170 (T/C), rs2145288 (A/C), rs2935752 (A/C), (A/G), rs74338736 (A/C), rs10851726 (T/C), rs4610906 (T/C), rs59485211 (T/C), rs7060015 (T/G), rs75710780 (T/G), rs6520908 (T/C), rs487011 (T/G), rs1383699 (A/C), rs67516871 (A/G), rs114106519 (T/C), rs7220091 (A/G), rs12489026 (A/G), rs876270 (T/C), rs4968161 (T/C), rs62056907 (A/G), rs2235013 (T/C), rs16878812 (A/G), rs6549407 (A/G), rs28381848 (A/G), rs79723704 (A/C), rs72814052 (A/G), rs10152908 (T/C), rs172769 (A/C), rs78596668 (T/C), rs73307922 (T/C), rs3842 (A/G), rs7210584 (A/C), rs62402121 (T/C), rs55709291 (A/G), rs72747088 (A/G), rs929610 (G/C), rs6766242 (T/C), rs1468552 (G/C), rs78838114 (T/C), rs62489862 (T/C), rs894342 (A/G), rs58882373 (T/C), rs3811939 (A/G), rs6984688 (T/G), rs1018160 (T/C), rs76602912 (A/G), rs80067508 (A/G), rs74888440 (T/C), rs12481583 (T/C), rs66794218 (A/G), rs16946701 (A/G), rs75726724 (A/G), rs67959715 (T/A), rs11871392 (T/G), rs2044070 (A/G), rs77612799 (T/C), rs6743702 (T/C), rs616870 (T/C), rs79590198 (A/G), rs75715199 (A/G), rs13087555 (T/C), rs4869618 (T/C), rs117397046 (A/G), rs8042817 (A/G), rs2258097 (T/C), rs2260882 (C/G), rs532996 (A/G), rs11747040 (T/C), rs10034039 (T/G), rs116909369 (A/G), rs79134986 (A/G), rs117615688 (T/C), rs8032253 (T/C), rs12818653 (T/A), rs4587884 (A/C), rs77122853 (T/C), rs117615061 (T/C), rs74682905 (A/G), rs2257468 (T/C), rs2032582 (T/G), rs2235015 (T/G), rs2729794 (T/C), rs77549514 (A/G), rs74790420 (A/C), rs73129579 (T/C), rs12913346 (A/C), rs117560908 (T/C), rs72747091 (A/G), rs2935751 (A/G), rs4331446 (A/G), rs7523266 (T/C), rs7648662 (T/C), rs117034065 (A/G), rs4836256 (T/C), rs80238698 (T/C), rs3730173 (T/C), rs11687884 (T/C), rs72693005 (T/C), rs2589476 (T/C), rs9813396 (T/C), rs10482667 (A/G), rs72784444 (A/G), rs75074511 (T/C), rs7951003 (A/G), rs79584784 (A/G), rs2214102 (T/C), rs28811003 (A/G), rs6100261 (A/T), rs77152456 (A/G), rs66624622 (T/G), rs140302965 (A/G), rs11653269 (T/C), rs74405057 (A/G), rs7121 (A/G), rs16977818 (A/C), rs12490095 (T/C), rs118003903 (A/G), rs62377761 (T/C), P1_M_061510_6_34_M (–/CACTTACCTTCTTTGTGCCACAGTTTCCCTATCTAAAACACAAGGTTATCAGTTATC AACATCTCTTGGGATTGTGAGGACTAAAGTAATGCACATAAAG), rs 375115639 (–/AAATTACCCTGTTAGGTTTCAATGAAACACCTTTTCTCTTGTAACAAACATCTCCTC CA AGCTAGAATTTCAAAACAG), rs1002204 (A/C), rs10062367 (A/G), rs10482642 (A/G), rs10482658 (A/G), rs1053989 (A/C), rs10851628 (T/C), rs10947562 (T/C), rs11069612 (A/G), rs11071351 (T/C), rs11091175 (A/G), rs11638450 (T/C), rs11715827 (T/G), rs11745958 (T/C), rs11834041 (A/G), rs1202180 (T/C), rs12054781 (A/G), rs12539395 (A/G), rs12720066 (T/G), rs1279754 (A/C), rs12872047 (T/C), rs12876742 (A/C), rs12917505 (A/G), rs13066950 (T/G), rs13229143 (C/G), rs1383707 (T/C), rs1441824 (T/C), rs1652311 (A/G), rs17064 (T/A), rs17100236 (A/G), rs17149699 (A/G), rs1724386 (A/G), rs17250255 (A/G), rs17327624 (T/G), rs17616338 (A/G), rs17687796 (A/G), rs17740874 (T/C), rs17763104 (T/C), rs1880748 (T/C), rs1882478 (A/G), rs1944887 (T/C), rs2028629 (A/G), rs2143404 (A/G), rs2173530 (T/C), rs220806 (T/C), rs2235047 (A/C), rs2242071 (A/G), rs2257474 (T/C), rs2295583 (A/T), rs234629 (T/C), rs234630 (A/G), rs2436401 (A/G), rs258750 (T/C), rs2589487 (T/C), rs28364018 (T/G), rs28381774 (T/C), rs28381784 (A/G), rs2963155 (A/G), rs3133622 (T/G), rs32897 (T/C), rs33388 (A/T), rs3730168 (T/C), rs3735833 (T/G), rs3777747 (A/G), rs3786066 (T/C), rs3798346 (T/C), rs3822736 (A/G), rs389035 (T/C), rs3924144 (A/G), rs4148737 (T/C), rs4148749 (G/C), rs417968 (T/C), rs4458144 (T/C), rs4515335 (T/C), rs4728699 (A/G), rs4758040 (A/G), rs4812040 (A/G), rs4912650 (T/G), rs4957891 (T/C), rs5906392 (A/G), rs6026561 (T/C), rs6026565 (T/A), rs6026567 (A/G), rs6026593 (A/G), rs6092704 (T/G), rs6100260 (A/G), rs6128461 (T/C), rs6415328 (T/C), rs6610868 (T/C), rs6686061 (A/C), rs6730350 (T/G), rs6746197 (T/C), rs6963426 (T/C), rs7121326 (T/C), rs7721799 (A/G), rs7787082 (T/C), rs7799592 (A/C), rs796245 (T/C), rs809482 (A/C), rs8125112 (T/C), rs919196 (A/G), rs920750 (T/C), rs9332385 (A/G), rs930473 (T/G), rs9324921 (A/C), rs9348979 (A/G), rs9571939 (A/C), and rs9892359 (T/C); (b) at least one polymorphism genotype being in linkage disequilibrium with any one of the polymorphism genotypes of (a); or (c) a combination of (a) and (b). In one embodiment of this aspect, the method further comprises predicting the treatment response from the presence or absence of the polymorphism genotypes of (a), (b), or (c). In a preferred embodiment, the method of detecting a polymorphism genotype associated with a treatment response of a subject to treatment with a CRHR1 antagonist comprises providing a biological sample obtained from the subject, and detecting the presence or absence of one or more polymorphism genotypes in the biological sample, wherein the one or more polymorphism genotypes comprise: (a) at least one genotype selected from the group consisting of rs11715827 (T/G), rs2044070 (A/G), rs2028629 (A/G) and rs6026567 (A/G) as disclosed in Table 2, optionally (b) in combination with at least one polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2. In a further preferred embodiment, the method further comprises predicting the treatment response from the presence or absence of the polymorphism genotypes of (a), optionally in combination with (b).

In another aspect, the invention provides a method of treating a condition which is treatable by a CRHR1 antagonist in a subject in need thereof, comprising administering an effective amount of a CRHR1 antagonist to the subject, wherein the subject has been predicted to respond, or has an increased likelihood of responding, to treatment with a CRHR1 antagonist, as determined by the method of predicting a treatment response described above, wherein the CRHR1 antagonist is a compound of Formula I, as defined herein, or any one of "formulae I-VI" as disclosed at pages 2-6 and 12-48 of WO 2013/160317 (A2)(PCT/EP2013/058413). In another aspect, the invention provides a method of treating a condition which is treatable by a CRHR1 antagonist in a subject in need thereof, comprising administering an effective amount of a CRHR1 antagonist to the subject, wherein at least one polymorphism genotype associated with a treatment response of the subject to treatment with a CRHR1 antagonist has been detected, as determined by the method for detecting a polymorphism genotype associated with a treatment response, wherein the CRHR1 antagonist is a compound of Formula I, as defined herein, or any one of "formulae I-VI" as disclosed at pages 2-6 and 12-48 of WO 2013/160317 (A2) (PCT/EP2013/058413). Likewise, a CRHR1 antagonist for use in treating a condition which is treatable by a CRHR1 antagonist in a subject in need thereof is provided, wherein the subject has been predicted to respond, or has an increased likelihood of responding, to treatment with a CRHR1 antagonist, as determined by the method of predicting a treatment response described above, wherein the CRHR1 antagonist is a compound of Formula I, as defined herein, or any one of "formulae I-VI" as disclosed at pages 2-6 and 12-48 of WO 2013/160317 (A2) (PCT/EP2013/058413). In an alternative aspect, the invention provides a method of treating a condition which is treatable by a CRHR1 antagonist in a subject in need thereof, comprising administering an effective amount of a CRHR1 antagonist to the subject, wherein the subject has been predicted to respond, or has an increased likelihood of responding, to treatment with a CRHR1 antagonist, as determined by the method of predicting a treatment response described above, wherein the CRHR1 antagonist is selected from the group consisting of a Type I CRHR1 antagonist, a bicyclic Type II CRHR1 antagonist, an atypical CRHR1 antagonist, a cyclohexyl amide CRHR1 antagonist. In another aspect, the invention provides a method of treating a condition which is treatable by a CRHR1 antagonist in a subject in need thereof, comprising administering an effective amount of a CRHR1 antagonist to the subject, wherein at least one polymorphism genotype associated with a treatment response of the subject to treatment with a CRHR1 antagonist has been detected, as determined by the method for detecting a polymorphism genotype associated with a treatment response, wherein the CRHR1 antagonist is selected from the group consisting of a Type I CRHR1 antagonist, a bicyclic Type II CRHR1 antagonist, an atypical CRHR1 antagonist, a cyclohexyl amide CRHR1 antagonist. Likewise, a CRHR1 antagonist for use in treating a condition which is treatable by a CRHR1 antagonist in a subject in need thereof is provided, wherein the subject has been predicted to respond, or has an increased likelihood of responding, to treatment with a CRHR1 antagonist, as determined by the method of predicting a treatment response described above, wherein the CRHR1 antagonist is selected from the group consisting of a Type I CRHR1 antagonist, a bicyclic Type II CRHR1 antagonist, an atypical CRHR1 antagonist, a cyclohexyl amide CRHR1 antagonist. In embodiments, when a favorable treatment predictive response is determined based on a polymorphism(s) described herein, then the subject can be administered a dosage of treatment that is less than the amount of a dosage of treatment required by an individual not having the polymorphism(s).

The above aspects of the invention can be put into practice in any one of the following embodiments.

In one embodiment, providing a biological sample comprises extraction and/or purification of nucleic acids such as DNA or RNA, in particular genomic DNA from the subject's sample. In one embodiment, the detecting step can comprise amplification of nucleic acids extracted and/or purified from the sample obtained from the subject, and optionally clean-up of amplified products. The detecting step can further comprise fragmentation of amplified nucleic acids, or labelling of amplified nucleic acids.

In one embodiment, the detecting step can comprise specific hybridization of at least one polynucleotide to a nucleic acid comprising at least one polymorphism genotype selected from the group disclosed in Table 2 herein. Hybridization can be achieved by mixing and heating the at least one polynucleotide and the sample nucleic acid to a temperature at which denaturation occurs, e.g., at about 90-95° C. and subsequent incubation at a temperature at which hybridization occurs, e.g., at about 45-55° C. in buffer conditions suitable for specific hybridization. In one embodiment the polynucleotide is labelled. The polynucleotide can be a primer or probe. Specifically, in some embodiments, the detecting step comprises a method selected from the group consisting of allele-specific oligonucleotide (ASO)-dot blot analysis, primer extension assays, iPLEX polymorphism/SNP genotyping, dynamic allele-specific hybridization (DASH) genotyping, the use of molecular beacons, tetra primer ARMS PCR, a flap endonuclease invader assay, an oligonucleotide ligase assay, PCR-single strand conformation polymorphism (SSCP) analysis, quantitative real-time PCR assay, polymorphism/SNP microarray based analysis, restriction enzyme fragment length polymorphism (RFLP) analysis, targeted resequencing analysis and/or whole genome sequencing analysis.

In one embodiment, the predicting step comprises: (a) determining whether the subject will respond, or has an increased likelihood of responding to the treatment with a CRHR1 antagonist; and/or (b) determining whether the subject will not respond, or has a decreased likelihood of responding to the treatment with a CRHR1 antagonist. The determining step may further comprise, but is not limited to, one or more statistical analysis methods selected from the group consisting of artificial neural network learning, decision tree learning, decision tree forest learning, linear discriminant analysis, non-linear discriminant analysis, genetic expression programming, relevance vector machines, linear models, generalized linear models, generalized estimating equations, generalized linear mixed models, the elastic net, the lasso support vector machine learning. Bayesian network learning, probabilistic neural network learning, clustering, and regression analysis. The predicting step may also comprise providing a value indicative of the subject being responsive, or having an increased likelihood of responding to the treatment with a CRHR1 antagonist; and/or providing a value indicative of the subject being non-responsive, or having a decreased likelihood of responding to the treatment with a CRHR1 antagonist.

In one embodiment, the one or more polymorphism genotypes comprise at least two, at least three, at least four, at least five, at least six, at least seven, at least eight, at least nine, at least ten, at least 15, at least 19, at least 20, at least 30, at least 40, at least 50, at least 60, at least 70, at least 80, at least 90, at least 100, at least 200, or all (a) polymorphism genotypes selected from the group consisting of the polymorphism genotypes disclosed in Table 2, (b) polymorphism genotypes being in linkage disequilibrium with the polymorphism genotypes disclosed in Table 2; or (c) a combination of (a) and (b). In a further preferred embodiment, the one or more polymorphism genotypes comprise at least two, at least three, at least four or all polymorphism genotypes selected from the group consisting of rs11715827 (T/G), rs2044070 (A/G), rs2028629 (A/G) and rs6026567 (A/G) as disclosed in Table 2, optionally in combination with at least one, at least two, at least three, at least four, at least five, at least six, at least seven, at least eight, at least nine, at least ten, at least 11, at least 12, at least 13, at least 14, at least 15, polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2.

In a specific embodiment, the one or more polymorphism genotypes comprise (a) at least two polymorphism genotypes selected from the group consisting of the polymorphism genotypes disclosed in Table 2. (b) at least two polymorphism genotypes being in linkage disequilibrium with the polymorphism genotypes disclosed in Table 2; or (c) a combination of (a) and (b). Exemplary sets of at least two polymorphism genotypes useful in the methods of the invention are disclosed in Table 5. Therefore, the specific combinations of at least two polymorphism genotypes disclosed in Table 5 are used in specific embodiments of the invention, while further combinations of at least two polymorphism genotypes are expressly contemplated. Preferred combinations of at least two polymorphism genotypes are selected from the group of polymorphism genotypes selected from rs11715827 (T/G), rs2044070 (A/G), rs2028629 (A/G) and rs6026567 (A/G) as disclosed in Table 2, optionally in combination with at least one polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2.

In another specific embodiment, the one or more polymorphism genotypes comprise (a) at least four polymorphism genotypes selected from the group consisting of the polymorphism genotypes disclosed in Table 2, (b) at least four polymorphism genotypes being in linkage disequilibrium with the polymorphism genotypes disclosed in Table 2, or (c) a combination of (a) and (b). Exemplary sets of at least four polymorphism genotypes useful in the methods of the invention are disclosed in Table 6. Therefore, the specific combinations of at least four polymorphism genotypes disclosed in Table 6 are used in specific embodiments of the invention, while further combinations of at least four polymorphism genotypes are expressly contemplated. Preferred combinations of at least four polymorphism genotypes are selected from the group of polymorphism genotypes selected from rs11715827 (T/G), rs2044070 (A/G), rs2028629 (A/G) and rs6026567 (A/G) as disclosed in Table 2, optionally in combination with at least one polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2.

In another specific embodiment, the one or more polymorphism genotypes comprise (a) at least eight polymorphism genotypes selected from the group consisting of the polymorphism genotypes disclosed in Table 2. (b) at least eight polymorphism genotypes being in linkage disequilibrium with the polymorphism genotypes disclosed in Table 2, or (c) a combination of (a) and (b). Exemplary sets of at least eight polymorphism genotypes useful in the methods of the invention are shown in Table 7. Therefore, the specific combinations of at least eight polymorphism genotypes disclosed in Table 7 are used in specific embodiments of the invention, while further combinations are expressly contemplated. Preferred combinations of at least eight polymorphism genotypes are selected from the group of polymorphism genotypes selected from rs11715827 (T/G), rs2044070 (A/G), rs2028629 (A/G) and rs6026567 (A/G) as disclosed in Table 2, in combination with at least four polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2.

In another embodiment, the one or more polymorphism genotypes comprise (a) at least 16 polymorphism genotypes selected from the group consisting of the polymorphism genotypes disclosed in Table 2, (b) at least 16 polymorphism genotypes being in linkage disequilibrium with the polymorphism genotypes disclosed in Table 2, or (c) a combination of (a) and (b). Preferred combinations of at least 16 polymorphism genotypes are selected from the group of polymorphism genotypes selected from rs11715827 (T/G), rs2044070 (A/G), rs2028629 (A/G) and rs6026567 (A/G) as disclosed in Table 2, in combination with at least 12 polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2. In another embodiment, the one or more polymorphism genotypes comprise (a) at least 32 polymorphism genotypes selected from the group consisting of the polymorphism genotypes disclosed in Table 2. (b) at least 16 polymorphism genotypes being in linkage disequilibrium with the polymorphism genotypes disclosed in Table 2, or (c) a combination of (a) and (b). In another embodiment, the one or more polymorphism genotypes comprise at least 150 polymorphism genotypes selected from the group consisting of the polymorphism genotypes disclosed in Table 2. (b) at least 16 polymorphism genotypes being in linkage disequilibrium with the polymorphism genotypes disclosed in Table 2, or (c) a combination of (a) and (b). In another embodiment, the one or more polymorphism genotypes comprise all polymorphism genotypes disclosed in Table 2.

In some embodiments, the method can include detecting the presence or absence of (a) one or more of the polymorphism genotypes disclosed in Tables 2, 5, 6, or 7. (b) one or more polymorphism genotypes being in linkage disequilibrium with the polymorphism genotypes disclosed in Tables 2, 5, 6, or 7, or (c) a combination of (a) and (b), predicting that the subject will respond, or is likely to respond to treatment with a CRHR1 antagonist and selecting a treatment with a CRHR1 agent for the subject. The method can further include administering the CRHR1 antagonist to the subject. In the preferred embodiment of the invention, the method can include detecting the presence or absence of (a) one or more of the polymorphism genotypes selected from the group consisting in rs2028629 (A/G), rs6026567 (A/G), rs11715827 (T/G) and rs2044070 (A/G) as disclosed in Table 2, optionally (b) in combination with at least one of the polymorphism genotypes selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2, predicting that the subject will respond, or is likely to respond to treatment with a CRHR1 antagonist and selecting a treatment with a CRHR1 agent for the subject. The method can further include administering the CRHR1 antagonist to the subject.

In some embodiments, the predicting step can include creating a record indicating that the subject will respond, or is likely to respond to treatment with a CRHR1 antagonist. The record can be created on a computer readable medium.

In some embodiments, the method can include detecting the presence or absence of (a) one or more of any of the polymorphism genotypes disclosed in Tables 2, 5, 6 or 7, (b) one or more polymorphism genotypes being in linkage disequilibrium with the polymorphism genotypes disclosed in Tables 2, 5, 6, or 7, or (c) a combination of (a) and (b), predicting that the subject will not respond, or is not likely to respond to a treatment with a CRHR1 antagonist and selecting a treatment with treatment with a non-CRHR1 antagonist for the subject. The method can further include administering the treatment with the non-CRHR1 antagonist to the subject. In the preferred embodiment of the invention, the method can include detecting the presence or absence of (a) one or more of the polymorphism genotypes selected from the group consisting in rs2028629 (A/G), rs6026567 (A/G), rs11715827 (T/G) and rs2044070 (A/G) as disclosed in Table 2, optionally (b) in combination with at least one of the polymorphism genotypes selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2, predicting that the subject will not respond, or is not likely to respond to treatment with a CRHR1 antagonist and selecting a treatment with treatment with a non-CRHR1 antagonist for the subject. The method can further include administering the treatment with the non-CRHR1 antagonist to the subject.

In some embodiments, the method can include creating a record indicating that the subject will not respond, or is not likely to respond to a treatment with a CRHR1 antagonist. The record can be created on a computer readable medium.

In one embodiment, the subject is a mammal. Preferably, in all aspects of the invention, the subject is human.

In one embodiment, the subject has a condition which is treatable by a treatment with a CRHR1 antagonist, as described herein. The condition can be characterized, caused or accompanied by CRH overproduction or over-activity. The condition can be characterized, caused or accompanied by ACTH overproduction or over-activity. The condition can be characterized, caused or accompanied by over-activity of the Hypothalamic-pituitary-adrenal (HPA) axis.

In another embodiment, the subject has and/or the treatment is a treatment of a condition selected from the group consisting of anxiety symptoms, generalized anxiety disorder, panic, phobias, obsessive-compulsive disorder, post-traumatic stress disorder, sleep disorders such as insomnia, hypersomnia, narcolepsy, idiopathic hypersomnia, excessive amounts of sleepiness, lack of alertness, lack of attentiveness, absentmindedness and/or lack of or aversion to movement or exercise, sleep disorders induced by stress, pain perception such as fibromyalgia, mood disorders such as depressive symptoms, including major depression, single episode depression, recurrent depression, child abuse induced depression, mood disorders associated with premenstrual syndrome, and postpartum depression, dysthymia, bipolar disorders, cyclothymia, chronic fatigue syndrome, stress-induced headache, eating disorders such as anorexia and bulimia nervosa, hemorrhagic stress, stress-induced psychotic episodes, endocrine disorders involving ACTH overproduction, ACTH over-activity, e.g., adrenal disorders, including, but not limited to congenital adrenal hyperplasia (CAH), euthyroid sick syndrome, syndrome of inappropriate antidiarrheic hormone (ADH), obesity, infertility, head traumas, spinal cord trauma, ischemic neuronal damage (e.g., cerebral ischemia such as cerebral hippocampal ischemia), excitotoxic neuronal damage, epilepsy, senile dementia of the Alzheimers type, multi-infarct dementia, amyotrophic lateral sclerosis, chemical dependencies and addictions (e.g., dependencies on alcohol, nicotine, cocaine, heroin, benzodiazepines, or other drugs), drug and alcohol withdrawal symptoms, hypertension, tachycardia, congestive heart failure, osteoporosis, premature birth, and hypoglycaemia, inflammatory disorders such as rheumatoid arthritis and osteoarthritis, pain, asthma, psoriasis and allergies, irritable bowel syndrome, Crohn's disease, spastic colon, post-operative ileus, ulcer, diarrhea, stress-induced fever, human immunodeficiency virus (HIV) infections, neurodegenerative diseases such as Alzheimer's disease, Parkinson's disease and Huntington's disease, gastrointestinal diseases, stroke, stress induced immune dysfunctions, muscular spasms, urinary incontinence.

In a specific embodiment, the subject has and/or the treatment is a treatment of depressive symptoms, anxiety symptoms or both depressive symptoms and anxiety symptoms. In another specific embodiment, the subject has and/or the treatment is a treatment of depressive disorder, anxiety disorder or both depressive disorder and anxiety disorder. In another specific embodiment, the subject has and/or the treatment is a treatment of a sleep disorder.

In contrast to the prior art, the present invention identifies sets of polymorphisms indicative of a clinical response in subjects which are in need of a treatment with a CRHR1 antagonist. Therefore, in all aspects of the invention, the treatment response to treatment with the CRHR1 antagonist is preferably a clinical response. Generally, the clinical response can be a prevention, alteration, alleviation or complete remission of a clinical parameter in any of the above conditions. In particular, the clinical response can be a prevention, alteration, alleviation or complete remission of depressive symptoms and/or anxiety symptoms, or a decrease in adverse effects resulting from the treatment.

In some embodiments, the clinical response is a prevention, alteration, alleviation or complete remission of depressive symptoms, as determined using a scale selected from the group consisting of the Hamilton Depression Rating Scale (HAM-D), the Beck Depression Inventory (BDI), the Montgomery-Asberg Depression Scale (MADRS), the Geriatric Depression Scale (GDS), and/or the Zung Self-Rating Depression Scale (ZSRDS).

In some embodiments, the clinical response is a prevention, alteration, alleviation or complete remission of anxiety symptoms, as determined using a scale selected from the group consisting of Hamilton Anxiety Rating Scale (HAM-A) and/or the State-Trait Anxiety Rating Scale (STAI).

Any of the methods described herein can further include a step of prescribing a treatment with a CRHR1 antagonist or non-CRHR1 antagonist (the choice of which depends upon the outcome of the predictive methods described herein) for the subject.

In all aspects, the sample obtained from the subject can comprise any type of cells containing nucleic acids from the subject, in particular genomic DNA. Specifically, the sample can be, e.g., a buccal sample, a blood sample, a tissue sample, a formalin-fixed, paraffin-embedded tissue sample, or a hair follicle. The sample obtained from the subject can comprise purified nucleic acids, such as purified genomic DNA.

In any of the above aspects, a CRHR1 antagonist can be any compound capable of binding directly or indirectly to a CRHR1 so as to modulate any of its known biological activity receptor mediated activity, as is commonly known in the art. For instance, CRHR1 antagonists will specifically bind to CRHR1 with a $K_D$ of 1 μM or less, preferably with a $K_D$ of 100 nM or less and/or specifically inhibit CRH binding to CRHR1 in vitro with $K_i$ values of 1 μM or less, preferably with $K_i$ values of 100 nM or less. Alternatively or in addition, a CRHR1 antagonist will also inhibit cAMP accumulation and adrenocorticotropic hormone (ACTH) production in vitro and/or attenuate CRH and ACTH production in vivo.

In some embodiments of any of the above aspects, the CRHR1 antagonist can be a compound of Formula (I)

(I)

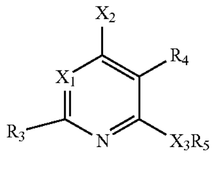

or a pharmaceutically acceptable salt thereof, wherein $X_1$ is —$CR_6$ or N;

$X_2$ is —$NR_1R_2$, —$CR_1R_2R_9$, —$C(=CR_2R_{10})R_1$, —$NHCHR_1R_2$, —$OCHR_1R_2$, —$SCHR_1R_2$, —$CHR_2OR_{10}$, —$CHR_2SR_{10}$, —$C(S)R_2$ or —$C(O)R_2$;

$X_3$ is NH, O, S, —N($C_1$-$C_2$ alkyl) or —$C(R_{11}R_{12})$, wherein $R_{11}$ and $R_{12}$ are each, independently, hydrogen, trifluoromethyl or methyl, or one of $R_{11}$ and $R_{12}$ is cyano and the other is hydrogen or methyl, or $X_3$ is N and $X_3$ and $R_4$ form a 5-membered ring substituted at $X_3$ with $R_5$;

$R_1$ is $C_1$-$C_6$ alkyl which may optionally be substituted with one or two substituents $R_7$ independently selected from the group consisting of hydroxy, fluoro, chloro, bromo, iodo, $CF_3$, $C_3$-$C_8$ cycloalkyl, $C_1$-$C_4$ alkoxy, —O—CO—($C_1$-$C_4$ alkyl), —O—CO—NH($C_1$-$C_4$ alkyl), —O—CO—N($C_1$-$C_4$ alkyl)($C_1$-$C_2$ alkyl), —NH($C_1$-$C_4$ alkyl), —N($C_1$-$C_2$ alkyl)($C_1$-$C_4$ alkyl), —S($C_1$-$C_4$ alkyl), —N($C_1$-$C_4$ alkyl)CO($C_1$-$C_4$ alkyl), —NHCO($C_1$-$C_4$ alkyl), —COO($C_1$-$C_4$ alkyl), —CONH($C_1$-$C_4$ alkyl), —CON($C_1$-$C_4$ alkyl)($C_1$-$C_2$ alkyl), CN, $NO_2$, —SO($C_1$-$C_4$ alkyl) and —$SO_2$ ($C_1$-$C_4$ alkyl), and wherein said $C_1$-$C_6$ alkyl and the ($C_1$-$C_4$) alkyl moieties in the foregoing $R_7$ groups may optionally contain one carbon-carbon double or triple bond;

$R_2$ is $C_1$-$C_{12}$ alkyl, $C_1$-$C_{12}$ alkoxyalkyl, aryl or —($C_1$-$C_4$ alkylene) aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, oxadiazolyl or benzoxazolyl; 3- to 8-membered cycloalkyl or —($C_1$-$C_6$ alkylene) cycloalkyl, wherein one or two of the ring carbons of said cycloalkyl having at least 4 ring members and the cycloalkyl moiety of said —($C_1$-$C_6$ alkylene)cycloalkyl having at least 4 ring members may optionally be replaced by an oxygen or sulfur atom or by N—$R_8$ wherein $R_8$ is hydrogen or $C_1$-$C_4$ alkyl; and wherein each of the foregoing $R_2$ groups may optionally be substituted with from one to three substituents independently selected from chloro, fluoro and $C_1$-$C_4$ alkyl, or with one substituent selected from bromo, iodo, $C_1$-$C_6$ alkoxy, —O—CO—($C_1$-$C_6$ alkyl), —O—CO—N($C_1$-$C_4$ alkyl)($C_1$-$C_2$ alkyl), —S($C_1$-$C_6$ alkyl), CN, $NO_2$, —SO($C_1$-$C_4$ alkyl), and —$SO_2$ ($C_1$-$C_4$ alkyl), and wherein said $C_1$-$C_{12}$ alkyl and/or the $C_1$-$C_4$ alkylene moiety of said —($C_1$-$C_4$ alkylene) aryl may optionally contain one carbon-carbon double or triple bond;

or —$NR_1R_2$ or —$CR_1R_2R_9$ may form a saturated 5- to 8-membered ring which may optionally contain one or two carbon-carbon double bonds and/or in which one or two of the ring carbons may optionally be replaced by an oxygen, nitrogen or sulfur atom and which may be substituted with at least one substituent;

$R_3$ is methyl, ethyl, fluoro, chloro, bromo, iodo, cyano, methoxy, $OCF_3$, methylthio, methylsulfonyl, $CH_2OH$, or $CH_2OCH_3$;

$R_4$ is hydrogen, $C_1$-$C_4$ alkyl, fluoro, chloro, bromo, iodo, $C_1$-$C_4$ alkoxy, trifluoromethoxy, —$CH_2OCH_3$, —$CH_2OCH_2CH_3$, —$CH_2CH_2OCH_3$, —$CH_2OCF_3$, $CF_3$, amino, nitro, —NH($C_1$-$C_4$ alkyl), —$N(CH_3)_2$, —$NHCOCH_3$—$NHCONHCH_3$, —$SO_n$($C_1$-$C_4$ alkyl) wherein n is 0, 1 or 2, hydroxy, —CO($C_1$-$C_4$ alkyl), —CHO, cyano or —COO($C_1$-$C_4$ alkyl) wherein said $C_1$-$C_4$ alkyl may optionally contain one double or triple bond and/or may optionally be substituted with one substituent selected from hydroxy, amino, —$NHCOCH_3$, —NH($C_1$-$C_2$ alkyl), —N($C_1$-$C_2$ alkyl)$_2$, —COO($C_1$-$C_4$ alkyl), —CO($C_1$-$C_4$ alkyl), $C_1$-$C_3$ alkoxy, $C_1$-$C_3$ thioalkyl, fluoro, chloro, cyano and nitro;

$R_5$ is phenyl, naphthyl, thienyl, benzothienyl, pyridyl, quinolyl, pyrazinyl, pyrimidyl, furanyl, benzofuranyl, benzothiazolyl, or indolyl, wherein each of the above groups $R_5$ is substituted with from one to three substituents independently selected from fluoro, chloro, $C_1$-$C_6$ alkyl and $C_1$-$C_6$ alkoxy, or with one substituent selected from hydroxy, iodo, bromo, formyl, cyano, nitro, trifluoromethyl, amino, ($C_1$-$C_6$ alkyl)O($C_1$-$C_6$) alkyl, —$NHCH_3$, —$N(CH_3)_2$, —COOH, —COO($C_1$-$C_4$ alkyl), —CO($C_1$-$C_4$ alkyl), —$SO_2$NH($C_1$-$C_4$ alkyl), —$SO_2$N($C_1$-$C_4$ alkyl)($C_1$-$C_2$ alkyl), —$SO_2NH_2$, —$NHSO_2$ ($C_1$-$C_4$ alkyl), —S($C_1$-$C_6$ alkyl) and $SO_2$ ($C_1$-$C_6$ alkyl), and wherein the $C_1$-$C_4$ alkyl and the $C_1$-$C_6$ alkyl moieties of the foregoing $R_5$ groups may optionally be substituted with one or two fluoro groups or with one substituent selected from hydroxy, amino, methylamino, dimethylamino and acetyl;

$R_6$ is hydrogen, methyl, fluoro, chloro, bromo, iodo, cyano, hydroxy, —O($C_1$-$C_4$ alkyl), —C(O)($C_1$-$C_4$ alkyl), —C(O)O($C_1$-$C_4$ alkyl), —$OCF_3$, $CF_3$, —$CH_2OH$, —$CH_2OCH_3$ or —$CH_2OCH_2CH_3$;

$R_9$ is hydrogen, hydroxy, fluoro, or methoxy;

$R_{10}$ is hydrogen or $C_1$-$C_4$ alkyl.

Further, CRHR1 antagonists can encompass compounds of Formula (I) as defined above, wherein $X_1$ is —$CR_6$. Optionally, $X_1$ is —$CR_6$, wherein $R_6$ is hydrogen.

In a further embodiment, the 5- to 8-membered ring formed by —$NR_1R_2$ or —$CR_1R_2R_9$ of the compound of Formula (I) as defined above is substituted with at least one substituent selected from $C_1$-$C_4$ alkyl or with a 4-8 membered ring, which may be saturated or may contain one to three double bonds and in which one carbon atom may be replaced by CO or $SO_2$ and one to four carbon atoms may optionally be replaced by nitrogen.

In a specific embodiment, $X_2$ of the compound of Formula (I) as defined above is —$NHCHR_1R_2$, —$OCHR_1R_2$ or —$NR_1R_2$.

Optionally, in the compounds of Formula (I) as defined above-$NHCHR_1R_2$ is-$NHCH(CH_2OCH_3)_2$, —$NHCH(CH_2OCH_3)(CH_2CH_3)$, —$NHCH(CH_2CH_3)_2$, $NHCH(CH_2CH_2OCH_3)_2$ or —$NHCHR_1R_2$, wherein $R_1$ is ethyl and $R_2$ is oxadiazolyl substituted with methyl, or —$NR_1R_2$ is —$N(CH_2CH_3)(CH_3)$, —$N(CH_2CH_2CH_3)_2$, —$N(CH_2CH_2CH_3)(CH_2$-cyclopropyl), —$N(CH_2CH_3)(CH_2CH_2CH_2CH_3)$, —$N(CH_2CH_2OCH_3)_2$, or —$N(CH_2CH_2OCH_3)(CH_2CH_2CH_3)$, or —$OCHR_1R_2$ is —$OCH(CH_2CH_3)_2$, —$OCH(CH_2CH_3)$ $CH_3$, —$OCH(CH_2CH_3)(CH_2CH_2CH_3)$, —$OCH(CH_2CH_3)(CH_2OCH_3)$.

In another embodiment, $R_3$ and $R_4$ of the compound of Formula (I) as defined above are methyl.

In a further embodiment, $X_3$ of the compound of Formula (I) as defined above is O.

In another embodiment, $R_5$ of the compound of Formula (I) as defined above is phenyl substituted with from one to three substituent(s) independently selected from the group $CH_3$, $CH_2CH_3$, $OCH_3$, Cl, F, $CF_3$.

In a specific embodiment of any of the above aspects, the CRHR1 antagonist is a compound of the Formula (VI)

(VI)

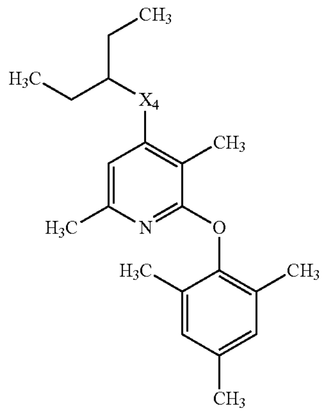

or a pharmaceutically acceptable salt thereof, wherein $X_4$ is O or NH.

In some embodiments of the methods of predicting, or the methods of detecting as described herein, the CRHR1 antagonist is a compound of Formulae I or VI, as defined above, or any one of "formulae I-VI" as disclosed at pages 2-6 and 12-48 of WO 2013/160317 (A2) (PCT/EP2013/058413) or a pharmaceutically acceptable salt thereof.

In alternative embodiments of the methods of predicting, or the methods of detecting as described herein, the CRHR1 antagonist is selected from the group consisting of GW876008 (Emicerfont), GSK-561679 (NBI-77860, Verucerfont), GSK586529, BMS-562,086 (Pexacerfont), NBI-30775 (R-121919), NBI-34101, CP-316,311, CP-376,395, PF-00572778, NVP-AAG561, Ono-2333 MS, E2508, E2009, R317573 (JNJ19567470, CRA5626), R278995 (CRA0450), CRA-1000, CRA-1001, CP154,526, Antalarmin, DMP-695, DMP-696, DMP-904, SC-241, BMS-561388, NBI30545, PD-171729, NBI34041, NBI35965, SN003, NBI-27914, trans-2-chloro-N-(4-((5-fluoro-4-methyl-pyridin-2-ylamino)-methyl)-cyclohexyl)-5-(trifluoromethyl)-benzamide, SSR-125543, or a pharmaceutically acceptable salt thereof.

In preferred embodiments of the methods of predicting, or the methods of detecting, as described herein, the CRHR1 antagonist is selected from the group consisting of BMS-562,086 (Pexacerfont), CP-316,311, Ono-2333 MS, GW876008 (Emicerfont), GSK-561679 (NBI-77860, Verucerfont), NBI-30775 (R-121919), DMP-696, and SSR-125543, or a pharmaceutically acceptable salt thereof. In preferred embodiments of the methods of predicting, or the methods of detecting, as described herein, the CRHR1 antagonist is SSR-125543. In one embodiment of the method of treatment, the CRHR1 antagonist is not SSR-125543. In a preferred embodiment of all aspects, the CRHR1 antagonist is BMS-562,086 (Pexacerfont). In another preferred embodiment of all aspects, the CRHR1 antagonist is CP-316,311. In another preferred embodiment of all aspects, the CRHR1 antagonist is ONO-2333 MS. In another preferred embodiment of all aspects, the CRHR1 antagonist is GW876008 (Emicerfont). In another preferred embodiment of all aspects, the CRHR1 antagonist is GSK-561679 (Verucerfont). In another preferred embodiment of all aspects, the CRHR1 antagonist is NBI-30775 (R121919). In another preferred embodiment of all aspects, the CRHR1 antagonist is DMP-696.

In another aspect, the disclosure provides a composition comprising at least one polynucleotide capable of specifically hybridizing to nucleic acids comprising: (a) at least one polymorphism genotype selected from the group consisting of rs34169260 (A/G), rs796287 (A/C), rs56149945 (A/G), rs6190 (T/C), rs7179092 (T/C), rs7614867 (A/G), rs920640 (T/C), rs7167722 (T/C), rs920638 (T/C), rs7165629 (T/C), rs80049044 (T/A), rs16941058 (A/G), rs112015971 (A/G), rs10894873 (T/C), rs117455294 (T/G), rs1170303 (T/C), rs16940681 (C/G), rs968519 (T/C), rs28381866 (T/C), rs79320848 (T/G), rs114653646 (T/G), rs2589496 (T/C), rs10482650 (A/G), rs17614642 (A/G), rs73200317 (T/C), rs1380146 (T/A), rs735164 (T/C), rs730976 (T/G), rs55934524 (T/G), rs4570614 (A/G), rs4458044 (C/G), rs77850169 (A/G), rs35339359 (A/G), rs34800935 (T/C), rs72945439 (T/C), rs113959523 (A/G), rs116798177 (A/G), rs11247577 (T/G), rs75869266 (T/C), rs74372553 (T/C), rs11691508 (A/G), rs6493965 (A/G), rs4869476 (T/C), rs3730170 (T/C), rs2145288 (A/C), rs2935752 (A/C), (A/G), rs74338736 (A/C), rs10851726 (T/C), rs4610906 (T/C), rs59485211 (T/C), rs7060015 (T/G), rs75710780 (T/G), rs6520908 (T/C), rs487011 (T/G), rs1383699 (A/C), rs67516871 (A/G), rs114106519 (T/C), rs7220091 (A/G), rs12489026 (A/G), rs876270 (T/C), rs4968161 (T/C), rs62056907 (A/G), rs2235013 (T/C), rs16878812 (A/G), rs6549407 (A/G), rs28381848 (A/G), rs79723704 (A/C), rs72814052 (A/G), rs10152908 (T/C), rs172769 (A/C), rs78596668 (T/C), rs73307922 (T/C), rs3842 (A/G), rs7210584 (A/C), rs62402121 (T/C), rs55709291 (A/G), rs72747088 (A/G), rs929610 (G/C), rs6766242 (T/C), rs1468552 (G/C), rs78838114 (T/C), rs62489862 (T/C), rs894342 (A/G), rs58882373 (T/C), rs3811939 (A/G), rs6984688 (T/G), rs1018160 (T/C), rs76602912 (A/G), rs80067508 (A/G), rs74888440 (T/C), rs12481583 (T/C), rs66794218 (A/G), rs16946701 (A/G), rs75726724 (A/G), rs67959715 (T/A), rs11871392 (T/G), rs2044070 (A/G), rs77612799 (T/C), rs6743702 (T/C), rs616870 (T/C), rs79590198 (A/G), rs75715199 (A/G), rs13087555 (T/C), rs4869618 (T/C), rs117397046 (A/G), rs8042817 (A/G), rs2258097 (T/C), rs2260882 (C/G), rs532996 (A/G), rs11747040 (T/C), rs10034039 (T/G), rs116909369 (A/G), rs79134986 (A/G), rs117615688 (T/C), rs8032253 (T/C), rs12818653 (T/A), rs4587884 (A/C), rs77122853 (T/C), rs117615061 (T/C), rs74682905 (A/G), rs2257468 (T/C), rs2032582 (T/G), rs2235015 (T/G), rs2729794 (T/C), rs77549514 (A/G), rs74790420 (A/C), rs73129579 (T/C), rs12913346 (A/C), rs117560908 (T/C), rs72747091 (A/G), rs2935751 (A/G), rs4331446 (A/G), rs7523266 (T/C), rs7648662 (T/C), rs117034065 (A/G), rs4836256 (T/C), rs80238698 (T/C), rs3730173 (T/C), rs11687884 (T/C), rs72693005 (T/C), rs2589476 (T/C), rs9813396 (T/C), rs10482667 (A/G), rs72784444 (A/G), rs75074511 (T/C), rs7951003 (A/G), rs79584784 (A/G), rs2214102 (T/C), rs28811003 (A/G), rs6100261 (A/T), rs77152456 (A/G), rs66624622 (T/G), rs140302965 (A/G), rs11653269 (T/C), rs74405057 (A/G), rs7121 (A/G), rs16977818 (A/C), rs12490095 (T/C), rs118003903 (A/G), rs62377761 (T/C), P1_M_061510_6_34_M (–/CACTTAC CTTCTTTGTGC-CACAGTTTCCCTATCTAAAACACAAGGTTATCAGT-TATCAACATCTC TTGGGATTGTGAGGACTAAAG-TAATGCACATAAAG), rs375115639 (–/AAAT-TACCCTGTTAGGTTTCAATGAAACACCTTTTCT-CTTGTAACAAACATCTCC TCCAAGCTAGAATTT-CAAAACAG), rs1002204 (A/C), rs10062367 (A/G), rs10482642 (A/G), rs10482658 (A/G), rs1053989 (A/C), rs10851628 (T/C), rs10947562 (T/C), rs11069612 (A/G), rs11071351 (T/C), rs11091175 (A/G), rs11638450 (T/C), rs11715827 (T/G), rs11745958 (T/C), rs11834041 (A/G), rs1202180 (T/C), rs12054781 (A/G), rs12539395 (A/G), rs12720066 (T/G), rs1279754 (A/C), rs12872047 (T/C), rs12876742 (A/C), rs12917505 (A/G), rs13066950 (T/G), rs13229143 (C/G), rs1383707 (T/C), rs1441824 (T/C), rs1652311 (A/G), rs17064 (T/A), rs17100236 (A/G), rs17149699 (A/G), rs1724386 (A/G), rs17250255 (A/G), rs17327624 (T/G), rs17616338 (A/G), rs17687796 (A/G), rs17740874 (T/C), rs17763104 (T/C), rs1880748 (T/C), rs1882478 (A/G), rs1944887 (T/C), rs2028629 (A/G), rs2143404 (A/G), rs2173530 (T/C), rs220806 (T/C), rs2235047 (A/C), rs2242071 (A/G), rs2257474 (T/C), rs2295583 (A/T), rs234629 (T/C), rs234630 (A/G), rs2436401 (A/G), rs258750 (T/C), rs2589487 (T/C), rs28364018 (T/G), rs28381774 (T/C), rs28381784 (A/G), rs2963155 (A/G), rs3133622 (T/G), rs32897 (T/C), rs33388 (A/T), rs3730168 (T/C), rs3735833 (T/G), rs3777747 (A/G), rs3786066 (T/C), rs3798346 (T/C), rs3822736 (A/G), rs389035 (T/C), rs3924144 (A/G), rs4148737 (T/C), rs4148749 (G/C), rs417968 (T/C), rs4458144 (T/C), rs4515335 (T/C), rs4728699 (A/G), rs4758040 (A/G), rs4812040 (A/G), rs4912650 (T/G), rs4957891 (T/C), rs5906392 (A/G), rs6026561 (T/C), rs6026565 (T/A), rs6026567 (A/G), rs6026593 (A/G), rs6092704 (T/G), rs6100260 (A/G), rs6128461 (T/C), rs6415328 (T/C), rs6610868 (T/C), rs6686061 (A/C), rs6730350 (T/G), rs6746197 (T/C), rs6963426 (T/C), rs7121326 (T/C), rs7721799 (A/G), rs7787082 (T/C), rs7799592 (A/C), rs796245 (T/C), rs809482 (A/C), rs8125112 (T/C), rs919196 (A/G), rs920750 (T/C), rs9332385 (A/G), rs930473 (T/G), rs9324921 (A/C), rs9348979 (A/G), rs9571939 (A/C), and rs9892359 (T/C), as disclosed in Table 2; (b) at least one polymorphism genotype being in linkage disequilibrium with any one of the polymorphism genotypes of (a), or (c) a combination of (a) and (b). In a preferred aspect, the disclosure provides a composition comprising at least one polynucleotide capable of specifically hybridizing to nucleic acids comprising: (a) at least one polymorphism genotype selected from the group consisting of rs11715827 (T/G), rs2044070 (A/G), rs2028629 (A/G) and rs6026567 (A/G) as disclosed in Table 2, optionally (b) in combination with at least one polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2. In one embodiment, the composition comprises less than 100,000, less than 90,000, less than 80,000, less than 70,000, less than 60,000, less than 50,000, less than 40,000, less than 30,000, less than 20,000, less than 15,000, less than 10,000, less than 5,000, less than 4,000, less than 3,000, less than 2,000, less than 1,500, less than 1,000, less than 750, less than 500, less than 200, less than 100, or less than 50 different polynucleotides in total. In some embodiments, the composition comprises at least two, at least three, at least four, at least five, at least six, at least seven, at least eight, at least nine, at least 10, at least 11, at least 12, at least 15, at least 19, at least 20, or at least 30, or at least 50, or at least 100, or at least 200, or 274 polynucleotides capable of specifically hybridizing to nucleic acids comprising each of at least two, at least three, at least four, at least five, at least six, at least seven, at least eight, at least nine, at least 10, at least 11, at least 12, at least 15, at least 19, at least 20, or at least 30, or at least 50, or at least 100, or at least 200, or 274 (a) polymorphism genotypes as disclosed in Table 2, preferably one or more polymorphism genotypes selected from the group consisting of rs11715827 (T/G), rs2044070 (A/G), rs2028629 (A/G) and rs6026567 (A/G) as disclosed in Table 2, optionally in combination with one or more polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2. (b) polymorphism genotypes being in linkage disequilibrium with any one of the polymorphism genotypes of (a), or (c) a combination of (a) and (b).

In a specific embodiment, the disclosure provides a composition containing at least two polynucleotides capable of specifically hybridizing to nucleic acids comprising (a) each of at least two polymorphism genotypes selected from the group consisting of the polymorphism genotypes as disclosed in Table 2, preferably one or more polymorphism genotypes selected from the group consisting of rs11715827 (T/G), rs2044070 (A/G), rs2028629 (A/G) and rs6026567 (A/G) as disclosed in Table 2, optionally in combination with one or more polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2, (b) each of at least two polymorphism genotypes being in linkage disequilibrium with any one of the polymorphism genotypes of (a), or (c) a combination of (a) and (b). In another specific embodiment, the disclosure provides a composition containing at least four polynucleotides capable of specifically hybridizing to (a) each of at least four polymorphism genotypes selected from the group consisting of the polymorphism genotypes as disclosed in Table 2, preferably one or more polymorphism genotypes selected from the group consisting of rs11715827 (T/G), rs2044070 (A/G), rs2028629 (A/G) and rs6026567 (A/G) as disclosed in Table 2, optionally in combination with one or more polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2, (b) each of at least four polymorphism genotypes being in linkage disequilibrium with any one of the polymorphism genotypes of (a), or (c) a combination of (a) and (b). In another specific embodiment, the disclosure provides a composition containing at least eight polynucleotides capable of specifically hybridizing to (a) each of at least eight polymorphism genotypes selected from the group consisting of the polymorphism genotypes as disclosed in Table 2, preferably one or more polymorphism genotypes selected from the group consisting of rs11715827 (T/G), rs2044070 (A/G), rs2028629 (A/G) and rs6026567 (A/G) as disclosed in Table 2, optionally in combination with one or more polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2, (b) each of at least eight polymorphism genotypes being in linkage disequilibrium with any one of the polymorphism genotypes of (a), or (c) a combination of (a) and (b). In another specific embodiment, the disclosure provides a composition containing at least 16 polynucleotides capable of specifically hybridizing to each of at least 16 polymorphism genotypes selected from the group consisting of the polymorphism genotypes as disclosed in Table 2, preferably one or more polymorphism genotypes selected from the group consisting of rs11715827 (T/G), rs2044070 (A/G), rs2028629 (A/G) and rs6026567 (A/G) as disclosed in Table 2, optionally in combination with one or more polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2, (b) each of at least 16 polymorphism genotypes being in linkage disequilibrium with any one of the polymorphism genotypes of (a), or (c) a combination of (a) and (b). In another specific embodiment, the disclosure provides a composition containing at least 32 polynucleotides capable of specifically hybridizing to (a) each of at least 32 polymorphism genotypes selected from the group consisting of the polymorphism genotypes as disclosed in Table 2, (b) each of at least 32 polymorphism genotypes being in linkage disequilibrium with any one of the polymorphism genotypes of (a), or (c) a combination of (a) and (b). In another specific embodiment, the disclosure provides a composition containing at least 150 polynucleotides capable of specifically hybridizing to (a) each of at least 150 polymorphism genotypes selected from the group consisting of the polymorphism genotypes as disclosed in Table 2, (b) each of at least 150 polymorphism genotypes being in linkage disequilibrium with any one of the polymorphism genotypes of (a), or (c) a combination of (a) and (b). In another specific embodiment, the disclosure provides a composition containing 274 polynucleotides capable of specifically hybridizing to each of the 274 polymorphism genotypes as disclosed in Table 2.

In some embodiments, the at least one polynucleotide capable of specifically hybridizing to the polymorphism genotypes is selected from the group consisting of the polynucleotides disclosed as "AlleleA Probe" in Table 2. In a preferred embodiment, the at least one polynucleotide capable of specifically hybridizing to the polymorphism genotypes is selected from the group consisting of the polynucleotides disclosed as "AlleleA Probe" of one or more polymorphism genotypes selected from the group consisting of rs11715827 (T/G), rs2044070 (A/G), rs2028629 (A/G) and rs6026567 (A/G) as disclosed in Table 2 and optionally in combination with the polynucleotides disclosed as "AlleleA Probe" of one or more polymorphism genotypes selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2. In particular, the composition can comprise all of the polynucleotides disclosed as "AlleleA Probe" in Table 2, preferably all the of the polynucleotides disclosed as "AlleleA Probe" of the polymorphism genotypes selected from the group consisting of rs11715827 (T/G), rs2044070 (A/G), rs2028629 (A/G) and rs6026567 (A/G) as disclosed in Table 2 and optionally in combination with the polynucleotides disclosed as "AlleleA Probe" of one or more polymorphism genotypes selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2.

In any of the compositions described above, the at least one polynucleotide can be bound to a solid support. The solid support can be in the form of an array on a microarray chip, a particle (e.g., an encoded, magnetic, or magnetic and encoded particle), or any other solid support described herein.

In yet another aspect, the disclosure provides a kit useful in determining the presence or absence of one or more polymorphism genotypes. The kit can include any of the compositions described above and, optionally, instructions for detecting one or more polymorphism genotypes. The kit can also include, e.g., one or more additional reagents for detecting the presence or absence of the one or more polymorphism genotypes described herein. For example, the kit can include primers (e.g., random hexamers or oligo (dT) primers), reverse transcriptase, a DNA polymerase (e.g., Taq polymerase), T4 polynucleotide kinase, one or more detectable labels (such as any described herein), or any other reagents described herein.

In some embodiments, the compositions, kits or arrays described above contain less than 100,000 different polynucleotides. In some embodiments, the compositions, kits or arrays described above contain less than 90,000; less than 80,000; less than 70,000; less than 60,000; less than 50,000; less than 40,000; less than 30,000; less than 20,000; less than 15,000; less than 10,000; less than 5,000; less than 4,000; less than 3,000; less than 2,000; less than 1,500; less than 1,000; less than 750; less than 500, less than 200, less than 100, or less than 50 different polynucleotides.

In yet another aspect, the disclosure provides a use of a composition, kit or array as described herein for predicting the treatment response of a subject to a treatment with a CRHR1 antagonist, wherein the composition, kit or array is used to detect the presence or absence of one or more polymorphism genotypes within a sample obtained from a subject. In some embodiments, the composition, kit or array is used in a method of predicting a treatment response of a subject to a treatment with a CRHR1 antagonist as described herein. In some embodiments, the composition, kit or array is used in a method of detecting a polymorphism genotype associated with a treatment response of a subject to treatment with a CRHR1 antagonist as described herein.

BRIEF DESCRIPTION OF THE DRAWINGS

FIG. 1 shows a time course curve of the clinical response of depressive patients as measured by the HAM-D scale upon treatment using placebo, or using an exemplary CRHR1 antagonist, wherein the surveyed subjects were predicted to positively respond to CRHR1 antagonist treatment using the method of prediction. The dashed line indicates a significant effect in treatment response at day 42 (p-value <0.01).

DETAILED DESCRIPTION OF THE INVENTION

General Definitions

The term "comprise" or "comprising" as used herein is to be construed as "containing" or "including" and does generally not exclude other elements or steps, but encompasses the term "consisting of" as an optional, specific embodiment. Thus, a group defined as comprising a certain number of embodiments, is also to be construed as a disclosure of a group which optionally consists only of these embodiments. Where an indefinite or a definite article is used when referring to a singular noun such as "a" or "an" or "the", it includes a plural form of that noun unless specifically stated. Vice versa, when the plural form of a noun is used it refers also to the singular form. For example, when polymorphism genotypes are mentioned, this is also to be understood as a single polymorphism genotype.

Furthermore, the terms "first", "second", "third" or "(a)", "(b)", "(c)" and the like in the description and in the claims are used for distinguishing between elements and not necessarily for describing a sequential or chronological order. It is to be understood that the terms so used can be interchangeable under appropriate circumstances and that the embodiments of the invention described herein are capable of operation in other sequences than described or illustrated herein.

"Corticotropin releasing hormone" or "CRH" is used synonymously to the term "corticotropin releasing factor" or "CRF" herein, and refers to the known human 41 aa peptide or its mammalian homologues. The term "corticotropin releasing hormone receptor 1" or "CRHR1" refers to the receptor which binds to CRH and is used synonymously to the term "corticotropin-releasing factor receptor 1", or CRF—R1, or CRFR-1 herein.

A "CRHR1 antagonist", as used herein, refers to a compound capable of binding directly or indirectly to CRHR1 so as to modulate the receptor mediated activity. The CRHR1 mediated activity may be exerted on a downstream target within the signalling pathway of CRHR1. A "downstream target" may refer to a molecule such as an endogenous molecule (e.g. peptide, protein, lipid, nucleic acid or oligonucleotide), that is regulated by CRHR1 directly or indirectly, comprising direct or indirect modulation of the activity and/or expression level and/or localization, degradation or stability of the downstream target. A CRHR1 antagonist can be tested by any in vitro or in vivo test known in the art to be indicative of CRHR1 inhibition. For instance, CRHR1 antagonists will specifically bind to CRHR1 with a $K_D$ of 1 μM or less, preferably with a $K_D$ of 100 nM or less and/or specifically inhibit CRH binding to CRHR1 in vitro with an $IC_{50}$ value of 1 μM or less, preferably with $IC_{50}$ value of 100 nM or less. Alternatively or in addition, a CRHR1 antagonist can inhibit cellular, CRHR1-mediated cAMP accumulation and/or attenuate CRH and ACTH production in vivo.

Several groups of CRHR1 antagonists are well known in the literature and are disclosed in the patent literature, e.g., in WO 94/13676, EP 0 773 023, WO 2004/047866, WO 2004/094420, WO 98/03510, WO 97/029109, WO 2006/044958, WO 2001/005776 and WO 95/033750, WO 2009/008552, WO 2010/015655 all of which are herein incorporated by reference. Further exemplary groups of CRHR1 antagonists are reviewed and disclosed in the scientific literature, e.g., in Williams, Expert Opin Ther Pat. 2013; 23(8):1057-68 (in particular compounds 1-48 as disclosed therein); Zorilla and Koob, Drug Discovery Today, 2010, 371-383 (in particular FIG. 1 and Tables 1-3 thereof); all of which are herein incorporated by reference in their entirety. Exemplary CRHR1 antagonist comprise, but are not limited to, GW876008 (Emicerfont), GSK-561679 (NBI-77860, Verucerfont), GSK586529, BMS-562,086 (Pexacerfont), NBI-30775 (R-121919), NBI-34101, CP-316,311, CP-376,395, PF-00572778, NVP-AAG561, Ono-2333 MS, E2508, E2009, R317573 (JNJ19567470, CRA5626), R278995 (CRA0450), CRA-1000, CRA-1001, CP154,526, Antalarmin, DMP-695, DMP-696, DMP-904, SC-241, BMS-561388, NBI30545, PD-171729, NBI34041, NBI35965, SN003, NBI-27914, trans-2-chloro-N-(4-((5-fluoro-4-methyl-pyridin-2-ylamino)-methyl)-cyclohexyl)-5-(trifluoromethyl)-benzamide. SSR-125543. Ono-2333 Ms, NBI-34101. PF-00572778. GSK-561579 and GSK586529 are described by Zorilla and Koob (Drug Discovery Today. 2010, 371-383) as corticotropin releasing factor receptor antagonists tested in clinical trials. Exemplary CRHR1 antagonists are depicted in Table 1.

TABLE 1
| Exemplary CRHR1 antagonists | |
|---|---|
| Structure | Name (synonym)/reference |
| 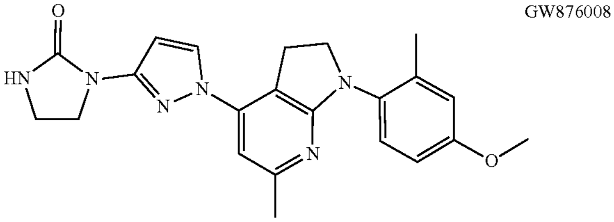 | GW876008 (Emicerfont) |
| 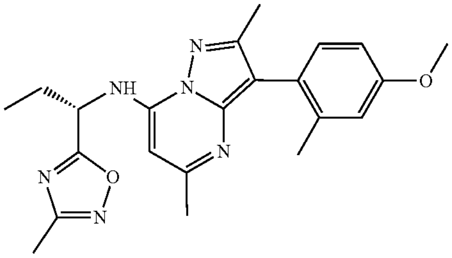 [SMILES: CC[C@H](Nc1cc(C)nc2c(-c3ccc(OC)cc3C)c(C)nn12)c1nc(C)no1] | GSK-561679 (NBI-77860, Verucerfont) |
| 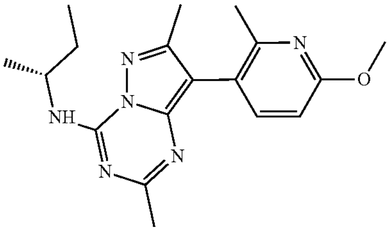 [SMILES: CC[C@@H](C)Nc1nc(C)nc2c(-c3ccc(OC)nc3C)c(C)nn12] | BMS-562,086 (Pexacerfont) |
| 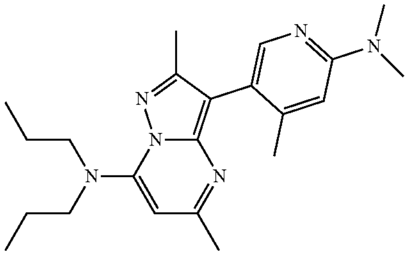 | NBI-30775 (R-121919) |
| 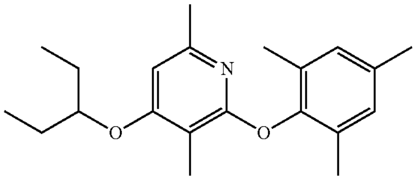 [SMILES: CCC(CC)Oc1cc(C)nc(Oc2c(C)cc(C)cc2C)c1C] | CP-316,311 |
| 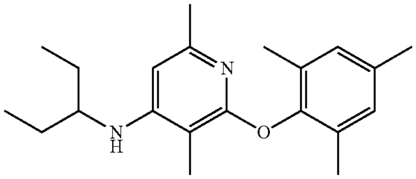 [SMILES: CCC(CC)Nc1cc(C)nc(Oc2c(C)cc(C)cc2C)c1C] | CP-376,395 |

TABLE 1-continued
Exemplary CRHR1 antagonists
| Structure | Name (synonym)/reference |
| --- | --- |
| 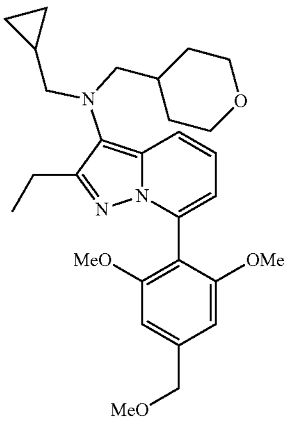 [SMILES: CCc1nn2c(-c3c(OC)cc(COC)cc3OC)cccc2c1N(CC1CCOCC1)CC1CC1] | E2508 |
| 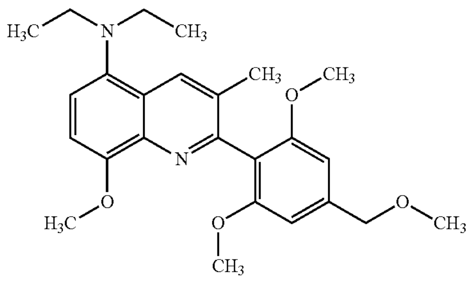 [SMILES: CCN(CC)c1ccc(OC)c2nc(-c3c(OC)cc(COC)cc3OC)c(C)cc12] | E2009 Terauchi et al., 244th ACS National Meeting, Aug. 19-23, 2012, Poster Presentation & Abstract, 2 pp. |
| 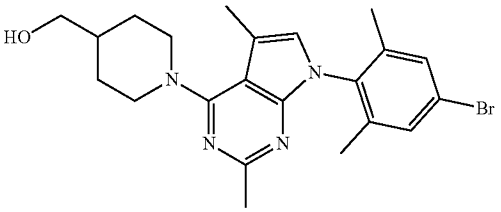 [SMILES: Cc1nc(N2CCC(CO)CC2)c2c(C)cn(-c3c(C)cc(Br)cc3C)c2n1] | R317573 (JNJ19567470, CRA5626, TAI-041) |
| 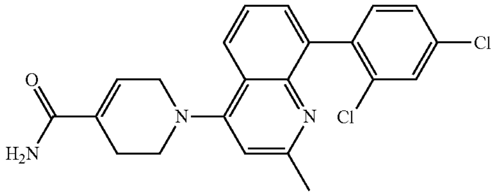 [SMILES: Cc1cc(N2CC=C(C(N)=O)CC2)c2cccc(-c3ccc(Cl)cc3Cl)c2n1] | R278995 (CRA0450) |
| 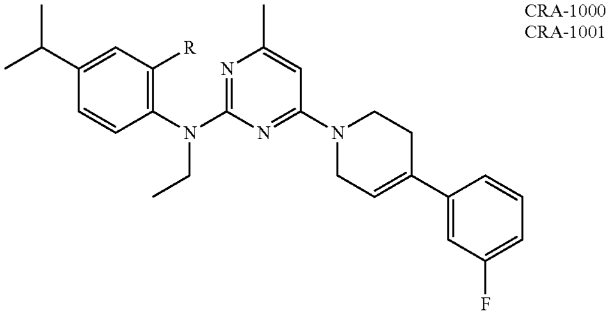 | CRA-1000 (R = S—$CH_3$)<br>CRA-1001 (R = Br) |

TABLE 1-continued
| Structure | Name (synonym)/reference |
|---|---|
| Exemplary CRHR1 antagonists | |
| 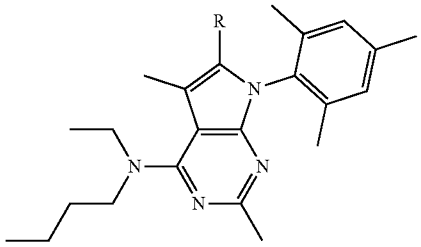 | CP154,526 (R = H)<br>Antalarmin (R = $CH_3$) |
| 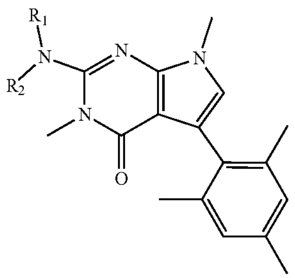 | Compounds 16a-e<br>K. Aso et al./Bioorg. Med. Chem. Lett. 21 (2011) 2365-2371 |
| 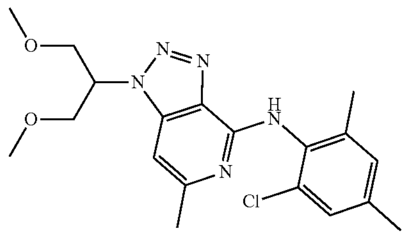 | DMP-695 |
| 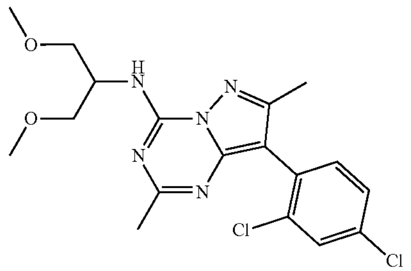 [SMILES: COCC(COC)Nc1nc(C)nc2c(-c3ccc(Cl)cc3Cl)c(C)nn12] | DMP-696 |
| 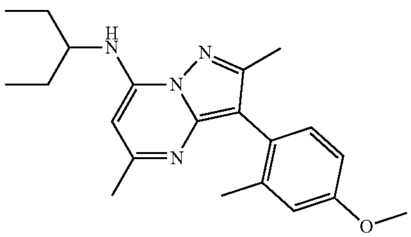 [SMILES: CCC(CC)Nc1cc(C)nc2c(-c3ccc(OC)cc3C)c(C)nn12] | DMP-904 |

TABLE 1-continued
| Exemplary CRHR1 antagonists | |
|---|---|
| Structure | Name (synonym)/reference |
| 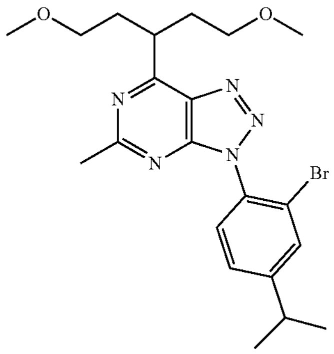 [SMILES: COCCC(CCOC)c1nc(C)nc2c1nnn2-c1ccc(C(C)C)cc1Br] | SC-241 |
| 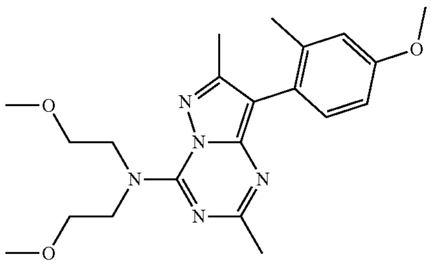 | BMS-561388 |
| 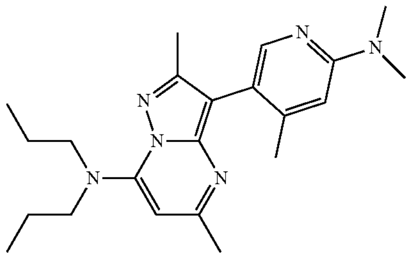 | NBI30545 |
| 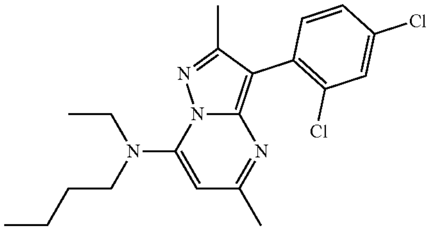 [SMILES: CCCCN(CC)c1cc(C)nc2c(-c3ccc(Cl)cc3Cl)c(C)nn12] | PD-171729 |
| 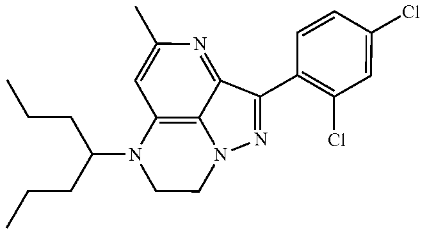 [SMILES: CCCC(CCC)N1CCn2nc(-c3ccc(Cl)cc3Cl)c3nc(C)cc1c32] | NBI34041 |

TABLE 1-continued
| Structure | Name (synonym)/reference |
| --- | --- |
| 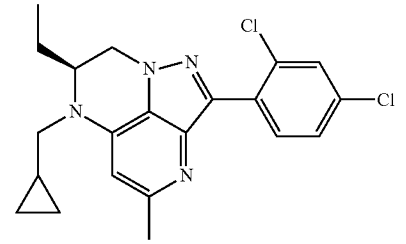 [SMILES: CC[C@H]1Cn2nc(-c3ccc(Cl)cc3Cl)c3nc(C)cc(c32)N1CC1CC1] | NBI35965 |
| 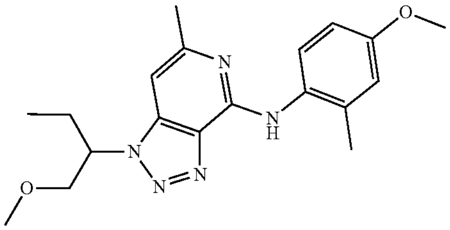 | SN003 |
| 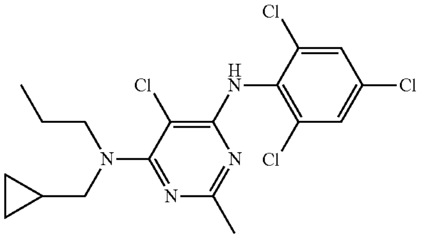 [SMILES: CCCN(CC1CC1)c1nc(C)nc(Nc2c(Cl)cc(Cl)cc2Cl)c1Cl] | NBI-27914 |
| 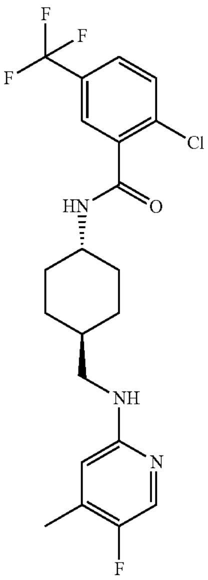 [SMILES: Cc1cc(NC[C@H]2CC[C@H](NC(=O)c3cc(C(F)(F)F)ccc3Cl)CC2)ncc1F] | trans-2-chloro-N-(4-((5-fluoro-4-methyl-pyridin-2-ylamino)-methyl)-cyclohexyl)-5-(trifluoromethyl)-benzamide Compound 46 in Williams Expert Opin Ther Pat, 2013, 23(8):1057-68); WO 2010/015655 |
Exemplary CRHR1 antagonists TABLE 1-continued

| Exemplary CRHR1 antagonists | |
|---|---|
| Structure | Name (synonym)/reference |
| 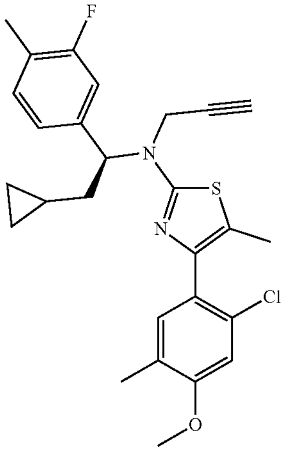 | SSR-125543 |

Most of the non-peptidic CRHR1 antagonists can be described by a pharmacophore model comprising a lipophilic top group, a heterocyclic core containing an invariable hydrogen bond acceptor, which is almost always a heterocyclic nitrogen, and a lipophilic, usually aromatic, bottom group. The terms "Type I CRHR1 antagonist", "Type II CRHR1 antagonist", "monocyclic Type II CRHR1 antagonist", "bicyclic Type II CRHR1 antagonist", "atypical CRHR1 antagonist" or "cyclohexyl amide CRHR1 antagonist", as used herein, is synonymous to "Type I $CRF_1$ antagonist", "Type II $CRF_1$ antagonist", "monocyclic Type II $CRF_1$ antagonist", "bicyclic Type II $CRF_1$ antagonist", "atypical $CRF_1$ antagonist" or "cyclohexyl amide $CRF_1$ antagonist", respectively, referring to known and readily available compounds as defined in Williams, Expert Opin Ther Pat. 2013; 23(8):1057-68, incorporated herein by reference in its entirety. In specific embodiments, Type I CRHR1 antagonists are compounds 1-33, monocyclic Type II CRHR1 antagonists are compounds 34-36, bicyclic Type II CRHR1 antagonists are compounds 37-41, atypical CRHR1 antagonists are compounds 42-45, or cyclohexyl amide CRHR1 antagonists are compounds 46-48, respectively, as disclosed in FIGS. 1-11 of Williams, Expert Opin Ther Pat. 2013; 23(8):1057-68, incorporated herein by reference in its entirety. Exemplary "Type I CRHR1 antagonists" may be characterized in that the heterocyclic hydrogen bond acceptor and the bottom group are connected by a two-atom linker as exemplified by CRHR1 antagonists R-121919, NBI-30545, CP-154526, DMP-696, pexacerfont (BMS-562086), emicerfont (GW876008), or verucerfont (GSK561679). Type II CRH1R antagonists may be characterized by a one-atom linker between hydrogen bond acceptor and the bottom group. Any pharmaceutically acceptable salt of a CRHR1 antagonist described herein is encompassed by the present disclosure.

Methods of Predicting Treatment Response to CRHR1 Treatment

In one aspect, the present invention provides methods for predicting a treatment response of a subject (such as a human patient) to a treatment with a CRHR1 antagonist, which can include one or more CRHR1 antagonists. Thus, methods of the invention are useful in selecting appropriate therapeutic modalities (e.g., a treatment with a CRHR1 antagonist or a treatment with a non-CRHR1 antagonist) for subjects suffering from conditions generally treatable by a CRHR1 antagonist, for instance psychiatric disorders such as depressive symptoms or anxiety symptoms.

Specifically, in this aspect, the method of the invention can be used for predicting a treatment response of a subject to treatment with a CRHR1 antagonist, the method comprising providing a biological sample obtained from the subject, detecting the presence or absence of one or more polymorphism genotypes in the biological sample, wherein the one or more polymorphism genotypes comprise: (a) at least one polymorphism genotype selected from the group consisting of the polymorphism genotypes disclosed in Table 2, preferably at least one polymorphism genotypes selected from the group consisting of rs11715827 (T/G), rs2044070 (A/G), rs2028629 (A/G) and rs6026567 (A/G), optionally in combination with at least one polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C), (b) at least one polymorphism genotype being in linkage disequilibrium with any one of the polymorphism genotypes of (a); or (c) a combination of (a) and (b), and predicting the treatment response from the presence or absence of the one or more polymorphism genotypes of (a), (b), or (c).

In a preferred aspect, the present invention provides a method of treatment of a subject comprising: detecting the presence or absence of one or more polymorphism genotypes in a biological sample from the subject, wherein the one or more polymorphism genotypes comprise: (a) at least one polymorphism genotype selected from the group consisting of rs11715827, rs2044070, rs2028629 and rs6026567, optionally (b) in combination with at least one polymorphism genotype selected from the group consisting of rs17740874, rs3811939, rs1882478, rs2235013, rs2214102, rs6415328, rs77152456, rs66794218, rs2589476, rs118003903, rs11871392, rs2589487, rs74338736, rs6026593 and rs6520908; predicting an increased likelihood of positive response of the subject to treatment with a CRHR1 antagonist based on the presence or absence of the one or more polymorphism genotypes; and administering to the subject having a predicted increased likelihood of positively responding an effective amount of the CRHR1 antagonist.

In another preferred aspect, the present invention provides a method of using a kit comprising at least one polynucleotide capable of specifically hybridizing to a nucleic acid comprising: (a) at least one polymorphism genotype selected from the group consisting of rs11715827, rs2044070, rs2028629 and rs6026567, optionally (b) in combination with at least one polymorphism genotype selected from the group consisting of rs17740874, rs3811939, rs1882478, rs2235013, rs2214102, rs6415328, rs77152456, rs66794218, rs2589476, rs118003903, rs11871392, rs2589487, rs74338736, rs6026593 and rs6520908, and one or more additional reagents for detecting the presence or absence of the one or more polymorphism genotypes; optionally comprising instructions for detecting the presence or absence of the at least one polymorphism genotype in a sample obtained from a subject; the method comprising predicting the treatment response of a subject to a treatment with a non-peptidic CRHR1 antagonist, and administering to the subject predicted to have a positive treatment response an effective amount of a non-peptidic CRHR1 antagonist.

In a still further preferred aspect, the present invention provides a method of treatment of a subject positively responsive to treatment with a non-peptidic CRHR1 antagonist, the method comprising: detecting the presence or absence of one or more polymorphism genotypes in a biological sample obtained from the subject, wherein the one or more polymorphism genotypes comprise: (a) at least one polymorphism genotype selected from the group consisting of rs11715827, rs2044070, rs2028629 and rs6026567, optionally (b) in combination with at least one polymorphism genotype selected from the group consisting of rs17740874, rs3811939, rs1882478, rs2235013, rs2214102, rs6415328, rs77152456, rs66794218, rs2589476, rs118003903, rs11871392, rs2589487, rs74338736, rs6026593 and rs6520908; —predicting an increased likelihood of positive response of the subject to treatment with a non-peptidic CRHR1 antagonist based on the presence or absence of the one or more polymorphism genotypes; and administering to the subject having a predicted increased likelihood of positively responding an effective amount of the non-peptidic CRHR1 antagonist.

A "subject", as used herein, can generally be any mammal, in which one or more polymorphism genotypes as disclosed in Table 2, in particular one or more polymorphism genotypes selected from the group consisting of rs11715827 (T/G), rs2044070 (A/G), rs2028629 (A/G) and rs6026567 (A/G), optionally in combination with at least one polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C), or polymorphism genotypes being in linkage disequilibrium with any one of the polymorphism genotypes of Table 2 are conserved or homologous. In particular, the term "subject" includes a human subject, and any model organism such as mice, rats, cats, dogs, simians, cattle. Preferably, the subject is a human subject.

A "treatment with a CRHR1 antagonist", as used herein, refers to the treatment of a condition in the subject which can be treated by administration of a CRHR1 antagonist, as is made plausible herein or in the prior art. "Conditions treatable with a CRHR1 antagonist", as used herein, are conditions which can generally be treated by administration of a CRHR1 antagonist and/or are commonly characterized, caused or accompanied by CRH over-activity, by ACTH over-activity and/or by over-activity of the Hypothalamic-pituitary-adrenal (HPA) axis.

The term "CRH over-activity" is used herein synonymously to the terms "CRH system over-activity", "CRH hyperactivity", "CRH hyperdrive" or "central CRH hyperdrive". An indication for CRH over-activity may be an increase in activity or concentration of CRH or of one or several molecules downstream of the CRHR1 receptor, that are activated or whose concentration is increased based on the activation of CRHR1 receptor upon CRH binding, for instance, but not being limited to, ACTH. A further indication for CRH over-activity may be a decrease in activity or concentration of one or several molecules downstream of the CRHR1 receptor, that are inactivated or whose concentration is decreased resulting from the activation of CRHR1 receptor upon CRH binding. For instance, the concentrations or activities of adrenocorticotrophin (ACTH) and/or cortisol can be used for determining a value indicative for CRH over-activity. The CRH over-activity in each patient may be determined by a CRH test as described in Holsboer et al., N Engl J Med. 1984; 311(17):1127, or by a combined dexamethasone suppression/CRH stimulation test (dex/CRH test) as described in Heuser et al., J Psychiatr Res 1994, 28 (4): 341-56; both incorporated herein by reference in their entirety.

In particular, conditions which can be treated using a CRHR1 antagonist in a subject comprise, but are not limited to, behavioural disorders, neuropsychiatric disorders, mood disorders, neurological disorders, neurodegenerative disorders, endocrine disorders, inflammatory or stress-induced immune disorders, CRH-related cardiovascular diseases or metabolic diseases. Specifically, such conditions comprise anxiety symptoms, generalized anxiety disorder, panic, phobias, obsessive-compulsive disorder, post-traumatic stress disorder, sleep disorders such as insomnia, hypersomnia, narcolepsy, idiopathic hypersomnia, excessive amounts of sleepiness, lack of alertness, lack of attentiveness, absent-mindedness and/or lack of or aversion to movement or exercise, sleep disorders induced by stress, pain perception such as fibromyalgia, mood disorders such as depressive symptoms, including major depression, single episode depression, recurrent depression, child abuse induced depression, mood disorders associated with premenstrual syndrome, and postpartum depression, dysthymia, bipolar disorders, cyclothymia, chronic fatigue syndrome, stress-induced headache, eating disorders such as anorexia and bulimia nervosa, hemorrhagic stress, stress-induced psychotic episodes, endocrine disorders involving ACTH overproduction, ACTH over-activity, e.g., adrenal disorders, including, but not limited to congenital adrenal hyperplasia (CAH), euthyroid sick syndrome, syndrome of inappropriate antidiarrheic hormone (ADH), obesity, infertility, head traumas, spinal cord trauma, ischemic neuronal damage (e.g., cerebral ischemia such as cerebral hippocampal ischemia), excitotoxic neuronal damage, epilepsy, senile dementia of the Alzheimers type, multi-infarct dementia, amyotrophic lateral sclerosis, chemical dependencies and addictions (e.g., dependencies on alcohol, nicotine, cocaine, heroin, benzodiazepines, or other drugs), drug and alcohol withdrawal symptoms, hypertension, tachycardia, congestive heart failure, osteoporosis, premature birth, and hypoglycaemia, inflammatory disorders such as rheumatoid arthritis and osteoarthritis, pain, asthma, psoriasis and allergies, irritable bowel syndrome, Crohn's disease, spastic colon, post-operative ileus, ulcer, diarrhea, stress-induced fever, human immunodeficiency virus (HIV) infections, neurodegenerative diseases such as Alzheimer's disease, Parkinson's disease and Huntington's disease, gastrointestinal diseases, stroke, stress induced immune dysfunctions, muscular spasms, urinary incontinence. In a specific embodiment, the subject has and/or the treatment is a treatment of depressive symptoms, anxiety symptoms or both depressive symptoms and anxiety symptoms. The depressive and/or anxiety symptoms can be symptoms of a depressive disorder, an anxiety disorder or both a depressive disorder and anxiety disorder. In another specific embodiment, the subject has and/or the treatment is a treatment of a sleep disorder.

A "treatment response", as used herein, generally refers to any measurable response specific for the treatment with one or more CRHR1 antagonist and/or the condition being treated, during and/or shortly after treatment as compared to before said treatment. Generally, the treatment response can be a biological response or a clinical response. A biological response would include, for example, any alteration in CRH over-activity, as defined above.

Preferably, according to the invention, the treatment response is a clinical treatment response. A "clinical treatment response", as used herein, refers to a prevention, alteration, alleviation or complete remission, as measured by the alteration in severity and/or frequency of relapse of individual symptoms and/or the mean change on a diagnostic marker or scale of any type commonly used in assessing clinical responses in the conditions described herein, see, for instance, Harrison's Principles of Internal Medicine, $18^{th}$ ed./editors Longo et al., Mcgraw-Hill Publ. Comp, NY, US (2011), as incorporated herein by reference in its entirety. A clinical treatment response can also include an alteration, increase or decrease in adverse effects resulting from the treatment with a CRHR1 antagonist. Predicting a clinical response, or lack thereof, is expressly distinguished from predicting merely biological responses, since a clinical response is to be seen as target variable directly linked to treatment success, or failure, respectively. Therefore, while biological responses can also be predicted by the methods described herein, the methods of the invention are particularly suited for predicting a clinical response, as defined above.

In preferred embodiments, the clinical response can be a prevention, alteration, alleviation or complete remission of depressive symptoms and/or anxiety symptoms. In preferred embodiments, the clinical response can be a prevention, alteration, alleviation or complete remission of a sleep disorder. Depressive symptoms comprise, but are not limited to, low mood, low self-esteem, loss of interest or pleasure, psychosis, poor concentration and memory, social isolation, psychomotor agitation/retardation, thoughts of death or suicide, significant weight change (loss/gain), fatigue, and feeling of worthlessness. The depressive symptoms can last for weeks to lifelong with periodic reoccurring depressive episodes. For the diagnosis of the depression mode (e.g. moderate or severe depression) the Hamilton Depression Rating Scale (HAM-D)(Hamilton, J Neurol Neurosurg Psychiatry, 1960) may be used. In addition or alternatively, the depression mode may be also rated by alternative scales as the Beck Depression Inventory (BDI), the Montgomery-Asberg Depression Scale (MADRS), the Geriatric Depression Scale (GDS), and/or the Zung Self-Rating Depression Scale (ZSRDS). Therefore, in some embodiments, the clinical response is a prevention, alteration, alleviation or complete remission of depressive symptoms as determined using a scale selected from the group consisting of HAM-D, BDI, MADRS, GDS, ZSRDS.

Anxiety symptoms comprise, but are not limited to, panic disorders, generalized anxiety disorder, phobias and post-traumatic stress disorder, avoidance behavior which may lead to social isolation, physical ailments like tachycardia, dizziness and sweating, mental apprehension, stress and/or tensions. The severity of anxiety symptoms ranges from nervousness and discomfort to panic and terror in subjects. Anxiety symptoms may persist for several days, weeks, or even months and years, if not suitably treated. The severity of anxiety symptoms may be measured by the Hamilton Anxiety Rating Scale (HAM-A) and/or the State-Trait Anxiety Rating Scale (STAI). Therefore, in some embodiments, the clinical response is a prevention, alteration, alleviation or complete remission of anxiety symptoms as determined using a scale selected from the group consisting of HAM-A and STAI. Sleep disorders comprise, but are not limited to, insomnia, hypersomnia, narcolepsy, idiopathic hypersomnia, excessive amounts of sleepiness, lack of alertness, lack of attentiveness, absentmindedness and/or lack of or aversion to movement or exercise, sleep disorders induced by stress.

"Alteration", as used herein, refers to any change in a clinical response as defined above. "Alleviation", as used herein, refers to any amelioration in a clinical response, including partial amelioration of one or more symptoms, temporary disappearance of one or more symptoms, wherein relapse is not excluded, as well as complete remission of one or more symptoms. "Complete remission" refers to disappearance of all manifestations and symptoms of a disease to be treated, as described herein.

The present disclosure identifies sets of polymorphism genotypes that are predictive for the treatment response of a subject to treatment with a CRHR1 antagonist. Thus, the presence of one or more of these polymorphism genotypes can be used to predict the likelihood of responding or not responding to treatment with a CRHR1 antagonist in a subject.

The term "polymorphism", as used herein, refers to a sequential variation of a genomic allele at the same locus within a population of subjects and having a certain frequency in the population, including deletions/insertions (designated "[−/I]" herein), point mutations and translocations. The term "polymorphism", as used herein, in particular includes, but is not limited to, single nucleotide polymorphisms (SNPs). For instance, as used herein, the term "polymorphism" can also include polymorphic deletions, or insertions, respectively, of more than one nucleotide. The term "single nucleotide polymorphism" or "SNP" is well understood by the skilled person and refers to a point mutation of a genomic allele at the same locus within a population of subjects and having a certain frequency in a population. The term "genotype", as used herein, encompasses one or both genomic alleles at the same locus of a subject. The term "polymorphism genotype" or "SNP genotype", as used herein, refers to the presence of a polymorphism or SNP within the genotype of a subject, either in one or both genomic alleles at the same locus. The allele being present in the majority of the population, is also referred to herein as wild-type allele or major allele. As used herein, this state is defined as the "absence of one or more polymorphism genotypes". The nucleotide being present in the minority of the population is also referred to herein as the variation, point mutation, mutated nucleotide or minor allele. As used herein this state is defined as "presence of one or more polymorphism genotype". For instance, P_ID 1 as identified in Table 2 below, (rs34169260, TOP. [A/G]) exhibits a variation to nucleotide G instead of the wild-type nucleotide A. Typically, a polymorphism or SNP genotype occurs in a certain percentage of a population, for example in at least 5% or at least 10% of a population. In other words, the minor allele frequency (MAF) is equal or higher than about 0.05 or about 0.10 (MAF>0.05 or MAF>0.10).

Theoretically, a wild-type allele could be mutated to three alternative nucleotides. However, a mutation to a first nucleotide within germline cells of an individual which persists within a population occurs very rarely. The chance of the same nucleotide being mutated to yet another nucleotide and again persisting within a population is virtually non-existent and can be therefore neglected. Therefore, as used herein, a certain nucleotide position in the genome of an individual can only have the above two states, namely the wild-type state (absence of a polymorphism genotype from both alleles of a single subject) and the mutated state (presence of a polymorphism genotype in one or both alleles of a single subject). The presence of a polymorphism genotype in both alleles may have a higher predictive value than the presence of a polymorphism genotype in one allele only, the other allele comprising a wild-type genotype. The presence or absence of a polymorphism genotype on one or two alleles may be associated with an algorithm for predicting the treatment response to CRHR1 antagonists as described herein.

Sets of polymorphism genotypes useful in methods for predicting a treatment response are disclosed in Table 2. Table 2 provides a consecutively numbered identifier (P_ID) for internal reference, an rs-identifier (rs_ID), as commonly known in polymorphism databases such as NCBI's dbSNP or NCBI's Blast, the polymorphism (P, indicated in bold and defined as [wild-type/variation]), the strand designation (Str, see, e.g., Illumina Inc. "TOP/BOT" Strand and "A/B" Allele—A guide to Illumina's method for determining Strand and Allele for the GOLDENGATE and INFINIUM Assays", Technical Note, C 2006; illumina.com/documents/products/technotes/technote_topbot.pdf; incorporated by reference herein in its entirety), specific probe sequences for the respective allele in humans (AlleleA Probe, see also SEQ ID NOs: 275-548), a human chromosomal identifier (Chr), and a reference to the sequence of the genomic flanking sequence in humans (TopGenomicSequence), as disclosed in SEQ ID NOs: 1-274. A person skilled in the art is able to derive the exact position and polymorphism genotype sequence from the rs-nomenclature identified in Table 2 from suitable database entries and associated information systems, e.g. the NCBI's Single Nucleotide Polymorphism database (dbSNP; ncbi.nlm.nih.gov/SNP/), or the NCBI's standard nucleotide BLAST database (blast.ncbi.nlm.nih-.gov/Blast.cgi?PAGE_TYPE=BlastSearch) even where the nomenclature, or the surrounding sequence elements were subject to alterations over time. The NCBI's databases which are well known and commonly used by the skilled person, allow information extraction of the exact polymorphic site ("the nucleotide associated with the SNP") for any of the polymorphism genotypes identified in Table 2, either by using the AlleleA Probe information (via the NCBI's nucleotide BLAST database) or by entering the rs-identifiers (re_ID) information of Table 2 (via the NCBI's dbSNP database). In the approach using the nucleotide blast database (blast.ncbi.nlm.nih.gov/Blast.cgi?PAGE_TYPE=BlastSearch) the skilled person can extract for each of the polymorphism genotypes of Table 2 the relevant AlleleA Probe sequence information (column 4 of Table 2) and enter the sequence in the database search filed choosing the database search set "human genomic plus transcripts". The obtained search result provides the respective Primary Assembly information of the specific genomic sequence (under the section "sequence producing significant alignment"). From the link to the Primary Assembly the genomic position of the polymorphic site on the respective chromosome can be exactly identified. The skilled person is aware that the polymorphic site is positioned one base after the last base of the AlleleA Probe as identified in Table 2. For instance, P_ID 146 as identified in Table 2 below, (re2589476, [T/C]) exhibit an AlleleA Probe sequence being CTCCTCATTATTCGCTTCTGCTGTAACTGCACC-TATGGTAACCCAGGTGC. By denoting the variable nucleotide as Y the sequence including the variable nucleotide is given as the same sequence with a "Y" at the end following the terminal "GC". This searching approach works regardless of Top or Bottom assignments, as known by the skilled in the art. Further, the skilled person is able to recognize if the information is presented in the sequence as given or on the complementary strand. In the alternative approach using the dbSNP database (ncbi.nlm.nih.gov/SNP/) the skilled person can enter in the search field of the database the SNP rs_ID name of the polymorphism genotype as identified in column 2 of Table 2 and can, thus, run the search for obtaining the relevant information on the polymorphic position on the respective chromosome. Finally, the skilled person will also know that for sequences such as P_ID 166 which are common structural variants (SV), a specialized database for SVs (NCBI's dbVar database; ncbi.nlm.nih.gov/dbvar/variants/nssv16186739/) is used for the relevant information. Also from these databases, a person skilled in the art will know to genotype the polymorphism form the available information based on his routine work. Further, the polymorphism information P as indicated in Table 2 also provides information which of the alleles, i.e. the wild-type allele or the mutation variant, is associated with a positive prediction that the subject will respond or is likely to respond to treatment with a CRHR1 antagonist. In particular, for each of the polymorphism genotypes identified in Table 2 below, in the column P, the allele which is highlighted by underlining, represents the allele which is predictive for a positive treatment response or an increased likelihood of positive treatment response with a CRHR1 antagonist.

TABLE 2

Polymorphism genotypes as used herein

| P_ID | rs_ID | Str | P | AlleleA Probe | Chr | TopGenomic Sequence |
|---|---|---|---|---|---|---|
| 1 | rs34169260 | TOP | [A/G] | AGGACTCTATGGCTTCCTTCATGTCATCGTCCA CTCTGCCAAGGGATTTA | 17 | SEQ ID NO: 1 |

TABLE 2-continued

Polymorphism genotypes as used herein

| P_ID | rs_ID | Str | P | AlleleA Probe | Chr | TopGenomic Sequence |
|---|---|---|---|---|---|---|
| 2 | rs796287 | TOP | [A/C] | ACGACAGAGATGAATTGAGGGGACAAATGTCAG AGCTCACAGACGACTGT | 2 | SEQ ID NO: 2 |
| 3 | rs56149945 | TOP | [A/G] | TCAGAAGCCTATTTTTAATGTCATTCCACCAAT TCCCGTTGGTTCCGAAA | 5 | SEQ ID NO: 3 |
| 4 | rs6190 | BOT | [T/C] | TCACAGTAGCTCCTCCTCTTAGGGTTTTATAGA AGTCCATCACATCTCCC | 5 | SEQ ID NO: 4 |
| 5 | rs7179092 | BOT | [T/C] | TTGCATTCTCTCCTAGCACTCCAGTAAATAAAC TATAGTCCTGGTCAAGT | 15 | SEQ ID NO: 5 |
| 6 | rs7614867 | TOP | [A/G] | ATTCCCAATATTCGTATATGTATTTATAAATTA CATAATGGGCAGGGTGC | 3 | SEQ ID NO: 6 |
| 7 | rs920640 | BOT | [T/C] | AGTGCTTTTTGAGAGGTATGAACTTACTCCATA CTACTTACATCTGCTAA | 15 | SEQ ID NO: 7 |
| 8 | rs7167722 | BOT | [T/C] | TGACTTCTAATTACAGGCAAAATCAACCTTAAT AAGAACAGGCGTTACTA | 15 | SEQ ID NO: 8 |
| 9 | rs920638 | BOT | [T/C] | TACTATTCTGTTCATAAGGTACACTTCTTTTTA GGGCACACTACCTTGGG | 15 | SEQ ID NO: 9 |
| 10 | rs7165629 | BOT | [T/C] | AGGTGGGATAAACAGAAGCAGCATAACGTGTCT TGATGTGTGCTGTTTAG | 15 | SEQ ID NO: 10 |
| 11 | rs80049044 | BOT | [T/A] | TTGTCATGCAGCAGGTTAACTATGCTTTCTGGA GAAGGTGTCAGCCAACT | 4 | SEQ ID NO: 11 |
| 12 | rs16941058 | TOP | [A/G] | CCCTCCAGCTGAATGATTTTTGTCTGTGCCTGG CCCAGTCCCTGAGTCCA | 17 | SEQ ID NO: 12 |
| 13 | rs112015971 | TOP | [A/G] | GTGAAAATGCATTTTCCCCCTATTCCTTCTGGA AAGCAACATTAGGGTCC | 20 | SEQ ID NO: 13 |
| 14 | rs10894873 | BOT | [T/C] | TGCTCACCACAGTCCTCATATCCTTAAAGGGAC ACCCTAGTGATTACTGA | 11 | SEQ ID NO: 14 |
| 15 | rs117455294 | BOT | [T/G] | CAGTCCCGCCTGCTTGGATCTGACGAGCGTGCC GATTCGGTCCGAAAATC | 20 | SEQ ID NO: 15 |
| 16 | rs1170303 | BOT | [T/C] | AGAGCACTAACTCTGGAGAGTAAGGATCTGAGT GTAAGTCACCGCTGTGT | 4 | SEQ ID NO: 16 |
| 17 | rs16940681 | TOP | [C/G] | AAGCAGTCCACAGCAGTCTGAGCTGGCAGGTCA TGGAGCAGCCCCCAAAC | 17 | SEQ ID NO: 17 |
| 18 | rs968519 | BOT | [T/C] | GTAAAGAACAGGGGGAGATAATGATCAGTAAAA TCACAGCAGGGTGAGGG | 20 | SEQ ID NO: 18 |
| 19 | rs28381866 | BOT | [T/C] | TATTTAGGTAGTTGACCACTTCAGCATTCTAGG TACAATAACGTTAGCCC | 7 | SEQ ID NO: 19 |
| 20 | rs79320848 | BOT | [T/G] | AGAACAAAGCCAGGACAAGGTACAAGGTGACCC CAGCAAATTTCCTTTTC | 20 | SEQ ID NO: 20 |
| 21 | rs114653646 | BOT | [T/G] | TGCTAGAAGCTTATCAACTGCATTAATCTTTTT AAAAACACTTTTAGTTT | 7 | SEQ ID NO: 21 |
| 22 | rs2589496 | BOT | [T/C] | TCTCACCTTCTCCAGGTGCACGGTAGGTGCTGT GTAAATTAACGACTTCA | 17 | SEQ ID NO: 22 |
| 23 | rs10482650 | TOP | [A/G] | GCCTCCTGCTAGACAATTAGCTTTATCCATGAG TTACCAAAGAGGGAGCC | 5 | SEQ ID NO: 23 |
| 24 | rs17614642 | TOP | [A/G] | ACCAAAATCTATAAACAATAAGGAACTGTGGTT GTTTGCTGCAAATAACT | 6 | SEQ ID NO: 24 |
| 25 | rs73200317 | BOT | [T/C] | TCAAGAGTTGGGAATGATGAGGGCATGTACTGT GACTGGCACACAGAATG | 7 | SEQ ID NO: 25 |
| 26 | rs1380146 | BOT | [T/A] | AGTGccTAcTATGTGcTAGTcccTAGTGAcATG AGAGTGAGGAAGGCAGT | 12 | SEQ ID NO: 26 |

TABLE 2-continued

Polymorphism genotypes as used herein

| P_ID | rs_ID | Str | P | AlleleA Probe | Chr | TopGenomic Sequence |
|---|---|---|---|---|---|---|
| 27 | rs735164 | BOT | [T/C] | CCTTATTTCAAGGTCGGGGTCAAGGTGGTCAAA AGAACTGTTTTGCTCTC | 16 | SEQ ID NO: 27 |
| 28 | rs730976 | BOT | [T/G] | AAGGGTATTTATACCTTTGCCTTTCCGCCTCAA CCATTGGAACCTGGGAC | 5 | SEQ ID NO: 28 |
| 29 | rs55934524 | BOT | [T/G] | AGCCTCTCTGGGTCCTTGGGGAGCATGAGGATC CTGCAGAAAGCAGAGTG | 17 | SEQ ID NO: 29 |
| 30 | rs4570614 | TOP | [A/G] | ATGCTCTCTGAACACTATGACCTCTGATTATTT ATCAACCTCCAAGAGCT | 11 | SEQ ID NO: 30 |
| 31 | rs4458044 | TOP | [C/G] | CCCCTCTTCTGTGAGAGCCAAACAGAGCCCTTC CTGAGTCCCATCCATTC | 17 | SEQ ID NO: 31 |
| 32 | rs77850169 | TOP | [A/G] | TCTGGGTCCTTTTCATTGCTCTACAAAGAATCC TTTCTTCCTCCCAGGCC | 17 | SEQ ID NO: 32 |
| 33 | rs35339359 | TOP | [A/G] | CATCAATGCCCACGCTACACGAGGCATACTAGA CAGTCGCTGCCTAAGCC | 17 | SEQ ID NO: 33 |
| 34 | rs34800935 | BOT | [T/C] | TCAAGAGTAACAGTATGCCCTGCATTAACAGGG ATAATATATAAGAAAAA | 7 | SEQ ID NO: 34 |
| 35 | rs72945439 | BOT | [T/C] | GAATTTATTACTCCTGGGAGGATTCTGCTCACC ACTGGCAACTATGACCA | 2 | SEQ ID NO: 35 |
| 36 | rs113959523 | TOP | [A/G] | CATCATGATGTAATGTAGTCATATAGACTAGGA CACTTAGATTAGCCCCC | 20 | SEQ ID NO: 36 |
| 37 | rs116798177 | TOP | [A/G] | GGTTTTAGTATTGCAATGTGGAATCCAAAACTG TTATCAATGAACTTTTG | 5 | SEQ ID NO: 37 |
| 38 | rs11247577 | BOT | [T/G] | TGGGTGAGGGAACCGTTAGTGCCATCCTGAGGC CCCGTGTCAGGAAATAT | 17 | SEQ ID NO: 38 |
| 39 | rs75869266 | BOT | [T/C] | ACTGAACTCCCCATCACAAATCTGTATGCTTTA TTAGAAAGTAAAACTCT | 15 | SEQ ID NO: 39 |
| 40 | rs74372553 | BOT | [T/C] | AGTAAAACAGACGACGGGATCCCCAGACGCTGC ACATCAGCACCAGGAGC | 17 | SEQ ID NO: 40 |
| 41 | rs11691508 | TOP | [A/G] | CACACTAATATTCAAACATCCTTGACCTCATCT CATATAAATAAATCCAA | 2 | SEQ ID NO: 41 |
| 42 | rs6493965 | TOP | [A/G] | CCAAGATTCTGGATGTCTTTAAGGTAACAAGTG TCCATGTTGTTCCTTGA | 15 | SEQ ID NO: 42 |
| 43 | rs4869476 | BOT | [T/C] | GAAGCGAAAATAGCTATGCACCAAATCTCTGCA GGCATTTCATTGAGTAC | 5 | SEQ ID NO: 43 |
| 44 | rs3730170 | BOT | [T/C] | TGAATGACAGTGTTGTTGATTAGTTCAAGCTCT TGCCTTTCTCTAAACTT | 20 | SEQ ID NO: 44 |
| 45 | rs2145288 | TOP | [A/C] | GATCTTAGCCAAGGCAGGAAAGCACACGATCAG GTAACCTCCAGATTCAC | 20 | SEQ ID NO: 45 |
| 46 | rs2935752 | TOP | [A/C] | TTACTCGCATTAACTCTTTCAATTTCACAACAA ATCTAAGAAAAAATGCAA | 8 | SEQ ID NO: 46 |
| 47 | rs146512400 | TOP | [A/G] | AGTCTAAAACACTATCATCTCCTCCTGGATTAC TGCAACAGACTCCTTCT | 7 | SEQ ID NO: 47 |
| 48 | rs62057097 | BOT | [T/C] | TCTGCCCTAAATATTCCCTGTTCGGTGGGGTTT GGCGGTCCAGCAGCCCT | 17 | SEQ ID NO: 48 |
| 49 | rs115061314 | BOT | [T/C] | CCATGCGTGTTGGAAGTATTTCTCTTGTTCTCC TGCTTTTAGAAAGCCAT | 6 | SEQ ID NO: 49 |
| 50 | rs34113594 | BOT | [T/G] | CTTCTGACCCTCGCCGTCCTAGAACCAACGGCC CCTCGGTGTCTGGTCCT | 17 | SEQ ID NO: 50 |
| 51 | rs61751173 | TOP | [A/G] | AAAGCTCTAATACCACCTAAAACCATTTCTGTT CTCTACCTCTGTCATTA | 5 | SEQ ID NO: 51 |

TABLE 2-continued

Polymorphism genotypes as used herein

| P_ID | rs_ID | Str | P | AlleleA Probe | Chr | TopGenomic Sequence |
|---|---|---|---|---|---|---|
| 52 | rs74338736 | TOP | [A/C] | ACAGGTTCTATATCTTTAGATGGTAAATTAAAA ATTCCTGGCTGAATTTG | 20 | SEQ ID NO: 52 |
| 53 | rs10851726 | BOT | [T/C] | AATGTGAGTAGATTCCAACCTTTATCCATTCCA TTCACATTTACCTTCTC | 15 | SEQ ID NO: 53 |
| 54 | rs4610906 | BOT | [T/C] | TTGTTTAAAGCTGCTGCAGGTATACTCTTTGGA GGCTAATAATAAAGAAC | X | SEQ ID NO: 54 |
| 55 | rs59485211 | BOT | [T/C] | TGGAGTAGTCTTCTTCTAGCCCTTGCATGACCT CTCTTACTTCACCCATA | X | SEQ ID NO: 55 |
| 56 | rs7060015 | BOT | [T/G] | CTTCCACCTGCTGCACTCCAATATAGCCACTAT GTTCGGCTATATATATA | X | SEQ ID NO: 56 |
| 57 | rs75710780 | BOT | [T/G] | TAGAGAGTAATGTGGTGGGTGTGCTGTGTCAGA AAGGCTTCACTAGCAGT | 6 | SEQ ID NO: 57 |
| 58 | rs6520908 | BOT | [T/C] | CTAATTTGATCAATGAATCACTGCTAGCATGTG AATGTCCATAATGGATA | X | SEQ ID NO: 58 |
| 59 | rs487011 | BOT | [T/G] | TTATTAGAGGTAAACATAGAGATAAGCCCCTAA TAAAATAGTAGCTGGAG | X | SEQ ID NO: 59 |
| 60 | rs1383699 | TOP | [A/C] | AGTGTTAATTCTCTAAGAGGAAAATGTCATTTC TCCAAAACAAAACTTTA | 4 | SEQ ID NO: 60 |
| 61 | rs67516871 | TOP | [A/G] | GTAACAAGGTTACCTCCAGAAAAAAAGGCTATT GCTGAACAGAGGCTTTC | X | SEQ ID NO: 61 |
| 62 | rs114106519 | BOT | [T/C] | AAGAGAGAAAAATATTTTTAAGTGAAAAGGAAC AAAACTATTCTATACGA | 7 | SEQ ID NO: 62 |
| 63 | rs7220091 | TOP | [A/G] | GGCTCACACCGAGATCAATCCATGATGACAGCA CTTCATGGCCCGTCTCA | 17 | SEQ ID NO: 63 |
| 64 | rs12489026 | TOP | [A/G] | GATAATCTAATTCATCTAACTTGCTTTACAAAT GAGGAAACTGATAATCC | 3 | SEQ ID NO: 64 |
| 65 | rs876270 | BOT | [T/C] | GTGGACCCTTTGAGTGGTTACAGACGGGCCTCA GGATTGGTGTTATTTAA | 12 | SEQ ID NO: 65 |
| 66 | rs4968161 | BOT | [T/C] | AACAGGGGCCACTGTCTGTTTCCCATGGTATCT ATAGGGCCTGGTGGACA | 17 | SEQ ID NO: 66 |
| 67 | rs62056907 | TOP | [A/G] | AGGGGTCAAGATACAAGGAGTCACCAAAGAATG CAGAAGAGACAAGTTCA | 17 | SEQ ID NO: 67 |
| 68 | rs2235013 | BOT | [T/C] | CCTTTTCTAAGACCAATATTAACAAGAATTAGT AGTAGAATGTTCTTATG | 7 | SEQ ID NO: 68 |
| 69 | rs16878812 | TOP | [A/G] | TGTTGCTAATCCCAACCAGCATGATTTACGGGA AGTAAATCATCTATGAC | 6 | SEQ ID NO: 69 |
| 70 | rs6549407 | TOP | [A/G] | GCCTGTCTCACAAACATTGGGTTCTATAGACGC TCCTAGATTGCATTTTC | 3 | SEQ ID NO: 70 |
| 71 | rs28381848 | TOP | [A/G] | CCCAGTGCCTTGACAGGGTATGGGGGGACCTGC ATGACTAGCATTAAATG | 7 | SEQ ID NO: 71 |
| 72 | rs79723704 | TOP | [A/C] | TAACCAGGGATCTGTGCGTTTTGCTATAATTCA GAAAGTAGCAGACTACT | 20 | SEQ ID NO: 72 |
| 73 | rs72814052 | TOP | [A/G] | AAAAGTCGGTTCGAGAACCCAGGTGGAAAATAG ATTGAGGGAAGCAAAAC | 17 | SEQ ID NO: 73 |
| 74 | rs10152908 | BOT | [T/C] | GAGTAAGAGTTAATCACTTCCACTGTGCACTTG TTTATTCCAAGTAGAAA | 15 | SEQ ID NO: 74 |
| 75 | rs172769 | TOP | [A/C] | CTCTGGACATCTTCAGAGGGTCCCACTTTAGAC TTCACTGATCTCTTTTT | 2 | SEQ ID NO: 75 |
| 76 | rs78596668 | BOT | [T/C] | TCACACTTTACATTTATTATTTCCAGTAAGGGA TATAGCTAAGATAGTTA | 6 | SEQ ID NO: 76 |

TABLE 2-continued

Polymorphism genotypes as used herein

| P_ID | rs_ID | Str | P | AlleleA Probe | Chr | TopGenomic Sequence |
|---|---|---|---|---|---|---|
| 77 | rs73307922 | BOT | [T/C] | CAGTTTGATGAATGGCAAAATCGTTCAAATGGA AAAGAGGAGAGAGATAG | 20 | SEQ ID NO: 77 |
| 78 | rs3842 | TOP | [A/G] | TTCGTAATTAAAGGAACAGAGTGAGAGACATCA TCAAGTGGAGAGAAATC | 7 | SEQ ID NO: 78 |
| 79 | rs7210584 | TOP | [A/C] | AGCCAGGGTTGAAGTCACTCACGGGTCCTCTCC GAGAACTCGAGTGGTGA | 17 | SEQ ID NO: 79 |
| 80 | rs62402121 | BOT | [T/C] | CAAAGGTGATATGCATTTTAAATTTGATAGTTA TTGCCCAACTGTCTTTA | 6 | SEQ ID NO: 80 |
| 81 | rs55709291 | TOP | [A/G] | CCCTCAGGCTGCTTGTTACCGTGGAAGCTTCCT GAACTCTCTCCAGACCC | 17 | SEQ ID NO: 81 |
| 82 | rs72747088 | TOP | [A/G] | TTTTCATTTTTCTCTTCCCAACCCAATCCCCTC TCTCTAAATCTTGGTAT | 15 | SEQ ID NO: 82 |
| 83 | rs929610 | BOT | [G/C] | TTCAATATATGTTTTCTGAACACCTTCTGTGTT CAAGGCACCATGCTGGG | 14 | SEQ ID NO: 83 |
| 84 | rs6766242 | BOT | [T/C] | CCCTTGCATGTTCACCTTGTTATGTGTACTTTC ATCTCAATTGCCAGTTA | 3 | SEQ ID NO: 84 |
| 85 | rs1468552 | BOT | [G/C] | AAAGTATCTCCCCAAATCATTCCCAAACACTAC AAAGGTAGTGCCATCAG | 16 | SEQ ID NO: 85 |
| 86 | rs78838114 | BOT | [T/C] | TGCTCTAAAACTAATTTGCTTGAAGTGTACAGA ATGGAATTCGGGAAGGA | 15 | SEQ ID NO: 86 |
| 87 | rs62489862 | BOT | [T/C] | ATCACTTTTCCATGAAATTGTCTTTGCATTAGC AAAATGAATCAAGCATA | 7 | SEQ ID NO: 87 |
| 88 | rs894342 | TOP | [A/G] | TTGGTGATGCTGATAGTTGGAGATACCCAGACA GATAAGGTATATTGCCC | 15 | SEQ ID NO: 88 |
| 89 | rs58882373 | BOT | [T/C] | ATCAATATGACTGGTGTCCTTCAGGAATGTGGT AGCACAGTGAAAAAGGT | 3 | SEQ ID NO: 89 |
| 90 | rs3811939 | TOP | [A/G] | GCAGTAGGGGACTGGCTGCCGAGGGGGCATCTA GATTGAGATAGGTGGGA | 5 | SEQ ID NO: 90 |
| 91 | rs6984688 | BOT | [T/G] | ATTGGCAAAAGTGCTCATTCTGGAAAAACAAAG AAGTGAGAAAGTGGATG | 8 | SEQ ID NO: 91 |
| 92 | rs1018160 | BOT | [T/C] | ATTCTAAAGCTTTGTGTGGTCCACCATGATCAC CTTTTCCTGCTTCCCCC | 5 | SEQ ID NO: 92 |
| 93 | rs76602912 | TOP | [A/G] | GCTCCATTTTCTTTGAGGTACATCAACATCAAT AACAGATCAATGGACCC | 20 | SEQ ID NO: 93 |
| 94 | rs80067508 | TOP | [A/G] | AGCCTGACCTCATGGCTTAGCTGTGCCTCCTGG ACACCATCCCTCTCTGC | 17 | SEQ ID NO: 94 |
| 95 | rs74888440 | BOT | [T/C] | TTCTGAAAGTCACAGCCCAGGGATTCAGACCCA CTAAAAAAAACTGAGAT | 5 | SEQ ID NO: 95 |
| 96 | rs12481583 | BOT | [T/C] | ACTACATTACATCATGATGTATTGATTGCCTCT GGCCTAGGAATCTGCAG | 20 | SEQ ID NO: 96 |
| 97 | rs66794218 | TOP | [A/G] | CCACTCATATGTCTGTTCTCACTCAGAGGTGAG GCCCTGTGTCTTCAGCC | 17 | SEQ ID NO: 97 |
| 98 | rs16946701 | TOP | [A/G] | GGGGGACAGAGAAGTAACGTCACAAGATTTTAA GCTTGGGCCAGATATGG | 15 | SEQ ID NO: 98 |
| 99 | rs75726724 | TOP | [A/G] | AAGTAGAGCAGAAAGGGCAAGCAGAGAACTAGA CAGAGAAGACAGATGAC | 15 | SEQ ID NO: 99 |
| 100 | rs67959715 | BOT | [T/A] | TGGCTGCCTCTAGGGCAAGAAGACTGGGGATAT CACCATGGGCTCAATGT | 13 | SEQ ID NO: 100 |
| 101 | rs11871392 | BOT | [T/G] | CCAAGTCCTTCTACCTCCCTGGGTGAGGGAACC GTTAGTGCCATCCTGAG | 17 | SEQ ID NO: 101 |

TABLE 2-continued

Polymorphism genotypes as used herein

| P_ID | rs_ID | Str | P | AlleleA Probe | Chr | TopGenomic Sequence |
|---|---|---|---|---|---|---|
| 102 | rs2044070 | TOP | [A/G] | AATCTTGGGGAATCTGAGTTTATTAGAGGAATG TAGGGAGGAAGCAGGCT | 15 | SEQ ID NO: 102 |
| 103 | rs77612799 | BOT | [T/C] | TATCATATGCTCTAGTGACTTCATCAAGACAGT CTAAAGGAAGATGGGCC | 6 | SEQ ID NO: 103 |
| 104 | rs6743702 | BOT | [T/C] | CAGAAACACCTTTAATGTTTTTATTTCTATGAA TATTCTCCTAATGATTA | 2 | SEQ ID NO: 104 |
| 105 | rs616870 | BOT | [T/C] | TTAAAATGAGATCCCTTCCAACATGCTTTGCTG AGCCAGATTTATAAAAT | 3 | SEQ ID NO: 105 |
| 106 | rs79590198 | TOP | [A/G] | TAGTACAGTAAGGGCAAAGGGCACTGCAATTGC TATTAAACTGTAAGAAG | 5 | SEQ ID NO: 106 |
| 107 | rs75715199 | TOP | [A/G] | ATCCCCCGGAACTGGGGGAATTTCCAGGCACAT GAGGCTCTGTCAACCCA | 17 | SEQ ID NO: 107 |
| 108 | rs13087555 | BOT | [T/C] | AGCCACTTAAAATAAATTTTTCCAGCAGTTATT CATTTAGTGCCAAAATA | 3 | SEQ ID NO: 108 |
| 109 | rs4869618 | BOT | [T/C] | GCAGGGGCACATGCAATTGCCATTTAAAAATGA GGTCTGGCATGGCCAGA | 5 | SEQ ID NO: 109 |
| 110 | rs117397046 | TOP | [A/G] | GTACCACAGCTCCCAGCTGCATGTACTTTAAAA ATGTGTCTAAGCCAGGC | 17 | SEQ ID NO: 110 |
| 111 | rs8042817 | TOP | [A/G] | TGCAAACAGAAAAATCAGAACCTGCTCATGCTG CCATATTAATAGGAACC | 15 | SEQ ID NO: 111 |
| 112 | rs2258097 | BOT | [T/C] | TAACTACACACTCAAGGCTCCCTCTCAAAGTCT CAAACCTTACAACTTCC | 17 | SEQ ID NO: 112 |
| 113 | rs2260882 | TOP | [C/G] | AATACAGCCATGCGCTACCTACTGGCATTCCCG TCAGTGCGTACACGATC | 17 | SEQ ID NO: 113 |
| 114 | rs532996 | TOP | [A/G] | AACTGCTTTCCTCATTGGCTTGGTCTCCATAGT GATTCATTTTGCTGTAA | 13 | SEQ ID NO: 114 |
| 115 | rs11747040 | BOT | [T/C] | TGGAAATTTTTTTGTAATTAGAAATGACCTAAA GGATAGTTTCTATTCTT | 5 | SEQ ID NO: 115 |
| 116 | rs10034039 | BOT | [T/G] | ATTGATTTTTATGTCAGCAATCTTCCAATCTTG TTAATTCTAAAATACTT | 4 | SEQ ID NO: 116 |
| 117 | rs116909369 | TOP | [A/G] | GCCTAAGCTGAACCTGAGAGGTGAGGAAAACAG ACCAAGCTGACCAAACC | 17 | SEQ ID NO: 117 |
| 118 | rs79134986 | TOP | [A/G] | GCGAACTGTGGAGTATCTCAGTAAGAGTGTTAG GAGGAATATTTTATAGG | 6 | SEQ ID NO: 118 |
| 119 | rs117615688 | BOT | [T/C] | ACAACAACAAATCTCAAACAACTGTTCTGCCAA TGGGGTGGAGCACCTTT | 17 | SEQ ID NO: 119 |
| 120 | rs8032253 | BOT | [T/C] | TGATGATTTTCCAGCATGGCAATGGTAAAGCTG CAAATAAAAAGCAGCCA | 15 | SEQ ID NO: 120 |
| 121 | rs12818653 | BOT | [T/A] | TTCTTTTCTCCAAGCAAAAGAGAGAAGAGTTTA TTTCATTCTCAGCAGCT | 12 | SEQ ID NO: 121 |
| 122 | rs4587884 | TOP | [A/C] | GGCAAAAGCAGAGATGTGAGCTGTAAATTTGAA TGAAGGACCAGATAGAA | 14 | SEQ ID NO: 122 |
| 123 | rs77122853 | BOT | [T/C] | TAGGAACATAAAAGTTCAGATGTTAGTAGGACT AATAAAAAGTTATTGTT | 20 | SEQ ID NO: 123 |
| 124 | rs117615061 | BOT | [T/C] | TTTTTCAGGTCTAGCTTAACCAAAACACTTAAA ACTGTTACCAAAAAACT | 20 | SEQ ID NO: 124 |
| 125 | rs74682905 | TOP | [A/G] | CAAATAAATAAACTTTAAAGAAATGGCCAACTT GGGAAGGACATTAGGCC | 7 | SEQ ID NO: 125 |
| 126 | rs2257468 | BOT | [T/C] | CAGTCCAACAACCAGTTCCAGAAGATCTCAGAG GTAGGCCGCTCCCCACA | 17 | SEQ ID NO: 126 |

TABLE 2-continued

Polymorphism genotypes as used herein

| P_ID | rs_ID | Str | P | AlleleA Probe | Chr | TopGenomic Sequence |
|---|---|---|---|---|---|---|
| 127 | rs2032582 | BOT | [T/G] | TGAAAATGTTGTCTGGACAAGCACTGAAAGATA AGAAAGAACTAGAAGGT | 7 | SEQ ID NO: 127 |
| 128 | rs2235015 | BOT | [T/G] | GATTCATTTTTACATGTTTATTTTTAATGGAGA CTAAAGAGACATAAATG | 7 | SEQ ID NO: 128 |
| 129 | rs2729794 | BOT | [T/C] | TCTTGATTCAATTGGAAGTAACTGAGAGGTATA TCACATGTTGTGATTCA | 15 | SEQ ID NO: 129 |
| 130 | rs77549514 | TOP | [A/G] | TGCTCCATAACACAAATAATTTCATTCTTCTTC CTTTCTTGCCGAGTAGT | 2 | SEQ ID NO: 130 |
| 131 | rs74790420 | TOP | [A/C] | ATGAGCAAGGAGGCCAAAACCCTGCGTGGACGG TCTGCTTCCCTGCCCTT | 17 | SEQ ID NO: 131 |
| 132 | rs73129579 | BOT | [T/C] | GAGTGCCAAATATGTGCCCTTCCCCGTGGGGAA GACAAAAGTATGAGACA | 20 | SEQ ID NO: 132 |
| 133 | rs12913346 | TOP | [A/C] | TATTTTTAGCAGCCTATGGATTCTAGGAGTGAC CCAGCTCCAGGGATAGG | 15 | SEQ ID NO: 133 |
| 134 | rs117560908 | BOT | [T/C] | CATGAGGAAAGGCTGCAACTTTGAGCTCCCTCT TTAGCTAGGGAGCCTCC | 17 | SEQ ID NO: 134 |
| 135 | rs72747091 | TOP | [A/G] | AGCATTAATGAAGCACAGGGCCTATCACGCAGT CAGGCTCAGTATAAGGT | 15 | SEQ ID NO: 135 |
| 136 | rs2935751 | TOP | [A/G] | CATACTCAAATTGATACACAGCCTTTGTCCTGA GTGTTTGTCTTCCAAAA | 8 | SEQ ID NO: 136 |
| 137 | rs4331446 | TOP | [A/G] | AGAGTAGTATTGCTTAAAAACTGCTCCAACCAC TTCTTAAACCTGAAACC | 2 | SEQ ID NO: 137 |
| 138 | rs7523266 | BOT | [T/C] | TCGGCCAAAATCAGGGACAAGGATGACATGCCA TTGCTTACCAACTGCTA | 1 | SEQ ID NO: 138 |
| 139 | rs7648662 | BOT | [T/C] | CCGTTGTGCAAACTCCAGAAAGGGCATCTCTCT GTCCCACTCCCCCATTA | 3 | SEQ ID NO: 139 |
| 140 | rs117034065 | TOP | [A/G] | ATCTGCGTAAATTGCTGCATCTCTCTTGGCCTC AGTTTTCTTAGCCACAC | 15 | SEQ ID NO: 140 |
| 141 | rs4836256 | BOT | [T/C] | GTAAGTGCCAGCTACTATTATTTAGGAGGCTAA GGCTCTAGGTGATGAGG | 5 | SEQ ID NO: 141 |
| 142 | rs80238698 | BOT | [T/C] | TGCCACCCTATGGCATTCTTGTTGTGTAATGAA ATAACTCTCCTATGAAA | 7 | SEQ ID NO: 142 |
| 143 | rs3730173 | BOT | [T/C] | CTGCGCTTGCCCAGGAGGCCCTGGTCTGCACTG TTTATAGAGAAGAACCC | 20 | SEQ ID NO: 143 |
| 144 | rs11687884 | BOT | [T/C] | TTAGGAAAGTTCTGTACAGATATGTGTAATCCA GCATCTGTTTATCTATT | 2 | SEQ ID NO: 144 |
| 145 | rs72693005 | BOT | [T/C] | AATGATGGAAAAAACTGCAGCGCACGGTGGAAA TGTCTACTTTGTATGCA | 4 | SEQ ID NO: 145 |
| 146 | rs2589476 | BOT | [T/C] | CTCCTCATTATTCGCTTCTGCTGTAACTGCACC TATGGTAACCCAGGTGC | 17 | SEQ ID NO: 146 |
| 147 | rs9813396 | BOT | [T/C] | AAGTGCTCTGTAACCAAATATTTTGGAAATGCT GAGTTGTACCAAGTTGG | 3 | SEQ ID NO: 147 |
| 148 | rs10482667 | TOP | [A/G] | TTTTGAAATTTCCATTATATGCAAAGCCCATGA AAGGCTAAATATCAGTT | 5 | SEQ ID NO: 148 |
| 149 | rs72784444 | TOP | [A/G] | GTTTGTAAATGCACACTGTTGGGGGAACCCTCT TCCTAGTCCTTGTTTCC | 5 | SEQ ID NO: 149 |
| 150 | rs75074511 | BOT | [T/C] | TGGGCGAGAACTTATTCCTCAGGCCATTAGATT CCCTAATGCTGCACCTT | 17 | SEQ ID NO: 150 |
| 151 | rs7951003 | TOP | [A/G] | GCCATGGGCAAAAACAGCTCAGGTAGTAATGAA GGTGTGGCTATAGCTGA | 11 | SEQ ID NO: 151 |

TABLE 2-continued

| Polymorphism genotypes as used herein | | | | | | |
|---|---|---|---|---|---|---|
| P_ID | rs_ID | Str | P | AlleleA Probe | Chr | TopGenomic Sequence |
| 152 | rs79584784 | TOP | [A/G] | ACATCAAACTAAATTACATCATCAGAGTAAAGA GACAATTTACAAAAAGG | 7 | SEQ ID NO: 152 |
| 153 | rs2214102 | BOT | [T/C] | AAAAAGTTCTTCTTCTTTGCTCCTCCATTGCGG TCCCCTTCAAGATCCAT | 7 | SEQ ID NO: 153 |
| 154 | rs28811003 | TOP | [A/G] | CTGGCTCCAGGCAAAGAATACTACCAGCAACAA AGAGGAACATTTCAGAT | 15 | SEQ ID NO: 154 |
| 155 | rs6100261 | TOP | [A/T] | GGACTAGCCTGCTGCTTCATTTCCCCCCTCCTC TGCAGCCGATTTCAGAA | 20 | SEQ ID NO: 155 |
| 156 | rs77152456 | TOP | [A/G] | ATATTAGTAACCTGGAAAACATACATGGAGGTA TGTTCATTAACGGCAGT | 15 | SEQ ID NO: 156 |
| 157 | rs66624622 | BOT | [T/G] | ATGGGAAGAGCTGGATTTTTGTCGTGGAGTAAA GGAGAGGGAATCAAGAA | 5 | SEQ ID NO: 157 |
| 158 | rs140302965 | TOP | [A/G] | AAAATCATAGAAATTGTGTCTAAGGATATGCTT TGGGATATTTGGACTTC | 7 | SEQ ID NO: 158 |
| 159 | rs11653269 | BOT | [T/C] | CATAAACCAAAGGGATCTTCTCTACTCGTGCGT CCCTAGTCTCTCTCCCC | 17 | SEQ ID NO: 159 |
| 160 | rs74405057 | TOP | [A/G] | GCTGCCTGTACTAGTGATAGTGAGGCTCACTAC CATCCACCACCTAAATT | 20 | SEQ ID NO: 160 |
| 161 | rs7121 | TOP | [A/G] | GTGTAGCTTACGGGAGGGAAGTCAAAGTCAGGC ACGTTCATCACACTCAG | 20 | SEQ ID NO: 161 |
| 162 | rs16977818 | TOP | [A/C] | CTCATTGTAAGATTCAAAAACATTCCAGCTTAC AAAACATATCCAGCTTA | 15 | SEQ ID NO: 162 |
| 163 | rs12490095 | BOT | [T/C] | TTTGCAAGGCAATTTGTTCTACTGCTGGACAGC TTCATGTTTAATGTTTT | 3 | SEQ ID NO: 163 |
| 164 | rs118003903 | TOP | [A/G] | CTATATTTGAACAAGCTTCTGGGTAATATTTAT GACAGGGAAGTCTTGAG | 17 | SEQ ID NO: 164 |
| 165 | rs62377761 | BOT | [T/C] | CTGTGAACCAGGCACTGTTTGAAATGTTCCATT TATTGACTTATTTAAGT | 5 | SEQ ID NO: 165 |
| 166 | P1_M_061510_ 6_34_M | MINUS | [-/I*] | ACTACTACTAATGTTGAAAGTATACCATGTAAC AGGCACTGTACAAAGCC | 6 | SEQ ID NO: 166 |
| 167 | rs375115639 | MINUS | [-/I*] | TTTTGGGTTTTGTTGCTAGCATAAAAATTATTA CCTAGTGGATGGTAACA | 6 | SEQ ID NO: 167 |
| 168 | rs1002204 | TOP | [A/C] | TTTTTTTTTCATTTGAAGTAAATATCCACCTTT GTATCTAATTTTGCATT | 7 | SEQ ID NO: 168 |
| 169 | rs10062367 | TOP | [A/G] | TTATTTTTTAATAGTGTTCTTGCACATGAGGAG AAAGACTGAATTCAATT | 5 | SEQ ID NO: 169 |
| 170 | rs10482642 | TOP | [A/G] | CGTGTCACTTCGTTTGACTTCAGCTGGGAACAT GCATATCAGTCGACTCA | 5 | SEQ ID NO: 170 |
| 171 | rs10482658 | TOP | [A/G] | ATCGTCACACAGTTTTAAGACAAATGTTTTTAC CTATTTGACCTAGTCTG | 5 | SEQ ID NO: 171 |
| 172 | rs1053989 | TOP | [A/C] | TGTGCTACAAACCTGAAACTGGTAAGACAAGCA CAAAGCAACGTGCAATA | 5 | SEQ ID NO: 172 |
| 173 | rs10851628 | BOT | [T/C] | CTTGGATGGAGGCTCAGGGAGCCAAAGGCAAAT GTCTTCATAGAACCAGG | 15 | SEQ ID NO: 173 |
| 174 | rs10947562 | BOT | [T/C] | ATCATGAATTAAACAAATTAATTTATGTATTTT GTTTTGAGTCAGTGTCT | 6 | SEQ ID NO: 174 |
| 175 | rs11069612 | TOP | [A/G] | ACATGTGACCAACAAGATAATTATGAAACCTGA CTGCTGGATATGCTGAT | 13 | SEQ ID NO: 175 |
| 176 | rs11071351 | BOT | [T/C] | GTCTTTTGGAAAATGCAATCTGCCACTCTGTGC AATGGAAAACCACTGCA | 15 | SEQ ID NO: 176 |

TABLE 2-continued

Polymorphism genotypes as used herein

| P_ID | rs_ID | Str | P | AlleleA Probe | Chr | TopGenomic Sequence |
|---|---|---|---|---|---|---|
| 177 | rs11091175 | TOP | [A/G] | TTATTAATATTAGCCTTTCTTCTCTCCCCGTTT ATGCTTTGGTGGGTACT | X | SEQ ID NO: 177 |
| 178 | rs11638450 | BOT | [T/C] | TTTGGTTTGGGTTTTGTTTGGCAGAGGCAGAAT AGAATAAAGAACATGGG | 15 | SEQ ID NO: 178 |
| 179 | rs11715827 | BOT | [T/G] | AGAATTATTGCTGCACAATTCTTATGAAACCGA ACTAGAGCTACACTATT | 3 | SEQ ID NO: 179 |
| 180 | rs11745958 | BOT | [T/C] | CAGGCAGATCACTTGACGTGAGGAGTTCAAGTG AGGAGTTCAAGTCCAGC | 5 | SEQ ID NO: 180 |
| 181 | rs11834041 | TOP | [A/G] | ACAAACAAACTGAGGTTTAGGTTTAGGTAGCTG GAGTTTATAGGCATGGC | 12 | SEQ ID NO: 181 |
| 182 | rs1202180 | BOT | [T/C] | TCTGGAATAATAGTTACATTTGCTACATCCCTT TCTAGCGTCAACTCACT | 7 | SEQ ID NO: 182 |
| 183 | rs12054781 | TOP | [A/G] | CATAATGTGATGCCATATTAAACTGTAATCACC TTTCCACCAAACTAATA | 5 | SEQ ID NO: 183 |
| 184 | rs12539395 | TOP | [A/G] | CAAAATTCATATGTTGATACCTAATCTCCAAAG CAATAGTATTAAGGGTG | 7 | SEQ ID NO: 184 |
| 185 | rs12720066 | BOT | [T/G] | AATACTGTTTGGTATGGCAAGACAGTATTGGTT TTGGTTCAAGTGCTCCT | 7 | SEQ ID NO: 185 |
| 186 | rs1279754 | TOP | [A/C] | TTGGTTTTCCTGGGTGGGGAAGGGTGCTGGCCT CATTCACAACAGCAGAT | 5 | SEQ ID NO: 186 |
| 187 | rs12872047 | BOT | [T/C] | GGGAAAGACAGAGTGAGAGAAAGAGAGAGTTAG CCTCTACATATTATAAG | 13 | SEQ ID NO: 187 |
| 188 | rs12876742 | TOP | [A/C] | GCAGAGAGAGCCCTGTCTCAAAACAGATTTCTG AGTGTGGCTTCTGTCCA | 13 | SEQ ID NO: 188 |
| 189 | rs12917505 | TOP | [A/G] | TCTCGTAGCTGAGAGAGTCATGACTATGGCGTG TTCTCTGTACTCTGAGG | 15 | SEQ ID NO: 189 |
| 190 | rs13066950 | BOT | [T/G] | CTCAAGCAGAAGGAATCTCTCCCCATAGCCGCT ATAGTTTCAAATGTGCT | 3 | SEQ ID NO: 190 |
| 191 | rs13229143 | TOP | [C/G] | GTGAGGATAGGTAGCTTTTCTTACTCACTGTTG TTACCAGTACCTAGAAC | 7 | SEQ ID NO: 191 |
| 192 | rs1383707 | BOT | [T/C] | ACGAGCTTGTCATTCTGTAAATGACATATTCAT ATTCTTGGTATTGTACA | 4 | SEQ ID NO: 192 |
| 193 | rs1441824 | BOT | [T/C] | CAAGGTTAAAATTCCCGCATTGTGGGCCTTGTA GCTTTCATGTCTTAATG | 15 | SEQ ID NO: 193 |
| 194 | rs1652311 | TOP | [A/G] | GGATTTTGGCCATTCTAAGAGATGTGCAGTAGT AACTCAGTGTTTTATTT | 2 | SEQ ID NO: 194 |
| 195 | rs17064 | BOT | [T/A] | CTGAAGACTCTGAACTTGACTGAGGAAATGTTA AACAGATACCTCTTCAT | 7 | SEQ ID NO: 195 |
| 196 | rs17100236 | TOP | [A/G] | AACATTCCATTATCCTATTGTTCATTCTTTGGA GCTGTGATTTGTTTAAT | 5 | SEQ ID NO: 196 |
| 197 | rs17149699 | TOP | [A/G] | AGCTTCGGTGAATATTAGAATGGCCTCAAGAGC TAGTAAAAAACACAGCC | 7 | SEQ ID NO: 197 |
| 198 | rs1724386 | TOP | [A/G] | AGGCATATGGGGAAAAAATAAGGCAGGAAAGGA AGACGGAAAATGCTGTG | 17 | SEQ ID NO: 198 |
| 199 | rs17250255 | TOP | [A/G] | TTGGTTTTATAAAGGATCTAAGTGTTTGGAAAG GTGTGGGACCATGTACT | 7 | SEQ ID NO: 199 |
| 200 | rs17327624 | BOT | [T/G] | ACATGCTCTGCATGCTTTGACAGTACAGTGTAT AGAATAGACACAAAACT | 7 | SEQ ID NO: 200 |
| 201 | rs17616338 | TOP | [A/G] | TAAGGTTGTATCATCTACCTGTAGTCACTGCAG TCAGCTGAATTTTACCA | 4 | SEQ ID NO: 201 |

TABLE 2-continued

Polymorphism genotypes as used herein

| P_ID | rs_ID | Str | P | AlleleA Probe | Chr | TopGenomic Sequence |
|---|---|---|---|---|---|---|
| 202 | rs17687796 | TOP | [A/G] | CTCTGTAGCCACACAGATGCCAACAGCTGGCAC TTGTCCAAGAAACATGT | 17 | SEQ ID NO: 202 |
| 203 | rs17740874 | BOT | [T/C] | AGAATGGGTCACTTGTTAGAAACAGTCAAGGAT ACATACAAACAGTGGAA | 2 | SEQ ID NO: 203 |
| 204 | rs17763104 | BOT | [T/C] | CCAAGAGTGGTGAAGCCTTCCTGTTTACAGAGG ATTTTCATATCTGTTAT | 17 | SEQ ID NO: 204 |
| 205 | rs1880748 | BOT | [T/C] | ACACCCATGGGGCCAAGCCAGGAGCAGTCACCA CAGCCAACCTGCAGGCT | 17 | SEQ ID NO: 205 |
| 206 | rs1882478 | TOP | [A/G] | TATTCTAAGGAAGTGCCCCCTAAAACAAAGCTC AGGAGCCTCAACCCGGC | 7 | SEQ ID NO: 206 |
| 207 | rs1944887 | BOT | [T/C] | TCCCAACATCAAAAGGCAAATTCTTGCCCCACT TTTACAGATGAGAGCGC | 11 | SEQ ID NO: 207 |
| 208 | rs2028629 | TOP | [A/G] | TACCATGGGAAACAGACAGTGGCCCCTGTTCTC AAGTGGCTTAGACTCTA | 17 | SEQ ID NO: 208 |
| 209 | rs2143404 | TOP | [A/G] | CTTATTGGCCCTAAGTAAATCTTAGGTTAGGTA GAGCTCAGTTCCCAGGG | 6 | SEQ ID NO: 209 |
| 210 | rs2173530 | BOT | [T/C] | GTATTTTTAGGAACATTCAGGAAAACAGGTAAA GGGTATTCAGGAATTCA | 13 | SEQ ID NO: 210 |
| 211 | rs220806 | BOT | [T/C] | GGCCTTCCTCACTCTGACGGTGAGTTCCAGAGG ACAGGGATTTGTGGTTG | 6 | SEQ ID NO: 211 |
| 212 | rs2235047 | TOP | [A/C] | TGGTTGCTAATTTCTCTTCACTTCTGGGAAACC AGCCCCTTATAAATCAA | 7 | SEQ ID NO: 212 |
| 213 | rs2242071 | TOP | [A/G] | AACACAGAGCAGTATGTACAGGACAGCGTTAGA ATATACCAGAGAACAAG | 2 | SEQ ID NO: 213 |
| 214 | rs2257474 | BOT | [T/C] | AAACACACCTGTCACCCACGACCCTGGCATAGG GCATCGTGAACCCATCA | 17 | SEQ ID NO: 214 |
| 215 | rs2295583 | TOP | [A/T] | ATAGTATTCTGTTCTTCAGGGAGTTGTGGGTTC GGATCTGTGCAAAGATA | 20 | SEQ ID NO: 215 |
| 216 | rs234629 | BOT | [T/C] | TAGGAATCAGGGAACTCTAGATGCGTCTAGCAG CTAGCCTGTGGCCTCGA | 20 | SEQ ID NO: 216 |
| 217 | rs234630 | TOP | [A/G] | TTCAAATTGCTTGATTAAAATGGCAAACAGTTT GAAAATTGTATACCTCT | 20 | SEQ ID NO: 217 |
| 218 | rs2436401 | TOP | [A/G] | GGATAATGGAAAAGGGGGTTTCTCCCAAGTAGA GAACTTAAACAGTGTGA | 5 | SEQ ID NO: 218 |
| 219 | rs258750 | BOT | [T/C] | CACCTAGTCATGTGTATATAAAATCACCATGTT ATTACAGAATTTAGTAA | 5 | SEQ ID NO: 219 |
| 220 | rs2589487 | BOT | [T/C] | CAATCTATTTTCCACCTGGGTTCTCGAACCGAC TTTTCCTCCCTCTCTTC | 17 | SEQ ID NO: 220 |
| 221 | rs28364018 | BOT | [T/G] | GGGTCTTCCTACGGGACTGCCTTAGACGTGCTG GGCTTTGGCCTCAGTGA | 8 | SEQ ID NO: 221 |
| 222 | rs28381774 | BOT | [T/C] | AGTTTTGGTTGGGGAGGACAATGCCAGGTTAAC AGACACTTAATATACAT | 7 | SEQ ID NO: 222 |
| 223 | rs28381784 | TOP | [A/G] | AAAGAGAGTGGAAGTACCAGGTGGGCAAAGTTT ACAATTTTAAGTAGGAT | 7 | SEQ ID NO: 223 |
| 224 | rs2963155 | TOP | [A/G] | ATGATTCTTTCCATGACACCTAGTGCCCTTCTC CATCTAGAGCTACCTCT | 5 | SEQ ID NO: 224 |
| 225 | rs3133622 | BOT | [T/G] | AAATGAACTCAGCAATGAAATGGAACAAGCTAT CCATACATGCAGCAATT | 8 | SEQ ID NO: 225 |
| 226 | rs32897 | BOT | [T/C] | CCATCATTGCCTGGCTGTTGAAGCAGTTCTTGA CATTTTAAAGTAATATG | 5 | SEQ ID NO: 226 |

TABLE 2-continued

Polymorphism genotypes as used herein

| P_ID | rs_ID | Str | P | AlleleA Probe | Chr | TopGenomic Sequence |
|---|---|---|---|---|---|---|
| 227 | rs33388 | TOP | [A/T] | TTGCTACAAGGAGGATTATGGGTGAAAGTCATGGATGGATTATGAGTTAA | 5 | SEQ ID NO: 227 |
| 228 | rs3730168 | BOT | [T/C] | GATGGACATCACTGAAATGTAGTTTTGCCTGAAGTGTGGTTTGGATGCTC | 20 | SEQ ID NO: 228 |
| 229 | rs3735833 | BOT | [T/G] | CTTGTTTGTGTATGATACATGAAGTAGAATTCATACAGCACAAGTACTTT | 8 | SEQ ID NO: 229 |
| 230 | rs3777747 | TOP | [A/G] | GAAATTCTCCATAATTTCTGATCCACTCTTACATTCCTCTCCTTTCCAGC | 6 | SEQ ID NO: 230 |
| 231 | rs3786066 | BOT | [T/C] | GGGGGCTGGGGGGAAGTCCCGGGACAGGTGCATGTCATCAACACGACTGT | 17 | SEQ ID NO: 231 |
| 232 | rs3798346 | BOT | [T/C] | AGATCTTTTCAGGCATAAAAGTTGTCAATAGGTTTTCATAAATTTCTAGG | 6 | SEQ ID NO: 232 |
| 233 | rs3822736 | TOP | [A/G] | CCCTTGCACAGGCACAGCTATAATTTTTGTCTCTCTTCTGTTGGAAAGGT | 5 | SEQ ID NO: 233 |
| 234 | rs389035 | BOT | [T/C] | GTGGTTTCTAATGATTTAATACCATCCCCCAGGGTGCTCTTCTTGTGATA | 2 | SEQ ID NO: 234 |
| 235 | rs3924144 | TOP | [A/G] | GAATATTGAAGGTAGCCAGAAAAGAAAAAAAGGCACATTGCATGCAGAGG | 2 | SEQ ID NO: 235 |
| 236 | rs4148737 | BOT | [T/C] | ATGGCAGTTCATTGCTTTACTATTTGGACATTTCAAACTGTCCCAAGGTG | 7 | SEQ ID NO: 236 |
| 237 | rs4148749 | BOT | [G/C] | TTTTTTCAAACCTTTAAACAACAGTCCCACTTGGATAAAGTCTGAGAGCG | 7 | SEQ ID NO: 237 |
| 238 | rs417968 | BOT | [T/C] | ATAGCCTAACTTTCCCCCCGAAGCTTCCCAAGCCCTCATGATATCTATTA | 17 | SEQ ID NO: 238 |
| 239 | rs4458144 | BOT | [T/C] | ACCTGAGAATTCTCACCCATCCAATTCTACTTGATATGGGATTCCTCTAA | 2 | SEQ ID NO: 239 |
| 240 | rs4515335 | BOT | [T/C] | AATGGGCATGATCTCACTCACATGGAACAGGATCTCTTTCCTTGTTAGCA | 5 | SEQ ID NO: 240 |
| 241 | rs4728699 | TOP | [A/G] | AGTCACAGAAACATAGCAAGCCCTTGAAATCAGGCTTTCTGACTTTGTCT | 7 | SEQ ID NO: 241 |
| 242 | rs4758040 | TOP | [A/G] | CACCTACACACATGCATGCACACACACATGGCCTCTCTCTCCAGGCTTCT | 11 | SEQ ID NO: 242 |
| 243 | rs4812040 | TOP | [A/G] | CGTACAGACCTGGTCCAAAAATTCCAATTTCATAGGTGTGGAGTTTTCAT | 20 | SEQ ID NO: 243 |
| 244 | rs4912650 | BOT | [T/G] | CAAACAACCACCACATCAAAATAATAGCAAAGACAACAACTAATACTAAT | 5 | SEQ ID NO: 244 |
| 245 | rs4957891 | BOT | [T/C] | ATAGTAAGTTTTAAAGTAAGAGGTCAGAAACATATGTTACTTTACAAACA | 5 | SEQ ID NO: 245 |
| 246 | rs5906392 | TOP | [A/G] | TTATGTAGCAGGTCCTGATGTAACAGAATTAAGATTGCAGGTGGGATTGG | X | SEQ ID NO: 246 |
| 247 | rs6026561 | BOT | [T/C] | TCCCTAGAACAGCAGGACCTGCGAAACTCTGAGGCCGCTTTGTGAGGTCC | 20 | SEQ ID NO: 247 |
| 248 | rs6026565 | BOT | [T/A] | TTGAAAAGAGAAACCCACAGGGCTTTCTGCTTAAATCCCTCGGACACAGT | 20 | SEQ ID NO: 248 |
| 249 | rs6026567 | TOP | [A/G] | TAAGGATGGGACCCCTACTGTCCATCTCAGGCTCAGCACTGCCTTGGGGC | 20 | SEQ ID NO: 249 |
| 250 | rs6026593 | TOP | [A/G] | CTTCTACATCTTAGCTCACCTGTCCTCACAAATAAACATCACTCTTGAAT | 20 | SEQ ID NO: 250 |
| 251 | rs6092704 | BOT | [T/G] | TTGTTGAAATGTGACCACGAACTAGGTCTTAACCTAGCAAATTCACAAAT | 20 | SEQ ID NO: 251 |

TABLE 2-continued

Polymorphism genotypes as used herein

| P_ID | rs_ID | Str | P | AlleleA Probe | Chr | TopGenomic Sequence |
|---|---|---|---|---|---|---|
| 252 | rs6100260 | TOP | [A/G] | CTTTCTAAACACTAGCAGCCCAGAATTCTCAGG CCACTTTTGGGCATTGT | 20 | SEQ ID NO: 252 |
| 253 | rs6128461 | BOT | [T/C] | GTCTATGAATTGGTGAATCAGCCAAGTGAATGC TTCAAAAACTGGGACTC | 20 | SEQ ID NO: 253 |
| 254 | rs6415328 | BOT | [T/C] | CCTCCTGAGATGAACATCGTGAGGAGTAAATAG AGATGCTATTCTCAGCT | 7 | SEQ ID NO: 254 |
| 255 | rs6610868 | BOT | [T/C] | AACTCCGATTAATCACTAGTTGTTCACACCAAA AACCCAAGTGCCATTAC | X | SEQ ID NO: 255 |
| 256 | rs6686061 | TOP | [A/C] | TCACCAAGTCTGGTTGTCCCAGTCTCCTATCTC TGTCTGTTCCTCTCCTC | 1 | SEQ ID NO: 256 |
| 257 | rs6730350 | BOT | [T/G] | ATGAGTTGGAATTGCATAATGGGTAGATGCTGA TGCTGGAGAACTTTGAG | 2 | SEQ ID NO: 257 |
| 258 | rs6746197 | BOT | [T/C] | GTCATTGACTCGACTATAATTTTCCAAACTACC TAAACGTGTTATATCAT | 2 | SEQ ID NO: 258 |
| 259 | rs6963426 | BOT | [T/C] | TGATGATTAGGAGTCTGATGGAGGAAAGTAATT TTAAAACAACTTAATGG | 7 | SEQ ID NO: 259 |
| 260 | rs7121326 | BOT | [T/C] | TGGGGTTTTATTTGCTTTTTTCCCAGTTTCTTA GATGTAAAGTTAGGTTA | 11 | SEQ ID NO: 260 |
| 261 | rs7721799 | TOP | [A/G] | GGAACTCTGACGCAATCCAGGGCCGAGGAAAAA TGATTAAAACCCAACAA | 5 | SEQ ID NO: 261 |
| 262 | rs7787082 | BOT | [T/C] | TACTGCAGTGAGTTCAAGTGTTGTACCTGCTTA AAATGCAGTGACACTAA | 7 | SEQ ID NO: 262 |
| 263 | rs7799592 | TOP | [A/C] | GGCAGAGGGAACAGCTTGTGCAAAGGCCCTGGG GCAGGCCAAGGGCAGAG | 7 | SEQ ID NO: 263 |
| 264 | rs796245 | BOT | [T/C] | AAAAGAGGATGGCTGGTTTATCTCAAGTAATCA GACATTTAATAATAATA | 2 | SEQ ID NO: 264 |
| 265 | rs809482 | TOP | [A/C] | GTGCTATTTTGTTGCTGTTAGGTCTATTTTCTT CATCTGTTATTTCGCAT | 2 | SEQ ID NO: 265 |
| 266 | rs8125112 | BOT | [T/C] | GCCTGGGGGAGCGGGGAATCGCTTTTCGCCGGC CTCCGCGTAACCTTGTT | 20 | SEQ ID NO: 266 |
| 267 | rs919196 | TOP | [A/G] | GGCTCAACGGAAGTGACCGTCCCACAGTTATGC AGCACTAAGTCAATGGC | 20 | SEQ ID NO: 267 |
| 268 | rs920750 | BOT | [T/C] | TTGTGACAGGTCCCAGCGTGAACACGCACGCCC TAGCCGGGCCCCAAACC | 17 | SEQ ID NO: 268 |
| 269 | rs9332385 | TOP | [A/G] | AAGGGGACCGCAATGGAGGAGCAAAGAAGAAGA ACTTTTTTAAACTGAAC | 7 | SEQ ID NO: 269 |
| 270 | rs930473 | BOT | [T/G] | GCTGACTTCTTGACTGCAGCCACAGGAAGGACT CAACCCAGGACCATCCA | 15 | SEQ ID NO: 270 |
| 271 | rs9324921 | TOP | [A/C] | AATTTTTCAATGGTAAACAGACCAGAGTTATTC TAAGAAATTATGAAAAG | 5 | SEQ ID NO: 271 |
| 272 | rs9348979 | TOP | [A/G] | AGGATTTCAAGACTTGCCTGAGCAACATAATGA GATGCCCTCTCTCAAAA | 6 | SEQ ID NO: 272 |
| 273 | rs9571939 | TOP | [A/C] | AGCAAGCAGAAAACAAACAACTTCATTAAAAAT GAGCAGAGGACCTGAAC | 13 | SEQ ID NO: 273 |
| 274 | rs9892359 | BOT | [T/C] | TTCTGAGACCTTCTTGCCCCTTTGTTTCTAAGC CCAGGGCCACAATTCCC | 17 | SEQ ID NO: 274 |

*[-/I*] designates an allelic deletion/insertion polymorphism as defined in the respective SEQ ID NOs: 166 and 167

Further useful combinations of more than one polymorphism genotype are disclosed in Tables 5, 6, and 7 below, which all refer to the consecutively numbered, internal polymorphism-identifier (P_ID) of Table 2 to specify the genotype identity.

For the purposes of the present invention, the one or more polymorphism genotypes described above may be represented, for instance, within a nucleic acid of a length of, e.g., 1 nt, 2 nt, 3 nt, 4 nt, 5 nt, 10 nt, 15 nt, 20 nt, 25 nt, 30 nt, 35 nt, 40 nt, 45 nt, 50 nt, 60 nt, 70 nt, 80 nt, 90 nt, 100 nt, 200 nt, 300 nt, 400 nt, 500 nt, 1000 nt, 2000 nt, or more or any length in between these lengths. The nucleic acid may be any nucleic acid molecule, e.g. a DNA molecule, e.g., a genomic DNA molecule or a cDNA molecule, an RNA molecule, or a derivative thereof. The one or more polymorphism genotypes may further be represented by translated forms of the nucleic acid, e.g. a peptide or protein, as long as the polymorphic modification leads to a corresponding modification of the peptide or protein. Corresponding information is readily available in the art, e.g., from databases such as the NCBI dbSNP repository or the NCBI Genbank.

The polymorphism genotypes as described herein may be present on both strands of genomic DNA or its derivatives, i.e. on the chromosomal/genomic 5'→3' strand and/or the chromosomal/genomic 3'→5' strand. For example, a polymorphism can be present on the 5'→3' strand as A, it is present on the 3'→5' strand as T and vice versa. Also the insertion or deletion of bases may be detected on both DNA strands, with correspondence as defined above. For analytic purposes, the strand identity may be defined, or fixed, or may be chosen at will, e.g. in dependence on factors such the availability of binding elements, GC-content etc. Furthermore, for more universally applicable designation, a polymorphism genotype may be defined on both strands at the same time, or using the commonly known designations, such as the "probe/target"-designation, the "plus (+)/minus (−)"-designation, the "TOP/BOT"-designation or the "forward/reverse"-designation, as described in Nelson et al., Trends Genet. 2012, 28(8):361-3, or Illumina Inc. "*TOP/BOT" Strand and "A/B" Allele—A guide to Illumina's method for determining Strand and Allele for the GOLDENGATE and INFINIUM Assays*", Technical Note, © 2006; illumina.com/documents/products/technotes/technote_topbot.pdf, both incorporated by reference herein in their entirety. For the sake of unambiguity in polymorphism genotype designation, e.g., the "TOP/BOT"-designation can be used to identify the polymorphism genotypes in Table 2 above. In the alternative, the probe sequence or the genomic flanking sequences can be used to identify the polymorphism genotypes in Table 2 above.

A "polymorphic site" or "polymorphic variant" as used herein relates to the position of a polymorphism or SNP as described herein within the genome or portion of a genome of a subject, or within a genetic element derived from the genome or portion of a genome of a subject.

"Linkage disequilibrium" as used herein refers to co-inheritance of two or more alleles at frequencies greater than would be expected from the separate frequencies of occurrence of each allele in the corresponding control population. The expected frequency of occurrence of two or more alleles that are inherited independently is the population frequency of the first allele multiplied by the population frequency of the second allele. Alleles or polymorphisms that co-occur at expected frequencies are said to be in linkage equilibrium. Polymorphisms in linkage disequilibrium with a polymorphism of Table 2 can be identified by methods known to one skilled in the art. For example, Devlin and Risch (Genomics 1995, 29(2):311-22; incorporated herein by reference in its entirety) provide guidance for determining the parameter delta (also referred to as "r") as a standard measure of the linkage disequilibrium. Gabriel et al. (Science 2002, 296 (5576):2225-9; incorporated herein by reference in its entirety) provides instructions for finding the maximal $r^2$ value in populations for disease gene mapping. Further, Carlson et al. (Am J Hum Genet 2004; 74(1):106-120) disclose methods for selecting and analyzing polymorphisms based on linkage disequilibrium for disease gene association mapping. Stoyanovich and Pe'er (Bioinformatics, 2008, 24(3):440-2; incorporated herein by reference in its entirety) show that polymorphisms in linkage disequilibrium with identified polymorphisms have virtually identical response profiles. Currently, several databases provide datasets that can be searched for polymorphisms in strong linkage disequilibrium, which can be accessed by the following addresses: 1000.genomes.org, hapmap.org, broadinsitute.org/mpg/snap. An example workflow for determining polymorphisms in linkage disequilibrium to a specific polymorphism is outlined in Uhr et al. (Neuron 2008, 57 (2): 203-9; incorporated herein by reference in its entirety). Preferably, the linkage disequilibrium referred to herein is strong linkage disequilibrium. "Strong linkage disequilibrium", as used herein, means that the polymorphism is in linkage disequilibrium with an $r^2$ higher than 0.7 or higher than 0.8 in the tested population or an ethnically close reference population with the identified polymorphism.

A "sample obtained from a subject" as used herein may be any sample any biological sample comprising a bodily fluid, cell, tissue, or fraction thereof, which includes analyte biomolecules of interest such as nucleic acids (e.g., DNA or RNA). For instance, the sample obtained from the subject can be a buccal sample, a blood sample, plasma, serum, semen, sputum, cerebral spinal fluid, tears, a tissue sample, a formalin-fixed, paraffin-embedded tissue sample, or a hair follicle. Such samples are routinely collected, processed, preserved and/or stored by methods well known in the art. A biological sample can be further fractionated, if desired, to a fraction containing particular cell types. If desired, a sample can be a combination of samples from a subject such as a combination of a tissue and fluid sample.

In some embodiments, the subject's nucleic acid or DNA is extracted, isolated, and/or purified from the sample by any method commonly known in the art prior to polymorphism and/or SNP genotyping analysis. The term "isolated nucleic acid molecule", as used herein, refers to a nucleic acid entity, e.g. DNA, RNA etc, being substantially free of other biological molecules, such as, proteins, lipids, carbohydrates, other nucleic acids or other material, such as cellular debris and growth media. Generally, the term "isolated" is not intended to refer to the complete absence of such material, or to the absence of water, buffers, or salts, unless they are present in amounts which substantially interfere with the methods of the present invention. In alternative embodiments, detection of one or more polymorphism genotypes may also be performed by using a non-extracted, non-isolated or non-purified sample. In some embodiments, DNA amplification by any suitable method known in the art is used prior to the detection of one or more polymorphism genotypes.

The term "detecting the presence or absence of one or more polymorphism/SNP genotypes" is used herein synonymously to a "polymorphism/SNP genotyping analysis" and refers to a step of determining in one or several patients the presence or absence of at least one polymorphism/SNP genotype, typically several polymorphism/SNP genotypes, or all polymorphism/SNP genotypes disclosed in Table 2, or, in some embodiments, all (known) polymorphism/SNP genotypes of the human genome, including endogenous and exogenous regions. In a preferred embodiment, the term refers to a step of determining in one or several patients the presence or absence of at least one polymorphism/SNP genotype selected from the group consisting of rs11715827 (T/G), rs2044070 (A/G), rs2028629 (A/G) and rs6026507 (A/G) as disclosed in Table 2, optionally in combination with one or more polymorphism/SNP genotypes selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2. In particular, detecting the presence or absence of one or more polymorphism genotypes as used herein may not be limited to the CRHR1 gene or to genes of the CRH pathway, but can encompass a genome-wide screening for polymorphism genotypes.

A detection step or polymorphism/SNP genotyping analysis can be performed by any suitable method known in the art. Such methods include, but are not limited to, PCR-related methods using polymorphism/SNP-specific primers and/or probes, a primer extension reaction, polymorphism/SNP microarrays analysis, sequencing analysis, mass spectrometry, 5'-nuclease assays, allele specific hybridization, high-throughput/multiplex variants of these techniques or combinations thereof, as described in the prior art, for example in Rampal, DNA Arrays: Methods and Protocols (Methods in Molecular Biology) 2010; Graham & Hill, DNA Sequencing Protocols (Methods in Molecular Biology) 2001; Schuster, Nat. Methods, 2008 and Brenner, Nat. Biotech., 2000; Mardis, Annu Rev Genomics Hum Genet., 2008, which are incorporated herein by reference. Genome-wide arrays can be purchased from different suppliers such as Illumina or Affymetrix. For primer selection, multiplexing and assay design, and the mass-extension for producing primer extension products the MassARRAY Assay Designer software may be used using the sequences presented in Table 2 as input. The MassARRAY Typer 3.4 software may be used for genotype calling.

For example, the presence or absence of a polymorphism genotype can be detected by determining the nucleotide sequence at the respective locus and may be carried out by allele-specific oligonucleotide (ASO)-dot blot analysis, primer extension assays, iPLEX polymorphism/SNP genotyping, dynamic allele-specific hybridization (DASH) genotyping, the use of molecular beacons, tetra primer ARMS PCR, a flap endonuclease invader assay, an oligonucleotide ligase assay, PCR-single strand conformation polymorphism (SSCP) analysis, quantitative real-time PCR assay, polymorphism/SNP microarray based analysis, restriction enzyme fragment length polymorphism (RFLP) analysis, targeted resequencing analysis and/or whole genome sequencing analysis. In some embodiments, any of the methods described herein can comprise the determination of the haplotype for two copies of the chromosome comprising the polymorphism genotypes identified herein.

In another example, genomic DNA isolated from a biological sample can be amplified using PCR as described above. The amplicons can be detectably-labeled during the amplification (e.g., using one or more detectably labeled dNTPs) or subsequent to the amplification. Following amplification and labeling, the detectably-labeled-amplicons are then contacted with a plurality of polynucleotides, containing one or more of a polynucleotide (e.g., an oligonucleotide) being capable of specifically hybridizing to a corresponding amplicon containing a specific polymorphism, and where the plurality contains many probe sets each corresponding to a different, specific polymorphism. Generally, the probe sets are bound to a solid support and the position of each probe set is predetermined on the solid support. The binding of a detectably-labeled amplicon to a corresponding probe of a probe set indicates the presence of a nucleic acid containing the polymorphism so amplified in the biological sample. Suitable conditions and methods for detecting a polymorphism or SNP using nucleic acid arrays are further described in, e.g., Lamy et al. (2006) Nucleic Acids Research 34(14):e100; European Patent Publication No. 1234058; U.S. Publication Nos. 2006/0008823 and 2003/0059813; and U.S. Pat. No. 6,410,231; the disclosures of each of which are incorporated herein by reference in their entirety.

In yet another example, MALDI-TOF (matrix-assisted laser desorption ionization time of flight) mass spectrometry on the Sequenom platform (San Diego, USA) may be used to detect one or more polymorphism genotypes.

Polynucleotides for use in detection of one or more of the polymorphism genotypes disclosed in Tables 2, 5, 6 or 7 are capable of specifically hybridizing to nucleic acids comprising said one or more polymorphism genotypes and can comprise the nucleic acid sequences of the polymorphism genotypes themselves, including up and/or downstream, flanking sequences, e.g., as hybridization polynucleotide probes or primers (e.g., for amplification or reverse transcription). "Capable of specifically hybridizing", as used herein, refers to capability of hybridization under stringent conditions in any one of the methods of detection involving hybridization disclosed herein, as known to one skilled in the art. In that sense, primers and probes useful in such detection methods are particular polynucleotides capable of specifically hybridizing.

Primers or probes should contain a sequence of sufficient length and complementarity to a corresponding polymorphism locus to specifically hybridize with that locus under suitable hybridization conditions. For example, the polymorphism probes can include at least one (e.g., at least two, at least three, at least four, at least five, at least six, at least seven, at least eight, at least nine, at least 10, at least 11, at least 12, at least 15, at least 20, at least 25, at least 30, at least 35, at least 40, at least 45, at least 50, or 55 or more) nucleotides 5' or 3' to the polymorphism of interest. The polymorphic site of each probe (i.e., the polymorphism region) is generally flanked on one or both sides by sequence that is common among the different alleles. In specific embodiments, the polynucleotides capable of specifically hybridizing to the polymorphism genotypes are selected from the group consisting of the polynucleotides disclosed as "AlleleA Probe" in Table 2. The term "primer" may denote an oligo- or polynucleotide that acts as an initiation point of nucleotide synthesis under conditions in which synthesis of a primer extension product complementary to a nucleic acid strand is induced. The term "probe" may denote an oligonucleotide that is capable of specifically hybridizing to a target nucleic acid under suitable conditions, e.g., stringent conditions suitable for allele-specific hybridization. Primers and probes can be designed such are suitable for discriminating between wild-type allele or mutated allele of the position of a polymorphism to be analyzed, as described, e.g., by Coleman, and Tsongalis, Molecular Diagnostics: For the Clinical Laboratorian, 2007; Weiner et al. Genetic Variation: A Laboratory Manual, 2010, which are incorporated herein by reference.

Any of the methods of detecting a polymorphism can, optionally, be performed in multiplex formats that allow for rapid preparation, processing, and analysis of multiple samples, see above.

The detected polymorphism genotypes may be represented by values 0, 1 or 2. The value "O" may indicate that the polymorphism is present on none of the two homologous chromosomes, or in no allele, or is absent. The value "1" may indicate that the polymorphism is present on one of the two homologous chromosomes, or in one allele, or that the polymorphism genotype is heterozygous. The value "2" may indicate that the polymorphism is present on both homologous chromosomes, or in both alleles, or that the polymorphism genotype is homozygous.

The term "predicting a treatment response from the presence or absence of the one or more polymorphism genotypes", as used herein, generally refers to a prediction step that provides a reasonably high prediction performance by associating the presence or absence of a polymorphism genotype with a treatment response. Similarly, the term "polymorphism genotype associated with a treatment response of a subject to treatment with a CRHR1 antagonist", as used herein, generally refers to a polymorphism genotype being predicted to be associated with a treatment response with a reasonably high prediction performance. Specifically, the predicting step may comprise determining whether the subject will respond, or has an increased likelihood of responding to the treatment with a CRHR1 antagonist; and/or (b) determining whether the subject will not respond, or has a decreased likelihood of responding to the treatment with a CRHR1 antagonist. This is generally achieved herein by associating the presence or absence of the one or more polymorphism genotypes as a variable with a value indicative for treatment response within an algorithm for predicting a treatment response to a treatment with a CRHR1 antagonist, which is commonly a computer-implemented algorithm. The evaluation of the performance of the algorithm may depend on the problem the algorithm is applied for. If the algorithm is used to identify patients that are likely to respond to treatment with CRHR1 antagonists, the performance is preferably expressed by a high accuracy and/or sensitivity and/or precision. If patients should be identified which are likely not to respond to the treatment with CRHR1 antagonists, specificity and/or negative predictive value can be statistical measures to describe the performance of the prediction algorithm. For optimizing the prediction performance of the method of predicting a treatment response, a step of determining and/or optimizing the algorithm by a machine-learning method in a first subset of the test set and testing the prediction performance in an second independent subset of the test set may be carried out and repeated based on different numbers and groups of polymorphism genotypes, until the desired prediction performance is reached. Specifically, the algorithm for predicting may comprise a classification function (also known as binary classification test), which can comprise one or more statistical analysis methods and/or machine learning methods which are available to one of skill in the art. Specifically, statistical analysis methods and/or machine learning methods to be used in the invention may be selected from the group consisting of artificial neural network learning, decision tree learning, decision tree forest learning, linear discriminant analysis, non-linear discriminant analysis, genetic expression programming, relevance vector machines, linear models, generalized linear models, generalized estimating equations, generalized linear mixed models, the elastic net, the lasso support vector machine learning, Bayesian network learning, probabilistic neural network learning, clustering, and regression analysis, e.g., as described and exemplified herein. Statistical methods and/or machine learning methods from the group mentioned above may exist in different variants, especially applying or not applying prior and posterior weights in the analysis leading to solutions which may be applicable in different settings and may lead to models with more or less explanatory variables. The results of single methods may be used in a method called "ENSEMBLE learning" in which the results of several single analysis with one of the methods mentioned above are combined to arrive at a better prediction using either simply majority vote or using one of the machine learning algorithms with the results of the single analyses again as input to that specific algorithm.

In an exemplary embodiment of the method of the invention, the number of minor alleles for both polymorphism rs74888440 (P1) and rs9813396 (P2) is coded as a numeric variable, which can take one of the following values: 0, 1 or 2, denoting the two variables thus created as V1 for rs74888440 and V2 for rs9813396. Each subject is designated a value of the predictive quantitative variable PQV such that PQV=0.3205619+(0.2923413*V1)+(0.2362708*V2)+(−0.0104643*V1*V2). Depending on whether a subject's PQV is above or below a value of 0.5, that person is then predicted to not to respond, or to have a decreased likelihood of responding to a treatment with a CRHR1 antagonist (if PQV<=0.5), or to respond, or to have an increased likelihood of responding to a treatment with a CRHR1 antagonist (if PQV>0.5). For example, a subject who has no minor alleles at either of the two polymorphisms (homozygous for the common allele at both loci, such that V1=V2=0) is designated a PQV of 0.3205619 and is consequently predicted to be a non-responder. In another example, a subject who is heterozygous at P1 (V1=1) and homozygous for P2 (V2=2) is then designated a PQV of (0.3205619)+(0.2923413*1)+(0.2362708*2)+(−0.0104643*1*2)=1.064516 and is, in consequence, predicted to be a responder. In this example, a sensitivity of 0.6285714 and a specificity of 0.6626506 is reached.

In another exemplary embodiment of the method of the invention, the number of minor alleles for both SNPs rs74888440 (P1) and rs220806 (P2) is coded as a numeric variable, which can take one of the following values: 0, 1 or 2, denoting the two variables thus created as V1 for rs74888440 and V2 for rs220806. Each subject is designated a value of the predictive quantitative variable PQV such that PQV=0.539548+(0.460452*V1)+(−0.1765537*V2)+(−0.1567797*V1*V2). Depending on whether a subject's PQV is above or below a value of 0.5, that subject is then predicted to not to respond, or to have a decreased likelihood of responding to a treatment with a CRHR1 antagonist (if PQV<=0.5), or to respond, or to have an increased likelihood of responding to a treatment with a CRHR1 antagonist (if PQV>0.5). For example, a subject who has no minor alleles at either of the two SNPs (homozygous for the common allele at both loci, such that V1=V2=0) is designated a PQV of 0.539548 and is consequently predicted to be a responder. In another example, a subject who is heterozygous at SNP1 (V1=1) and homozygous for SNP2 (V2=2) is then designated a PQV of (0.539548)+(0.460452*1)+(−0.1765537*2)+(−0.1567797*1*2)=0.3333333 and is, in consequence, predicted to be a non-responder. In this example, a sensitivity of 0.6857143 and a specificity of 0.626506 is reached.

In a similar manner, one of skill in the art, having the polymorphisms of Table 2 and the additional information above at hand, will readily derive suitable methods, combinations of methods, parameters and/or coefficients such as those exemplified herein, for use in the methods of the invention, achieving a high performance of prediction.

Preferably, the prediction of the treatment response is made with a high accuracy, sensitivity, precision, specificity and/or negative predictive value.

"Accuracy", "sensitivity", "precision", "specificity" and "negative predictive value" are exemplary statistical measure of the performance of the prediction algorithm. In the following, examples are given for determining the performance of the prediction algorithm.

As used herein, accuracy may be calculated as (number of true positives+number of true negatives)/(number of true positives+number of false positives+number of true negatives+number of false negatives), e.g., (number of patients correctly diagnosed as responding to CRHR1 antagonist+number of patients correctly diagnosed as not responding to CRHR1 antagonist)/(number of patients correctly diagnosed as responding to CRHR1 antagonist+number of patients wrongly diagnosed as responding to CRHR1 antagonist+number of patients correctly diagnosed as not responding to CRHR1 antagonist+number of patients wrongly diagnosed as not responding to CRHR1 antagonist). In some embodiments, the accuracy of prediction is higher than 50%, at least 60%, at least 70%, at least 80% or at least 90%.

As used herein, sensitivity may be calculated as (true positives)/(true positives+false negatives), e.g., (number of patients correctly diagnosed as responding to CRHR1 antagonist)/(number of patients correctly diagnosed as responding to CRHR1 antagonist+number of patients wrongly diagnosed as not responding to CRHR1 antagonist). In some embodiments, the sensitivity of prediction is higher than 50%, at least 60%, at least 70%, at least 80% or at least 90%.

As used herein, precision (also referred to as positive predictive value) may be calculated as (true positives)/(true positives+false positives), e.g.: (number of patients correctly diagnosed as responding to CRHR1 antagonist)/(number of patients correctly diagnosed as responding to CRHR1 antagonist+number of patients wrongly diagnosed as responding to CRHR1 antagonist). In some embodiments, the precision of prediction is higher than 50%, at least 60%, at least 70%, at least 80% or at least 90%.

As used herein, specificity is calculated as (true negatives)/(true negatives+false positives), e.g.: (number of patients correctly diagnosed as not responding to CRHR1 antagonist)/(number of patients correctly diagnosed as not responding to CRHR1 antagonist+number of patients wrongly diagnosed as responding to CRHR1 antagonist). In some embodiments, the specificity of prediction is higher than 50%, at least 60%, at least 70%, at least 80%, at least 85%, or at least 90%.

As used herein, negative predictive value is calculated as (true negatives)/(true negatives+false negatives), e.g.: (number of patients correctly diagnosed as not responding to CRHR1 antagonist)/(number of patients correctly diagnosed as not responding to CRHR1 antagonist+number of patients wrongly diagnosed as not responding to CRHR1 antagonist). In some embodiments, the negative predictive value is higher than 50%, at least 60%, at least 70%, at least 80% or at least 90%.

Other statistical measures useful for describing the performance of the prediction algorithm are geometric mean of sensitivity and specificity, geometric mean of positive predictive value and negative predictive value, F-measure and area under ROC curve, and the positive and negative likelihood ratios, the false discovery rate and Matthews correlation coefficient. These measures and method for their determination are well known in the art.

In general, a prediction algorithm with high sensitivity may have low specificity and vice versa. For the purposes of the present invention, it is generally preferable that the prediction algorithm is based on a number of polymorphism genotypes selected from Table 2 sufficient to achieve a sensitivity and specificity of higher than 50% each, optionally at least 60% each, at least 70% each, at least 80% each, or at least 90% each. In a preferred embodiment of the present invention, the prediction algorithm is based on a number of polymorphism genotypes selected from the group consisting of rs11715827 (T/G), rs2044070 (A/G), rs2028629 (A/G) and rs6026567 (A/G) from Table 2, optionally in combination with one or more polymorphism genotypes selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2 sufficient to achieve a sensitivity and specificity of higher than 50% each, optionally at least 60% each, at least 70% each, at least 80% each, or at least 90% each.

For a prediction whether a patient will respond, or has an increased likelihood of responding to a treatment with a CRHR1 antagonist, the prediction algorithm may be based on a number of polymorphisms sufficient to achieve a prediction sensitivity and/or precision of higher than 50%, optionally at least 60%, at least 70%, at least 80%, or at least 90%.

For the prediction whether the subject will not respond, or has a decreased likelihood of responding to a treatment with a CRHR1 antagonist, the prediction algorithm may be based on a number of polymorphisms sufficient to achieve a prediction specificity and/or negative predictive value of higher than 50%, optionally at least 60%, at least 70%, at least 80%, at least 85%, or at least 90%.

For a prediction whether a patient responds to a treatment with CRHR1 antagonists or not, the prediction algorithm may be based on a number of polymorphisms sufficient to achieve sensitivity and/or precision and/or specificity and/or negative predictive value of higher than 50%, optionally at least 60%, at least 70%, at least 80%, or at least 90%.

Based on the disclosure of the present invention, in particular of the highly useful set of polymorphism genotypes disclosed in Table 2, the skilled person in the art is enabled to employ the statistical analysis methods and/or machine-learning methods disclosed herein and to identify suitable parameters for further improving the prediction performance, as defined above. The whole statistical workflow can be automated by the use of an algorithm as described above, implemented and/or stored on a machine-readable medium, e.g., implemented and/or stored on a computer.

Typically, at least 1, at least 2, at least 3, at least 4, at least 5, at least 6, at least 7, at least 8, at least 9, at least 10, at least 19, at least 20, at least 30, at least 50, at least 100, at least 100, at least 200 or all polymorphism genotypes disclosed in Table 2 are used for predicting the treatment response to a CRHR1 antagonist. In a very preferred embodiment of the invention, at least 1, at least 2, at least 3 or at least 4 polymorphism genotypes selected from the group consisting of rs11715827 (T/G), rs2044076 (A/G), rs2028629 (A/G) and rs6026567 (A/G) as disclosed in Table 2 are used for predicting the treatment response to a CRHR1 antagonist, optionally in combination with at least 1, at least 2, at least 3, at least 4, at least 5, at least 6, at least 7, at least 8, at least 9, at least 10, at least 11, at least 12, at least 13, at least 14 or all polymorphism genotypes selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2

Using various such polymorphism genotype sets and statistical analysis methods as described above, the present invention consistently achieves a high predictive performance in directly predicting a clinical response. For instance, Example 1 describes a study with clinical data from 300 enrolled patients, wherein 150 polymorphism genotypes were used in a method for predicting the clinical treatment response of subjects to a treatment with a CRHR1 antagonist. Therein, a sensitivity of about 78% and a specificity of about 73% was observed, which is considered to reflect a superior reliability in predicting both true positive responses and true negative responses. Further, Example 2 provides examples of minimal subsets of only one, two, four or eight polymorphism genotypes selected from the group of polymorphism genotypes disclosed in Table 2, achieving a performance of predicting a clinical treatment response with values for specificity and sensitivity which are still higher than 60%, or even higher than 70%. Predictive performance in terms of sensitivity and specificity can be further increased to at least 75% each, e.g., by including specific combinations of 32 polymorphism genotypes, as is also shown in Example 2. Further, Example 3 describes an example of a specific set of the four polymorphism genotypes rs2028629 (A/G), rs6026567 (A/G), rs17715827 (T/G) and rs2044070 (A/G) selected from the group of polymorphism genotypes disclosed in Table 2, for which a particular high performance of predicting an outcome of clinical treatment response of subjects to a treatment with a CRHR1 antagonist, particularly SSR-125543, was observed. Predicted performance in terms of sensitivity and specificity was even increased by including to these four polymorphism genotypes combinations of at least one and preferably all polymorphism genotypes selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2, with values for sensitivity higher than 90% and values of specificity higher than 85%.

Furthermore, in patients with depressive symptoms and/or anxiety symptoms, another embodiment of the method for predicting a treatment response to CRHR1 antagonists, the method of predicting a treatment response as described above may be also accompanied by analyzing the rapid-eye-movement (REM) sleep, e.g. during night sleep of a patient in a sleep EEC. In some embodiments, an alteration in REM sleep may serve as an additional biomarker to identify subjects who would benefit from treatment with a CRHR1 antagonist. REM sleep typically comprises a characteristic coincidence of nearly complete muscle atonia, a waking-like pattern of brain oscillations and rapid eye movements (REMs). The amount of REMs during consecutive REM sleep episodes is usually increasing throughout the night. Single and short REMs with low amplitude can be characteristic for initial parts of REM sleep. The amount of REMs, in particular within the first REM sleep episode, can be of clinical relevance. Recent clinical and animal data supports the correlation of REM density with an increased CRH activity. For example, Kimura et al. (Mol. Psychiatry, 2010) showed that mice overexpressing CRH in the forebrain exhibit constantly increased rapid eye movement (REM) sleep compared to wildtype mice. In addition, it could be shown that treatment with the CRHR1 antagonist DMP696 could reverse the REM enhancement. Further, the polymorphism analysis and REM density analysis as described herein may be combined for predicting the response of patients with depressive symptoms and/or anxiety symptoms to treatment with a CRHR1 antagonist. The REM analysis may be carried out before, concomitant or after the polymorphism analysis. For example, the REM density analysis may be carried out on subjects that where identified by the polymorphism analysis as responding, or having an increased likelihood of responding to the treatment with a CRHR1 antagonist; or as not responding, or having a decreased likelihood of responding to the treatment with a CRHR1 antagonist. The recording of a “sleep-EEG” (also referred to “polysomatic recordings”) may comprise electroencephalography (EEG), vertical and horizontal electrooculugraphy (EOG), electromyography (EMG) and/or electrocardiogram EOG, muscle activities of right and left eye may be recorded by electrooculograms (one or typically two channels) in order to visualize the phasic components of REM sleep. “REM analysis” or “analyzing the rapid-eye-movement (REM)” may refer to a method comprising recoding of muscle activities of right and left eye by EOG and then analyzing the electrooculogram. The recognition of REM in the electrooculogram may be done manually, for example by standard guidelines Rechtschaffen and Kales, 1968, Bethesda, MD: National Institute of Neurological Diseases and Blindness, incorporated herein by reference in its entirety.

Methods of Treatment

In a further aspect, the present invention also provides methods of treating a condition treatable by treatment with a CRHR1 antagonist in a subject in need thereof, comprising administering an effective amount of a CRHR1 antagonist to a subject in need thereof, wherein the subject has been predicted to respond, or has an increased likelihood of responding, to treatment with a CRHR1 antagonist, as determined by the method described above, and wherein the CRHR1 antagonist is a compound of Formula I, as defined herein, or any one of “formulae I-VI” as disclosed at pages 2-6 and 12-48 of WO 2013/160317 (A2) (PCT/EP2013/058413). Likewise the invention features a CRHR1 antagonist for use in treating a condition treatable by treatment with a CRHR1 antagonist in a subject in need thereof, wherein the subject has been predicted to respond, or has an increased likelihood of responding, to treatment with a CRHR1 antagonist, as determined by the method described above, and wherein the CRHR1 antagonist is a compound of Formula I, as defined herein, or any one of “formulae I-VI” as disclosed at pages 2-6 and 12-48 of WO 2013/160317 (A2)(PCT/EP2013/058413).

Conditions which are treatable by a treatment with a CRHR1 antagonist are generally defined above. Specific conditions comprise, but are not limited to, behavioural disorders, psychiatric disorders, mood disorders, neurological disorders, neurodegenerative disorders, inflammatory or stress-induced immune disorders, CRH-related cardiovascular diseases or metabolic diseases. Specifically, such conditions comprise anxiety symptoms, generalized anxiety disorder, panic, phobias, obsessive-compulsive disorder, post-traumatic stress disorder, sleep disorders induced by stress, pain perception such as fibromyalgia, mood disorders such as depressive symptoms, including major depression, single episode depression, recurrent depression, child abuse induced depression, mood disorders associated with premenstrual syndrome, and postpartum depression, dysthymia, bipolar disorders, cyclothymia, chronic fatigue syndrome, stress-induced headache, eating disorders such as anorexia and bulimia nervosa, hemorrhagic stress, stress-induced psychotic episodes, euthyroid sick syndrome, syndrome of inappropriate antidiarrheic hormone (ADH), obesity, infertility, head traumas, spinal cord trauma, ischemic neuronal damage (e.g., cerebral ischemia such as cerebral hippocampal ischemia), excitotoxic neuronal damage, epilepsy, senile dementia of the Alzheimers type, multi-infarct dementia, amyotrophic lateral sclerosis, chemical dependencies and addictions (e.g., dependencies on alcohol, nicotine, cocaine, heroin, benzodiazepines, or other drugs), drug and alcohol withdrawal symptoms, hypertension, tachycardia, congestive heart failure, osteoporosis, premature birth, and hypoglycaemia, inflammatory disorders such as rheumatoid arthritis and osteoarthritis, pain, asthma, psoriasis and allergies, irritable bowel syndrome, Crohn's disease, spastic colon, post-operative ileus, ulcer, diarrhea, stress-induced fever, human immunodeficiency virus (HIV) infections, neurodegenerative diseases such as Alzheimer's disease, Parkinson's disease and Huntington's disease, gastrointestinal diseases, stroke, stress induced immune dysfunctions, muscular spasms, urinary incontinence. In a preferred embodiment, the condition is selected from the groups consisting of depressive symptoms, anxiety symptoms or both depressive symptoms and anxiety symptoms.

Any CRHR1 antagonist as generally defined by Formula I herein, or any one of "formulae I-VI" as disclosed at pages 2-6 and 12-48 of WO 2013/160317 (A2) (PCT/EP2013/058413) can be used in the method of treatment. In a specific embodiment of the method of treatment, the CRHR1 antagonist is selected from the group consisting of a Type I CRHR1 antagonist, a bicyclic Type II CRHR1 antagonist, an atypical CRHR1 antagonist or a cyclohexyl amide CRHR1 antagonist. In another specific embodiment of the method of treatment, the CRHR1 antagonist is selected from the group consisting of GW876008 (Emicerfont), GSK-561679 (NBI-77860, Verucerfont), GSK586529, BMS-562,086 (Pexacerfont), NBI-30775 (R-121919), NBI-34101, CP-316,311, CP-376,395, PF-00572778, NVP-AAG561, Ono-2333 MS, E2508, E2009, R317573 (JNJ19567470, CRA5626), R278995 (CRA0450), CRA-1000, CRA-1001, CP154,526, Antalarmin, DMP-695, DMP-696, DMP-904, SC-241, BMS-561388, NBI30545, PD-171729, NBI34041, NBI35965, SN003, NBI-27914, trans-2-chloro-N-(4-((5-fluoro-4-methyl-pyridin-2-ylamino)-methyl)-cyclohexyl)-5-(trifluoromethyl)-benzamide, or a pharmaceutically acceptable salt thereof. In one embodiment of the method of treatment, the CRHR1 antagonist is not SSR-125543.

It will be appreciated that reference to treatment is intended to include prevention as well as the partial alleviation, or full remission of symptoms.

CRHR1 antagonists may be administered as the raw chemical but the active ingredient is preferably formulated in a pharmaceutical composition suitable for administration by any convenient route, preferably in a form suitable for use in human medicine. The treatment can comprise any suitable route of administration, such as oral, buccal, parenteral, topical (including ophthalmic and nasal), depot or rectal administration or in a form suitable for administration by inhalation or insufflation (either through the mouth or nose) administration of the CRHR1 antagonist.

CRHR1 antagonists can be administered at any suitable efficacious dose, which one skilled in the art will readily adapt, e.g., to the specific condition to be treated. For many therapeutic indications as encompassed herein, a dose of about 1 mg to about 2000 mg per day, about 2 mg to about 1000 mg per day, about 5 mg to about 500 mg per day, about 10 mg to about 250 mg, or about 20 to about 100 mg daily will be efficacious. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected. Thus, for parenteral administration a daily dose will typically be in the range of 1 to about 100 mg, preferably 1 to 80 mg per day. For oral administration a daily dose will typically be within the range of 1 to 300 mg e.g. 1 to 100 mg of a CRHR1 antagonist. For instance, in treating depressive symptoms and/or anxiety symptoms, daily oral doses of about 10 mg, about 20 mg, or about 100 mg of a CRHR1 antagonist can be efficacious.

Compositions, Kits and Arrays and Uses Thereof

The disclosure further provides compositions comprising polynucleotides (e.g., probes), as well as kits and arrays. Polynucleotide compositions, kits, and arrays are useful in, e.g., detecting the presence of (a) one or more polymorphism genotypes as disclosed in Table 2, preferably one or more polymorphism genotypes selected from the group consisting of rs11715827 (T/G), rs2044070 (A/G), rs2028629 (A/G) and rs6026567 (A/G) as disclosed in Table 2, optionally in combination with one or more polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2. (b) one or more polymorphism genotypes being in linkage disequilibrium with any one of the polymorphism genotypes of (a), or a combination of (a) and (b). The compositions, kits and arrays are further useful for predicting the treatment response of a subject to treatment with a CRHR1 antagonist.

The compositions, kits or arrays can include at least one polynucleotide capable of specifically hybridizing to a nucleic acid comprising: (a) at least one polymorphism genotype as disclosed in Table 2; preferably one or more polymorphism genotypes selected from the group consisting of rs11715827 (T/G), rs2044070 (A/G), rs2028629 (A/G) and rs6026567 (A/G) as disclosed in Table 2, optionally in combination with one or more polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2. (b) at least one polymorphism genotype being in linkage disequilibrium with any one of the polymorphism genotypes of (a), or (c) a combination of (a) and (b). In one embodiment, the at least one polynucleotide comprises less than 100,000, less than 90,000, less than 80,000, less than 70,000, less than 60,000, less than 50,000, less than 40,000, less than 30,000, less than 20,000, less than 15,000, less than 10,000, less than 5,000, less than 4,000, less than 3,000, less than 2,000, less than 1,500, less than 1,000, less than 750, less than 500, less than 200, less than 100, or less than 50 different polynucleotides in total. Specifically, the compositions, kits or arrays can include at least two, at least three, at least four, at least five, at least six, at least seven, at least eight, at least nine, at least 10, at least 11, at least 12, at least 15, at least 20, or at least 30, or at least 50, or at least 100, or at least 200, or 274 polynucleotides capable of specifically hybridizing to each of at least two, at least three, at least four, at least five, at least six, at least seven, at least eight, at least nine, at least 10, at least 11, at least 12, at least 15, at least 20, or at least 30, or at least 50, or at least 100, or at least 200, or 274 of (a) at least one polymorphism genotype as disclosed in Table 2; preferably one or more polymorphism genotypes selected from the group consisting of rs11715827 (T/G), rs2044070 (A/G), rs2028629 (A/G) and rs6026567 (A/G) as disclosed in Table 2, optionally in combination with one or more polymorphism genotype selected from the group consisting of rs17740874 (T/C), rs3811939 (A/G), rs1882478 (A/G), rs2235013 (T/C), rs2214102 (T/C), rs6415328 (T/C), rs77152456 (A/G), rs66794218 (A/G), rs2589476 (T/C), rs118003903 (A/G), rs11871392 (T/G), rs2589487 (T/C), rs74338736 (A/C), rs6026593 (A/G) and rs6520908 (T/C) as disclosed in Table 2; (b) at least one polymorphism genotype being in linkage disequilibrium with any one of the polymorphism genotypes of (a), or (c) a combination of (a) and (b).

A polynucleotide can include a coding sequence or non-coding sequence (e.g., exons, introns, or 5' or 3' regulatory sequences). The polynucleotide can also be single or double-stranded and of variable length. In some embodiments, the length of one strand of a polynucleotide capable of specifically hybridizing to a nucleic acid comprising: (a) at least one a polymorphism genotype as disclosed in Table 2; (b) at least one polymorphism genotype being in linkage disequilibrium with any one of the polymorphism genotypes of (a), or (c) a combination of (a) and (b) can be about six nucleotides (e.g., about seven nucleotides, about eight nucleotides, about nine nucleotides, about 10 nucleotides, about 12 nucleotides, about 13 nucleotides, about 14 nucleotides, about 15 nucleotides, about 20 nucleotides, about 25 nucleotides, about 30 nucleotides, about 35 nucleotides, about 40 nucleotides, about 50 nucleotides, about 75 nucleotides, about 100 nucleotides, or about 150 or more nucleotides) in length. As is commonly known in the art, a longer polynucleotide often allows for higher stringency hybridization and wash conditions. The polynucleotide can be DNA, RNA, modified DNA or RNA, or a hybrid, where the nucleic acid contains any combination of deoxyribo- and ribo-nucleotides, and any combination of uracil, adenine, thymine, cytosine and guanine, as well as other bases such as inosine, xanthine, and hypoxanthine.

The polynucleotides can be attached to a solid support, e.g., a porous or non-porous material that is insoluble. The polynucleotides can be arranged in an array on the solid support, e.g., in a microarray. A solid support can be composed of a natural or synthetic material, an organic or inorganic material. The composition of the solid support on which the polynucleotide sequences are attached by either 5' or 3' terminal attachment generally depend on the method of attachment (e.g., covalent attachment). Suitable solid supports include, but are not limited to, plastics, resins, polysaccharides, silica or silica-based materials, functionalized glass, modified silicon, carbon, metals, inorganic glasses, membranes, nylon, natural fibers such as silk, wool and cotton, or polymers. The material comprising the solid support can have reactive groups such as carboxy, amino, or hydroxyl groups, which are used for attachment of the polynucleotides. Polymeric solid supports can include, e.g., polystyrene, polyethylene glycol tetraphthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, polypropylene, (poly)tetrafluoroethylene, (poly) vinylidenefluoride, polycarbonate, or polymethylpentene (see, e.g., U.S. Pat. No. 5,427,779, the disclosure of which is hereby incorporated by reference in its entirety). Alternatively, polynucleotides can be attached to the solid support without the use of such functional groups.

Arrays of polynucleotides can also be conjugated to solid support particles. Many suitable solid support particles are known in the art and illustratively include, e.g., particles, such as LUMINEX-type encoded particles, magnetic particles, and glass particles. Exemplary particles that can be used can have a variety of sizes and physical properties. Particles can be selected to have a variety of properties useful for particular experimental formats. For example, particles can be selected that remain suspended in a solution of desired viscosity or to readily precipitate in a solution of desired viscosity. Particles can be selected for ease of separation from sample constituents, for example, by including purification tags for separation with a suitable tag-binding material, paramagnetic properties for magnetic separation, and the like. In some embodiments, encoded particles are used. Each particle includes a unique code (such as a bar code, luminescence code, fluorescence code, a nucleic acid code, and the like). Encoding can be used to provide particles for evaluating different nucleic acids in a single biological sample. The code is embedded (for example, within the interior of the particle) or otherwise attached to the particle in a manner that is stable through hybridization and analysis. The code can be provided by any detectable means, such as by holographic encoding, by a fluorescence property, color, shape, size, weight, light emission, quantum dot emission and the like to identify particle and thus the capture probes immobilized thereto. Encoding can also be the ratio of two or more dyes in one particle that is different than the ratio present in another particle. For example, the particles may be encoded using optical, chemical, physical, or electronic tags. Examples of such coding technologies are optical bar codes fluorescent dyes, or other means. In some embodiments, the particle code is a nucleic acid, e.g., a single stranded nucleic acid.

Different encoded particles can be used to detect or measure multiple nucleic acids (e.g., polymorphism genotypes or mRNAs) in parallel, so long as the encoding can be used to identify the polynucleotide (corresponding to an analyte nucleic acid) on a particular particle, and hence the presence or amount of the analyte nucleic acid (e.g., a polymorphism genotypes or mRNA from a biological sample) being evaluated. A sample can be contacted with a plurality of such coded particles. When the particles are evaluated, e.g., using a fluorescent scanner, the particle code is read as is the fluorescence associated with the particle from any probe used to evaluate modification of the intact substrate associated with the particles.

One exemplary platform utilizes mixtures of fluorescent dyes impregnated into polymer particles as the means to identify each member of a particle set to which a specific capture probe has been immobilized. Another exemplary platform uses holographic barcodes to identify cylindrical glass particles. For example, Chandler et al. (U.S. Pat. No. 5,981,180) describes a particle-based system in which different particle types are encoded by mixtures of various proportions of two or more fluorescent dyes impregnated into polymer particles. Soini (U.S. Pat. No. 5,028,545) describes a particle-based multiplexed assay system that employs time-resolved fluorescence for particle identification. Fulwyler (U.S. Pat. No. 4,499,052) describes an exemplary method for using particle distinguished by color and/or size. U.S. Publication Nos. 2004-0179267, 2004-0132205, 2004-0130786, 2004-0130761, 2004-0126875, 2004-0125424, and 2004-0075907 describe exemplary particles encoded by holographic barcodes.

U.S. Pat. No. 6,916,661 describes polymeric microparticles that are associated with nanoparticles that have dyes that provide a code for the particles. The polymeric microparticles can have a diameter of less than one millimeter, e.g., a size ranging from about 0.1 to about 1,000 micrometers in diameter, e.g., 3-25 μm or about 6-12 μm. The nanoparticles can have, e.g., a diameter from about 1 nanometer (nm) to about 100,000 nm in diameter, e.g., about 10-1,000 nm or 200-500 nm.

An "array", as used herein, refers to a plurality of polynucleotides comprised in the composition or kit being immobilized at predetermined positions on a solid support such that each polynucleotide can be identified by its position.

The compositions, kits and arrays can be, but are not necessarily used in genome-wide genotyping analysis, but for efficient, low cost, and application-specific genotyping analysis, tailored to be used in the methods of predicting a treatment response to a treatment with a CRHR1 antagonist, as disclosed herein. Thus, in some embodiments of any of the compositions, kits and arrays described herein, the array of polynucleotides has less than 100,000 (e.g., less than 90,000; less than 80,000; less than 70,000; less than 60,000; less than 50,000; less than 40,000; less than 30,000; less than 20,000; less than 15,000; less than 10,000; less than 5,000; less than 4,000; less than 3,000; less than 2,000; less than 1,500; less than 1,000; less than 750; less than 500, less than 200, less than 100, or less than 50) different polynucleotides.

The kits described above can, optionally, contain instructions for detecting the presence or absence of the at least one polymorphism genotype in a sample obtained from a subject. In some embodiments, the kits can include one or more reagents for processing a biological sample. For example, a kit can include reagents for isolating mRNA or genomic DNA from a biological sample and/or reagents for amplifying isolated mRNA (e.g., reverse transcriptase, primers for reverse transcription or PCR amplification, or dNTPs) and/or genomic DNA. The kits can also, optionally, contain one or more reagents for detectably-labeling an mRNA, mRNA amplicon, genomic DNA or DNA amplicon, which reagents can include, e.g., an enzyme such as a Klenow fragment of DNA polymerase, T4 polynucleotide kinase, one or more detectably-labeled dNTPs, or detectably-labeled gamma phosphate ATP (e.g., 33P-ATP). In some embodiments, the kits can include a software package for analyzing the results of, e.g., a microarray analysis. The kits described herein can also, optionally, include instructions for administering a CRHR1 antagonist where presence or absence of one or more polymorphism genotypes detectable by the plurality of polynucleotides or the array predicts that a subject will response to a CRHR1 antagonist.

The following are examples of the practice of the invention. They are not to be construed as limiting the scope of the invention in any way.

EXAMPLES

Example 1

Based on basic science studies, the role of CRH was recognized as causal for signs and symptoms prevalent in depression, rendering blocking of CRH/CRHR1 signalling as a viable treatment option. Further clinical findings have found that CRH is elevated in a subgroup of patients with depression, where CRH causes core symptoms. Compound SSR-125543 has been developed elsewhere as a specific CRHR1 antagonist blocking the effect of CRH. A clinical trial evaluating the efficacy and tolerability of SSR-125543 in comparison to placebo and a standard antidepressant has been carried out previously without having predicted the treatment response according to the invention. However, based on additional studies (not published), it was recognized that among patients diagnosed with major depression, only a fraction of 20-30% has central CRH over-activity. Thus, a substantial fraction of non-stratified patients might not show a treatment response, in view of about 70-80% of patients treated with the CRHR1 antagonist not having a central CRH increase. Given the pharmacological specificity, only patients with central CRH-over-activity are likely to benefit from CRHR1 antagonists, such as SSR-125543.

Here, a method of predicting a clinical treatment response (e.g., as measured by the HAM-D score) has been devised, which detects one or more polymorphism genotypes selected from the polymorphism genotypes disclosed in Table 2, using a chip containing probes specific for these polymorphism genotypes, allowing for identification of depressive patients being likely to respond to a treatment with a CRHR1 antagonist such as SSR-125543. DNA samples obtained from 300 subjects enrolled in the earlier clinical trial, as mentioned above, were extensively analyzed by polymorphism genotyping. Using a machine-learning algorithm as described herein, polymorphism genotypes predictive of a response to SSR-125543 were identified, as disclosed in Table 2. Further, 150 or more polymorphism genotypes of this set were used to further "train" the algorithm, assisted by common machine-learning algorithms as described herein, and to test the prediction. Thus, having the set of useful polymorphism genotypes as disclosed in Table 2, at hand, a prediction algorithm can be readily devised, which provides superior prediction of a clinical response with high sensitivity and specificity. As is shown in Table 3, test predictions of a clinical response with a sensitivity of about 78% and a specificity of about 73% have been achieved.

TABLE 3

| | | Observed phenotype | |
|---|---|---|---|
| | | Good response | Poor response |
| Test prediction | Good response | 21 | 13 |
| | Poor response | 6 | 36 |
| | | Sensitivity 78% | Specificity 73% |

To exclude the possibility that the polymorphism genotypes disclosed herein are merely identifying patients that are good responders to any kind of drug intervention, the performance of the method among patients treated with the standard antidepressant escitalopram used as comparator in the earlier clinical trial has also been tested. The sensitivity was 50%, and specificity was 43%, and thus insensitive and unspecific regarding prediction of response to a standard antidepressant, see Table 4. Therefore, the present method is to be considered highly specific for predicting the response to CRHR1 antagonists.

TABLE 4

| | | Observed phenotype | |
|---|---|---|---|
| | | Good response | Poor response |
| Test prediction | Good response | 23 | 17 |
| | Poor response | 23 | 13 |
| | | Sensitivity | Specificity |
| | | 50% | 43% |

The above results were further challenged by considering a "lucky split" between the training and the testing cohort. Another 10.000 random splits were calculated which corroborated the initial result, achieving an odds ratio of 5, which indicates that chances of non-response are 5 times higher if the CRH genotyping analysis described herein predicts poor response. Transforming these findings into a time course curve where those depressed patients that where tested positive in the CRH genotyping analysis and treated with SSR-125543 were compared with patients treated by placebo resulted in a clear superiority of the investigational drug, see FIG. 1. The time course curves revealed a marked difference between placebo and SSR-125543 beginning after 2 weeks of treatment, as measured using, e.g., the HAM-D scale. The difference in response between patients treated with SSR-125543 and those under placebo is significant (p<0.01). In essence, subjects which are tested positive using the method of prediction described herein, based on a CRH genotyping analysis using 150 of the polymorphism genotypes disclosed in Table 2, constitute 28% of the overall patient sample and 78% patients from this sample were responders when treated with SSR-125543.

Example 2

To further evaluate the usefulness of the set of polymorphism genotypes provided in Table 2, further predictions have been tested using minimal subsets selected as prediction variables. As few as singular polymorphism genotypes selected from Table 2, as well as subsets of two, four or eight polymorphism genotypes selected from Table 2 proved useful in the method of predicting a clinical response, e.g., as measured by the HAM-D scale.

Treatment response to an anti-depressant therapy comprising SSR-125543 was predicted based on the same patient data of the earlier clinical trial and polymorphism genotyping set as described above, using statistical tools selected from the group consisting of random forests, support vector machines, neural networks, linear discriminant analyses, clustering methods such as k-nearest neighbours and their respective derivatives, linear models and their derivatives, as well as their combinations.

Surprisingly, even this univariate, bivariate, quadrivariate or octovariate analyses using combinations of polymorphism genotypes as disclosed in Tables 2, 5-7 herein, yielded clinical response predictions of a quality significantly better (i.e. both sensitivity and specificity >50%) than randomness, based on assessing the P-value of concordance between observed and predicted outcome in a 10-fold cross-validation procedure.

In particular, a total number of 78 singular polymorphism genotypes was identified with nominally significant P-values. Of those, 46 yielded a specificity and sensitivity of >50% each in predicting a clinical response. One singular polymorphism yielded both a sensitivity and specificity of higher than 60% each in predicting a clinical response.

Of all tested combinations of two of the univariate significantly predicting polymorphisms, 237 exhibited both a sensitivity and specificity of at least 60% each in predicting a clinical response. Finally, a number of 46 tested combinations of two of the univariate significantly predicting polymorphism genotypes yielded a sensitivity and specificity beyond 65% each in predicting a clinical response, see Table 5.

TABLE 5

| Bivariate sets of polymorphism genotypes | | | | | | |
|---|---|---|---|---|---|---|
| P_ID1 | P_ID2 | rs_p1 | p2 | p-value | sensitivity | specificity |
| 11 | 181 | rs74888440 | rs9813396 | 0.00027897 | 0.62857143 | 0.6626506 |
| 11 | 192 | rs74888440 | rs72693005 | 0.00060709 | 0.67142857 | 0.60240964 |
| 11 | 207 | rs74888440 | rs220806 | 0.00010088 | 0.68571429 | 0.62650602 |
| 11 | 218 | rs74888440 | rs1944887 | 0.00015583 | 0.62857143 | 0.6746988 |
| 11 | 226 | rs74888440 | rs532996 | 0.00082753 | 0.62857143 | 0.63855422 |
| 11 | 227 | rs74888440 | rs9571939 | 0.00082753 | 0.62857143 | 0.63855422 |
| 11 | 228 | rs74888440 | rs2173530 | 0.00082753 | 0.62857143 | 0.63855422 |
| 11 | 244 | rs74888440 | rs2044070 | 0.00352822 | 0.62857143 | 0.60240964 |
| 11 | 245 | rs74888440 | rs920640 | 0.00352822 | 0.62857143 | 0.60240964 |
| 112 | 175 | rs2260882 | rs7648662 | 2.12E−05 | 0.64285714 | 0.69879518 |
| 112 | 237 | rs2260882 | rs12917505 | 0.00090174 | 0.61428571 | 0.65060241 |
| 112 | 238 | rs2260882 | rs16977818 | 2.19E−05 | 0.71428571 | 0.62650602 |
| 112 | 240 | rs2260882 | rs10851628 | 0.00039921 | 0.65714286 | 0.62650602 |
| 112 | 243 | rs2260882 | rs6493965 | 0.00137357 | 0.62857143 | 0.62650602 |
| 112 | 245 | rs2260882 | rs920640 | 0.0006793 | 0.65714286 | 0.61445783 |
| 112 | 246 | rs2260882 | rs920638 | 0.00202984 | 0.64285714 | 0.60240964 |
| 112 | 250 | rs2260882 | rs735164 | 0.00383837 | 0.61428571 | 0.61445783 |
| 112 | 277 | rs2260882 | rs2044230 | 0.00048656 | 0.62857143 | 0.65060241 |
| 116 | 179 | rs2257474 | rs6549407 | 0.00352822 | 0.62857143 | 0.60240964 |
| 116 | 182 | rs2257474 | rs12489026 | 0.00030332 | 0.61428571 | 0.6746988 |
| 116 | 191 | rs2257474 | rs1383699 | 7.55E−05 | 0.71428571 | 0.60240964 |
| 116 | 234 | rs2257474 | rs8042817 | 0.00011443 | 0.67142857 | 0.63855422 |
| 116 | 235 | rs2257474 | rs28811003 | 0.00039921 | 0.65714286 | 0.62650602 |
| 121 | 127 | rs2028629 | rs79320848 | 0.00383837 | 0.61428571 | 0.61445783 |
| 121 | 184 | rs2028629 | rs11715827 | 0.00015583 | 0.62857143 | 0.6746988 |
| 121 | 185 | rs2028629 | rs58882373 | 0.00015583 | 0.62857143 | 0.6746988 |
| 121 | 191 | rs2028629 | rs1383699 | 0.00082753 | 0.62857143 | 0.63855422 |
| 121 | 202 | rs2028629 | rs4836256 | 2.30E−05 | 0.62857143 | 0.71084337 |
| 121 | 233 | rs2028629 | rs929610 | 4.11E−05 | 0.64285714 | 0.68674699 |

TABLE 5-continued

| Bivariate sets of polymorphism genotypes | | | | | | |
|---|---|---|---|---|---|---|
| P_ID1 | P_ID2 | rs_p1 | p2 | p-value | sensitivity | specificity |
| 121 | 237 | rs2028629 | rs12917505 | 7.00E−05 | 0.65714286 | 0.6626506 |
| 121 | 238 | rs2028629 | rs16977818 | 7.75E−05 | 0.64285714 | 0.6746988 |
| 121 | 239 | rs2028629 | rs11071351 | 0.00112948 | 0.65714286 | 0.60240964 |
| 121 | 240 | rs2028629 | rs10851628 | 3.32E−06 | 0.7 | 0.6746988 |
| 121 | 241 | rs2028629 | rs930473 | 7.72E−06 | 0.68571429 | 0.6746988 |
| 121 | 242 | rs2028629 | rs1441824 | 0.00011443 | 0.67142857 | 0.63855422 |
| 121 | 243 | rs2028629 | rs6493965 | 1.53E−05 | 0.68571429 | 0.6626506 |
| 121 | 244 | rs2028629 | rs2044070 | 3.32E−06 | 0.7 | 0.6746988 |
| 121 | 245 | rs2028629 | rs920640 | 3.72E−05 | 0.65714286 | 0.6746988 |
| 121 | 246 | rs2028629 | rs920638 | 3.32E−06 | 0.7 | 0.6746988 |
| 123 | 218 | rs4812040 | rs1944887 | 0.00125068 | 0.64285714 | 0.61445783 |
| 123 | 235 | rs4812040 | rs28811003 | 0.00052981 | 0.61428571 | 0.6626506 |
| 127 | 192 | rs79320848 | rs72693005 | 0.00035634 | 0.67142857 | 0.61445783 |
| 127 | 207 | rs79320848 | rs220806 | 0.00025408 | 0.64285714 | 0.65060241 |
| 127 | 218 | rs79320848 | rs1944887 | 0.00030332 | 0.61428571 | 0.6746988 |
| 132 | 184 | rs6026567 | rs11715827 | 2.69E−06 | 0.61428571 | 0.75903614 |
| 132 | 185 | rs6026567 | rs58882373 | 1.22E−05 | 0.61428571 | 0.73493976 |
| 132 | 213 | rs6026567 | rs2935752 | 0.00030332 | 0.61428571 | 0.6746988 |
| 132 | 214 | rs6026567 | rs2935751 | 0.00030332 | 0.61428571 | 0.6746988 |
| 132 | 237 | rs6026567 | rs12917505 | 4.82E−05 | 0.61428571 | 0.71084337 |
| 132 | 238 | rs6026567 | rs16977818 | 9.16E−05 | 0.61428571 | 0.69879518 |
| 132 | 239 | rs6026567 | rs11071351 | 0.00242522 | 0.61428571 | 0.62650602 |
| 132 | 240 | rs6026567 | rs10851628 | 7.00E−05 | 0.65714286 | 0.6626506 |
| 132 | 241 | rs6026567 | rs930473 | 0.00030332 | 0.61428571 | 0.6746988 |
| 132 | 244 | rs6026567 | rs2044070 | 0.00027897 | 0.62857143 | 0.6626506 |
| 133 | 190 | rs968519 | rs1383707 | 0.00016904 | 0.61428571 | 0.68674699 |
| 133 | 238 | rs968519 | rs16977818 | 0.00052981 | 0.61428571 | 0.6626506 |
| 133 | 240 | rs968519 | rs10851628 | 9.16E−05 | 0.61428571 | 0.69879518 |
| 133 | 241 | rs968519 | rs930473 | 9.16E−05 | 0.61428571 | 0.69879518 |
| 133 | 243 | rs968519 | rs6493965 | 9.16E−05 | 0.61428571 | 0.69879518 |
| 133 | 245 | rs968519 | rs920640 | 0.00052981 | 0.61428571 | 0.6626506 |
| 141 | 157 | rs6092704 | rs2242071 | 0.0006793 | 0.65714286 | 0.61445783 |
| 141 | 181 | rs6092704 | rs9813396 | 4.11E−05 | 0.71428571 | 0.61445783 |
| 141 | 187 | rs6092704 | rs10034039 | 0.00012826 | 0.65714286 | 0.65060241 |
| 141 | 190 | rs6092704 | rs1383707 | 0.00012826 | 0.65714286 | 0.65060241 |
| 141 | 191 | rs6092704 | rs1383699 | 0.00202984 | 0.64285714 | 0.60240964 |
| 141 | 212 | rs6092704 | rs3133622 | 0.00383837 | 0.61428571 | 0.61445783 |
| 141 | 259 | rs6092704 | rs487011 | 0.00149683 | 0.61428571 | 0.63855422 |
| 155 | 207 | rs7523266 | rs220806 | 0.00090174 | 0.61428571 | 0.65060241 |
| 156 | 207 | rs6686061 | rs220806 | 0.00090174 | 0.61428571 | 0.65060241 |
| 157 | 215 | rs2242071 | rs4570614 | 0.00352822 | 0.62857143 | 0.60240964 |
| 168 | 192 | rs809482 | rs72693005 | 0.00352822 | 0.62857143 | 0.60240964 |
| 176 | 234 | rs616870 | rs8042817 | 0.00593832 | 0.61428571 | 0.60240964 |
| 179 | 223 | rs6549407 | rs876270 | 0.00039921 | 0.65714286 | 0.62650602 |
| 179 | 224 | rs6549407 | rs11834041 | 0.00020436 | 0.67142857 | 0.62650602 |
| 179 | 248 | rs6549407 | rs7165629 | 0.00015717 | 0.7 | 0.60240964 |
| 180 | 187 | rs6766242 | rs10034039 | 4.11E−05 | 0.71428571 | 0.61445783 |
| 180 | 220 | rs6766242 | rs7121326 | 0.00082753 | 0.62857143 | 0.63855422 |
| 180 | 223 | rs6766242 | rs876270 | 7.75E−05 | 0.64285714 | 0.6746988 |
| 180 | 224 | rs6766242 | rs11834041 | 3.72E−05 | 0.65714286 | 0.6746988 |
| 180 | 227 | rs6766242 | rs9571939 | 0.00593832 | 0.61428571 | 0.60240964 |
| 180 | 234 | rs6766242 | rs8042817 | 0.00030332 | 0.61428571 | 0.6746988 |
| 180 | 235 | rs6766242 | rs28811003 | 0.00090174 | 0.61428571 | 0.65060241 |
| 182 | 187 | rs12489026 | rs10034039 | 2.94E−05 | 0.68571429 | 0.65060241 |
| 182 | 188 | rs12489026 | rs17616338 | 0.00052981 | 0.61428571 | 0.6626506 |
| 182 | 218 | rs12489026 | rs1944887 | 0.00383837 | 0.61428571 | 0.61445783 |
| 182 | 224 | rs12489026 | rs11834041 | 4.82E−05 | 0.61428571 | 0.71084337 |
| 184 | 218 | rs11715827 | rs1944887 | 0.00082753 | 0.62857143 | 0.63855422 |
| 184 | 219 | rs11715827 | rs10894873 | 0.00383837 | 0.61428571 | 0.61445783 |
| 184 | 236 | rs11715827 | rs894342 | 4.48E−05 | 0.62857143 | 0.69879518 |
| 184 | 237 | rs11715827 | rs12917505 | 2.30E−05 | 0.62857143 | 0.71084337 |
| 184 | 238 | rs11715827 | rs16977818 | 2.30E−05 | 0.62857143 | 0.71084337 |
| 184 | 239 | rs11715827 | rs11071351 | 8.72E−06 | 0.67142857 | 0.68674699 |
| 184 | 240 | rs11715827 | rs10851628 | 1.14E−05 | 0.62857143 | 0.72289157 |
| 184 | 241 | rs11715827 | rs930473 | 4.82E−05 | 0.61428571 | 0.71084337 |
| 184 | 242 | rs11715827 | rs1441824 | 2.30E−05 | 0.62857143 | 0.71084337 |
| 184 | 243 | rs11715827 | rs6493965 | 9.16E−05 | 0.61428571 | 0.69879518 |
| 184 | 244 | rs11715827 | rs2044070 | 4.48E−05 | 0.62857143 | 0.69879518 |
| 184 | 245 | rs11715827 | rs920640 | 1.06E−05 | 0.64285714 | 0.71084337 |
| 184 | 246 | rs11715827 | rs920638 | 2.12E−05 | 0.64285714 | 0.69879518 |
| 185 | 219 | rs58882373 | rs10894873 | 0.00137357 | 0.62857143 | 0.62650602 |
| 185 | 234 | rs58882373 | rs8042817 | 0.00149683 | 0.61428571 | 0.63855422 |
| 185 | 236 | rs58882373 | rs894342 | 0.00015583 | 0.62857143 | 0.6746988 |
| 185 | 237 | rs58882373 | rs12917505 | 1.14E−05 | 0.62857143 | 0.72289157 |
| 185 | 238 | rs58882373 | rs16977818 | 2.30E−05 | 0.62857143 | 0.71084337 |
| 185 | 239 | rs58882373 | rs11071351 | 8.72E−06 | 0.67142857 | 0.68674699 |

TABLE 5-continued

Bivariate sets of polymorphism genotypes

| P_ID1 | P_ID2 | rs_p1 | p2 | p-value | sensitivity | specificity |
|---|---|---|---|---|---|---|
| 185 | 240 | rs58882373 | rs10851628 | 1.14E−05 | 0.62857143 | 0.72289157 |
| 185 | 241 | rs58882373 | rs930473 | 4.82E−05 | 0.61428571 | 0.71084337 |
| 185 | 242 | rs58882373 | rs1441824 | 2.30E−05 | 0.62857143 | 0.71084337 |
| 185 | 243 | rs58882373 | rs6493965 | 4.48E−05 | 0.62857143 | 0.69879518 |
| 185 | 244 | rs58882373 | rs2044070 | 4.48E−05 | 0.62857143 | 0.69879518 |
| 185 | 245 | rs58882373 | rs920640 | 4.48E−05 | 0.62857143 | 0.69879518 |
| 185 | 246 | rs58882373 | rs920638 | 4.48E−05 | 0.62857143 | 0.69879518 |
| 186 | 236 | rs12490095 | rs894342 | 2.57E−06 | 0.62857143 | 0.74698795 |
| 187 | 188 | rs10034039 | rs17616338 | 8.78E−05 | 0.7 | 0.61445783 |
| 187 | 193 | rs10034039 | rs1170303 | 0.00090174 | 0.61428571 | 0.65060241 |
| 187 | 198 | rs10034039 | rs66624622 | 0.00015583 | 0.62857143 | 0.6746988 |
| 187 | 215 | rs10034039 | rs4570614 | 0.00052981 | 0.61428571 | 0.6626506 |
| 187 | 216 | rs10034039 | rs4758040 | 0.00014215 | 0.64285714 | 0.6626506 |
| 187 | 239 | rs10034039 | rs11071351 | 0.00030332 | 0.61428571 | 0.6746988 |
| 188 | 191 | rs17616338 | rs1383699 | 0.00018028 | 0.68571429 | 0.61445783 |
| 189 | 218 | rs80049044 | rs1944887 | 0.00018028 | 0.68571429 | 0.61445783 |
| 190 | 193 | rs1383707 | rs1170303 | 0.00039921 | 0.65714286 | 0.62650602 |
| 190 | 212 | rs1383707 | rs3133622 | 1.61E−06 | 0.75714286 | 0.62650602 |
| 190 | 216 | rs1383707 | rs4758040 | 0.00039921 | 0.65714286 | 0.62650602 |
| 190 | 234 | rs1383707 | rs8042817 | 1.53E−05 | 0.74285714 | 0.60240964 |
| 190 | 237 | rs1383707 | rs12917505 | 0.00027897 | 0.62857143 | 0.6626506 |
| 190 | 242 | rs1383707 | rs1441824 | 0.00149683 | 0.61428571 | 0.63855422 |
| 190 | 252 | rs1383707 | rs4610906 | 0.00090174 | 0.61428571 | 0.65060241 |
| 191 | 216 | rs1383699 | rs4758040 | 0.00137357 | 0.62857143 | 0.62650602 |
| 191 | 234 | rs1383699 | rs8042817 | 0.00015717 | 0.7 | 0.60240964 |
| 191 | 235 | rs1383699 | rs28811003 | 0.00031476 | 0.68571429 | 0.60240964 |
| 191 | 237 | rs1383699 | rs12917505 | 2.19E−05 | 0.71428571 | 0.62650602 |
| 191 | 238 | rs1383699 | rs16977818 | 4.03E−06 | 0.74285714 | 0.62650602 |
| 191 | 240 | rs1383699 | rs10851628 | 2.19E−05 | 0.71428571 | 0.62650602 |
| 191 | 241 | rs1383699 | rs930473 | 0.00010088 | 0.68571429 | 0.62650602 |
| 191 | 242 | rs1383699 | rs1441824 | 0.00112948 | 0.65714286 | 0.60240964 |
| 191 | 243 | rs1383699 | rs6493965 | 1.14E−05 | 0.71428571 | 0.63855422 |
| 191 | 244 | rs1383699 | rs2044070 | 0.0006793 | 0.65714286 | 0.61445783 |
| 191 | 245 | rs1383699 | rs920640 | 1.14E−05 | 0.71428571 | 0.63855422 |
| 191 | 246 | rs1383699 | rs920638 | 3.27E−06 | 0.75714286 | 0.61445783 |
| 191 | 259 | rs1383699 | rs487011 | 4.11E−05 | 0.71428571 | 0.61445783 |
| 192 | 252 | rs72693005 | rs4610906 | 0.00202984 | 0.64285714 | 0.60240964 |
| 192 | 259 | rs72693005 | rs487011 | 1.53E−05 | 0.74285714 | 0.60240964 |
| 193 | 218 | rs1170303 | rs1944887 | 0.00112948 | 0.65714286 | 0.60240964 |
| 193 | 259 | rs1170303 | rs487011 | 0.00137357 | 0.62857143 | 0.62650602 |
| 198 | 226 | rs66624622 | rs532996 | 0.00039921 | 0.65714286 | 0.62650602 |
| 198 | 227 | rs66624622 | rs9571939 | 0.00039921 | 0.65714286 | 0.62650602 |
| 198 | 228 | rs66624622 | rs2173530 | 0.00137357 | 0.62857143 | 0.62650602 |
| 199 | 259 | rs72784444 | rs487011 | 0.00149683 | 0.61428571 | 0.63855422 |
| 201 | 237 | rs62377761 | rs12917505 | 0.00060709 | 0.67142857 | 0.60240964 |
| 201 | 238 | rs62377761 | rs16977818 | 0.00137357 | 0.62857143 | 0.62650602 |
| 201 | 244 | rs62377761 | rs2044070 | 0.00052981 | 0.61428571 | 0.6626506 |
| 202 | 206 | rs4836256 | rs730976 | 0.00593832 | 0.61428571 | 0.60240964 |
| 202 | 218 | rs4836256 | rs1944887 | 0.00016904 | 0.61428571 | 0.68674699 |
| 202 | 225 | rs4836256 | rs67959715 | 0.00044281 | 0.64285714 | 0.63855422 |
| 202 | 236 | rs4836256 | rs894342 | 7.00E−05 | 0.65714286 | 0.6626506 |
| 202 | 237 | rs4836256 | rs12917505 | 1.82E−06 | 0.68571429 | 0.69879518 |
| 202 | 238 | rs4836256 | rs16977818 | 2.12E−05 | 0.64285714 | 0.69879518 |
| 202 | 239 | rs4836256 | rs11071351 | 0.00044281 | 0.64285714 | 0.63855422 |
| 202 | 240 | rs4836256 | rs10851628 | 4.11E−05 | 0.64285714 | 0.68674699 |
| 202 | 241 | rs4836256 | rs930473 | 4.27E−06 | 0.67142857 | 0.69879518 |
| 202 | 242 | rs4836256 | rs1441824 | 0.00012826 | 0.65714286 | 0.65060241 |
| 202 | 243 | rs4836256 | rs6493965 | 4.27E−06 | 0.67142857 | 0.69879518 |
| 202 | 244 | rs4836256 | rs2044070 | 1.73E−05 | 0.67142857 | 0.6746988 |
| 202 | 245 | rs4836256 | rs920640 | 8.72E−06 | 0.67142857 | 0.68674699 |
| 202 | 246 | rs4836256 | rs920638 | 8.72E−06 | 0.67142857 | 0.68674699 |
| 206 | 218 | rs730976 | rs1944887 | 0.00242522 | 0.61428571 | 0.62650602 |
| 211 | 235 | rs3735833 | rs28811003 | 8.47E−05 | 0.62857143 | 0.68674699 |
| 213 | 233 | rs2935752 | rs929610 | 0.00149683 | 0.61428571 | 0.63855422 |
| 213 | 236 | rs2935752 | rs894342 | 0.00011443 | 0.67142857 | 0.63855422 |
| 213 | 237 | rs2935752 | rs12917505 | 9.69E−06 | 0.65714286 | 0.69879518 |
| 213 | 238 | rs2935752 | rs16977818 | 4.73E−06 | 0.65714286 | 0.71084337 |
| 213 | 239 | rs2935752 | rs11071351 | 0.00014215 | 0.64285714 | 0.6626506 |
| 213 | 240 | rs2935752 | rs10851628 | 4.73E−06 | 0.65714286 | 0.71084337 |
| 213 | 241 | rs2935752 | rs930473 | 1.06E−05 | 0.64285714 | 0.71084337 |
| 213 | 242 | rs2935752 | rs1441824 | 6.25E−05 | 0.67142857 | 0.65060241 |
| 213 | 243 | rs2935752 | rs6493965 | 1.06E−05 | 0.64285714 | 0.71084337 |
| 213 | 244 | rs2935752 | rs2044070 | 9.69E−06 | 0.65714286 | 0.69879518 |
| 213 | 245 | rs2935752 | rs920640 | 9.69E−06 | 0.65714286 | 0.69879518 |
| 213 | 246 | rs2935752 | rs920638 | 4.48E−05 | 0.62857143 | 0.69879518 |
| 214 | 236 | rs2935751 | rs894342 | 0.00044281 | 0.64285714 | 0.63855422 |

TABLE 5-continued

| Bivariate sets of polymorphism genotypes | | | | | | |
|---|---|---|---|---|---|---|
| P_ID1 | P_ID2 | rs_p1 | p2 | p-value | sensitivity | specificity |
| 214 | 237 | rs2935751 | rs12917505 | 9.69E−06 | 0.65714286 | 0.69879518 |
| 214 | 238 | rs2935751 | rs16977818 | 4.73E−06 | 0.65714286 | 0.71084337 |
| 214 | 239 | rs2935751 | rs11071351 | 0.00014215 | 0.64285714 | 0.6626506 |
| 214 | 240 | rs2935751 | rs10851628 | 2.30E−05 | 0.62857143 | 0.71084337 |
| 214 | 241 | rs2935751 | rs930473 | 1.06E−05 | 0.64285714 | 0.71084337 |
| 214 | 242 | rs2935751 | rs1441824 | 6.25E−05 | 0.67142857 | 0.65060241 |
| 214 | 243 | rs2935751 | rs6493965 | 4.82E−05 | 0.61428571 | 0.71084337 |
| 214 | 244 | rs2935751 | rs2044070 | 4.48E−05 | 0.62857143 | 0.69879518 |
| 214 | 245 | rs2935751 | rs920640 | 9.69E−06 | 0.65714286 | 0.69879518 |
| 214 | 246 | rs2935751 | rs920638 | 9.69E−06 | 0.65714286 | 0.69879518 |
| 215 | 218 | rs4570614 | rs1944887 | 0.00011443 | 0.67142857 | 0.63855422 |
| 215 | 237 | rs4570614 | rs12917505 | 0.00137357 | 0.62857143 | 0.62650602 |
| 215 | 240 | rs4570614 | rs10851628 | 0.00593832 | 0.61428571 | 0.60240964 |
| 215 | 246 | rs4570614 | rs920638 | 0.00149683 | 0.61428571 | 0.63855422 |
| 216 | 237 | rs4758040 | rs12917505 | 0.00202984 | 0.64285714 | 0.60240964 |
| 216 | 240 | rs4758040 | rs10851628 | 0.00112948 | 0.65714286 | 0.60240964 |
| 216 | 244 | rs4758040 | rs2044070 | 0.00352822 | 0.62857143 | 0.60240964 |
| 216 | 245 | rs4758040 | rs920640 | 0.00090174 | 0.61428571 | 0.65060241 |
| 216 | 246 | rs4758040 | rs920638 | 0.00052981 | 0.61428571 | 0.6626506 |
| 218 | 234 | rs1944887 | rs8042817 | 3.33E−05 | 0.67142857 | 0.6626506 |
| 218 | 259 | rs1944887 | rs487011 | 0.00593832 | 0.61428571 | 0.60240964 |
| 223 | 234 | rs876270 | rs8042817 | 0.00022908 | 0.65714286 | 0.63855422 |
| 223 | 235 | rs876270 | rs28811003 | 0.00039921 | 0.65714286 | 0.62650602 |
| 223 | 259 | rs876270 | rs487011 | 0.00075306 | 0.64285714 | 0.62650602 |
| 224 | 234 | rs11834041 | rs8042817 | 0.00011443 | 0.67142857 | 0.63855422 |
| 224 | 235 | rs11834041 | rs28811003 | 0.00020436 | 0.67142857 | 0.62650602 |
| 224 | 248 | rs11834041 | rs7165629 | 0.00039921 | 0.65714286 | 0.62650602 |
| 225 | 246 | rs67959715 | rs920638 | 5.82E−06 | 0.61428571 | 0.74698795 |
| 233 | 236 | rs929610 | rs894342 | 0.0006793 | 0.65714286 | 0.61445783 |
| 233 | 237 | rs929610 | rs12917505 | 7.72E−06 | 0.68571429 | 0.6746988 |
| 233 | 239 | rs929610 | rs11071351 | 0.00039921 | 0.65714286 | 0.62650602 |
| 233 | 240 | rs929610 | rs10851628 | 4.11E−05 | 0.64285714 | 0.68674699 |
| 233 | 243 | rs929610 | rs6493965 | 4.11E−05 | 0.64285714 | 0.68674699 |
| 233 | 244 | rs929610 | rs2044070 | 7.75E−05 | 0.64285714 | 0.6746988 |
| 233 | 245 | rs929610 | rs920640 | 1.73E−05 | 0.67142857 | 0.6746988 |
| 233 | 246 | rs929610 | rs920638 | 1.73E−05 | 0.67142857 | 0.6746988 |
| 234 | 237 | rs8042817 | rs12917505 | 0.00075306 | 0.64285714 | 0.62650602 |
| 234 | 240 | rs8042817 | rs10851628 | 0.00149683 | 0.61428571 | 0.63855422 |
| 237 | 239 | rs12917505 | rs11071351 | 6.46E−06 | 0.75714286 | 0.60240964 |
| 237 | 259 | rs12917505 | rs487011 | 6.73E−06 | 0.7 | 0.6626506 |
| 238 | 239 | rs16977818 | rs11071351 | 3.27E−06 | 0.75714286 | 0.61445783 |
| 238 | 259 | rs16977818 | rs487011 | 5.45E−07 | 0.72857143 | 0.6746988 |
| 239 | 240 | rs11071351 | rs10851628 | 3.27E−06 | 0.75714286 | 0.61445783 |
| 239 | 241 | rs11071351 | rs930473 | 7.95E−06 | 0.74285714 | 0.61445783 |
| 239 | 243 | rs11071351 | rs6493965 | 7.95E−06 | 0.74285714 | 0.61445783 |
| 239 | 244 | rs11071351 | rs2044070 | 3.27E−06 | 0.75714286 | 0.61445783 |
| 239 | 245 | rs11071351 | rs920640 | 3.27E−06 | 0.75714286 | 0.61445783 |
| 239 | 246 | rs11071351 | rs920638 | 3.27E−06 | 0.75714286 | 0.61445783 |
| 240 | 259 | rs10851628 | rs487011 | 5.45E−07 | 0.72857143 | 0.6746988 |
| 241 | 259 | rs930473 | rs487011 | 1.37E−06 | 0.71428571 | 0.6746988 |
| 242 | 259 | rs1441824 | rs487011 | 0.00018028 | 0.68571429 | 0.61445783 |
| 243 | 248 | rs6493965 | rs7165629 | 0.00352822 | 0.62857143 | 0.60240964 |
| 243 | 259 | rs6493965 | rs487011 | 1.73E−05 | 0.67142857 | 0.6746988 |
| 244 | 259 | rs2044070 | rs487011 | 6.73E−06 | 0.7 | 0.6626506 |
| 245 | 259 | rs920640 | rs487011 | 1.16E−06 | 0.72857143 | 0.6626506 |
| 246 | 259 | rs920638 | rs487011 | 1.16E−06 | 0.72857143 | 0.6626506 |

In higher order analyses, using sets of four and eight polymorphism genotypes selected from the group disclosed in Table 2, a complete enumeration becomes unpractical (over a million combinations for the sets of four and over 1010 for the set of eight polymorphism genotypes). Therefore, randomly sampled sets (1000 combinations each) of such cardinalities k are presented herein.

For k=4, 72.1% of tested polymorphism genotype combinations yield a sensitivity and specificity of higher than 50% each, 20.5% of polymorphism genotype combinations yield a sensitivity and specificity of higher than 60% each, and 5.8% of polymorphism genotype combinations yield a sensitivity and specificity of higher than 65% each in predicting a clinical response. Two quadrivariate combinations even yield at least 70% in both sensitivity and specificity in predicting a clinical response, see Table 6.

TABLE 6

| Quadrivariate sets of polymorphism genotypes | | | | | | |
|---|---|---|---|---|---|---|
| P_ID1 | P_ID2 | P_ID3 | P_ID4 | p-value | sensitivity | specificity |
| 233 | 123 | 121 | 127 | 8.72E−06 | 0.67142857 | 0.68674699 |
| 236 | 186 | 223 | 215 | 1.82E−06 | 0.68571429 | 0.69879518 |
| 202 | 215 | 184 | 233 | 9.40E−07 | 0.67142857 | 0.72289157 |
| 207 | 171 | 185 | 121 | 1.94E−07 | 0.65714286 | 0.75903614 |
| 240 | 207 | 141 | 157 | 8.01E−08 | 0.65714286 | 0.77108434 |
| 158 | 214 | 133 | 246 | 1.53E−05 | 0.68571429 | 0.6626506 |
| 241 | 219 | 188 | 127 | 8.72E−06 | 0.67142857 | 0.68674699 |
| 233 | 157 | 185 | 158 | 4.58E−08 | 0.78571429 | 0.65060241 |
| 188 | 225 | 223 | 237 | 7.45E−07 | 0.7 | 0.69879518 |
| 225 | 247 | 202 | 179 | 3.72E−05 | 0.65714286 | 0.6746988 |
| 157 | 213 | 219 | 218 | 7.00E−05 | 0.65714286 | 0.6626506 |
| 188 | 242 | 112 | 192 | 6.25E−05 | 0.67142857 | 0.65060241 |
| 237 | 226 | 158 | 216 | 6.25E−05 | 0.67142857 | 0.65060241 |
| 205 | 226 | 156 | 181 | 2.04E−06 | 0.67142857 | 0.71084337 |
| 191 | 239 | 226 | 234 | 0.00012826 | 0.65714286 | 0.65060241 |
| 116 | 243 | 246 | 158 | 2.24E−06 | 0.65714286 | 0.72289157 |
| 193 | 233 | 240 | 198 | 9.69E−06 | 0.65714286 | 0.69879518 |
| 202 | 141 | 204 | 160 | 7.00E−05 | 0.65714286 | 0.6626506 |
| 184 | 233 | 192 | 215 | 3.72E−05 | 0.65714286 | 0.6746988 |
| 191 | 188 | 159 | 243 | 2.94E−05 | 0.68571429 | 0.65060241 |
| 246 | 227 | 238 | 224 | 1.94E−07 | 0.65714286 | 0.75903614 |
| 202 | 241 | 224 | 183 | 3.90E−09 | 0.7 | 0.77108434 |
| 227 | 191 | 112 | 246 | 7.00E−05 | 0.65714286 | 0.6626506 |
| 252 | 161 | 192 | 240 | 4.55E−07 | 0.65714286 | 0.74698795 |
| 161 | 207 | 202 | 160 | 1.68E−07 | 0.75714286 | 0.6626506 |
| 212 | 243 | 190 | 116 | 4.95E−10 | 0.65714286 | 0.8313253 |
| 246 | 184 | 11 | 243 | 3.33E−05 | 0.67142857 | 0.6626506 |
| 184 | 241 | 259 | 187 | 7.00E−05 | 0.65714286 | 0.6626506 |
| 226 | 243 | 190 | 224 | 4.73E−06 | 0.65714286 | 0.71084337 |
| 237 | 157 | 240 | 160 | 1.53E−05 | 0.68571429 | 0.6626506 |
| 223 | 245 | 132 | 184 | 1.03E−06 | 0.65714286 | 0.73493976 |
| 188 | 207 | 182 | 228 | 1.03E−06 | 0.65714286 | 0.73493976 |
| 224 | 205 | 227 | 186 | 7.00E−05 | 0.65714286 | 0.6626506 |
| 223 | 176 | 245 | 206 | 4.73E−06 | 0.65714286 | 0.71084337 |
| 190 | 204 | 234 | 238 | 6.29E−08 | 0.7 | 0.73493976 |
| 201 | 192 | 240 | 187 | 1.73E−05 | 0.67142857 | 0.6746988 |
| 227 | 185 | 190 | 215 | 7.45E−07 | 0.7 | 0.69879518 |
| 185 | 241 | 202 | 186 | 1.93E−05 | 0.65714286 | 0.68674699 |
| 214 | 11 | 157 | 220 | 9.61E−07 | 0.74285714 | 0.65060241 |
| 242 | 190 | 192 | 245 | 2.86E−06 | 0.71428571 | 0.6626506 |
| 121 | 246 | 238 | 190 | 9.69E−06 | 0.65714286 | 0.69879518 |
| 223 | 157 | 241 | 190 | 1.82E−06 | 0.68571429 | 0.69879518 |
| 233 | 116 | 132 | 243 | 3.72E−05 | 0.65714286 | 0.6746988 |
| 218 | 158 | 250 | 244 | 9.40E−07 | 0.67142857 | 0.72289157 |
| 250 | 158 | 141 | 213 | 3.33E−05 | 0.67142857 | 0.6626506 |
| 240 | 215 | 213 | 158 | 9.69E−06 | 0.65714286 | 0.69879518 |
| 235 | 243 | 214 | 208 | 4.73E−06 | 0.65714286 | 0.71084337 |
| 202 | 244 | 234 | 127 | 1.33E−05 | 0.7 | 0.65060241 |
| 175 | 184 | 127 | 219 | 4.27E−06 | 0.67142857 | 0.69879518 |
| 190 | 240 | 212 | 223 | 1.81E−07 | 0.67142857 | 0.74698795 |
| 248 | 219 | 233 | 185 | 6.44E−07 | 0.71428571 | 0.68674699 |
| 184 | 234 | 205 | 244 | 9.69E−06 | 0.65714286 | 0.69879518 |
| 201 | 246 | 192 | 233 | 4.27E−06 | 0.67142857 | 0.69879518 |
| 251 | 245 | 191 | 176 | 1.82E−06 | 0.68571429 | 0.69879518 |
| 233 | 223 | 235 | 225 | 3.72E−05 | 0.65714286 | 0.6746988 |
| 237 | 220 | 236 | 192 | 9.69E−06 | 0.65714286 | 0.69879518 |
| 241 | 236 | 248 | 218 | 4.73E−06 | 0.65714286 | 0.71084337 |
| 252 | 218 | 219 | 239 | 6.98E−08 | 0.68571429 | 0.74698795 |

For k=8, 93.3% of tested polymorphism genotype combinations yield a sensitivity and specificity of higher than 50% each, 32.6% of polymorphism genotype yield a sensitivity and specificity of higher than 60% each, 8.7% of polymorphism genotype combinations yield a sensitivity and specificity of 65% each, and, finally, 0.5% (5 combinations) of octovariate polymorphism genotype combinations yield a sensitivity and specificity at least 70% in sensitivity and specificity in predicting a clinical response, see Table 7.

TABLE 7

| Octovariate sets of polymorphism genotypes | | | | | | | | | | |
|---|---|---|---|---|---|---|---|---|---|---|
| P_ID1 | P_ID2 | P_ID3 | P_ID4 | P_ID5 | P_ID6 | P_ID7 | P_ID8 | p-value | sensitivity | specificity |
| 201 | 198 | 191 | 248 | 176 | 213 | 220 | 239 | 3.85E−06 | 0.65714286 | 0.72289157 |
| 206 | 112 | 186 | 247 | 205 | 171 | 184 | 246 | 2.41E−05 | 0.65714286 | 0.68674699 |

TABLE 7-continued

Octovariate sets of polymorphism genotypes

| P_ID1 | P_ID2 | P_ID3 | P_ID4 | P_ID5 | P_ID6 | P_ID7 | P_ID8 | p-value | sensitivity | specificity |
|---|---|---|---|---|---|---|---|---|---|---|
| 188 | 243 | 227 | 191 | 240 | 202 | 242 | 176 | 3.85E−06 | 0.65714286 | 0.72289157 |
| 160 | 193 | 132 | 235 | 121 | 192 | 188 | 236 | 7.10E−07 | 0.67142857 | 0.73493976 |
| 246 | 112 | 237 | 220 | 190 | 185 | 116 | 186 | 6.78E−07 | 0.65714286 | 0.74698795 |
| 116 | 189 | 241 | 246 | 213 | 225 | 191 | 132 | 1.57E−08 | 0.68571429 | 0.77108434 |
| 132 | 202 | 236 | 245 | 184 | 193 | 192 | 198 | 4.11E−08 | 0.67142857 | 0.77108434 |
| 244 | 188 | 225 | 206 | 192 | 214 | 234 | 213 | 2.99E−07 | 0.68571429 | 0.73493976 |
| 235 | 214 | 211 | 156 | 245 | 190 | 188 | 237 | 1.66E−08 | 0.7 | 0.75903614 |
| 185 | 238 | 244 | 206 | 237 | 184 | 183 | 259 | 1.64E−06 | 0.65714286 | 0.73493976 |
| 185 | 168 | 191 | 193 | 184 | 160 | 238 | 141 | 1.93E−05 | 0.65714286 | 0.69879518 |
| 159 | 244 | 202 | 133 | 259 | 243 | 223 | 121 | 4.03E−06 | 0.67142857 | 0.71084337 |
| 211 | 238 | 235 | 158 | 228 | 218 | 214 | 189 | 4.11E−08 | 0.67142857 | 0.77108434 |
| 190 | 238 | 185 | 259 | 213 | 179 | 184 | 188 | 2.71E−07 | 0.65714286 | 0.75903614 |
| 11 | 157 | 223 | 188 | 236 | 185 | 244 | 201 | 2.41E−05 | 0.65714286 | 0.68674699 |
| 188 | 246 | 171 | 242 | 127 | 184 | 234 | 132 | 6.78E−07 | 0.65714286 | 0.74698795 |
| 240 | 158 | 112 | 235 | 259 | 242 | 226 | 205 | 1.06E−05 | 0.68571429 | 0.6746988 |
| 211 | 213 | 205 | 171 | 202 | 185 | 259 | 116 | 1.50E−07 | 0.72857143 | 0.69879518 |
| 187 | 121 | 250 | 116 | 233 | 243 | 198 | 220 | 7.46E−07 | 0.68571429 | 0.72289157 |
| 216 | 168 | 185 | 132 | 183 | 112 | 213 | 238 | 1.49E−08 | 0.67142857 | 0.78313253 |
| 157 | 248 | 236 | 259 | 171 | 238 | 239 | 192 | 4.86E−05 | 0.65714286 | 0.6746988 |
| 234 | 227 | 224 | 251 | 277 | 198 | 187 | 245 | 1.05E−07 | 0.65714286 | 0.77108434 |
| 237 | 223 | 11 | 215 | 116 | 218 | 182 | 233 | 1.49E−08 | 0.67142857 | 0.78313253 |
| 201 | 220 | 127 | 234 | 157 | 219 | 186 | 141 | 6.78E−07 | 0.65714286 | 0.74698795 |
| 218 | 247 | 193 | 241 | 192 | 236 | 224 | 186 | 2.84E−07 | 0.67142857 | 0.74698795 |
| 233 | 201 | 158 | 226 | 235 | 132 | 223 | 190 | 3.85E−06 | 0.65714286 | 0.72289157 |
| 225 | 186 | 156 | 241 | 204 | 214 | 218 | 212 | 2.71E−07 | 0.65714286 | 0.75903614 |
| 116 | 179 | 112 | 184 | 190 | 259 | 239 | 215 | 1.64E−06 | 0.65714286 | 0.73493976 |
| 121 | 252 | 186 | 189 | 241 | 133 | 141 | 223 | 1.41E−08 | 0.65714286 | 0.79518072 |
| 250 | 248 | 241 | 184 | 159 | 206 | 187 | 192 | 7.10E−07 | 0.67142857 | 0.73493976 |
| 168 | 277 | 250 | 238 | 245 | 218 | 227 | 184 | 1.57E−08 | 0.68571429 | 0.77108434 |
| 212 | 181 | 184 | 159 | 237 | 223 | 179 | 213 | 2.84E−07 | 0.67142857 | 0.74698795 |
| 241 | 219 | 175 | 187 | 156 | 233 | 157 | 184 | 2.99E−07 | 0.68571429 | 0.73493976 |
| 224 | 192 | 206 | 121 | 202 | 214 | 241 | 239 | 5.48E−09 | 0.68571429 | 0.78313253 |
| 241 | 192 | 214 | 141 | 179 | 227 | 212 | 121 | 8.76E−06 | 0.65714286 | 0.71084337 |
| 212 | 241 | 239 | 121 | 191 | 187 | 224 | 238 | 5.48E−09 | 0.68571429 | 0.78313253 |
| 245 | 225 | 236 | 132 | 160 | 211 | 244 | 238 | 2.85E−09 | 0.65714286 | 0.81927711 |
| 121 | 237 | 234 | 205 | 132 | 244 | 190 | 238 | 1.22E−07 | 0.7 | 0.73493976 |
| 121 | 220 | 241 | 245 | 219 | 214 | 248 | 132 | 8.76E−06 | 0.65714286 | 0.71084337 |
| 240 | 220 | 252 | 250 | 157 | 214 | 218 | 245 | 5.48E−09 | 0.68571429 | 0.78313253 |
| 193 | 211 | 179 | 132 | 185 | 246 | 238 | 240 | 2.85E−09 | 0.65714286 | 0.81927711 |
| 243 | 241 | 252 | 237 | 192 | 141 | 259 | 190 | 7.10E−07 | 0.67142857 | 0.73493976 |
| 227 | 190 | 213 | 250 | 191 | 218 | 214 | 248 | 4.91E−09 | 0.65714286 | 0.80722892 |
| 242 | 214 | 239 | 179 | 201 | 190 | 181 | 192 | 1.78E−11 | 0.7 | 0.8313253 |
| 224 | 121 | 259 | 246 | 207 | 228 | 204 | 219 | 3.85E−06 | 0.65714286 | 0.72289157 |
| 236 | 186 | 116 | 187 | 184 | 204 | 219 | 121 | 2.84E−07 | 0.67142857 | 0.74698795 |
| 179 | 11 | 239 | 184 | 159 | 202 | 123 | 185 | 4.33E−08 | 0.68571429 | 0.75903614 |
| 248 | 127 | 240 | 141 | 133 | 233 | 156 | 201 | 1.05E−07 | 0.65714286 | 0.77108434 |
| 185 | 237 | 188 | 191 | 247 | 189 | 216 | 158 | 2.84E−07 | 0.67142857 | 0.74698795 |
| 219 | 132 | 176 | 191 | 277 | 214 | 236 | 175 | 1.49E−08 | 0.67142857 | 0.78313253 |
| 133 | 241 | 214 | 220 | 189 | 191 | 233 | 211 | 6.78E−07 | 0.65714286 | 0.74698795 |
| 202 | 182 | 233 | 259 | 218 | 127 | 243 | 159 | 2.71E−07 | 0.65714286 | 0.75903614 |
| 189 | 238 | 216 | 223 | 214 | 158 | 190 | 179 | 2.85E−09 | 0.65714286 | 0.81927711 |
| 123 | 112 | 243 | 141 | 202 | 121 | 190 | 116 | 1.76E−08 | 0.71428571 | 0.74698795 |
| 237 | 193 | 116 | 185 | 228 | 202 | 186 | 132 | 2.71E−07 | 0.65714286 | 0.75903614 |
| 190 | 11 | 237 | 182 | 202 | 132 | 214 | 246 | 1.10E−07 | 0.67142857 | 0.75903614 |
| 214 | 237 | 224 | 218 | 250 | 181 | 155 | 160 | 3.92E−08 | 0.65714286 | 0.78313253 |
| 237 | 252 | 234 | 133 | 185 | 250 | 239 | 188 | 5.48E−09 | 0.68571429 | 0.78313253 |
| 188 | 228 | 245 | 185 | 248 | 234 | 161 | 224 | 4.03E−06 | 0.67142857 | 0.71084337 |
| 204 | 228 | 188 | 202 | 212 | 223 | 168 | 141 | 2.71E−07 | 0.65714286 | 0.75903614 |
| 206 | 238 | 186 | 245 | 191 | 220 | 155 | 192 | 6.78E−07 | 0.65714286 | 0.74698795 |
| 237 | 246 | 168 | 188 | 141 | 198 | 192 | 190 | 3.85E−06 | 0.65714286 | 0.72289157 |
| 223 | 252 | 190 | 160 | 205 | 212 | 184 | 233 | 4.03E−06 | 0.67142857 | 0.71084337 |
| 141 | 187 | 121 | 188 | 246 | 193 | 185 | 133 | 1.16E−07 | 0.68571429 | 0.74698795 |
| 218 | 238 | 228 | 234 | 184 | 213 | 132 | 248 | 1.10E−07 | 0.67142857 | 0.75903614 |
| 11 | 213 | 238 | 219 | 246 | 112 | 187 | 248 | 2.30E−05 | 0.67142857 | 0.6746988 |
| 121 | 190 | 160 | 213 | 184 | 239 | 246 | 189 | 1.10E−07 | 0.67142857 | 0.75903614 |
| 168 | 225 | 176 | 251 | 236 | 189 | 190 | 218 | 4.11E−08 | 0.67142857 | 0.77108434 |
| 235 | 116 | 187 | 250 | 168 | 220 | 238 | 190 | 6.78E−07 | 0.65714286 | 0.74698795 |
| 216 | 214 | 246 | 116 | 244 | 182 | 240 | 186 | 7.10E−07 | 0.67142857 | 0.73493976 |
| 208 | 188 | 187 | 218 | 245 | 238 | 199 | 157 | 1.64E−06 | 0.65714286 | 0.73493976 |
| 239 | 112 | 176 | 185 | 246 | 250 | 219 | 202 | 4.86E−05 | 0.65714286 | 0.6746988 |
| 250 | 220 | 233 | 127 | 224 | 116 | 226 | 237 | 1.72E−06 | 0.67142857 | 0.72289157 |
| 156 | 212 | 204 | 259 | 214 | 237 | 240 | 191 | 1.05E−07 | 0.65714286 | 0.77108434 |
| 259 | 204 | 213 | 228 | 180 | 218 | 242 | 193 | 1.72E−06 | 0.67142857 | 0.72289157 |
| 218 | 250 | 227 | 211 | 171 | 185 | 251 | 133 | 1.05E−07 | 0.65714286 | 0.77108434 |
| 176 | 202 | 185 | 187 | 277 | 248 | 233 | 189 | 1.72E−06 | 0.67142857 | 0.72289157 |
| 112 | 277 | 218 | 155 | 156 | 237 | 235 | 244 | 5.67E−10 | 0.67142857 | 0.81927711 |

TABLE 7-continued

| Octovariate sets of polymorphism genotypes | | | | | | | | | | |
|---|---|---|---|---|---|---|---|---|---|---|
| P_ID1 | P_ID2 | P_ID3 | P_ID4 | P_ID5 | P_ID6 | P_ID7 | P_ID8 | p-value | sensitivity | specificity |
| 187 | 252 | 240 | 116 | 175 | 184 | 239 | 242 | 2.84E−07 | 0.67142857 | 0.74698795 |
| 182 | 227 | 206 | 181 | 132 | 224 | 244 | 188 | 1.10E−07 | 0.67142857 | 0.75903614 |
| 239 | 238 | 214 | 223 | 242 | 218 | 186 | 192 | 1.66E−08 | 0.7 | 0.75903614 |
| 185 | 188 | 277 | 241 | 219 | 193 | 201 | 176 | 1.64E−06 | 0.65714286 | 0.73493976 |
| 116 | 233 | 199 | 247 | 183 | 238 | 214 | 180 | 4.11E−08 | 0.67142857 | 0.77108434 |
| 180 | 242 | 116 | 239 | 158 | 238 | 243 | 240 | 7.46E−07 | 0.68571429 | 0.72289157 |
| 234 | 237 | 193 | 235 | 224 | 179 | 190 | 233 | 3.92E−08 | 0.65714286 | 0.78313253 |

For k=32, 99.9% of tested polymorphism genotype combinations yield a sensitivity and specificity of higher than 50% each in specificity and sensitivity. 98.9% of tested polymorphism genotype combinations yield a sensitivity and specificity of higher than 60% each, 72.8% of tested polymorphism genotype combinations yield a sensitivity and specificity of higher than 65% each, 15.6% of tested polymorphism genotype combinations yield a sensitivity and specificity of higher than 70% each in predicting a clinical response. Finally, some of the tested polymorphism genotype combinations (0.3%) even yield a sensitivity and specificity of higher than 75% each (data not shown).

As will be understood from the above explanations and data in Table 5, Table 6, and Table 7, even minimal subsets of polymorphism genotypes selected from the particularly useful set of polymorphism genotypes disclosed in Table 2 already allow for predictions of a clinical response significantly better than 50% ("coin-flip"). Therefore, while the present invention ideally aims at predicting the treatment response to a CRHR1 antagonist with sensitivity and specificity of at least 75% each, at least 80% each, at least 85% each, or even at least 90% each, methods of prediction using smaller subsets, e.g., of only one, two, four, or eight polymorphism genotypes selected from the group consisting of the polymorphism genotypes disclosed in Table 2 already provide a significant performance in predicting clinical responses. A subset of k=32 polymorphism genotypes already comprises combinations yielding a sensitivity and specificity of at least 75% each in predicting a clinical response. The predictive performance can be further increased by including, e.g., 150 polymorphism genotypes, as has been done in Example 1, 200 polymorphism genotypes, 250 polymorphism genotypes or all polymorphism genotypes as disclosed in Table 2.

Example 3

To further evaluate the usefulness of specific set of polymorphism genotypes, a combination of 19 single nucleotide polymorphisms selected from the group polymorphism genotypes of Table 2 consisting of rs17740874, rs11715827, rs3811939, rs1882478, rs2235013, rs2214102, rs6415328, rs2044070, rs77152456, rs66794218, rs2589476, rs118003903, rs11871392, rs2589487, rs2028629, rs6026567, rs74338736, and rs6026593 has been found to be highly predictive for a clinical treatment response to a therapy comprising SSR-125543 or a pharmaceutically acceptable salt thereof.

Further, it was surprisingly found that of the above group of 19 SNPS, the four polymorphisms rs2028629, rs6026567, rs11715827 and rs2044070 as described in Table 2 show, considered on their own, significant evidence for being associated with a positive prediction of a response or a likelihood of response to a treatment with SSR-125543 or a pharmaceutically acceptable salt thereof. Interestingly and surprisingly, in all polymorphisms the allele G was found to be associated with a positive outcome, i.e. a good response or a good likelihood of response to the treatment.

The findings of prediction usefulness for these four polymorphism genotypes are described below. The data show that there is a significant evidence for association between response to treatment and each of the four polymorphism.

(i) rs2028629 rs2028629 (P_ID 208) is a polymorphism with the alleles A and G ([A/G]) as shown in Table 2. It was found that having at least one copy of the allele G (a person possessing genotypes AG or GG in contrast to the wild-type genotype AA) is positively associated with good response to treatment with SSR-125543 or a pharmaceutically acceptable salt thereof.

This is significant at a p-value of 0.0298 by logistic regression. The estimated odds ratio by logistic regression for having genotypes AG or GG in contrast to genotype AA given as its natural logarithm is 0.8172, corresponding to a value of 2.26 on the original scale. Predicting treatment response with polymorphism rs2028629 a sensitivity of 0.557 and of specificity of 0.626 was obtained.

(ii) rs6026567 rs6026567 (P_ID 249) is a polymorphism with the alleles A and G ([A/G]) as shown in Table 2. It was found that there is a positive correlation between the number of alleles G with good response to treatment with SSR-125543 or a pharmaceutically acceptable salt thereof.

This is significant at a p-value of 0.00129 by logistic regression. The estimated odds ratio by logistic regression per copy of allele G is 0.7795, corresponding to a value of 2.18 on the original scale. Predicting treatment response with polymorphism rs6026567 a sensitivity of 0.271 and of specificity of 0.904 was obtained.

(iii) rs11715827 rs11715827 (P_ID 179) is a polymorphism with the alleles G and T ([T/G]) as disclosed in Table 2. It was found that there is a positive correlation between the number of alleles G with good response to treatment with SSR-125543 or a pharmaceutically acceptable salt thereof.

This is significant at a p-value of 0.00023 by logistic regression. The estimated odds ratio by logistic regression per copy of allele G is 1.2267, corresponding to a value of 3.41 on the original scale. Predicting treatment response with polymorphism rs11715827 a sensitivity of 0.771 and of specificity of 0.506 was obtained.

(iv) rs2044070 rs2044070 (P_ID 102) is a polymorphism with the alleles A and G ([A/G]) as disclosed in Table 2. It was found that there is a positive correlation between the number of alleles G with good response to treatment with SSR-125543 or a pharmaceutically acceptable salt thereof.

This is significant at a p-value of 0.000129 by logistic regression. The estimated odds ratio by logistic regression per copy of allele G is 0.9558, corresponding to a value of 2.60 on the original scale. Predicting treatment response with polymorphism rs2044070 a sensitivity of 0.786 and of specificity of 0.530 was obtained.

Advantageously, the predictive properties to a treatment response of each one of the polymorphism rs2028629, rs6026567, rs11715827 and rs2044070 can be increased by combination of all of the four polymorphism genotypes, with the prediction response of each polymorphism genotype acting additively.

Thus, using the set of all of the four polymorphism genotypes rs2028629, rs6026567, rs11715827 and rs2044070, it is possible to create a classifier based on these four SNPs alone using logistic regression applying 10-fold cross validation in the building of the model. Combination of the four polymorphisms (with "good response to treatment" as the target category) yielded a sensitivity of 0.700 and a specificity of 0.759. The estimated log-odds ratios for the number of G-alleles in a person are 0.2205 for rs2028629, 0.7258 for rs6026567, 0.8733 for rs11715827 and 0.8065 for rs2044070, with the SNPs acting additively, so no interaction needs to be assumed for these four SNPs and for this predictor. The intercept in this model is negative and estimated as −1.2703.

The optimal threshold (obtained by aiming at maximum accuracy of prediction in the 10-fold cross validation) was found to be 0.512945 with patients obtaining a value equal to or above this threshold predicted to sow good response to treatment.

To illustrate this by an example, a person is genotyped and found to have genotype AG for rs2028629, AA for rs6026567, TT for rs11715827 and GG for rs2044070. This translates into 1 copy of a G-allele for rs2028629, 0 copies for rs6026567, 0 copies for rs11715827 and 2 copies for rs2044070. The predicted quantity (PQ) for this patient then is calculated as:

$$-1.2703+1*0.2205+0*0.7258+0*0.8733+2*0.8065=0.5632$$

As PQ for this patient is 0.5632 and thus above the threshold we predict this patient to show good response.

In another example, another person is genotyped and found to have genotype AA for rs2028629, AG for rs6026567, TT for rs11715827 and AA for rs2044070. This translates into 0 copies of a G-allele for rs2028629, 1 copy for rs6026567, 0 copies for rs11715827 and 0 copies for rs2044070. The predicted quantity (PQ) for this patient then is calculated as:

$$-1.2703+0*0.2205+1*0.7258+0*0.8733+0*0.8065=-0.5445$$

As PQ for this patient is-0.5445 and thus below the threshold we predict this patient to show poor response or, in other words, to not show good response.

Moreover, it was also surprisingly found that the level of treatment prediction can be further increased by combination of the four SNPs (rs2028629, rs6026567, rs11715827 and rs2044070) with one or more or all of the polymorphism genotypes rs17740874, rs3811939, rs1882478, rs2235013, rs2214102, rs6415328, rs77152456, rs66794218, rs2589476, rs118003903, rs11871392, rs2589487, rs74338736 and rs6026593.

Accordingly, the level of performance (sensitivity of 0.700; specificity of 0.759) can be further increased by using one or more of these specific 19 SNPs or the total set. Here it was found that using a probabilistic neural network as originally described by Specht (Specht D F. Probabilistic neural networks and the polynomial adaline as complementary techniques for classification. IEEE Trans Neural Netw. 1990; 1(1):111-121, which is incorporated by reference) and following the idea of neuron reduction as described by Kusy and Kluska (Kusy M, Kluska J. Assessment of prediction ability for reduced probabilistic neural network in data classification problems. Soft Computing. 2017; 21:199-212, which is incorporated by reference) as well as allowing for a different value of the smoothing parameter per variable (SNP) as described by Kusy and Zajdel (Kusy M, Zajdel R. Probabilistic neural network training procedure based on Q (0)-learning algorithm in medical data classification. Applied Intelligence. 2014; 21:837-854, which is incorporated by reference) an improved prediction as measured by sensitivity and specificity in leave-one-out cross validation is obtained. Particularly, values of 0.914 for sensitivity and 0.880 for specificity (adjusted to three informative digits) have been obtained. The AUC on the ROC for this model is 0.923, the positive predictive value 0.865, and the negative predictive value 0.924. Accuracy is estimated at 0.895.

As shown in Table 5, test prediction of a clinical response with a sensitivity of up to 91% and a specificity of up to 88% have been achieved.

TABLE 5

| | | Observed phenotype | |
|---|---|---|---|
| | | Good response to treatment | Poor Response to treatment |
| Test prediction | Good response to treatment | 64 | 10 |
| | Poor Response to treatment | 6 | 74 |
| | | Sensitivity 91.4% | Specificity 88.0% |

EQUIVALENTS

The foregoing exemplary embodiments are to be considered illustrative of, and not limiting to, the invention disclosed herein. It will be apparent to those skilled in the art that various modifications may be made without departing from the scope or spirit of the invention. Therefore, it will be appreciated that the scope of the present invention is primarily defined by the appended claims, and is not limited by the specific embodiments which have been presented as examples. All changes which come within the meaning and range of equivalency of the claims are intended to be encompassed.

What is claimed is:

1. A method of treatment of a subject comprising:

(a) detecting at least one polymorphism genotype selected from the group consisting of rs11715827 [G], rs2044070 [G], rs2028629 [G] and rs6026567 [G] in a biological sample from the subject;

(b) after step (a), diagnosing the subject as a CRHR1 antagonist responder, or having an increased likelihood of responding to a CRHR1 antagonist; and (c) administering a CRHR1 antagonist to the subject diagnosed as a CRHR1 antagonist responder.

2. The method of claim 1, wherein the diagnosing step comprises one or more statistical analysis method selected from the group consisting of artificial neural network learning, decision tree learning, decision tree forest learning, linear discriminant analysis, non-linear discriminant analysis, genetic expression programming, relevance vector machines, linear models, generalized linear models, generalized estimating equations, generalized linear mixed models, the elastic net, the lasso support vector machine learning, Bayesian network learning, probabilistic neural network learning, clustering, and regression analysis, optionally wherein the statistical analysis method is computer-implemented.

3. The method of claim 1, wherein the CRHR1 antagonist responder has a clinical response.

4. The method of claim 1, wherein the subject has depressive symptoms, anxiety symptoms or both depressive symptoms and anxiety symptoms or a sleep disorder; and/or wherein the CRHR1 antagonist treats depressive symptoms, anxiety symptoms or both depressive symptoms and anxiety symptoms or a sleep disorder.

5. The method of claim 3, wherein the clinical response is a prevention, alteration, alleviation or complete remission of depressive symptoms and/or anxiety symptoms or a sleep disorder.

6. The method of claim 3, wherein the clinical response is a prevention, alteration, alleviation or complete remission of depressive symptoms and/or anxiety symptoms as determined using a scale selected from the group consisting of HAM-D, BDI, MADRS, GDS, ZSRDS, HAM-A and STAI.

7. The method of claim 1, wherein the biological sample is a buccal or a blood sample.

8. The method of claim 1, wherein detecting comprises the use of one or more polynucleotides capable of specifically hybridizing to at least one nucleic acid comprising the one or more polymorphism genotypes.

9. The method of claim 1, wherein the subject diagnosed as a CRHR1 antagonist responder has a sensitivity of higher than 50% and a specificity of higher than 50%.

10. The method of claim 1, wherein the CRHR1 antagonist is selected from the group consisting of GW876008 (Emicerfont), GSK-561679 (NBI-77860, Verucerfont), GSK586529, BMS-562,086 (Pexacerfont), NBI-30775 (R-121919), NBI-34101, CP-316,311, CP-376,395, PF-00572778, NVP-AAG561, Ono-2333 MS, E2508, E2009, R317573 (JNJ19567470, CRA5626, TAI-041), R278995 (CRA0450), CRA-1000, CRA-1001, CP154,526, Antalarmin, DMP-695, DMP-696, DMP-904, SC-241, BMS-561388, NBI30545, PD-171729, NBI34041, NBI35965, SN003, NBI-27914, trans-2-chloro-N-(4-((5-fluoro-4-methyl-pyridin-2-ylamino)-methyl)-cyclohexyl)-5-(trifluoromethyl)benzamide, SSR-125543, or a pharmaceutically acceptable salt thereof.

11. The method of claim 1, wherein the CRHR1 antagonist is selected from the group consisting of a Type I CRHR1 antagonist, a bicyclic Type II CRHR1 antagonist, an atypical CRHR1 antagonist, and a cyclohexyl amide CRHR1 antagonist.

12. The method of claim 1, wherein the subject has a condition selected from the group consisting of depressive symptoms, anxiety symptoms, both depressive symptoms and anxiety symptoms, and a sleep disorder.

13. A method of treating comprising (a) detecting at least one polymorphism genotype selected from the group consisting of rs11715827 [G], rs2044070 [G], rs2028629 [G] and rs6026567 [G] in a biological sample from the subject, wherein detecting comprises using a kit comprising:

i) at least one polynucleotide capable of specifically hybridizing to a nucleic acid comprising—at least one polymorphism genotype selected from the group consisting of rs11715827 [G], rs2044070 [G], rs2028629 [G] and rs6026567 [G], and ii) one or more additional reagents for detecting the presence of the one or more polymorphism genotypes, (b) diagnosing the subject as a non-peptidic CRHR1 antagonist responder, or having an increased likelihood of responding to a non-peptidic CRHR1 antagonist; and (c) administering a non-peptidic CRHR1 antagonist to the subject diagnosed as a non-peptidic CRHR1 antagonist responder.

14. The method of claim 13, wherein the at least one polynucleotide is bound to a solid support.

15. The method of claim 13, wherein the at least one polynucleotide is bound to the solid support in the form of an array.

16. The method of claim 13, further comprising one or more reagents for isolating a nucleic acid from a sample.

17. The method of claim 13, further comprising a means for amplifying a nucleic acid.

18. The method of claim 13, wherein the kit is used to detect the presence or absence of one or more polymorphism genotypes within a sample obtained from a subject.

19. A method of treating comprising:

(a) detecting at least one polymorphism genotype selected from the group consisting of rs11715827 [G], rs2044070 [G], rs2028629 [G] and rs6026567 [G] in a biological sample;

(b) diagnosing the subject as a non-peptidic CRHR1 antagonist responder, or having an increased likelihood of responding to a non-peptidic CRHR1 antagonist; and (c) administering a non-peptidic CRHR1 antagonist to the subject diagnosed as a non-peptidic CRHR1 antagonist responder.

20. The method of claim 19, wherein the diagnosing step comprises one or more statistical analysis method selected from the group consisting of artificial neural network learning, decision tree learning, decision tree forest learning, linear discriminant analysis, non-linear discriminant analysis, genetic expression programming, relevance vector machines, linear models, generalized linear models, generalized estimating equations, generalized linear mixed models, the elastic net, the lasso support vector machine learning, Bayesian network learning, probabilistic neural network learning, clustering, and regression analysis, optionally wherein the statistical analysis method is computer-implemented.

21. The method of claim 19, wherein the non-peptidic CRHR1 antagonist responder has a clinical response.

22. The method of claim 19, wherein the subject has depressive symptoms, anxiety symptoms or both depressive symptoms and anxiety symptoms or a sleep disorder; and/or wherein the CRHR1 antagonist treats depressive symptoms, anxiety symptoms or both depressive symptoms and anxiety symptoms or a sleep disorder.

23. The method of claim 21, wherein the clinical response is a prevention, alteration, alleviation or complete remission of depressive symptoms and/or anxiety symptoms or a sleep disorder.

24. The method of claim 21, wherein the clinical response is a prevention, alteration, alleviation or complete remission of depressive symptoms and/or anxiety symptoms as determined using a scale selected from the group consisting of HAM-D, BDI, MADRS, GDS, ZSRDS, HAM-A and STAI.

25. The method of claim 19, wherein the biological sample is a buccal or a blood sample.

26. The method of claim 19, wherein detecting comprises the use of one or more polynucleotides capable of specifically hybridizing to at least one nucleic acid comprising the one or more polymorphism genotypes.

27. The method of claim 19, wherein the prediction that the subject will respond to a treatment with a non-peptidic CRHR1 antagonist has a sensitivity of higher than 50% and a specificity of higher than 50%.

28. The method of claim 19, wherein the non-peptidic CRHR1 antagonist is selected from the group consisting of GW876008 (Emicerfont), GSK-561679 (NBI-77860, Verucerfont), GSK586529, BMS-562,086 (Pexacerfont), NBI-30775 (R-121919), NBI-34101, CP-316,311, CP-376,395, PF-00572778, NVP-AAG561, Ono-2333 MS, E2508, E2009, R317573 (JNJ19567470, CRA5626, TAI-041), R278995 (CRA0450), CRA-1000, CRA-1001, CP154,526, Antalarmin, DMP-695, DMP-696, DMP-904, SC-241, BMS-561388, NBI30545, PD-171729, NBI34041, NBI35965, SN003, NBI-27914, trans-2-chloro-N-(4-((5-fluoro-4-methyl-pyridin-2-ylamino)-methyl)-cyclohexyl)-5-(trifluoromethyl)benzamide, SSR-125543, or a pharmaceutically acceptable salt thereof.

29. The method of claim 1, wherein the detecting step comprises amplification of nucleic acids extracted and/or purified from the biological sample obtained from the subject, and optionally clean-up of amplified products.

30. The method of claim 29, further comprising fragmentation of amplified nucleic acids and/or labelling of amplified nucleic acids.

31. The method of claim 11, wherein the detecting step comprises amplification of nucleic acids extracted and/or purified from the biological sample obtained from the subject, and optionally clean-up of amplified products.

32. The method of claim 31, further comprising fragmentation of amplified nucleic acids and/or labelling of amplified nucleic acids.

33. The method of claim 13, wherein the detecting step comprises amplification of nucleic acids extracted and/or purified from the biological sample obtained from the subject, and optionally clean-up of amplified products.

34. The method of claim 33, further comprising fragmentation of amplified nucleic acids and/or labelling of amplified nucleic acids.

35. The method of claim 19, wherein the detecting step comprises amplification of nucleic acids extracted and/or purified from the biological sample obtained from the subject, and optionally clean-up of amplified products.

36. The method of claim 35, further comprising fragmentation of amplified nucleic acids and/or labelling of amplified nucleic acids.

37. The method of claim 1, wherein the detecting step comprises specific hybridization of at least one polynucleotide, which is optionally labelled, to a nucleic acid comprising the one or more polymorphism genotypes.

38. The method of claim 37, wherein the polynucleotide is a primer or a probe.

39. The method of claim 37, wherein the at least one polynucleotide capable of specifically hybridizing to the polymorphism genotypes is selected from the group consisting of

AGAATTATTGCTGCACAATTCTTATGAAACCG-AACTAGAGCTACACTATT (SEQ ID NO:179),

AATCTTGGGGAATCTGAGTTTATTAGAG-GAATGTAGGGAGGAAGCAGGCT (SEQ ID NO:102),

TACCATGGGAAACAGACAGTGGCCCCTGTTCT-CAAGTGGCTTAGACTCTA (SEQ ID NO:208), and

TAAGGATGGGACCCCTACTGTCCATCTCAG-GCTCAGCACTGCCTTGGGGC (SEQ ID NO:249).

40. The method of claim 11, wherein the detecting step comprises specific hybridization of at least one polynucleotide to a nucleic acid comprising the one or more polymorphism genotypes.

41. The method of claim 40, wherein the polynucleotide is a primer or a probe.

42. The method of claim 40, wherein the at least one polynucleotide capable of specifically hybridizing to the polymorphism genotypes is selected from the group consisting of

AGAATTATTGCTGCACAATTCTTATGAAACCG-AACTAGAGCTACACTATT (SEQ ID NO:179),

AATCTTGGGGAATCTGAGTTTATTAGAG-GAATGTAGGGAGGAAGCAGGCT (SEQ ID NO:102),

TACCATGGGAAACAGACAGTGGCCCCTGTTCT-CAAGTGGCTTAGACTCTA (SEQ ID NO:208), and

TAAGGATGGGACCCCTACTGTCCATCTCAGG-CTCAGCACTGCCTTGGGGC (SEQ ID NO:249).

43. The method of claim 13, wherein the detecting step comprises specific hybridization of at least one polynucleotide to a nucleic acid comprising the one or more polymorphism genotypes.

44. The method of claim 43, wherein the polynucleotide is a primer or a probe.

45. The method of claim 43, wherein the at least one polynucleotide capable of specifically hybridizing to the polymorphism genotypes is selected from the group consisting of

AGAATTATTGCTGCACAATTCTTATGAAACCGA-ACTAGAGCTACACTATT (SEQ ID NO:179),

AATCTTGGGGAATCTGAGTTTATTAGAG-GAATGTAGGGAGGAAGCAGGCT (SEQ ID NO:102),

TACCATGGGAAACAGACAGTGGCCCCTGTTCT-CAAGTGGCTTAGACTCTA (SEQ ID NO:208), and

TAAGGATGGGACCCCTACTGTCCATCTCAGG-CTCAGCACTGCCTTGGGGC (SEQ ID NO:249).

46. The method of claim 19, wherein the detecting step comprises specific hybridization of at least one polynucleotide to a nucleic acid comprising the one or more polymorphism genotypes.

47. The method of claim 46, wherein the polynucleotide is a primer or a probe.

48. The method of claim 46, wherein the at least one polynucleotide capable of specifically hybridizing to the polymorphism genotypes is selected from the group consisting of

AGAATTATTGCTGCACAATTCTTATGAAACCG-AACTAGAGCTACACTATT (SEQ ID NO: 179),

AATCTTGGGGAATCTGAGTTTATTAGAG-GAATGTAGGGAGGAAGCAGGCT (SEQ ID NO:102),

TACCATGGGAAACAGACAGTGGCCCCTGTTCT-CAAGTGGCTTAGACTCTA (SEQ ID NO:208), and

TAAGGATGGGACCCCTACTGTCCATCTCAG-GCTCAGCACTGCCTTGGGGC (SEQ ID NO:249).

49. The method of claim 1, wherein the detecting step comprises a method selected from the group consisting of allele-specific oligonucleotide (ASO)-dot blot analysis, primer extension assays, iPLEX polymorphism/SNP genotyping, dynamic allele-specific hybridization (DASH) genotyping, the use of molecular beacons, tetra primer ARMS PCR, a flap endonuclease invader assay, an oligonucleotide ligase assay, PCR-single strand conformation polymorphism (SSCP) analysis, quantitative real-time PCR assay, polymorphism/SNP microarray based analysis, restriction enzyme fragment length polymorphism (RFLP) analysis, targeted resequencing analysis and whole genome sequencing analysis.

50. The method of claim 11, wherein the detecting step comprises a method selected from the group consisting of allele-specific oligonucleotide (ASO)-dot blot analysis, primer extension assays, iPLEX polymorphism/SNP genotyping, dynamic allele-specific hybridization (DASH) genotyping, the use of molecular beacons, tetra primer ARMS PCR, a flap endonuclease invader assay, an oligonucleotide ligase assay, PCR-single strand conformation polymorphism (SSCP) analysis, quantitative real-time PCR assay, polymorphism/SNP microarray based analysis, restriction enzyme fragment length polymorphism (RFLP) analysis, targeted resequencing analysis and whole genome sequencing analysis.

51. The method of claim 13, wherein the detecting step comprises a method selected from the group consisting of allele-specific oligonucleotide (ASO)-dot blot analysis, primer extension assays, iPLEX polymorphism/SNP genotyping, dynamic allele-specific hybridization (DASH) genotyping, the use of molecular beacons, tetra primer ARMS PCR, a flap endonuclease invader assay, an oligonucleotide ligase assay, PCR-single strand conformation polymorphism (SSCP) analysis, quantitative real-time PCR assay, polymorphism/SNP microarray based analysis, restriction enzyme fragment length polymorphism (RFLP) analysis, targeted resequencing analysis and whole genome sequencing analysis.

52. The method of claim 19, wherein the detecting step comprises a method selected from the group consisting of allele-specific oligonucleotide (ASO)-dot blot analysis, primer extension assays, iPLEX polymorphism/SNP genotyping, dynamic allele-specific hybridization (DASH) genotyping, the use of molecular beacons, tetra primer ARMS PCR, a flap endonuclease invader assay, an oligonucleotide ligase assay, PCR-single strand conformation polymorphism (SSCP) analysis, quantitative real-time PCR assay, polymorphism/SNP microarray based analysis, restriction enzyme fragment length polymorphism (RFLP) analysis, targeted resequencing analysis and whole genome sequencing analysis.

53. The method of claim 1, wherein the at least one polymorphism genotype comprises at least one polymorphism genotype selected from the group consisting of rs11715827 [G], rs2044070 [G], rs2028629 [G] and rs6026567 [G] in combination with at least one polymorphism genotype selected from the group consisting of rs17740874 [T], rs3811939 [G], rs1882478 [G], rs2235013 [T], rs2214102 [T], rs6415328 [C], rs77152456 [A], rs66794218 [A], rs2589476 [T], rs118003903 [G], rs11871392 [T], rs2589487 [C], rs74338736 [C], rs6026593 [G] and rs6520908 [T].

54. The method of claim 19, wherein the one or more polymorphism genotypes comprise at least one polymorphism genotype selected from the group consisting of rs11715827 [G], rs2044070 [G], rs2028629 [G] and rs6026567 [G] in combination with at least one polymorphism genotype selected from the group consisting of rs17740874 [T], rs3811939 [G], rs1882478 [G], rs2235013 [T], rs2214102 [T], rs6415328 [C], rs77152456 [A], rs66794218 [A], rs2589476 [T], rs118003903 [G], rs11871392 [T], rs2589487 [C], rs74338736 [C], rs6026593 [G] and rs6520908 [T].

55. The method of claim 53, wherein the at least one polymorphism genotype comprises:

(a) at least two;

(b) at least four;

(c) at least eight;

(d) at least sixteen; or (e) all of the polymorphism genotypes as defined in claim 53.

56. The method of claim 54, wherein the one or more polymorphism genotypes comprise:

(a) at least two;
(b) at least four;
(c) at least eight;
(d) at least sixteen; or
(e) all of the polymorphism genotypes as defined in claim 54.

57. The method of claim 13, wherein the kit comprises at least one polynucleotide capable of specifically hybridizing to a nucleic acid at least one polymorphism genotype selected from the group consisting of rs11715827 [G], rs2044070 [G], rs2028629 [G] and rs6026567 [G] in combination with at least one polynucleotide capable of specifically hybridizing to a nucleic acid at least one polymorphism genotype selected from the group consisting of rs17740874 [T], rs3811939 [G], rs1882478 [G], rs2235013 [T], rs2214102 [T], rs6415328 [C], rs77152456 [A], rs66794218 [A], rs2589476 [T], rs118003903 [G], rs11871392 [T], rs2589487 [C], rs74338736 [C], rs6026593 [G] and rs6520908 [T].

58. The method of claim 57, wherein said kit comprises:

(a) at least two;
(b) at least four;
(c) at least eight;
(d) at least 16; or
(e) 19 of the polynucleotides capable of specifically hybridizing to nucleic acids comprising each of the polymorphism genotypes as defined in claim 57.

* * * * *